(12) United States Patent
Hoveyda et al.

(10) Patent No.: US 10,017,468 B2
(45) Date of Patent: Jul. 10, 2018

(54) SUBSTITUTED PYRROLIDINES AS G-PROTEIN COUPLED RECEPTOR 43 AGONISTS

(71) Applicant: Ogeda SA, Gosselies (BE)

(72) Inventors: Hamid R. Hoveyda, Brussels (BE); Didier Schils, Loupoigne (BE); Ludivine Zoute, Vedrin (BE); Julien Parcq, Lille (FR)

(73) Assignee: Ogeda SA, Gosselies (BE)

( * ) Notice: Subject to any disclaimer, the term of this patent is extended or adjusted under 35 U.S.C. 154(b) by 0 days.

(21) Appl. No.: 15/624,290

(22) Filed: Jun. 15, 2017

(65) Prior Publication Data

US 2017/0283376 A1 Oct. 5, 2017

Related U.S. Application Data

(60) Division of application No. 13/526,337, filed on Jun. 18, 2012, now Pat. No. 9,695,120, which is a continuation of application No. PCT/EP2010/070040, filed on Dec. 17, 2010.

(60) Provisional application No. 61/376,013, filed on Aug. 23, 2010, provisional application No. 61/373,370, filed on Aug. 13, 2010.

(30) Foreign Application Priority Data

Dec. 18, 2009 (EP) .................. 09306270

(51) Int. Cl.
| | |
|---|---|
| C07D 295/10 | (2006.01) |
| C07D 207/16 | (2006.01) |
| C07D 277/06 | (2006.01) |
| C07D 401/04 | (2006.01) |
| C07D 401/06 | (2006.01) |
| C07D 401/12 | (2006.01) |
| C07D 403/10 | (2006.01) |
| C07D 403/14 | (2006.01) |
| C07D 405/10 | (2006.01) |
| C07D 407/06 | (2006.01) |
| C07D 409/10 | (2006.01) |
| C07D 413/10 | (2006.01) |
| C07D 413/12 | (2006.01) |

(52) U.S. Cl.
CPC ......... *C07D 207/16* (2013.01); *C07D 277/06* (2013.01); *C07D 401/04* (2013.01); *C07D 401/06* (2013.01); *C07D 401/12* (2013.01); *C07D 403/10* (2013.01); *C07D 403/14* (2013.01); *C07D 405/10* (2013.01); *C07D 407/06* (2013.01); *C07D 409/10* (2013.01); *C07D 413/10* (2013.01); *C07D 413/12* (2013.01)

(58) Field of Classification Search
CPC .................................................. C07D 295/10
USPC .......................................................... 548/530
See application file for complete search history.

(56) References Cited

U.S. PATENT DOCUMENTS

| | | | |
|---|---|---|---|
| 3,542,788 | A | 11/1970 | Chinn et al. |
| 4,098,680 | A | 7/1978 | Luckenbach |
| RE35,096 | E | 11/1995 | Taniguchi et al. |
| 7,459,472 | B2 | 12/2008 | Mjalli et al. |
| 7,576,175 | B2 | 8/2009 | Lam et al. |
| 2006/0199817 | A1 | 9/2006 | Tasker et al. |
| 2007/0082932 | A1 | 4/2007 | Jiaang et al. |
| 2007/0129335 | A1 | 6/2007 | Furukawa et al. |
| 2009/0233972 | A1 | 9/2009 | Or et al. |
| 2010/0074863 | A1 | 3/2010 | Or et al. |

FOREIGN PATENT DOCUMENTS

| | | |
|---|---|---|
| EP | 0168607 A1 | 1/1986 |
| JP | 51-93794 A | 8/1976 |
| JP | 3005469 B2 | 1/2000 |
| WO | WO-9320099 A2 | 10/1993 |
| WO | WO-9840373 A1 | 9/1998 |
| WO | WO-200185720 A1 | 11/2001 |
| WO | WO-2003037895 A1 | 5/2003 |
| WO | WO-2004060862 A2 | 7/2004 |
| WO | WO-2004062553 A2 | 7/2004 |
| WO | WO-200514533 A2 | 2/2005 |
| WO | WO-2005014534 A1 | 2/2005 |
| WO | WO-2006036688 A2 | 4/2006 |
| WO | WO-2009003009 A1 | 12/2008 |

OTHER PUBLICATIONS

Newsholme et al., Biochem J. 1961, 80, 655-662.
Prentki et al., Endocrine Rev. 2008, 29, 647-676.
Sellin et al., News Physiol. Sci. 1999, 14, 58-64.
McArthur et al., J. Lipid. Res. 1999, 40, 1371-1383.
Wild et al., Diabetes Care 2004, 27, 1047-1053.
Fraze et al., J. Clin. Endocrinol. Metab. 1985, 61, 807-811.
Anderson et al., J. Am. Coll. Nutr. 2004, 23, 5-17.
Berggren et al., Br. J. Nutr. 1996, 76, 287-294.

(Continued)

*Primary Examiner* — Douglas M Willis
(74) *Attorney, Agent, or Firm* — Locke Lord LLP; Nicholas J. DiCeglie, Jr.

(57) ABSTRACT

The present invention is directed to a process for the preparation of aryl-pyrrolidine carboxylic acid derivative compounds which are useful in treating metabolic diseases, said process consisting of coupling an aryl-pyrrolidine compound with an aryl carboxylic acid compound followed by alkaline or acidic treatment, hydrogenolysis or treatment with a fluoride of the ester intermediate to afford novel aryl-pyrrolidine carboxylic acid derivative compounds.

3 Claims, 2 Drawing Sheets

(56) References Cited

OTHER PUBLICATIONS

Sakakibara et al., *Biochem. Biophys. Res. Com* <http://Biochem.Biophys.Res.Com>. 2006, 344, 597-604.
Tenenbaum et al., Cardiov. Diab. 2006, 5:20.
Le Poul et al., J. Biol. Chem. 2003, 278, 25481-25489.
Covington et al., Biochem. Soc. Trans. 2006, 34, 770-773.
Rayasam et al., Exp. Opin. Ther. Targets 2007, 11, 661-671.
Regard et al., J. Clin. Invest. 2007, 117, 4034-4043.
Suokas et al., Alcohol. Clin. Exp. Res. 1988, 12, 52-58.
Laurent et al., Eur. J. Clin. Nut. 1995, 49, 484-491.
Ge et al., Endocrinology 2008, 149, 4519-4526.
Lee et al., Mol. Pharmacol. 2008, 74, 1599-1609.
Colandrea et al., Bioorg. Med. Chem. Lett. 2006, 16, 2905-2908.
Ying-Zi Xu et al., J. Org. Chem. 1999, 64, 4060-4078.
Johnson et al., *J. Org* <http://J.Org>. Chem. 2003, 68, 5300-5309.
Clapham et al., *J. Org* <http://J.Org>. Chem. 2008, 73, 2176-2181.
Burton et al., Bioorg. Med. Chem. Lett. 2005, 15, 1553-1556.
Refouvelet et al., J. Het. Chem. 2000, 37, 1425-1430.
Prabhakar et al., QSAR & Com. Sci. 2003, 22, 456-465.
Cossy et al., Synlett 1997, 905-906.
Wallén et al., Bio Med Chem 2003, 11, 3611-3619.
Hong et al., Endocrinology 2005, 146, 5092-5099.
Sato et al., Chem. Pharm. Bull. 1994, 42, 521-529.
Onomura, Osamu et al., Tetrahedron 2008, 64, 7498-7503.
K. M. Maslowski et al, "Regulation of inflammatory responses by gut microbiota and chemoattractant receptor GPR43", Nature, Oct. 2009, vol. 461, No. 7268, pp. 1282-1286.
Halab et al., "Effect of sequence on peptide geometry in 5-tert-butylprolyl type VI beta-turn mimics.", J. Am. Chem. Soc., vol. 124, N °11, Mar. 2002, pp. 2474-2484.
Liu T. et al,"Tumor necrosis factor-alpha expression in ischemic neurons", Stroke, vol. 25, N °7, Jul. 1994, pp. 1481-1488.
Chandrasekhar et al., "Arthritis induced by interleukin-1 is dependent on the site and frequency of intraarticular injection", Clinical Immunol. Immunopathol. vol. 55, N °3, Jun. 1990, pp. 382-400.
Firestein G.S. et al., "Stromelysin and tissue inhibitor of metalloproteinases gene expression in rheumatoid arthritis synovium", Am. J. Pathol., vol. 140, N °6, Jun. 1992, pp. 1309-1314.
Dinarello, "The biological properties of interleukin-1.", Eur. Cytokines Netw., vol. 5, N °6, Nov.-Dec. 1994, pp. 517-531.
Maini et al.; "Monoclonal anti-TNF alpha antibody as a probe of pathogenesis and therapy of rheumatoid disease", Immunological Reviews, Apr. 1995, pp. 195-223.
Senga et al., "LSSIG is a novel murine leukocyte-specific GPCR that is induced by the activation of STAT3", Blood, vol. 101, N °3, Feb. 2003, pp. 1185-1187.
Fuss, "Cytokine network in inflammatory bowel disease", Curr. Drug Targets Inflamm. Allergy, vol. 2, N °2, Jun. 2003, pp. 101-112.
Tedelind, S. et al.,"Anti-inflammatory properties of the short-chain fatty acids acetate and propionate: a study with relevance to inflammatory bowel disease.", World J. Gastroenterol., vol. 13, N °20, May 2007, pp. 2826-2832.
XP-02277781—Steinkopf, JLACBF: Justus Liebings Ann. Chem; 540; 1939; 1-5.
CAS Registry Database, RN: 1185864-08-7, entered STN: Sep. 21, 2009, accessed on Sep. 12, 2015.
Jordan, V. C. Nature Reviews: Drug Discovery, 2, 2003, 205.
Beausoleil, et al. Biopolymers, 53(3), 2000, 249-256.
Vippagunta, et al. Advanced Drug Delivery Reviews, 48, 2001, 18.
Wolff Manfred E., Ed. Burger's Medicinal Chemistry and Drug Discovery—Fifth Edition, vol. 1: Principles and Practice, New York: John Wiley & Sons, 1994, 975-977.
Kim, et al., Arch. Pharm. Res., vol. 35, No. 9, 1505-1509, 2012.
Bindels, et al., Trends in Pharmacological Sciences Apr. 2013, vol. 34, No. 4.
Wikipedia, Acyl, last modified Dec. 29, 2013.
IUPAC, downloaded Oct. 29, 2010, http://www.iupac.org/goldbook/A00123.pdf.
Hawley's Condensed Chem. Dict., 14th Ed., 2002.
Hackh's Chem. Dict., 3rd Ed., 1944, p. 18.

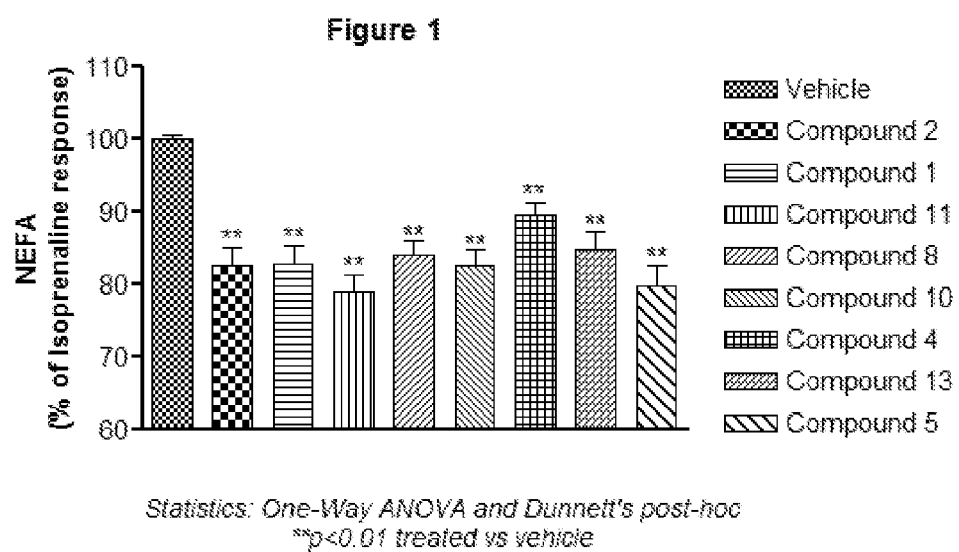

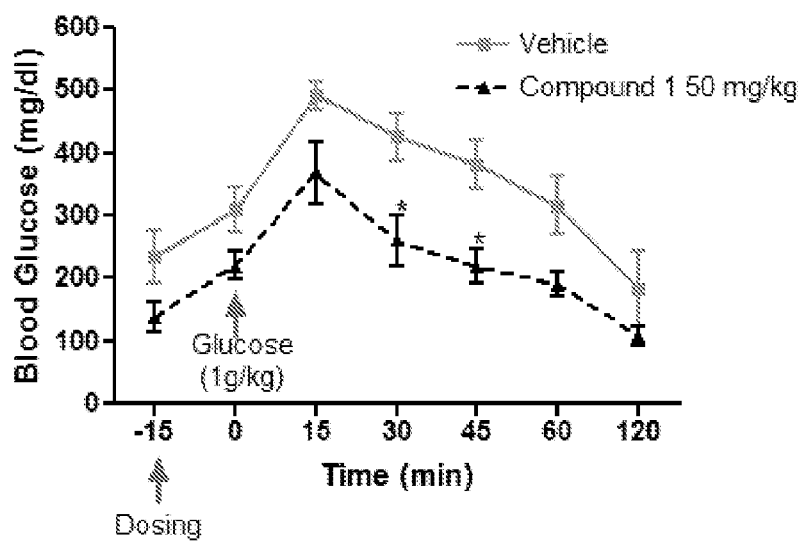
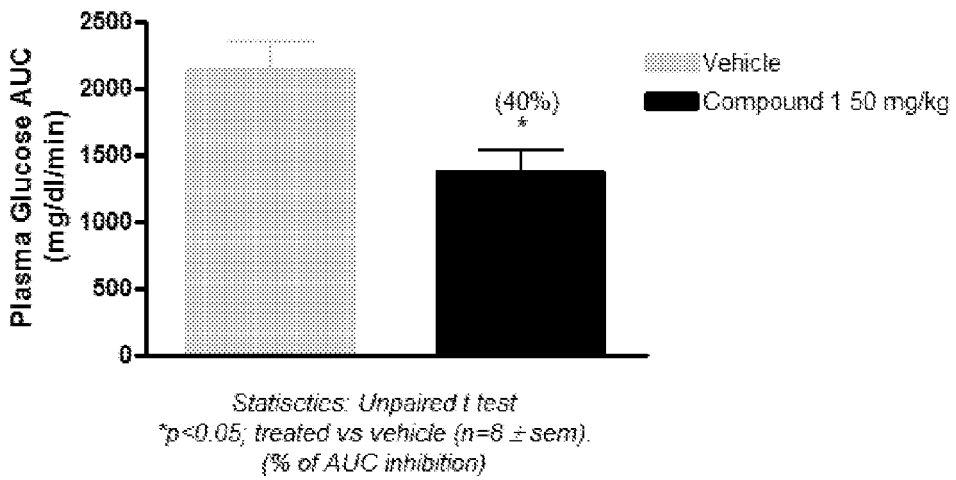

SUBSTITUTED PYRROLIDINES AS G-PROTEIN COUPLED RECEPTOR 43 AGONISTS

CROSS-REFERENCE TO RELATED APPLICATION

This application is a divisional application of U.S. patent application Ser. No. 13/526,337, filed Jun. 18, 2012, which is a continuation of PCT international application Ser. No. PCT/EP2010/070040, filed Dec. 17, 2010, designating the United States, which claims the benefit of European Application No. 09306270.1, filed on Dec. 18, 2009, U.S. Provisional Application 61/373,370, filed on Aug. 13, 2010, and U.S. Provisional Application No. 61/376,013, filed on Aug. 23, 2010. The entire contents of the aforementioned patent applications are incorporated herein by this reference.

The present invention relates to novel compounds including their pharmaceutically acceptable salts, solvates and prodrugs, which are agonists or partial agonists of G-protein coupled receptor 43 (GPR43) and are useful as therapeutic compounds, particularly in the treatment and/or prevention of Type 2 diabetes mellitus and conditions that are often associated with this disease including, lipid disorders such as dyslipidemia, hypertension, obesity, atherosclerosis and its sequelae.

BACKGROUND OF THE INVENTION

Under normal conditions, Free Fatty Acids (FFAs) are implicated in numerous physiological processes by serving as fuel in various metabolic pathways and/or acting as signaling molecules in different tissues such as the heart, liver, skeletal muscle, adipocytes and the pancreas (Newsholme et al., Biochem. J., 80 pp 655-662, 1961; Prentki et al., Endocrine Reviews, PubMed print ahead, 2008). Among FFAs, the short-chain fatty acids (SCFAs, carbon length C2-C6) are generated during anaerobic bacterial fermentation of fiber in the gut (Sellin et al., News. Physiol. Sci., 14, pp 58-64, 1999). Long-chain fatty acids (LCFAs, carbon length C14-C24) are products of dietary intake from adipose tissues and liver (McArthur et al., J. Lipid. Res., 40, pp 1371-1383, 1999).

Obesity is an increasing, worldwide public health problem associated with devastating pathologies such as type 2 diabetes (T2D) and dyslipidemia (Wild et al., Diabetes Care 27, pp 1047-1053, 2004). Dyslipidemia is characterized by high levels of triglycerides and/or LDL (bad cholesterol) or low levels of HDL (good cholesterol). Dyslipidemia is a key independent risk factor for cardiovascular diseases. It has long been suggested that FFAs are implicated in the regulation and/or genesis of these diseases (Fraze et al., J. Clin. Endocrinol. Metab., 61, pp 807-811, 1985). It is well established that regular intake of dietary fiber has several beneficial metabolic effects such as lowering of plasma cholesterol and triglyceride levels (Anderson et al., J. Am. Coll. Nutr., 23, pp 5-17, 2004). Specifically, dietary fiber has been shown to increase endogenous levels of SCFAs, leading to the suppression of cholesterol synthesis and improvement in glucose tolerance in rat (Berggren et al., Br. J. Nutr., 76, pp 287-294, 1996), as well as the reduction of hyperglycemia in a diabetic mice model (Sakakibara et al., Biochem. Biophys. Res. Com., 344, pp 597-604, 2006).

Drug therapies are available to address both T2D and dyslipidemia. Specifically, statins, fibrates and nicotinic acid or combinations thereof are often considered as a first line therapy in dyslipidemia whereas metformin, sulphonylureas and thiazolidinediones are three, widely-used classes of oral anti-diabetic drugs (Tenenbaum et al., Cardiovascular Diabetology, 5, pp 20-23, 2006). Although theses therapies are widespread in their use, the common appearance of adverse effects or lack of efficacy after long-term use causes concern. Moreover, the growing patient population suffering from T2D, dyslipidemia and associated metabolic diseases creates a demand for new entrants into this therapeutic market.

GPR43 (also named FFA2R) belongs to a subfamily of G-Protein-Coupled Receptors (GPCRs), including GPR40 and GPR41 that have been identified as receptor for FFAs (Le Poul et al., J. Biol Chem. 278, 25481-489, 2003; Covington et al., Biochemical Society transaction 34, 770-773, 2006). The 3 family members share 30 to 40% sequence identity with specificity toward different fatty acids carbon chain lengths, with SCFAs (short chain fatty acids: six carbons molecules or shorter) activating GPR41 and GPR43; and medium and long chain fatty acids (MCFA, LCFA) activating GPR40 (Rayasam et al., Expert Opinion on therapeutic targets, 11 661-671, 2007). C2 acetate and C3 propionate are the most potent activators of GPR43. GPR43 is mainly coupled with Gq-proteins, with some evidence for its possible coupling with Gi/o pathways as well.

GPR43 is strongly expressed in adipocytes. Also there is evidence suggesting that GPR43 is overexpressed in pancreatic β-cells in prediabetic states as shown in WO2006/036688A2. Recent papers confirmed the GPR43 expression in pancreatic islets (Ahren, Nature Reviews, 8 pp 396-385; 2009; Regard et al., J; Clin. Invst., 117 pp 4034-4043, 2007). In adipocyte cells, GPR43 is induced during the differentiation process and increased during the high fat feeding in rodents, suggesting that GPR43 may affect adipocyte functions (Hong et al., Endocrinology, 146 pp 5092-5099, 2005). Indeed, it has been reported that acetate and propionate may stimulate adipogenesis via GPR43. In addition siRNA results hinted that acetate and propionate may inhibit lipolysis in adipocytes via GPR43 activation (Hong et al., Endocrinology, 146 pp 5092-5099, 2005). It is interesting to note that the effect of acetate on reducing plasma free fatty acids level has been documented in humans (Suokas et al., Alcoholism, clinical and experimental research, 12 pp 52-58, 1988; Laurent et al., European journal of clinical nutrition, 49 pp 484-491, 1995). In addition, it has been shown that (i) adipocytes treated with GPR43 endogenous SCFA ligands exhibit a reduction in lipolytic activity and such inhibition of lypolysis is the result of GPR43 activation and (ii) GPR43 activation by acetate results in the reduction of plasma free fatty acids level in vivo (Ge et al., Endocrinology, 149 pp 4519-26, 2008). Recently two GPR43 positive allosteric modulator molecules have been shown able to inhibit the lipolysis in adipocytes similarly to that of GPR43 endogenous SCFA ligands (Lee et al., Mol Pharmacol, 74(6) pp 1599-1609, 2008). Such results suggest a potential role of GPR43 in regulating plasma lipid profiles and aspects of metabolic syndrome.

On this basis, new agonists or partial agonists of GPR43 may be of therapeutic value for T2D mellitus and conditions that are associated with this disease including, lipid disorders such as dyslipidemia, hypertension, obesity, atherosclerosis and its sequelae.

SUMMARY OF THE INVENTION

The invention encompasses compounds of general Formula I, their pharmaceutically acceptable salts, solvates and prodrugs as well as methods of use of such compounds or compositions comprising such compounds as modulators of GPR43 activity.

In a general aspect, the invention provides compounds of general formula I:

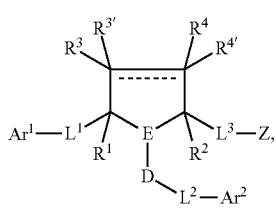

and pharmaceutically acceptable salts, solvates and prodrugs thereof,
wherein
$Ar^1$ is a 5- to 6-membered aryl or heteroaryl group, 3- to 8-membered cycloalkyl group, a 3- to 8-membered heterocycloalkyl group, or a linear or branched $C_3$-$C_6$ alkyl group, each of which being optionally substituted by one or more group(s) selected from halo, cyano, alkyl, hydroxyalkyl, haloalkyl, cycloalkyl, cycloalkylalkyl, alkenyl, alkynyl, heteroalkyl, heterocyclyl, heterocyclylalkyl, aryl, aralkyl, heteroaryl, heteroarylalkyl, hydroxyl, alkoxy, haloalkoxy, cycloalkyloxy, heterocyclyloxy, aryloxy, amino, alkylamino, aminoalkyl, carboxy, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonylsulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or two substituents form an alkylenedioxy group or a haloalkylenedioxy group, or two substituents form a cycloalkyl or heterocycloalkyl moiety together with the cycloalkyl or heterocycloalkyl group they are attached to, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo;
$L^1$ is a single bond, $C_1$-$C_3$ alkylene, $C_3$-$C_6$ cycloalkylene, $C_2$-$C_3$ alkenylene, $C_2$-$C_3$ alkynylene, each of which being optionally substituted by one or more group(s) selected from halo, alkyl, haloalkyl, hydroxyl, alkoxy, haloalkoxy, hydroxyalkyl, alkoxyalkyl;
$R^1$ is H, linear or branched $C_1$-$C_4$ alkyl;
E is N, C—$R^5$ where $R^5$ is H, linear or branched $C_1$-$C_4$ alkyl;
D is CO or D is where D is

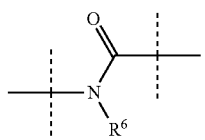

linked to E either on the nitrogen or the carbonyl and $R^6$ is H, alkyl, $C_2$-$C_4$ alkenyl, $C_2$-$C_4$ alkynyl, haloalkyl, cycloalkyl, cycloalkylalkyl, hydroxyalkyl or alkoxyalkyl, and under the condition that E is C—$R^5$;
$L^2$ is a single bond, $C_1$-$C_4$ alkylene, $C_3$-$C_6$ cycloalkylene, $C_2$-$C_3$ alkenylene, $C_2$-$C_3$ alkynylene each of which being optionally substituted by one or more group(s) selected from halo, alkyl, haloalkyl, hydroxyl, alkoxy, haloalkoxy, hydroxyalkyl or alkoxyalkyl;
$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, alkenyl, alkynyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, amino, alkylamino, aminoalkyl, arylcarbonyl, carboxy, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, oxo or two substituents form an alkylenedioxy group or a haloalkylenedioxy group, or two substituents form a cycloalkyl or heterocycloalkyl moiety together with the cycloalkyl or heterocyclyl group they are attached to, or fused to the aryl, heteroaryl, cycloalkyl or heterocyclyl group may be one or more cycloalkyl, aryl, heterocyclyl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, cycloalkylalkyl, heteroalkyl, hydroxyl, alkoxy, haloalkoxy, cycloalkyloxy, cycloalkylalkyloxy, aryloxy, aralkyloxy optionally substituted by a fluoro group, alkylamino, carboxy, alkoxycarbonyl, alkylcarbonyloxy, cycloalkylcarbonyloxy, amino, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, cycloalkylsulfonylamino, haloalkylsulfonylamino, oxo, aralkyl, heteroarylalkyl, alkoxyalkoxy, alkoxyalkyl, and haloalkoxyalkyl.

$R^2$ is H;

$L^3$ is a single bond, $C_1$-$C_3$ alkylene, $C_3$-$C_6$ cycloalkylene, $C_2$-$C_3$ alkenylene or $C_2$-$C_3$ alkynylene each of which being optionally substituted by one or more group(s) selected from halo, alkyl, haloalkyl, hydroxyl, alkoxy, haloalkoxy, hydroxyalkyl, alkoxyalkyl;

Z is selected from the group consisting of —COOR,

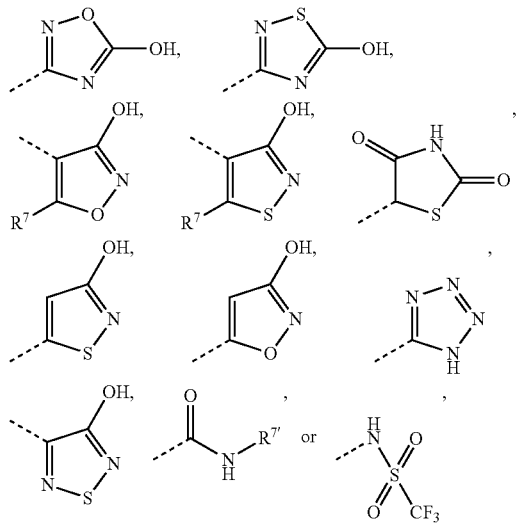

wherein R is H or linear or branched alkyl, aryl, acyloxyalkyl, dioxolene, $R^7$ is H, methyl or ethyl, and $R^{7'}$ is hydroxyl —$SO_2CH_3$, —$SO_2$cyclopropyl or —$SO_2CF_3$;

the bond represented by the dotted line is either absent or present;

$R^3$ is H, halo, cyano, alkyl, hydroxyalkyl, haloalkyl, cycloalkyl, cycloalkylalkyl, alkenyl, alkynyl, heteroalkyl, heterocyclyl, heterocyclylalkyl, aryl, aralkyl, heteroaryl, heteroarylalkyl, hydroxyl, alkoxy, alkoxyalkyl, haloalkoxy, cycloalkyloxy, heterocyclyloxy, aryloxy, amino, alkylamino, aminoalkyl, alkylcarbonyloxy, cycloalkylcarbonyloxy, heterocyclylcarbonyloxy, arylcarbonyloxy, heteroarylcarbonyloxy, arylalkyloxy, acetyl, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonylsulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo;

$R^{3'}$ is H or $C_1$-$C_4$ alkyl, or $R^{3'}$ is absent if the dotted line is present;

$R^4$ is H, halo, cyano, alkyl, hydroxyalkyl, haloalkyl, cycloalkyl, cycloalkylalkyl, heteroalkyl, heterocyclyl, heterocyclylalkyl, aryl, aralkyl, heteroaryl, heteroarylalkyl, hydroxyl, alkoxy, haloalkoxy, cycloalkyloxy, heterocyclyloxy, aryloxy, amino, alkylamino, aminoalkyl, carboxy, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonylsulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, or $R^4$ forms together with $R^3$ a cyclopropane ring optionally substituted by one or more group selected from halo, alkyl, haloalkyl, hydroxyl, alkoxy, or haloalkoxy, under the condition that the dotted line is absent;

$R^{4'}$ is H, $C_1$-$C_4$ alkyl, or $R^{4'}$ is absent if the dotted line is present;

under the condition that the compound of formula (I) is not
(2S)-methyl 1-benzoyl-5-mesitylpyrrolidine-2-carboxylate,
(2S)-methyl 1-benzoyl-5-(2,4,6-triethylphenyl)pyrrolidine-2-carboxylate,
(2S,5S)-1-benzoyl-5-mesitylpyrrolidine-2-carboxylic acid,
(2S)-methyl 1-benzoyl-5-propylpyrrolidine-2-carboxylate,
(2S,5S)-methyl 1-benzoyl-5-propylpyrrolidine-2-carboxylate, (2S,5R)-methyl 1-benzoyl-5-propylpyrrolidine-2-carboxylate,
(2S,5R)-5-(tert-butyl)-1-(4-phenylbutanoyl)pyrrolidine-2-carboxylic acid,
(2S,5R)-methyl 5-(tert-butyl)-1-(4-phenylbutanoyl)pyrrolidine-2-carboxylate,
(2R,5R)-1-(4-bromothiophene-2-carbonyl)-5-phenylpyrrolidine-2-carboxylic acid,
(2R,5S)-1-(3-bromo-2,6-dimethoxybenzoyl)-5-phenylpyrrolidine-2-carboxylic acid,
tert-butyl 2-[(2R,5S)-2-ethoxycarbonyl-5-phenyl-pyrrolidine-1-carbonyl]indoline-1-carboxylate,
(2R,5S)-1-(1-tert-butoxycarbonylindoline-2-carbonyl)-5-phenyl-pyrrolidine-2-carboxylic acid,
1-[7-(4-tert-butyl-phenoxy)-1-cyclopentylmethyl-isoquinoline-3-carbonyl]-(5R)-phenyl-pyrrolidine-(2S)-carboxylic acid.

Advantageously, the compounds of the invention or pharmaceutically acceptable salts, solvates and prodrugs thereof are those described above in respect to formula (I) with the following provisos:
$Ar^2$ is not phthalazin-6-yl, pyrido[2,3-d]pyridazin-2-yl, pyrido[2,3-d]pyridazin-3-yl, or pyrazino[2,3-d]pyridazin-2-yl; and/or
each of $R^3$ and $R^4$ is not a pyrimid-2-ylamino group substituted at position 6 by a bicyclic heteroaryl group, if the bond represented as a dotted line is absent; and/or
$R^3$ is not a mono substituted hydroxymethyl; and/or
The $D-L^2-Ar^2$ moiety is not

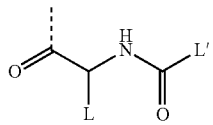

wherein L is H or alkyl and L' is selected from phenyl, naphtyl, indolyl, quinolyl, phenylamino.

In another aspect, the present invention provides a pharmaceutical composition comprising at least one compound according to the invention or a pharmaceutically acceptable salt or solvate thereof.

The invention also relates to the use of the above compounds or their pharmaceutically acceptable salts, solvates and prodrugs as modulators of GPR43, preferably as agonists or partial agonists of GPR43.

The invention further provides methods of treatment and/or prevention of type 11 diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH) comprising the administration of a therapeutically effective amount of a compound or pharmaceutically acceptable salt or solvate of formula (I), to a patient in need thereof. Preferably the patient is a warm-blooded animal, more preferably a human.

The invention also provides the use of a compound of formula (I) or a pharmaceutically acceptable salt or solvate thereof as a medicament. Preferably, the medicament is used for the treatment and/or prevention of type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

In a preferred embodiment the disease is type II diabetes, a lipid disorder such as dyslipidemia, hypertension, obesity, or atherosclerosis and its sequelae.

DETAILED DESCRIPTION OF THE INVENTION

As noted above, the invention relates to compounds of formula I, as well as their pharmaceutically acceptable salts, solvates and prodrugs.

Preferred compounds of formula I and pharmaceutically acceptable salts, solvates and prodrugs thereof are those wherein all the following descriptions are independently the dotted line is absent and E is N; and/or
$L^1$ is a single bond, preferably a single bond drawn as a solid wedge; and/or
$L^3$ is a single bond, preferably a single bond drawn as a solid wedge; and/or
Z is selected from the group consisting of —COOR wherein R is defined as above in respect to formula I, preferably Z is COOH; and/or
$R^3$ is H, halo, cyano, alkyl, hydroxyalkyl, haloalkyl, cycloalkyl, cycloalkylalkyl, alkenyl, alkynyl, heteroalkyl, 5-membered heterocyclyl, heterocyclylalkyl, aryl, aralkyl, 5-membered heteroaryl, heteroarylalkyl, hydroxyl, alkoxy, alkoxyalkyl, haloalkoxy, cycloalkyloxy, heterocyclyloxy, aryloxy, amino, alkylamino, aminoalkyl, alkylcarbonyloxy, cycloalkylcarbonyloxy, heterocyclylcarbonyloxy, arylcarbonyloxy, heteroarylcarbonyloxy, arylalkyloxy, acetyl, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, arylsulfonyl, sulfamoyl, alkylsulfamoyl, alkylsulfonylamino, cycloalkylsulfonylamino, haloalkylsulfonylamino or oxo, preferably $R^3$ is H, cyano, alkyl, haloalkyl, cycloalkylalkyl, heterocyclylalkyl, aralkyl, heteroarylalkyl, alkoxyalkyl, haloalkoxy, aminoalkyl, arylalkyloxy, acetyl, haloalkylcarbonylamino, alkylcarbonylaminoalkyl, carbamoylalkyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or a bicyclic ring made by an aryl, heteroaryl, cycloalkyl or heterocycloalkyl fused to one cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, or $R^3$ forms together with $R^4$ a cyclopropane ring substituted by one or more group selected from halo, haloalkyl, or haloalkoxy, under the condition that the bond represented by the dotted line is absent, more preferably $R^3$ is H, cyano, alkyl, preferably methyl, aralkyl, preferably benzyl, acetyl linked to the E containing ring by bond drawn as a dotted wedge, alkoxyalkyl preferably methoxymethyl, even more preferably $R^3$ is H; and/or $R^4$ is H, halo, cyano, alkyl, hydroxyalkyl, haloalkyl, cycloalkyl, cycloalkylalkyl, heteroalkyl, heterocyclyl, heterocyclylalkyl, aryl, aralkyl, heteroaryl, heteroarylalkyl, hydroxyl, alkoxy, haloalkoxy, cycloalkyloxy, heterocyclyloxy, aryloxy, amino, alkylamino, aminoalkyl, carboxy, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonylsulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, or $R^4$ forms together with $R^3$ a cyclopropane ring substituted by one or more haloalkyl, haloalkoxy, under the condition that the dotted line is absent, preferably $R^4$ is H, methyl or cyano, more preferably $R^4$ is H; and/or $R^{3'}$ and $R^{4'}$ are independently H or methyl, preferably $R^{3'}$ is H or methyl and $R^{4'}$ is H, more preferably $R^{3'}$ and $R^{4'}$ are both H; and/or D is CO and $L^2$ is a single bond; and/or $Ar^1$ is a 5- to 6-membered aryl or heteroaryl group, or a 3- to 6-membered cycloalkyl group, or a linear or branched $C_3$-$C_6$ alkyl group, each of which being optionally substituted by one or more group(s) selected from halo preferably bromo, chloro or fluoro, cyano, $C_1$-$C_4$ alkyl preferably methyl, $C_1$-$C_4$ hydroxyalkyl, $C_1$-$C_4$ haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, $C_1$-$C_4$ alkoxy preferably methoxy, $C_1$-$C_4$ haloalkoxy preferably $OCF_3$ or $OCHF_2$, $C_1$-$C_4$ alkylamino, alkylcarbonylamino, haloalkylcarbonylamino, cycloalkylcarbonylamino, heterocyclylcarbonylamino arylcarbonylamino, heteroarylcarbonylamino, $C_1$-$C_4$ alkylcarbonylaminoalkyl, carbamoyl, hydroxycarbamoyl, $C_1$-$C_4$ alkylcarbamoyl, arylcarbamoyl, heteroarylcarbamoyl, carbamoylalkyl, carbamoylamino, $C_1$-$C_4$ alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or two substituents form an alkylenedioxy group or a haloalkylenedioxy group, or two substituents form a cycloalkyl or heterocycloalkyl moiety together with the cycloalkyl group they are attached to, or fused to the aryl, heteroaryl or cycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, more preferably $Ar^1$ is a phenyl, pyridin-2-yl, pyridin-3-yl, cyclohexyl, cyclopentyl, isopropyl, isobutyl or isopentyl group, each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ haloalkyl preferably $CF_3$ or $CHF_2$, cycloalkyl, aryl preferably phenyl, heteroaryl, hydroxyl, $C_1$-$C_4$ alkoxy preferably methoxy, $C_1$-$C_4$ haloalkoxy preferably $OCF_3$ or $OCHF_2$, $C_1$-$C_4$ alkylamino, alkylcarbonylamino, carbamoyl, $C_1$-$C_4$ alkylcarbamoyl, carbamoylamino, $C_1$-$C_4$ alkylcarbamoylamino, alkylsulfonyl, sulfamoyl, alkylsulfamoyl, alkylsulfonylamino, or two substituents form an alkylenedioxy group or a haloalkylenedioxy group, still more preferably $Ar^1$ is a phenyl, cyclohexyl, isobutyl or isopentyl group, said phenyl or cyclohexyl, group being optionally substituted by one or more group(s) selected from halo preferably bromo, chloro or fluoro, cyano, $C_1$-$C_4$ alkyl preferably methyl, $C_1$-$C_4$ haloalkyl preferably $CF_3$ or $CHF_2$, cycloalkyl, aryl preferably phenyl, heteroaryl preferably hydroxyl, $C_1$-$C_4$ alkoxy preferably methoxy, $C_1$-$C_4$ haloalkoxy preferably $OCF_3$ or $OCHF_2$, $C_1$-$C_4$ alkylamino, alkylcarbonylamino, alkylsulfonyl, or two substituents form an alkylenedioxy group or a haloalkylenedioxy group, even more preferably $Ar^1$ is a phenyl or isobutyl group, said phenyl group being optionally substituted by one or more group(s) selected from halo preferably bromo, chloro or fluoro, cyano or $C_1$-$C_4$ alkyl preferably methyl, alkoxy preferably methoxy; and/or $R^1$ is H or methyl, preferably $R^1$ is H; and/or $R^2$ is H; and/or $Ar^2$ is an aryl or heteroaryl, cycloalkyl, heterocyclyl or $C_2$-$C_6$ alkyl group, each of which being optionally substituted by one or more group(s) selected from halo preferably chloro and fluoro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy preferably $OCF_3$ or $OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, oxo, or two substituents form an alkylenedioxy group or a haloalkylenedioxy group, or two substituents form a cycloalkyl or heterocycloalkyl moiety together with the cycloalkyl or heterocycloalkyl group they are attached to, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, nitro, alkyl, hydroxyalkyl, haloalkyl preferably $CF_3$, cyanomethyl, cycloalkyl, heterocyclyl, aryl optionally substituted by a chloro or methyl group, preferably phenyl, 4-chlorophenyl, heteroaryl, cycloalkylalkyl, heteroalkyl, hydroxyl, alkoxy, haloalkoxy preferably 1,1,1-trifluoroethyloxy, alkoxyalkyl preferably methoxymethyl, cycloalkyloxy, cycloalkylalkyloxy preferably cyclopropylmethyloxy, aryloxy, aralkyloxy optionally substituted with one fluoro, carboxy, alkoxycarbonyl, alkylcarbonyloxy, cycloalkylcarbonyloxy, amino, alkylamino, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl preferably (piperidin-1-yl)sulfonyl, (morpholin-4-yl)sulfonyl, arylsulfonyl preferably phenylsulfonyl, sulfamoyl, alkylsulfamoyl, alkylsulfonylamino, cycloalkylsulfonylamino, haloalkylsulfonylamino, oxo, aralkyl, heteroarylalkyl, alkoxyalkoxy, alkoxyalkyl, and haloalkoxyalkyl, more preferably $Ar^2$ is an aryl or heteroaryl preferably pyridyl, pyrazinyl, cycloalkyl, heterocyclyl or $C_2$-$C_6$ alkyl group, each of said aryl, heteroaryl, cycloalkyl and heterocyclyl groups being optionally substituted by one or more group (s) selected from halo preferably chloro and fluoro, cyano, nitro, alkyl, haloalkyl preferably $CF_3$ or $CHF_2$, heterocyclyl, aryl, aralkyl, heteroaryl, benzoxazol-2-yl, heteroarylalkyl, hydroxyl, alkoxy, haloalkoxy preferably $OCF_3$ or $OCHF_2$, alkoxyalkoxy, aryloxy, alkoxyalkyl, cycloalkylalkyloxy, arylalkyloxy, heteroarylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, cycloalkyl, cycloalkylalkyloxy, alkoxyalkoxy, aryloxy, aralkyloxy optionally substituted with one fluoro, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl preferably methyl, heterocyclyl preferably pyrrolidin-1-yl, 4-methylpiperidin-1-yl, aryl, heteroaryl preferably pyridinyl, pyrimidinyl, pyrazinyl, pyridazinyl, benzoxazol-2-yl, alkoxy preferably methoxy, ethoxy and isopropyloxy, alkoxyalkyl, cycloalkylalkyloxy, arylalkyloxy preferably benzyloxy, phenethyloxy and 3,3-diphenylpropan-1-oxy heteroarylalkyloxy preferably pyridylmethyloxy or pyridylethyloxy, aryloxyalkyl preferably phenoxymethyl, heteroaryloxyalkyl preferably pyridyloxymethyl, arylcarbonyl, or two substituents form an haloalkylenedioxy group each of said substituents being optionally substituted by one or more further substituents selected from halo preferably chloro or fluoro, more preferably fluoro, cyano, alkyl preferably methyl, cycloalkyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted with one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino.

In one embodiment, preferred compounds of Formula I are those of formula Ib:

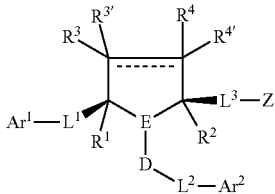

Ib and pharmaceutically acceptable salts, solvates and prodrugs thereof, wherein $Ar^1$ is as defined above in respect to formula I, preferably $Ar^1$ is a 5- to 6-membered aryl or heteroaryl group, or a 3- to 6-membered cycloalkyl group, or a linear or branched $C_3$-$C_6$ alkyl group, each of which being optionally substituted by one or more group(s) selected from halo preferably bromo, chloro or fluoro, cyano, $C_1$-$C_4$ alkyl, $C_1$-$C_4$ hydroxyalkyl, $C_1$-$C_4$ haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, $C_1$-$C_4$ alkoxy $C_1$-$C_4$ haloalkoxy preferably $OCF_3$ or $OCHF_2$, $C_1$-$C_4$ alkylamino, alkylcarbonylamino, haloalkylcarbonylamino, cycloalkylcarbonylamino, heterocyclylcarbonylamino arylcarbonylamino, heteroarylcarbonylamino, $C_1$-$C_4$ alkylcarbonylaminoalkyl, carbamoyl, hydroxycarbamoyl, alkylcarbamoyl, arylcarbamoyl, heteroarylcarbamoyl, carbamoylalkyl, carbamoylamino, $C_1$-$C_4$ alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or two substituents form an alkylenedioxy group or a haloalkylenedioxy group, or two substituents form a cycloalkyl or heterocycloalkyl moiety together with the cycloalkyl group they are attached to, or fused to the aryl or heteroaryl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, more preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl, phenyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;

$L^1$ is as defined above in respect to formula I, preferably $L^1$ is a single bond or a methylene optionally being substituted by one or more substituents selected from fluoro or methyl, more preferably $L^1$ is a single bond drawn as a solid or dotted wedge, even more preferably a single bond drawn as a solid wedge;

$R^1$ is as defined above in respect to formula I, preferably $R^1$ is H or methyl, more preferably $R^1$ is H;

E is as defined above in respect to formula I, preferably E is N;

D is as defined above in respect of formula I, preferably D is CO;

$L^2$ is as defined above in respect to formula I, preferably $L^2$ is a single bond, $C_1$-$C_3$ alkylene optionally being substituted by one or more substituents selected from fluoro or methyl, more preferably $L^2$ is a single bond;

$Ar^2$ is as defined above in respect to formula I, preferably $Ar^2$ is an aryl or heteroaryl, cycloalkyl, heterocyclyl or $C_2$-$C_6$ alkyl group, each of which being optionally substituted by one or more group(s) selected from halo preferably chloro and fluoro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy preferably $OCF_3$ or $OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, oxo, or two substituents form an alkylenedioxy group or a haloalkylenedioxy group, or two substituents form a cycloalkyl or heterocycloalkyl moiety together with the cycloalkyl or heterocyclyl group they are attached to, or fused to the aryl, heteroaryl, cycloalkyl or heterocyclyl group may be one or more cycloalkyl, aryl, hetcrocyclyl or heteroaryl moiety, each of said substituents being optionally substituted by one or more further substituents selected from halo, cyano, alkyl, hydroxyalkyl, alkoxyalkyl, haloalkyl, cyanomethyl, cycloalkyl, heterocyclyl, aryl optionally substituted by a chloro or methyl group, preferably phenyl, 4-chlorophenyl, 4-tolyl, heteroaryl, cycloalkylalkyl, heteroalkyl, aralkyl, heteroarylalkyl, hydroxyl, alkoxy, alkoxyalkyl preferably methoxymethyl, alkoxyalkoxy, haloalkoxy haloalkoxy preferably trifluoromethoxy, 1,1,1-trifluoroethyloxy, cycloalkyloxy, cycloalkylalkyloxy preferably cyclopropylmethyloxy, aryloxy, aralkyloxy optionally substituted by one fluoro, alkoxyalkyl, haloalkoxyalkyl, amino, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl preferably (piperidin-1-yl)sulfonyl, (morpholin-4-yl)sulfonyl, arylsulfonyl preferably phenylsulfonyl, sulfamoyl, alkylsulfamoyl, alkylsulfonylamino, cycloalkylsulfonylamino, haloalkylsulfonylamino, oxo, more preferably $Ar^2$ is an aryl or heteroaryl preferably pyridyl, pyrazinyl, cycloalkyl, heterocyclyl or $C_2$-$C_6$ alkyl group, each of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro or alkyl or cycloalkyl, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably $Ar^2$ is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1,1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, 4-(2,6-dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or Ar² is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro,2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6dimethoxypyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, 4-(4,6-dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^2$ is H;

$L^3$ is as defined above in respect to formula I, preferably $L^3$ is a single bond, $C_1$-$C_3$ alkylene optionally substituted by one or more group(s) selected from chloro, fluoro, alkyl preferably methyl, alkoxy preferably methoxy, or haloalkyl, preferably $L^3$ is a single bond, more preferably $L^3$ is a single bond drawn as a solid wedge;

Z is as defined above in respect to formula I, preferably Z is COOR where R is as defined above in respect of formula I, more preferably Z is COOH;

$R^3$ is as defined above in respect to formula I, preferably $R^3$ is H, cyano, alkyl, preferably methyl, aralkyl, preferably benzyl, hydroxyalkyl preferably hydroxymethyl, alkoxyalkyl preferably methoxymethyl, acetyl linked to the E containing ring by a bond drawn as a dotted wedge, arylsulfonyl preferably phenylsulfonyl, more preferably $R^3$ is H;

$R^{3'}$ is as defined above in respect of formula I, preferably $R^{3'}$ is H or methyl, more preferably $R^{3'}$ is H;

$R^4$ is as defined above in respect to formula I, preferably $R^4$ is H, cyano or methyl, more preferably $R^4$ is H;

$R^{4'}$ is as defined above in respect to formula I, preferably $R^{4'}$ is H or methyl, more preferably $R^{4'}$ is H;

the bond represented by the dotted line is either absent or present, preferably the dotted line is absent.

Particularly preferred compounds of formula Ib are those of formula Ib-1a

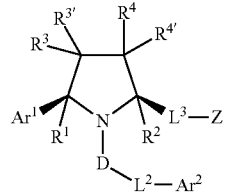

Ib-1a and pharmaceutically acceptable salts, solvates and prodrugs thereof, wherein $Ar^1$, $Ar^2$, $R^1$, $R^2$, $R^3$, $R^{3'}$, $R^4$, $R^{4'}$, $L^2$, $L^3$, D and Z are as defined above in respect of formula Ib.

Preferred compounds of formula Ib-1a are those of formula Ib-1b

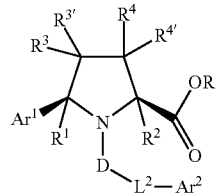

Ib-1b and pharmaceutically acceptable salts, solvates and prodrugs thereof, wherein $Ar^1$, $Ar^2$, $R^1$, $R^2$, $R^3$, $R^{3'}$, $R^4$, $R^{4'}$, $L^2$ and D are as defined above in respect of formula Ib and R is as defined above in respect of formula I.

Preferred compounds of formula Ib-1b are those of formula Ib-1c

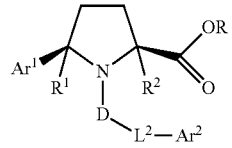

Ib-1c and pharmaceutically acceptable salts, solvates and prodrugs thereof, wherein $Ar^1$, $Ar^2$, $R^1$, $R^2$, $L^2$ and D are as defined above in respect of formula Ib and R is as defined above in respect of formula I.

Other preferred compounds of formula Ib-1b are those of formula Ib-1b'

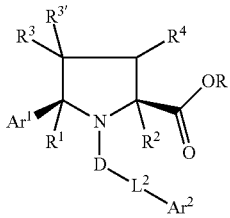

Ib-1b' and pharmaceutically acceptable salts, solvates and prodrugs thereof, wherein
R² is as defined above in respect of formula Ib and R is as defined above in respect of formula I;
R¹ is H;
D is C=O;
L² is single bond;
A¹ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy, preferably Ar¹ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably Ar¹ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably Ar¹ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably Ar¹ is isobutyl, cyclohexyl, phenyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably Ar¹ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;

Ar² is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, hetcroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl, cycloalkyl or heterocyclyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro or alkyl or cycloalkyl group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, alkoxyalkoxy, alkoxyalkyl, and haloalkoxyalkyl; preferably Ar² is an aryl or heteroaryl preferably pyridyl, pyrazinyl, cycloalkyl, heterocyclyl or $C_2$-$C_6$ alkyl group, each of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro or alkyl or cycloalkyl, amino, alkylcarbonylamino, carbamoyl, hydroxycarbamimidoyl, alkylsulfonyl, alkylsulfonylamino, still more preferably Ar² is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonylalkylsulfonylamino preferably methylsulfonylamino, (N-methyl-N-methylsulfonyl)amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably $Ar^2$ is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1,1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or $Ar^2$ is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro,2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxypyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, 4-(4,6-dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

$R^4$ is H, cyano, $C_1$-$C_4$ alkyl.

Preferred compounds of formula Ib-1c or Ib-1b' are those of formula Ib-1d

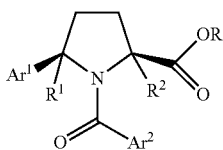

and pharmaceutically acceptable salts, solvates and prodrugs thereof, wherein $Ar^1$, $Ar^2$, $R^1$ and $R^2$ are as defined above in respect of formula Ib in case of preferred compounds of formula Ib-1c, or Ib-1b' in case of preferred compounds of formula Ib-1b', and R is as defined above in respect of formula I.

Preferred compounds of formula Ib-1d are those of formula Ib-1e

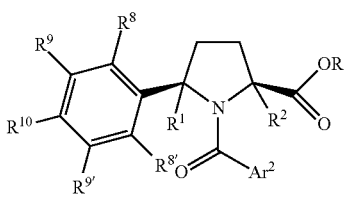

and pharmaceutically acceptable salts, solvates and prodrugs thereof, wherein $Ar^2$, $R^1$ and $R^2$ are as defined above in respect of formula Ib or Ib-1b';

R is as defined above in respect of formula I;

$R^8$, $R^{8'}$, $R^9$, $R^{9'}$ and $R^{10}$ are independently selected from H, halo preferably fluoro, chloro, bromo, cyano, alkyl, hydroxyalkyl, haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, haloalkoxy preferably $OCF_3$ or $OCHF_2$, heterocyclyloxy, alkylamino, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonylsulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, or one or more of $R^8$ and $R^9$, or $R^9$ and $R^{10}$, or $R^{10}$ and $R^{9'}$, or $R^{9'}$ and $R^{8'}$ form together a cycloalkyl, aryl, heterocycloalyl or heteroaryl moiety fused to the phenyl group they are attached to, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, preferably $R^8$, $R^{8'}$, $R^9$, $R^{9'}$ and $R^{10}$ are independently selected from H, halo preferably fluoro, chloro, bromo, cyano, alkyl, haloalkyl preferably $CF_3$ or $CHF_2$, cycloalkyl, aryl preferably phenyl, heteroaryl, hydroxyl, haloalkoxy preferably $OCF_3$ or $OCHF_2$, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy, haloalkoxy, more preferably $R^8$, $R^{8'}$, $R^9$, $R^{9'}$ and $R^{10}$ are independently selected from H, halo preferably bromo, fluoro or chloro, cyano, $C_1$-$C_4$ alkyl preferably methyl, aryl preferably phenyl, alkoxy preferably methoxy, still more preferably $R^8$, $R^{8'}$, $R^9$, $R^{9'}$ and $R^{10}$ are independently selected from H, halo preferably bromo, fluoro or chloro, alkyl preferably methyl, still more preferably $R^8$ is Br, Cl or F, preferably Cl and $R^{8'}$, $R^9$, $R^{9'}$ and $R^{10}$ are independently selected from H or F, or $R^9$ is Cl or F and $R^8$, $R^{8'}$, $R^{9'}$ and $R^{10}$ are H, or $R^9$ and $R^{9'}$ are F and $R^8$, $R^{8'}$ and $R^{10}$ are H, or $R^{10}$ is Cl or F and $R^8$, $R^{8'}$, $R^9$ and $R^{9'}$ are H, even more preferably $R^8$ is Br, Cl or F and $R^{8'}$, $R^9$, $R^{9'}$ and $R^{10}$ are H, or $R^8$ and $R^9$ are F and $R^{8'}$, $R^{9'}$ and $R^{10}$ are H, or $R^8$ and $R^{10}$ are F and $R^{8'}$, $R^9$ and $R^{9'}$ are H.

Preferred compounds of formula Ib-1e are those of formula Ib-1f

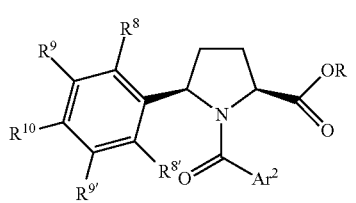

and pharmaceutically acceptable salts, solvates and prodrugs thereof, wherein
$Ar^2$ is as defined above in respect of formula Ib or Ib-1b';
R is as defined above in respect of formula I;
$R^8$, $R^{8'}$, $R^9$, $R^{9'}$ and $R^{10}$ are as defined above in respect of formula Ib-1e.

Preferred compounds of formula Ib-1f are those of formula Ib-1g

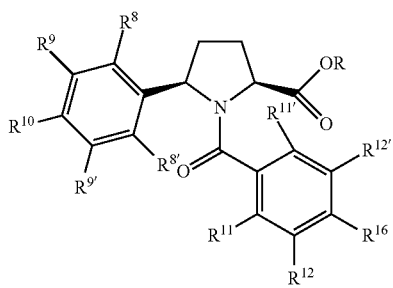

Ib-1g and pharmaceutically acceptable salts, solvates and prodrugs thereof, wherein
R is as defined above in respect of formula I;
$R^8$, $R^{8'}$, $R^9$, $R^{9'}$ and $R^{10}$ are as defined above in respect of formula Ib-1e;
$R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cyclo alkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or $OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkyloxycarbonyl, aminoalkylalkoxycarbonyl, cycloalkyloxycarbonyl, heterocyclyloxy carbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together a cycloalkyl, aryl, heterocycloalkyl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, cycloalkylalkyl, aralkyl, heteroarylalkyl, heteroalkyl, hydroxyl, alkoxy, alkoxyalkoxy, haloalkoxy preferably trifluoromethoxt, 1,1,1-trifluoroethyloxy, alkoxyalkyl, haloalkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, cycloalkylsulfonylamino, haloalkylsulfonylamino and oxo, preferably $R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy preferably 1,1,1-trifluoroethyloxy, alkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, cycloalkylcarbonyloxy, alkylcarbonylamino, haloalkylcarbonylamino, carbamoyl, hydroxycarbamoyl, alkylcarbamoyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, more preferably $R^{11}$, $R^{11'}$, $R^{12}$, $R^{12'}$ and $R^{16}$ are independently selected from H, halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, cycloalkylalkyloxy, arylalkyloxy, heteroarylalkyloxy, alkoxyalkyl, aryloxyalkyl, heteroaryloxyalkyl, arylcarbonyl, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl, or heteroaryl moiety fused to the phenyl group they are attached to, each of said substituents being optionally substituted by one or more further substituents selected from halo preferably chloro or fluoro, cyano, alkyl preferably methyl, ethyl, propyl, isopropyl, tert-butyl, cyanomethyl, cycloalkyl, heterocyclyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylamino, alkylcarbonylamino, carbamoyl, hydroxycarbamimidoyl, alkylsulfonyl, alkylsulfonylamino, still more preferably $R^{11}$, $R^{11'}$, $R^{12}$, $R^{12'}$ and $R^{16}$ are independently selected from H, halo preferably chloro and fluoro, cyano, nitro, alkyl preferably methyl, ethyl, isopropyl or isobutyl, haloalkyl preferably $CF_3$ or $CHF_2$, cycloalkyl preferably cyclohexyl, heterocyclyl preferably pyrrolidin-1-yl, 4-methylpiperidin-1-yl, aryl preferably phenyl, heteroaryl preferably thiophenyl, pyridinyl, pyrimidinyl, pyrazinyl, pyridazinyl, aralkyl preferably benzyl, alkoxy preferably methoxy, ethoxy or isopropyloxy, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridyloxymethyl, or two substituents form an haloalkylenedioxy group each of said substituents being optionally substituted by one or more further substituents selected from halo preferably chloro or fluoro, cyano, alkyl preferably methyl, haloalkyl preferably trifluoromethyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted by one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl) amino.

Preferred compounds of formula Ib-1g are those of formula Ib-1g1

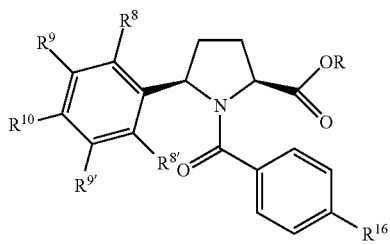

Ib-1g1 and pharmaceutically acceptable salts, solvates and prodrugs thereof, wherein
R is as defined above in respect of formula I;
$R^8$, $R^{8'}$, $R^9$, $R^{9'}$ and $R^{10}$ are as defined above in respect of formula Ib-1c;

$R^{16}$ is as defined above in respect to formula Ib-1g, preferably $R^{16}$ is selected from halo preferably chloro, alkyl preferably methyl or isobutyl, cycloalkyl preferably cyclohexyl, aryl preferably phenyl, heteroaryl preferably pyridyl, thiophen-3-yl, pyrimidinyl, pyrazinyl, pyridazinyl, aralkyl preferably benzyl, alkoxy preferably methoxy, isopropyloxy more preferably isopropyloxy, haloalkoxy, preferably $OCF_3$, $OCHF_2$, more preferably $OCF_3$, cycloalkylalkyloxy preferably cyclopropylmethyloxy, arylalkyloxy preferably phenethyloxy or benzyloxy, heteroarylalkyloxy preferably pyridylethyloxy, aryloxyalkyl preferably phenoxymethyl, heteroaryloxyalkyl preferably pyridyloxymethyl, arylcarbonyl preferably phenylcarbonyl, each of said substituents being optionally substituted by one or more further substituents selected from halo preferably chloro or fluoro, more preferably fluoro, cyano, alkyl preferably methyl, ethyl, propyl, isopropyl, tert-butyl, trifluoromethyl, cyanomethyl, cycloalkyl, aryl optionally substituted by a chloro or methyl group, hydroxyl, alkoxy preferably methoxy, ethoxy, isopropoxy, haloalkoxy preferably trifluoromethoxy, 1,1,1-trifluoroethyloxy, aryloxy preferably phenoxy, cycloalkylalkyloxy preferably cyclopropylmethyloxy, aralkyloxy optionally substituted by one fluoro preferably benzyloxy, 4-fluorobenzyloxy, alkoxyalkyl preferably methoxymethyl, alkoxyalkoxy preferably 2-methoxyethoxy, amino, alkylcarbonylamino preferably acetylamino, carbamoyl, carbamoylmethyloxy, carbamimidoyl, hydroxycarbamimidoyl, alkylsulfonylamino preferably methylsulfonylamino, (N-methyl-N-methylsulfonyl)amino, oxo, more preferably $R^{16}$ is selected from alkyl preferably isobutyl, or $R^{16}$ is alkoxy preferably isopropyloxy, or $R^{16}$ is heterocyclyl preferably pyrrolidin-1-yl, 4-methylpiperidin-1-yl, or $R^{16}$ is aryl preferably a phenyl, preferably a phenyl monosubstituted at position 2 by one group selected from halo preferably chloro or fluoro, more preferably fluoro, cyano, alkyl preferably methyl, alkoxy preferably methoxy, alkoxyalkyl preferably methoxymethyl, alkoxyalkoxy preferably 2-methoxyethoxy, or $R^{16}$ is 2,4-difluorophenyl, 2-fluoro-4-methoxyphenyl, 4-fluoro-2-methoxyphenyl, 2,3-dimethoxyphenyl, 3,4-dimethoxyphenyl, 3,5-dimethoxyphenyl, 2,5-dimethoxyphenyl, 2-methoxy-4-methylsulfonylaminophenyl, 4-acetylamino-2-methoxyphenyl, 4-amino-2-methoxyhenyl, 5-cyano-2,3-dimethoxyphenyl, 2-cyano-4,5-dimethoxyphenyl, 3,4,5-trimethoxyphenyl, 2-cyano-4-methoxyphenyl, 3-methylsulfonylaminophenyl, 4-methylsulfonylaminophenyl, 2-chloro-5-cyanophenyl, 2-cyano-4-trifluoromethylphenyl, 2-methyl-3-(N-methyl-N-methylsulfonyl)aminophenyl, 2-methoxy-4-(N-methyl-N-methylsulfonyl)aminophenyl, 4-methylsulfonylphenyl, 3-methylsulfonylaminophenyl, 4-methylsulfonylaminophenyl, 3-amino-2-methyl, 5-cyano-2-methylphenyl, 5-cyano-2-methoxyphenyl, 2-methyl-3-methylsulfonylamino, 3-cyano-2-methoxyphenyl, or $R^{16}$ is aralkyl preferably benzyl, or $R^{16}$ is heteroaryl preferably 4,6-dimethoxypyrimidin-2-yl, 2-methoxypyrimidin-3-yl, 2,4-dimethoxypyrimidin-5-yl, 2-methoxypyridin-3-yl, 2,6-dimethoxy-pyridin-3-yl, 2-(2-methoxyethoxy)-pyridin-3-yl, 2-methoxypyrimidin-5-yl, 2,4-dimethoxypyrimidin-6-yl, preferably 2-methoxypyrimidin-3-yl, (2,4-dimethoxy)pyrimidin-5-yl, 2-methoxypyrimidin-5-yl, 2,6-dimethoxy-pyridin-3-yl, more preferably (2,4-dimethoxy)pyrimidin-5-yl, 2,6-dimethoxy-pyridin-3-yl, 2-chloro-6-methoxypyrimidin-5-yl, 2-methoxy-6-methylpyridin-5-yl, 2,6-dimethylpyridin-5-yl, 2,6-dimethoxypyrimidin-5- yl, 4-methoxypyridin-3-yl, 2-methoxypyridin-5-yl, 2,4-dimethoxypyridin-5-yl, 2,6-dimethoxypyridazin-5-yl, 2,6-dimethoxypyridin-5-yl, 5-methoxypyridin-3-yl, 4,6-dimethoxypyrimidin-5-yl, 3-methoxypyridin-4-yl, 4-methoxypyridin-3-yl, or $R^{16}$ is, arylalkyloxy preferably phenethyloxy, benzyloxy, 2-fluorobenzyloxy, more preferably 2-fluorobenzyloxy, or $R^{16}$ is aryloxyalkyl preferably phenoxymethyl.

Preferred compounds of formula Ib-1g1 are those of formula Ib-1g1a

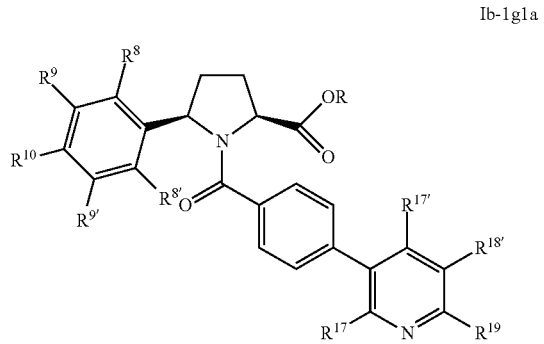

Ib-1g1a and pharmaceutically acceptable salts, solvates and prodrugs thereof, wherein R is as defined above in respect of formula I;

$R^8$, $R^{8'}$, $R^9$, $R^{9'}$ and $R^{10}$ are as defined above in respect of formula Ib-1e;

$R^{17}$, $R^{17'}$, $R^{18'}$ and $R^{19}$ are independently selected from H, halo preferably chloro and fluoro more preferably fluoro, cyano, alkyl preferably methyl, haloalkyl preferably $CF_3$ or $CHF_2$, cycloalkyl, cycloalkylalkyl, heteroalkyl, heterocyclyl, aryl, aralkyl, heteroaryl, heteroarylalkyl, hydroxyl, hydroxyalkyl, alkoxy preferably methoxy, ethoxy, isopropyloxy, haloalkoxy preferably $OCF_3$ or $OCHF_2$, alkoxyalkoxy, cycloalkyloxy, alkoxyalkyl, cycloalkylalkyloxy, aryloxy, aralkyloxy, haloalkoxyalkyl, alkylamino, alkylsulfonyl preferably methylsulfonyl, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino, preferably $R^{17}$, $R^{17'}$, $R^{18'}$ and $R^{19}$ are independently selected from H, halo preferably chloro and fluoro more preferably fluoro, cyano, alkyl preferably methyl, haloalkyl preferably $CF_3$ or $CHF_2$, cycloalkyl, heteroalkyl, heterocyclyl, aryl, heteroaryl, hydroxyl, alkoxy preferably methoxy, ethoxy, isopropyloxy, haloalkoxy preferably $OCF_3$ or $OCHF_2$, alkoxyalkoxy, cycloalkyloxy, alkoxyalkyl, cycloalkylalkyloxy, aryloxy, aralkyloxy, alkylamino, alkylsulfonyl preferably methylsulfonyl, alkylcarbonylamino, haloalkylcarbonylamino, carbamoyl, hydroxycarbamoyl, alkylcarbamoyl, carbamoylalkyl, carbamoylamino, alkylcarbamoylamino, haloalkylsulfonyl, cycloalkylsulfonyl, sulfamoyl, alkylsulfamoyl, alkylsulfonylamino, cycloalkylsulfonylamino, haloalkylsulfonylamino, more preferably $R^{17}$, $R^{17'}$, $R^{18'}$ and $R^{19}$ are independently selected from H, halo preferably chloro and fluoro more preferably chloro, cyano, alkyl preferably methyl, haloalkyl preferably $CF_3$ or $CHF_7$, alkoxy preferably methoxy, haloalkoxy preferably $OCF_3$ or $OCHF_2$, alkoxyalkoxy preferably (2-methoxy)ethoxy, alkylamino preferably dimethylamino, more preferably $R^{17'}$, $R^{18'}$ and $R^{19}$ are H and $R^{17}$ is methoxy, (2-methoxy)ethoxy or $R^{17}$, $R^{18'}$ and $R^{19}$ are H and $R^{17'}$ is methoxy, or $R^{17}$, $R^{17'}$ and $R^{18'}$ are H and $R^{19}$ is chloro, methyl, methoxy, dimethylamino, or $R^{17'}$ and $R^{18'}$ are H and: a) both $R^{17}$ and $R^{19}$ are methyl or methoxy, or b) $R^{17}$ is methyl and $R^{19}$ is methoxy, or $R^{17'}$, $R^{18'}$ and $R^{19}$ are H and $R^{18'}$ is methoxy even more preferably $R^{17'}$, $R^{18'}$ and $R^{19}$ are H and $R^{17}$ is methoxy, or $R^{17'}$ and $R^{18'}$ are H and: a) both $R^{17}$ and $R^{19}$ are methyl or methoxy, or b) $R^{17}$ is methyl and $R^{19}$ is methoxy, or $R^{17}$, $R^{17'}$ and $R^{19}$ are H and $R^{18'}$ is methoxy.

Other preferred compounds of formula Ib-1g are those of formula Ib-1g2

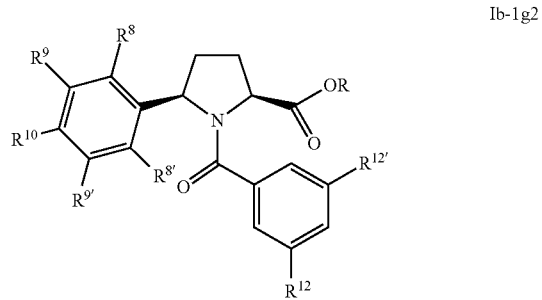

Ib-1g2 and pharmaceutically acceptable salts, solvates and prodrugs thereof, wherein

R is as defined above in respect of formula I;

$R^8$, $R^{8'}$, $R^9$, $R^{9'}$ and $R^{10}$ are as defined above in respect to formula Ib-1c;

$R^{12}$ and $R^{12'}$ are as defined above in respect to formula Ib-1g, preferably $R^{12}$ and $R^{12'}$ are independently selected from H, halo preferably chloro, cyano, nitro, alkyl preferably ethyl, isopropyl, haloalkyl preferably $CF_3$ or $CHF_2$, aryl preferably phenyl, hydroxyl, alkoxy preferably methoxy or ethoxy, haloalkoxy preferably $OCF_3$ or $OCHF_2$, alkoxyalkoxy, aryloxy, arylalkyloxy preferably phenethyloxy or benzyloxy, heteroarylalkyloxy, aryloxyalkyl, heteroaryloxyalkyl, each of said substituents being optionally substituted by one or more further substituents selected from halo preferably chloro or fluoro, alkoxy, alkyl, cycloalkyl, alkylsulfonyl preferably methylsulfonyl, more preferably $R^{12}$ is H or alkoxy preferably methoxy or ethoxy, more preferably methoxy and $R^{12'}$ is halo preferably chloro, alkoxy preferably methoxy or ethoxy, more preferably methoxy, arylalkyloxy preferably phenethyloxy, benzyloxy or 3,3-diphenylpropan-1-oxy, optionally substituted by halo preferably chloro or fluoro, alkoxy, alkyl, alkylsulfonyl preferably methylsulfonyl, even more preferably $R^{12}$ is methoxy and $R^{12'}$ is methoxy, chloro, benzyloxy, (4-chlorobenzyl)oxy, (4-methylsulfonylbenzyl)oxy.

Other preferred compounds of formula Ib-1g are those of formula Ib-1h

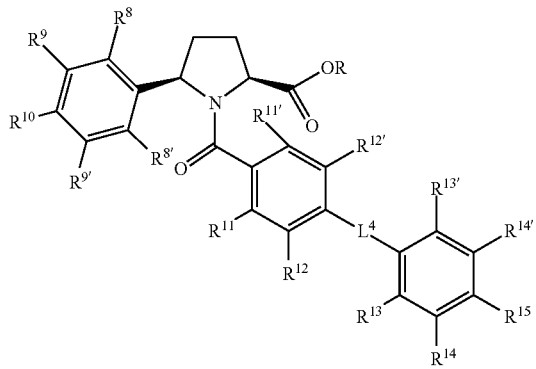

Ib-1h and pharmaceutically acceptable salts, solvates and prodrugs thereof, wherein R is as defined above in respect to formula I;

$R^8$, $R^{8'}$, $R^9$, $R^{9'}$ and $R^{10}$ are as defined above in respect to formula Ib-1e;

$L^4$ is a single bond, —C(O)—, —O—, —O—$C_1$-$C_3$-alkylene or —$C_1$-$C_3$-alkylene-O— optionally substituted by one or more group selected from fluoro or methyl, preferably $L^4$ is a single bond, —O—, —O—$C_1$-$C_2$-alkylene, —$C_1$-alkylene-O— optionally substituted by one or more group selected from fluoro or methyl, more preferably $L^4$ is a single bond, —$OCH_2$—, —$O(CH_2)_2$— or —$CH_2O$—;

$R^{11}$, $R^{11'}$, $R^{12}$ and $R^{12'}$ are as defined above in respect to formula Ib-1g, preferably $R^{11}$ and $R^{11'}$ are H and $R^{12}$ and $R^{12'}$ are independently selected from H, halo preferably chloro or fluoro, cyano, nitro, alkyl preferably methyl, ethyl, isopropyl, haloalkyl preferably $CF_3$ or $CHF_2$, hydroxyl, alkoxy preferably methoxy or ethoxy, haloalkoxy preferably $OCF_3$ or $OCHF_2$, alkoxyalkoxy, more preferably $R^{11}$ and $R^{11'}$ are H, $R^{12}$ is H, fluoro, chloro, methyl, —$CF_3$, alkoxy preferably methoxy or ethoxy, more preferably methoxy and $R^{12'}$is halo preferably chloro, alkoxy preferably methoxy or ethoxy, more preferably methoxy, or $R^{11}$, $R^{11'}$ and $R^{12'}$ are H and $R^{12}$ is fluoro, chloro, methyl, $CF_3$, methoxy, even more preferably $R^{11}$ and $R^{11'}$ are H, $R^{12}$ is H or methoxy and $R^{12'}$ is methoxy, chloro, or $R^{11}$, $R^{11'}$ and $R^{12'}$ are H and $R^{12}$ is fluoro, chloro, methyl, $CF_3$, methoxy;

$R^{13}$, $R^{13'}$, $R^{14}$, $R^{14'}$ and $R^{15}$ are independently selected from H, halo preferably chloro and fluoro more preferably fluoro, cyano, alkyl preferably methyl, ethyl, propyl, isopropyl, tert-butyl, haloalkyl preferably $CF_3$ or $CHF_2$, cyanomethyl, cycloalkyl, heteroalkyl, heterocyclyl, aryl, heteroaryl, hydroxyl, hydroxyalkyl, alkoxy preferably methoxy, haloalkoxy preferably $OCF_3$, $OCHF_2$, or 1,1,1-trifluoroethyloxy, alkoxyalkoxy, cycloalkyloxy, alkoxyalkyl, cycloalkylalkyloxy, aralkyloxy optionally substituted by one fluoro, haloalkoxyalkyl, amino, alkylamino, alkylcarbonylamino, haloalkylcarbonylamino, alkylcarbonylaminoalkyl, carbamoyl, hydroxycarbamoyl, alkylcarbamoyl, carbamoylalkyloxy, alkylcarbamoylamino, carbamimidoyl, hydroxycarbamimidoyl, alkylsulfonyl preferably methylsulfonyl, haloalkylsulfonyl, cycloalkylsulfonyl, sulfamoyl, alkylsulfamoyl, alkylsulfonylamino, cycloalkylsulfonylamino, haloalkylsulfonylamino, preferably $R^{13}$, $R^{13'}$, $R^{14}$, $R^{14'}$ and $R^{15}$ are independently selected from H, halo preferably chloro and fluoro more preferably fluoro, cyano, alkyl preferably methyl, ethyl, propyl, isopropyl, tert-butyl, haloalkyl preferably $CF_3$ or $CHF_2$, cycloalkyl, cycloalkylalkyl, heteroalkyl, heterocyclyl, aryl, aralkyl, heteroaryl, heteroarylalkyl, hydroxyl, hydroxyalkyl, alkoxy preferably methoxy, haloalkoxy preferably $OCF_3$, $OCHF_2$, or 1,1,1-trifluoroethyloxy, alkoxyalkoxy, cycloalkyloxy, alkoxyalkyl, cycloalkylalkyloxy, aralkyloxy optionally substituted by one fluoro, haloalkoxyalkyl, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl preferably methylsulfonyl, haloalkylsulfonyl, cycloalkylsulfonyl, sulfamoyl, alkylsulfamoyl, alkylsulfonylamino, cycloalkylsulfonylamino, haloalkylsulfonylamino, more preferably $R^{13}$, $R^{13'}$, $R^{14}$, $R^{14'}$ and $R^{15}$ are independently selected from H, halo preferably chloro and fluoro more preferably fluoro, cyano, alkyl preferably methyl, ethyl, propyl, isopropyl, tert-butyl, haloalkyl preferably —$CF_3$ or $CHF_2$, hydroxyl, hydroxyalkyl, alkoxy preferably methoxy, haloalkoxy preferably $OCF_3$ or $OCHF_2$, alkoxyalkoxy preferably 2-methoxyethoxy, cycloalkyloxy, cycloalkylalkyloxy, alkoxyalkyl preferably methoxymethyl, haloalkoxyalkyl, amino, alkylcarbonylamino preferably acetylamino, carbamoyl, hydroxycarbamimidoyl, alkylsulfonyl preferably methylsulfonyl, haloalkylsulfonyl, cycloalkylsulfonyl, alkylsulfonylamino preferably methylsulfonylamino, (N-methyl-N-methylsulfonyl)amino, still more preferably $R^{13}$, $R^{13'}$, $R^{14}$, $R^{14'}$ and $R^{15}$ are independently selected from H, halo preferably chloro and fluoro, more preferably fluoro, cyano, nitro, alkyl preferably methyl, haloalkyl preferably —$CF_3$ or —$CHF_2$, alkoxyalkyl preferably methoxymethyl, alkoxy preferably methoxy, cycloalkylalkyloxy preferably cyclopropylmethyloxy, haloalkoxy preferably $OCF_3$ or $OCHF_2$, alkoxyalkoxy preferably 2-methoxyethoxy, amino, alkylcarbonylamino preferably acetylamino, alkylsulfonyl preferably methylsulfonyl, alkylsulfonylamino preferably methylsulfonylamino, (N-methyl-N-methylsulfonyl)amino, even more preferably $R^{13}$, $R^{13'}$, $R^{14}$ and $R^{14'}$ are H and $R^{15}$ is H, chloro, methyl or methoxy, methylsulfonyl, methylsulfonylamino, preferably H, methylsulfonyl, methylsulfonylamino, or $R^{13'}$, $R^{14}$, $R^{14'}$ and $R^{15}$ are H and $R^{13}$ is methoxy or chloro, preferably chloro, or $R^{13}$, $R^{13'}$, $R^{14'}$ and $R^{15}$ are H and $R^{14}$ is methylsulfonylamino, or $R^{13'}$, $R^{14}$ and $R^{14'}$ are H and $R^{13}$ and $R^{15}$ are a) both F, or b) $R^{13}$ is F and $R^{15}$ is methoxy, or c) $R^{13}$ is methoxy and $R^{15}$ is F, or d) $R^{13}$ is methoxy and $R^{15}$ is acetylamino, or e) $R^{13}$ is methoxy and $R^{15}$ is amino, or f) $R^{13}$ is cyano and $R^{15}$ is methoxy, or g) $R^{13}$ is chloro and $R^{15}$ is cyano, or h) $R^{13}$ is cyano and $R^{15}$ is trifluoromethyl, or i) $R^{13}$ is methoxy and $R^{15}$ is (N-methyl-N-methylsulfonyl)amino, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13}$, $R^{13'}$ and $R^{14'}$ are H and $R^{14}$ and $R^{15}$ are both methoxy, or $R^{13'}$, $R^{14}$ and $R^{15}$ are H and $R^{13}$ and $R^{14'}$ are a) both methoxy, or b) $R^{14'}$ is methoxy and $R^{14'}$ is cyano, or c) $R^{14}$ is methyl and $R^{14'}$ is cyano, or $R^{13}$, $R^{13'}$ and $R^{15}$ are H and $R^{14}$ and $R^{14'}$ are both methoxy, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy.

Preferred compounds of formula Ib-1h are those of formula Ib-1h1

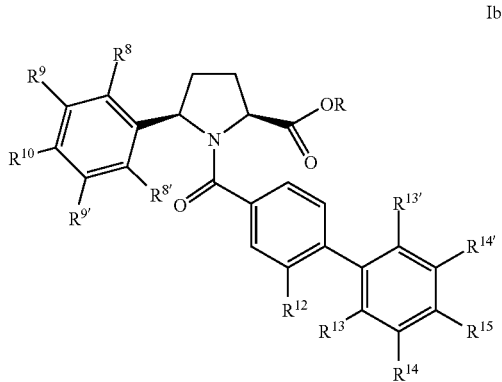

Ib-1h1 and pharmaceutically acceptable salts, solvates and prodrugs thereof, wherein

R is as defined above in respect to formula I;

$R^8$, $R^{8'}$, $R^9$, $R^{9'}$ and $R^{10}$ are as defined above in respect to formula Ib-1e;

$R^{12}$ is as defined above in respect to formula Ib-1h, preferably $R^{12}$ is H, fluoro, chloro, methyl, $CF_3$, nitro, cyano, methoxy or cyclopropylmethyloxy;

$R^{13}$, $R^{13'}$, $R^{14}$, $R^{14'}$ and $R^{15}$ are as defined above in respect to formula Ib-1h, preferably $R^{13'}$, $R^{14}$, $R^{14'}$ and $R^{15}$ are H and $R^{13}$ is chloro, cyano, hydroxyl, methyl, trifluoromethyl, cyanomethyl, methoxy, isopropoxy, isobutyloxy, $OCF_3$, cyclopropylmethyloxy, phenoxy, cyclopropylmethyloxy, benzyloxy, (4-fluorobenzyl)oxy, methoxymethyl, 2-methoxyethoxy, carbamoylmethyloxy, or $R^{13}$, $R^{13'}$, $R^{14'}$ and $R^{15'}$ are H and $R^{14}$ is chloro, methylsulfonylamino, or $R^{13}$, $R^{13'}$, $R^{14}$ and $R^{14'}$ are H and $R^{15}$ is chloro, methylsulfonylamino, $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{15}$ are H and both $R^{14}$ and $R^{14'}$ are fluoro, methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy, more preferably $R^{13'}$, $R^{14}$, $R^{14'}$ and $R^{15}$ are H and $R^{13}$ is chloro, cyano, trifluoromethyl, methoxy, isopropoxy, cyclopropylmethyloxy, or $R^{13}$, $R^{13'}$, $R^{14'}$ and $R^{15}$ are H and $R^{14}$ is chloro, or $R^{13}$, $R^{13'}$, $R^{14}$ and $R^{14'}$ are H and $R^{15}$ is chloro, methylsulfonylamino, or $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{14}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy.

Other preferred compounds of formula Ib-1g are those of formula Ib-1h'

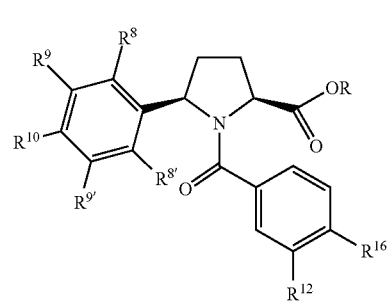

Ib-1h' and pharmaceutically acceptable salts, solvates and prodrugs thereof, wherein

R is as defined above in respect to formula I;

$R^8$, $R^{8'}$, $R^9$, $R^{9'}$ and $R^{10}$ are as defined above in respect to formula Ib-1e;

$R^{12}$ is as defined above in respect to formula Ib-1g, preferably $R^{12}$ is H, fluoro, chloro, methyl, $CF_3$, or methoxy more preferably $R^{12}$ is H or methoxy;

$R^{16}$ is selected from the group of heteroaryl moieties consisting of:

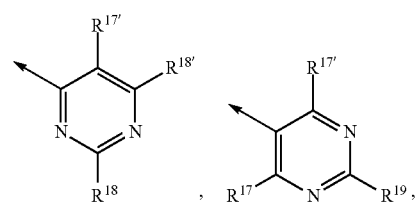

-continued

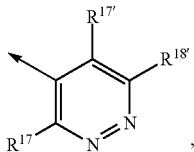

wherein
the arrow marks the attachment point to the phenyl ring;
$R^{17}$, $R^{17'}$, $R^{18}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$ or $CHF_2$, hydroxyl, hydroxyalkyl, alkoxy preferably methoxy, ethoxy, isopropyloxy, haloalkoxy preferably $OCF_3$, $OCHF_2$, or 1,1,1-trifluoroethyloxy, alkoxyalkoxy, cycloalkyloxy, alkoxyalkyl preferably methoxymethyl, cycloalkylalkyloxy preferably cyclopropylmethyloxy, aralkyloxy preferably benzyloxy, haloalkoxyalkyl, amino, alkylamino, alkylcarbonylamino, haloalkylcarbonylamino, alkylcarbonylaminoalkyl, carbamoyl, hydroxycarbamoyl, alkylcarbamoyl, carbamoylamino, alkylcarbamoylamino, carbamimidoyl, hydroxycarbamimidoyl, alkylsulfonyl preferably methylsulfonyl, haloalkylsulfonyl, sulfamoyl, alkylsulfamoyl, alkylsulfonylamino preferably methylsulfonylamino, (N-methyl-N-methylsulfonyl)amino, haloalkylsulfonylamino, preferably $R^{17}$, $R^{17'}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$, alkoxy preferably methoxy, ethoxy, isopropyloxy, haloalkoxy preferably $OCF_3$, $OCHF_2$, or 1,1,1-trifluoroethyloxy, alkoxyalkyl preferably methoxymethyl, aralkyloxy preferably benzyloxy, amino, alkylcarbonylamino, carbamoyl, carbamimidoyl, hydroxycarbamimidoyl, alkylsulfonyl preferably methylsulfonyl, alkylsulfonylamino preferably methylsulfonylamino, (N-methyl-N-methylsulfonyl)amino, more preferably $R^{17}$, $R^{17'}$, $R^{18'}$ and $R^{19}$ are independently selected from H, halo preferably chloro, alkoxy preferably methoxy, even more preferably $R^{17}$, $R^{17'}$, $R^{18'}$ and $R^{19}$ are independently selected from H, halo preferably chloro, alkoxy preferably methoxy;

Preferred compounds of formula Ib-1h' are those wherein $R^{10}$ is selected from 2-2-methoxypyrimidin-4-yl, 2,4-dibenzyloxypyrimidin-5-yl, 2,4-dimethoxypyrimidin-5-yl, 3,6-dimethoxypyridazin-5-yl, 2-methoxypyrimidin-5-yl, 2-methoxypyrimidin-3-yl.

Still other preferred compounds of formula Ib-1g are those of formula Ib-1h"

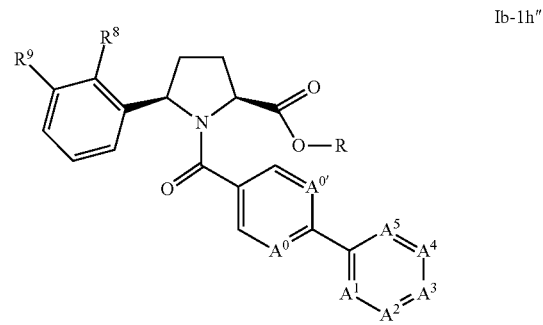

Ib-1h"

and pharmaceutically acceptable salts, solvates and prodrugs thereof, wherein
$R^8$ is F or Cl and $R^9$ is H, or both $R^8$ and $R^9$ are F;
R is H, methyl, ethyl or tert-butyl;
$A^0$, $A^{0'}$, $A^1$, $A^2$, $A^3$, $A^4$ and $A^5$ are selected from the combinations 1 to 24:

| Combination n° | $A^0$ | $A^{0'}$ | $A^1$ | $A^2$ | $A^3$ | $A^4$ | $A^5$ |
|---|---|---|---|---|---|---|---|
| 1 | CH | CH | C—$OCH_3$ | CH | C—$NHSO_2CH_3$ | CH | CH |
| 2 | CH | CH | C—$CH_3$ | C—$NHSO_2CH_3$ | CH | CH | CH |
| 3 | CH | CH | C—$OCH_3$ | N | CH | CH | CH |
| 4 | CH | CH | C—$OCH_3$ | N | C—$OCH_3$ | N | CH |
| 5 | C—$OCH_3$ | CH | CH | N | C—$OCH_3$ | N | CH |
| 6 | CH | CH | C—$OCH_3$ | N | N | C—$OCH_3$ | CH |
| 7 | CH | CH | C—$OCH_3$ | CH | CH | C—CN | CH |
| 8 | CH | CH | C—$CH_3$ | CH | CH | C—CN | CH |
| 9 | C—F | CH | C—$OCH_3$ | N | N | C—$OCH_3$ | CH |
| 10 | CH | CH | CH | N | CH | CH | C—$OCH_3$ |
| 11 | CH | CH | CH | CH | C—$NHSO_2CH_3$ | CH | CH |
| 12 | CH | CH | CH | C—$NHSO_2CH_3$ | CH | CH | CH |
| 13 | CH | CH | CH | N | C—$OCH_3$ | N | C—$OCH_3$ |
| 14 | N | C—$OCH_3$ | CH | CH | CH | CH | CH |
| 15 | CH | CH | C—$OCH_3$ | N | CH | N | CH |
| 16 | CH | C—$OCH_3$ | C—$OCH_3$ | CH | CH | CH | CH |
| 17 | C—$OCH_3$ | CH | CH | N | CH | CH | C—$OCH_3$ |
| 18 | C—$OCH_3$ | CH | C—$OCH_3$ | N | C—$OCH_3$ | N | CH |
| 19 | CH | CH | C—$OCH_3$ | CH | C—$NHCOCH_3$ | CH | CH |
| 20 | CH | CH | C—CN | CH | C—$OCH_3$ | C—$OCH_3$ | CH |
| 21 | CH | CH | C—$OCH_3$ | CH | C—$N(CH_3)SO_2CH_3$ | CH | CH |
| 22 | N | CH | C—$OCH_3$ | CH | C—$OCH_3$ | CH | CH |
| 23 | CH | CH | C—$OCH_3$ | N | CH | N | C—$OCH_3$ |
| 24 | CH | CH | C—$OCH_3$ | CH | N | CH | CH |

Still other preferred compounds of formula Ib-1g are those of formula Ib-1i

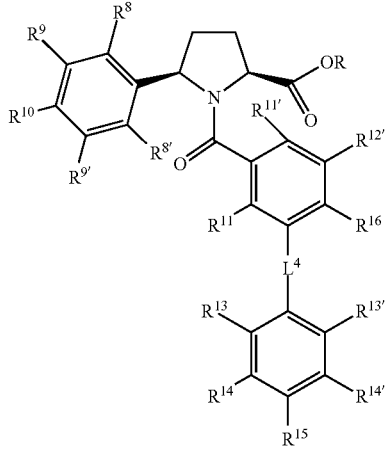

Ib-1i and pharmaceutically acceptable salts, solvates and prodrugs thereof, wherein R is as defined above in respect to formula I;

$R^8$, $R^{8'}$, $R^9$, $R^{9'}$ and $R^{10}$ are as defined above in respect to formula Ib-1f;

$L^4$, $R^{11}$, $R^{11'}$, $R^{12'}$, $R^{13}$, $R^{13'}$, $R^{14}$, $R^{14'}$ and $R^{15}$ is as defined above in respect to formula Ib-1h;

$R^{16}$ is as defined above in respect to formula Ib-1g, preferably $R^{16}$ is selected from H, halo preferably chloro or fluoro more preferably chloro, alkyl, haloalkyl preferably $CF_3$ or $CHF_2$, aryl, hydroxyl, alkoxy, haloalkoxy preferably $OCF_3$ or $OCHF_2$, alkoxyalkoxy, cycloalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, or $R^{16}$ forms together with $R^{12'}$ an alkylenedioxy group or a haloalkylenedioxy group, each of said substituents being optionally substituted by one or more further substituents selected from halo preferably chloro or fluoro, alkoxy, alkyl, alkylsulfonyl, more preferably $R^{16}$ is selected from H, halo preferably chloro and fluoro more preferably chloro, alkyl, haloalkyl preferably $CF_3$ or $CHF_2$, hydroxyl, alkoxy, haloalkoxy preferably $OCF_3$ or $OCHF_2$, alkoxyalkoxy, haloalkoxyalkyl, or $R^{16}$ forms together with $R^{12'}$ an alkylenedioxy group or a haloalkylenedioxy group, each of said substituents being optionally substituted by one or more further substituents selected from halo preferably chloro or fluoro, alkoxy, alkyl, cycloalkyl, alkylsulfonyl.

Other preferred compounds of formula Ib-1f are those of formula Ib-1j

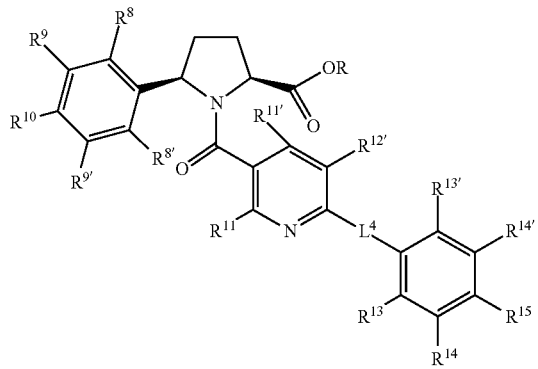

Ib-1j and pharmaceutically acceptable salts, solvates and prodrugs thereof, wherein R is as defined above in respect of formula I;

$R^8$, $R^{8'}$, $R^9$, $R^{9'}$ and $R^{10}$ are as defined above in respect of formula Ib-1f;

$L^4$ is as defined above in respect to formula Ib-1h, preferably $L^4$ is a single bond;

$R^{11}$ and $R^{11'}$ are as defined above in respect to formula Ib-1h, preferably and $R^{11'}$ are H;

$R^{12'}$ is as defined above in respect to formula Ib-1h, preferably $R^{12'}$ is H or methoxy, more preferably $R^{12'}$ is H;

$R^{13}$, $R^{13'}$, $R^{14}$, $R^{14'}$ and $R^{15}$ are as defined above in respect to formula Ib-1h, preferably $R^{13'}$, $R^{14}$, $R^{14'}$ and $R^{15}$ are H and $R^{13}$ is chloro, fluoro, methoxy, or $R^{13}$, $R^{13'}$, $R^{14'}$ and $R^{15}$ are H and $R^{14}$ is methoxy, or $R^{13'}$, $R^{14}$ and $R^{15}$ are H and a) both $R^{13}$ and $R^{14'}$ are chloro or b) $R^{13}$ is methoxy and $R^{14'}$ is cyano, or $R^{13'}$, $R^{14}$ and $R^{14'}$ are H and both $R^{13}$ and $R^{15}$ are methoxy more preferably $R^{13'}$, $R^{14}$, $R^{14'}$ and $R^{15}$ are H and $R^{13}$ is chloro, or $R^{13'}$, $R^{14}$ and $R^{15}$ are H and both $R^{13}$ and $R^{14'}$ are chloro.

Other preferred compounds of formula Ib-1f are those of formula Ib-1k

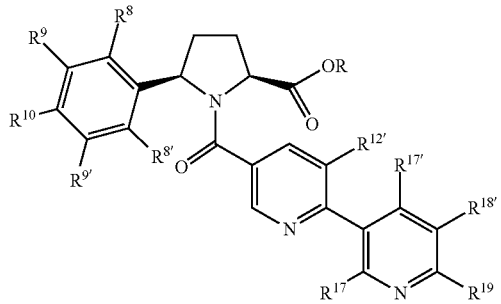

Ib-1k and pharmaceutically acceptable salts, solvates and prodrugs thereof, wherein R is as defined above in respect of formula I;

$R^8$, $R^{8'}$, $R^9$, $R^{9'}$ and $R^{10}$ are as defined above in respect of formula Ib-1e;

$R^{12'}$ is H, fluoro, chloro, $CF_3$, methyl or methoxy, preferably $R^{12'}$ is H or methoxy, more preferably $R^{12'}$ is methoxy;

$R^{17}$, $R^{17'}$, $R^{18'}$ and $R^{19}$ are independently selected from H, halo preferably chloro and fluoro, more preferably fluoro, cyano, nitro, alkyl preferably methyl, haloalkyl preferably CF₃ or CHF₂, alkoxyalkyl preferably methoxymethy, alkoxy preferably methoxy, cycloalkylalkyloxy preferably cyclopropylmethyloxy, haloalkoxy preferably OCF₃ or OCHF₂, alkoxyalkoxy preferably 2-methoxyethoxy, amino, alkylcarbonylamino preferably acetylamino, alkylsulfonyl preferably methylsulfonyl, alkylsulfonylamino preferably methylsulfonylamino, (N-methyl-N-methylsulfonyl)amino, preferably $R^{17'}$ and $R^{18'}$ are H and both $R^{17}$ and $R^{19}$ are methoxy.

Other preferred compounds of formula Ib-1f are those of formula Ib-1l

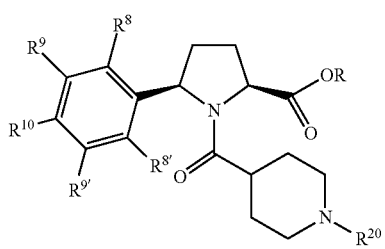

Ib-1l and pharmaceutically acceptable salts, solvates and prodrugs thereof, wherein R is as defined above in respect of formula I;

$R^8$, $R^{8'}$, $R^9$, $R^{9'}$ and $R^{10}$ are as defined above in respect of formula Ib-1e;

$R^{20}$ is an aryl or heteroaryl, each of said aryl or heteroaryl being optionally substituted by one or more substituent(s) selected from halo, alkyl, haloalkyl, cyano, nitro, phenyl optionally substituted by one chloro, alkoxy, heterocyclylsulfonyl, alkylsulfamoyl or alkylsulfonylamino, preferably $R^{20}$ is a phenyl optionally substituted by one or more substituent(s) selected from halo preferably chloro or fluoro, alkyl preferably methyl, haloalkyl preferably CF₃, cyano, nitro, alkoxy preferably methoxy, heterocyclylsulfonyl preferably (piperidin-1-yl)sulfonyl, (morpholin-4-yl)sulfonyl, alksulfamoyl preferably diethylaminosulfonyl, alkylsulfonylamino preferably methylsulfonylamino, or $R^{20}$ is 4-(4-chlorophenyl)thiazol-2-yl, or $R^{20}$ is a benzoxazol-2-yl, more preferably $R^{20}$ is 2-methoxyphenyl, 2-cyano-4-trifluoromethylphenyl, 2-chloro-4-trifluoromethylphenyl, 2-nitro-4-trifluoromethylphenyl, 2-nitro-4-(piperidin-1-yl)sulfonyl phenyl, 4-(morpholin-4-yl)sulfonylphenyl, 2-nitro-4-diethylaminosulfonyl phenyl, 2-nitro-4-tolyl, 2-cyano-4-nitrophenyl, 4-nitrophenyl, 2-fluoro-4-nitrophenyl, 3-methoxy-4-nitrophenyl, 5-chloro-2-nitrophenyl, 2-cyano-4-methylsulfonylaminophenyl, 2-cyano-4-methoxyphenyl, 2-methylsulfonylamino-4-trifluoromethylphenyl, 2-nitrophenyl, 4-cyanophenyl, 2-methoxy-4-trifluoromethylphenyl, or $R^{20}$ is 4-(4-chlorophenyl)thiazol-2-yl, or $R^{20}$ is a benzoxazol-2-yl, even more preferably $R^{20}$ is 2-cyano-4-trifluoromethylphenyl, 2-nitro-4-trifluoromethylphenyl, 2-methoxy-4-trifluoromethylphenyl.

Other preferred compounds of formula Ib are those of formula Ib-2

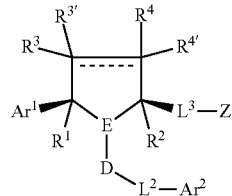

Ib-2 and pharmaceutically acceptable salts, solvates and prodrugs thereof, wherein $Ar^1$, $Ar^2$, $R^1$, $R^2$, $R^3$, $R^{3'}$, $R^4$, $R^{4'}$, $L^2$, $L^3$, D, E and Z are as defined above in respect of formula Ib; and the bond represented by the dotted line is either absent or present.

Preferred compounds of formula Ib-2 and pharmaceutically acceptable salts, solvates and prodrugs thereof are those wherein the dotted line is absent.

Further preferred compounds of formula Ib are those of formula Ib-3

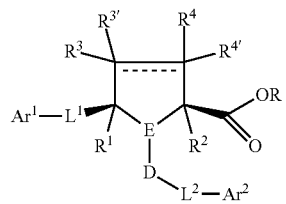

Ib-3 and pharmaceutically acceptable salts, solvates and prodrugs thereof, wherein $Ar^1$, $Ar^2$, $R^1$, $R^2$, $R^3$, $R^{3'}$, $R^4$, $R^{4'}$, $L^1$, $L^2$, D and E are as defined above in respect of formula Ib, R is as defined above in respect of formula I; and the bond represented by the dotted line is either absent or present.

Preferred compounds of formula Ib-3 and pharmaceutically acceptable salts, solvates and prodrugs thereof are those wherein dotted line is absent.

Yet other preferred compounds of formula Ib are those of formula Ib-4

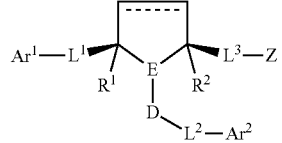

Ib-4 and pharmaceutically acceptable salts, solvates and prodrugs thereof, wherein $Ar^1$, $Ar^2$, $R^1$, $R^2$, $L^1$, $L^2$, $L^3$, D, E and Z are as defined above in respect of formula Ib; and the bond represented by the dotted line is either absent or present.

Preferred compounds of formula Ib-4 and pharmaceutically acceptable salts, solvates and prodrugs thereof are those wherein the dotted line is absent.

Further preferred compounds of formula Ib are those of formula Ib-5

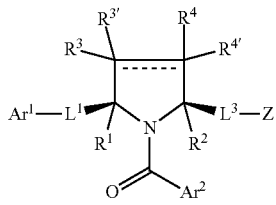

Ib-5 and pharmaceutically acceptable salts, solvates and prodrugs thereof, wherein
$Ar^1$, $Ar^2$, $L^1$, $L^3$, $R^1$, $R^2$, $R^3$, $R^{3'}$, $R^4$, $R^{4'}$ and Z are as defined above in respect of formula Ib; and
the bond represented by the dotted line is either absent or present.

Preferred compounds of formula Ib-5 and pharmaceutically acceptable salts, oleates and prodrugs thereof are those wherein the dotted line is absent.

Further preferred compounds of formula Ib are those of formula Ib-6

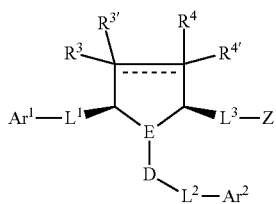

Ib-6 and pharmaceutically acceptable salts, solvates and prodrugs thereof, wherein
$Ar^1$, $Ar^2$, $L^1$, $L^2$, $L^3$, $R^3$, $R^{3'}$, $R^4$, $R^{4'}$, D, E and Z are as defined above in respect of formula Ib; and
the bond represented by the dotted line is either absent or present.

Preferred compounds of formula Ib-6 and pharmaceutically acceptable salts, solvates and prodrugs thereof are those wherein the dotted line is absent.

In yet another embodiment, preferred compounds of Formula I are those of formula Ic:

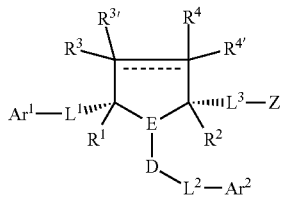

Ic and pharmaceutically acceptable salts, solvates and prodrugs thereof, wherein
$Ar^1$, $Ar^2$, $L^1$, $L^2$, $L^3$, $R^1$, $R^2$, $R^3$, $R^{3'}$, $R^4$, $R^{4'}$, D, E and Z are as defined above in respect of formula I; and
the bond represented by the dotted line is either absent or present.

Preferred compounds of formula Ic and pharmaceutically acceptable salts, solvates and prodrugs thereof are those wherein the dotted line is absent.

Other preferred compounds of formula Ic are those of formula Ic-1b':

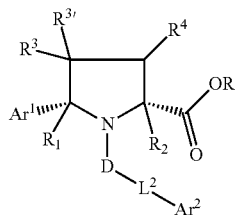

Ic-1b' and pharmaceutically acceptable salts, solvates and prodrugs thereof, wherein
$R^2$ is as defined above in respect of formula Ic and R is as defined above in respect of formula I;
$R^1$ is H;
D is C=O;
$L^2$ is single bond;
$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy, preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl, phenyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;
$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl, cycloalkyl or heterocyclyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro or alkyl or cycloalkyl group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, alkoxyalkoxy, alkoxyalkyl, and haloalkoxyalkyl; preferably $Ar^2$ is an aryl or heteroaryl preferably pyridyl, pyrazinyl, cycloalkyl, heterocyclyl or $C_2$-$C_6$ alkyl group, each of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro or alkyl or cycloalkyl, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenyl acetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonylalkylsulfonylamino preferably methylsulfonylamino, (N-methyl-N-methylsulfonyl) amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably $Ar^2$ is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1,1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1, 1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, 4-(2,6-dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or $Ar^2$ is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro,2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxypyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

$R^4$ is H, cyano, $C_1$-$C_4$ alkyl.

Preferred compounds of formula Ic-1b' are those of formula Ic-1g:

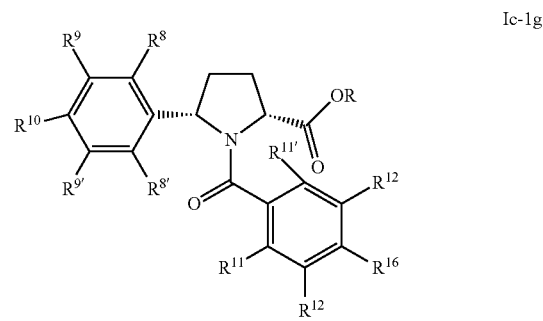

Ic-1g and pharmaceutically acceptable salts, solvates and prodrugs thereof, wherein R is as defined above in respect of formula I;

$R^8$, $R^{8'}$, $R^9$, $R^{9'}$ and $R^{10}$ are independently selected from H, halo preferably fluoro, chloro, bromo, cyano, alkyl, hydroxyalkyl, haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, haloalkoxy preferably $OCF_3$ or $OCHF_2$, heterocyclyloxy, alkylamino, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonylsulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, or one or more of $R^8$ and $R^9$, or $R^9$ and $R^{10}$, or $R^{10}$ and $R^{9'}$, or $R^{9'}$ and $R^{8'}$ form together a cycloalkyl, aryl, heterocycloalyl or heteroaryl moiety fused to the phenyl group they are attached to, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, preferably $R^8$, $R^{8'}$, $R^9$, $R^{9'}$ and $R^{10}$ are independently selected from H, halo preferably fluoro, chloro, bromo, cyano, alkyl, haloalkyl preferably $CF_3$ or $CHF_2$, cycloalkyl, aryl preferably phenyl, heteroaryl, hydroxyl, haloalkoxy preferably $OCF_3$ or $OCHF_2$, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy, haloalkoxy, more preferably $R^8$, $R^{8'}$, $R^9$, $R^{9'}$ and $R^{10}$ are independently selected from H, halo preferably bromo, fluoro or chloro, cyano, $C_1$-$C_4$ alkyl preferably methyl, aryl preferably phenyl, alkoxy preferably methoxy, still more preferably $R^8$, $R^{8'}$, $R^9$, $R^{9'}$ and $R^{10}$ are independently selected from H, halo preferably bromo, fluoro or chloro, alkyl preferably methyl, still more preferably $R^8$ is Br, Cl or F, preferably Cl and $R^{8'}$, $R^9$, $R^{9'}$ and $R^{10}$ are independently selected from H or F, or $R^9$ is Cl or F and $R^8$, $R^{8'}$, $R^{9'}$ and $R^{10}$ are H, or $R^9$ and $R^{9'}$ are F and $R^8$, $R^{8'}$ and $R^{10}$ are H, or $R^{10}$ is Cl or F and $R^8$, $R^{8'}$, $R^9$ and $R^{9'}$ are H, even more preferably $R^8$ is Br, Cl or F and $R^{8'}$, $R^9$, $R^{9'}$ and $R^{10}$ are H, or $R^8$ and $R^9$ are F and $R^{8'}$, $R^{9'}$ and $R^{10}$ are H, or $R^8$ and $R^{10}$ are F and $R^{8'}$, $R^9$ and $R^{9'}$ are H;

$R^{10}$, $R^{11}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkyloxycarbonyl, aminoalkylalkoxycarbonyl, cycloalkyloxycarbonyl, heterocyclyloxy carbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, aryl carbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together a cycloalkyl, aryl, heterocycloalkyl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, cycloalkylalkyl, aralkyl, heteroarylalkyl, heteroalkyl, hydroxyl, alkoxy, alkoxyalkoxy, haloalkoxy preferably trifluoromethoxt, 1,1,1-trifluoroethyloxy, alkoxyalkyl, haloalkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, cyclo alkylsulfonylamino, haloalkylsulfonylamino and oxo, preferably $R^{11}$, $R^{11'}$, $R^{12}$, $R^{12'}$ and $R^{16}$ are, independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, aryl carbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy preferably 1,1,1-trifluoroethyloxy, alkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, cycloalkylcarbonyloxy, alkylcarbonylamino, haloalkylcarbonylamino, carbamoyl, hydroxycarbamoyl, alkylcarbamoyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, more preferably $R^{11}$, $R^{11'}$, $R^{12}$, $R^{12'}$ and $R^{16}$ are independently selected from H, halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, cycloalkylalkyloxy, arylalkyloxy, heteroarylalkyloxy, alkoxyalkyl, aryloxyalkyl, heteroaryloxyalkyl, arylcarbonyl, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl, or heteroaryl moiety fused to the phenyl group they are attached to, each of said substituents being optionally substituted by one or more further substituents selected from halo preferably chloro or fluoro, cyano, alkyl preferably methyl, ethyl, propyl, isopropyl, tert-butyl, cyanomethyl, cycloalkyl, heterocyclyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylamino, alkylcarbonylamino, carbamoyl, hydroxycarbamimidoyl, alkylsulfonyl, alkylsulfonylamino, still more preferably $R^{11}$, $R^{11'}$, $R^{12}$, $R^{12'}$ and $R^{16}$ are independently selected from H, halo preferably chloro and fluoro, cyano, nitro, alkyl preferably methyl, ethyl, isopropyl or isobutyl, haloalkyl preferably $CF_3$ or $CHF_2$, cycloalkyl preferably cyclohexyl, heterocyclyl preferably pyrrolidin-1-yl, 4-methylpiperidin-1-yl, aryl preferably phenyl, heteroaryl preferably thiophenyl, pyridinyl, pyrimidinyl, pyrazinyl, pyridazinyl, aralkyl preferably benzyl, alkoxy preferably methoxy, ethoxy or isopropyloxy, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridyloxymethyl, or two substituents form an haloalkylenedioxy group each of said substituents being optionally substituted by one or more further substituents selected from halo preferably chloro or fluoro, cyano, alkyl preferably methyl, haloalkyl preferably trifluoromethyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted by one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino.

Preferred compounds of formula Ic-1g are those of formula Ic-1h1:

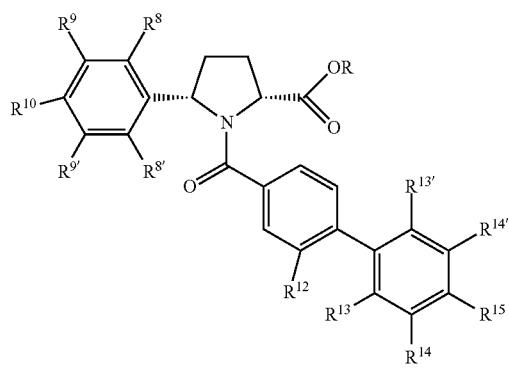

Ic-1h1 and pharmaceutically acceptable salts, solvates and prodrugs thereof, wherein

R is as defined above in respect to formula I;
$R^8$, $R^{8'}$, $R^9$, $R^{9'}$ and $R^{10}$ are as defined above in respect to formula Ic-1g;
$R^{12}$ is as defined above in respect to formula Ic-1g, preferably $R^{12}$ is H, fluoro, chloro, methyl, $CF_3$, nitro, cyano, methoxy or cyclopropylmethyloxy;
$R^{13}$, $R^{13'}$, $R^{14}$, $R^{14'}$ and $R^{15}$ are as defined above in respect to formula Ic-1g, preferably $R^{13'}$, $R^{14}$, $R^{14'}$ and $R^{15}$ are H and $R^{13}$ is chloro, cyano, hydroxyl, methyl, trifluoromethyl, cyanomethyl, methoxy, isopropoxy, isobutyloxy, $OCF_3$, cyclopropylmethyloxy, phenoxy, cyclopropylmethyloxy, benzyloxy, (4-fluorobenzyl)oxy, methoxymethyl, 2-methoxyethoxy, carbamoylmethyloxy, or $R^{13}$, $R^{13'}$, $R^{14'}$ and $R^{15}$ are H and $R^{14}$ is chloro, methylsulfonylamino, or $R^{13}$, $R^{13'}$, $R^{14}$ and $R^{14'}$ are H and $R^{15}$ is chloro, methylsulfonylamino, $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{13}$, $R^{13'}$ and $R^{15}$ are H and both $R^{13}$ and $R^{13'}$ are methoxy, or $R^{13}$, $R^{13'}$ and $R^{15}$ are H and both $R^{14}$ and $R^{14'}$ are fluoro, methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy, more preferably $R^{13'}$, $R^{14}$, $R^{14'}$ and $R^{15}$ are H and $R^{13}$ is chloro, cyano, trifluoromethyl, methoxy, isopropoxy, cyclopropylmethyloxy, or $R^{13}$, $R^{13'}$, $R^{14'}$ and $R^{15}$ are H and $R^{14}$ is chloro, or $R^{13}$, $R^{13'}$, $R^{14}$ and $R^{14'}$ are H and $R^{15}$ is chloro, methylsulfonylamino, or $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or h) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy.

Other preferred compounds of formula Ic-1g are those of formula Ic-1h':

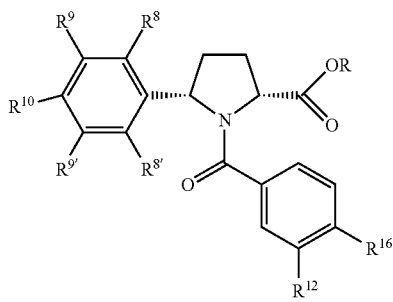

and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ic-1g;
$R^{12}$ is as defined above in respect to formula Ic-1g, preferably $R^{12}$ is H, fluoro, chloro, methyl, $CF_3$, or methoxy more preferably $R^{12}$ is H or methoxy;
$R^{16}$ is selected from the group of heteroaryl moieties consisting of:

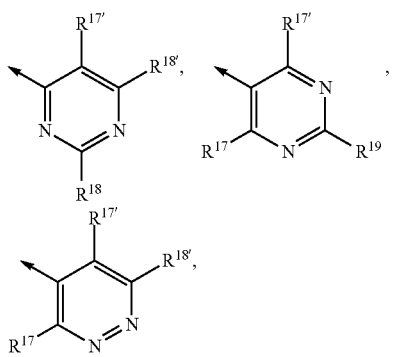

wherein
the arrow marks the attachment point to the phenyl ring;
$R^{17}$, $R^{17'}$, $R^{18}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$ or $CHF_2$, hydroxyl, hydroxyalkyl, alkoxy preferably methoxy, ethoxy, isopropyloxy, haloalkoxy preferably $OCF_3$, $OCHF_2$, or 1,1,1-trifluoroethyloxy, alkoxyalkoxy, cycloalkyloxy, alkoxyalkyl preferably methoxymethyl, cycloalkylalkyloxy preferably cyclopropylmethyloxy, aralkyloxy preferably benzyloxy, haloalkoxyalkyl, amino, alkylamino, alkylcarbonylamino, haloalkylcarbonylamino, alkylcarbonylaminoalkyl, carbamoyl, hydroxycarbamoyl, alkylcarbamoyl, carbamoylamino, alkylcarbamoylamino, carbamimidoyl, hydroxycarbamimidoyl, alkylsulfonyl preferably methylsulfonyl, haloalkylsulfonyl, sulfamoyl, alkylsulfamoyl, alkylsulfonylamino preferably methylsulfonylamino, (N-methyl-N-methylsulfonyl)amino, haloalkylsulfonylamino, preferably $R^{17}$, $R^{17'}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$, alkoxy preferably methoxy, ethoxy, isopropyloxy, haloalkoxy preferably $OCF_3$, $OCHF_2$, or 1,1,1-trifluoroethyloxy, alkoxyalkyl preferably methoxymethyl, aralkyloxy preferably benzyloxy, amino, alkylcarbonylamino, carbamoyl, carbamimidoyl, hydroxycarbamimidoyl, alkylsulfonyl preferably methylsulfonyl, alkylsulfonylamino preferably methylsulfonylamino, (N-methyl-N-methylsulfonyl)amino, more preferably $R^{17}$, $R^{17'}$, $R^{18'}$, and $R^{19}$ are independently selected from H, halo preferably chloro, alkoxy preferably methoxy, even more preferably $R^{17}$, $R^{17'}$, $R^{18'}$ and $R^{19}$ are independently selected from H, halo preferably chloro, alkoxy preferably methoxy;

Preferred compounds of formula Ic-1h' are those wherein $R^{16}$ is selected from 2-2-methoxypyrimidin-4-yl, 2,4-dibenzyloxypyrimidin-5-yl, 2,4-dimethoxypyrimidin-5-yl, 3,6-dimethoxypyridazin-5-yl, 2-methoxypyrimidin-5-yl, 2-methoxypyrimidin-3-yl.

In yet another embodiment, preferred compounds of Formula I are those of formula Id:

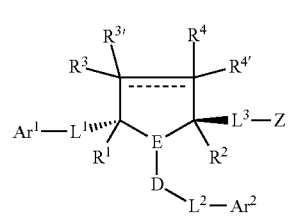

and pharmaceutically acceptable salts, solvates and prodrugs thereof, wherein
$Ar^1$, $Ar^2$, $L^1$, $L^2$, $L^3$, $R^1$, $R^2$, $R^3$, $R^{3'}$, $R^4$, $R^{4'}$, D, E and Z are as defined above in respect of formula I; and
the bond represented by the dotted line is either absent or present.

Preferred compounds of formula Id and pharmaceutically acceptable salts, solvates and prodrugs thereof are those wherein the dotted line is absent.

Other preferred compounds of formula Id are those of formula Id-1b':

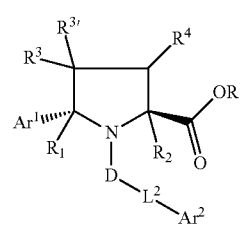

and pharmaceutically acceptable salts, solvates and prodrugs thereof, wherein
$R^2$ is as defined above in respect of formula Id and R is as defined above in respect of formula I;
$R^1$ is H;
D is C=O;
$L^2$ is single bond;
$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy, preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl, phenyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;

$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl, cycloalkyl or heterocyclyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro or alkyl or cycloalkyl group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, alkoxyalkoxy, alkoxyalkyl, and haloalkoxyalkyl; preferably $Ar^2$ is an aryl or heteroaryl preferably pyridyl, pyrazinyl, cycloalkyl, heterocyclyl or $C_2$-$C_6$ alkyl group, each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro or alkyl or cycloalkyl, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonylalkylsulfonylamino preferably methylsulfonylamino, (N-methyl-N-methylsulfonyl) amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably $Ar^2$ is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1,1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or $Ar^2$ is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro,2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxy-pyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

$R^4$ is H, cyano, $C_1$-$C_4$ alkyl.

Preferred compounds of formula Id-1b' are those of formula Id-1g:

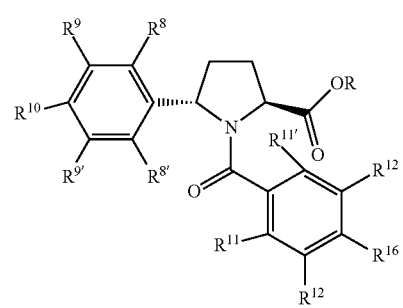

Id-1g and pharmaceutically acceptable salts, solvates and prodrugs thereof, wherein R is as defined above in respect of formula I;

$R^8$, $R^{8'}$, $R^9$, $R^{9'}$ and $R^{10}$ are independently selected from H, halo preferably fluoro, chloro, bromo, cyano, alkyl, hydroxyalkyl, haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, haloalkoxy preferably $OCF_3$ or $OCHF_2$, heterocyclyloxy, alkylamino, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonylsulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, or one or more of $R^8$ and $R^9$, or $R^9$ and $R^{10}$, or $R^{10}$ and $R^{9'}$, or $R^{9'}$ and $R^{8'}$ form together a cycloalkyl, aryl, heterocycloalyl or heteroaryl moiety fused to the phenyl group they are attached to, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, preferably $R^8$, $R^{8'}$, $R^9$, $R^{9'}$ and $R^{10}$ are independently selected from H, halo preferably fluoro, chloro, bromo, cyano, alkyl, haloalkyl preferably $CF_3$ or $CHF_2$, cycloalkyl, aryl preferably phenyl, heteroaryl, hydroxyl, haloalkoxy preferably $OCF_3$ or $OCHF_2$, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy, haloalkoxy, more preferably $R^8$, $R^{8'}$, $R^9$, $R^{9'}$ and $R^{10}$ are independently selected from H, halo preferably bromo, fluoro or chloro, cyano, $C_1$-$C_4$ alkyl preferably methyl, aryl preferably phenyl, alkoxy preferably methoxy, still more preferably $R^8$, $R^{8'}$, $R^9$, $R^{9'}$ and $R^{10}$ are independently selected from H, halo preferably bromo, fluoro or chloro, alkyl preferably methyl, still more preferably $R^8$ is Br, Cl or F, preferably Cl and $R^{8'}$, $R^9$, $R^{9'}$ and $R^{10}$ are independently selected from H or F, or $R^9$ is Cl or F and $R^8$, $R^{8'}$, $R^{9'}$ and $R^{10}$ are H, or $R^9$ and $R^{9'}$ are F and $R^8$, $R^{8'}$ and $R^{10}$ are H, or $R^{10}$ is Cl or F and $R^8$, $R^{8'}$, $R^9$ and $R^{9'}$ are H, even more preferably $R^8$ is Br, Cl or F and $R^{8'}$, $R^9$, $R^{9'}$ and $R^{10}$ are H, or $R^8$ and $R^9$ are F and $R^{8'}$, $R^{9'}$ and $R^{10}$ are H, or $R^8$ and $R^{10}$ are F and $R^{8'}$, $R^9$ and $R^{9'}$ are H;

$R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkyloxycarbonyl, aminoalkylalkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together a cycloalkyl, aryl, heterocycloalkyl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, cycloalkylalkyl, aralkyl, heteroarylalkyl, heteroalkyl, hydroxyl, alkoxy, alkoxyalkoxy, haloalkoxy preferably trifluoromethoxt, 1,1,1-trifluoroethyloxy, alkoxyalkyl, haloalkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, cycloalkylsulfonylamino, haloalkylsulfonylamino and oxo, preferably $R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —OCF₃ or —OCHF₂, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy preferably 1,1,1-trifluoroethyloxy, alkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, cycloalkylcarbonyloxy, alkylcarbonylamino, haloalkylcarbonylamino, carbamoyl, hydroxycarbamoyl, alkylcarbamoyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, more preferably $R^{11}$, $R^{11'}$, $R^{12}$, $R^{12'}$ and $R^{16}$ are independently selected from H, halo preferably chloro and fluoro, cyano, nitro, alkyl, haloalkyl preferably CF₃ or CHF₂, heterocyclyl, aryl, aralkyl, heteroaryl, heteroarylalkyl, hydroxyl, alkoxy, haloalkoxy preferably OCF₃ or OCHF₂, alkoxyalkoxy, aryloxy, cycloalkylalkyloxy, arylalkyloxy, heteroarylalkyloxy, alkoxyalkyl, aryloxyalkyl, heteroaryloxyalkyl, arylcarbonyl, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl, or heteroaryl moiety fused to the phenyl group they are attached to, each of said substituents being optionally substituted by one or more further substituents selected from halo preferably chloro or fluoro, cyano, alkyl preferably methyl, ethyl, propyl, isopropyl, tert-butyl, cyanomethyl, cycloalkyl, heterocyclyl, alkoxy preferably methoxy, ethoxy, isopropoxy, alkoxyalkyl, alkoxyalkoxy, cycloalkyloxy, aryloxy, aralkyloxy optionally substituted by one fluoro, amino, alkylamino, alkylcarbonylamino, carbamoyl, hydroxycarbamimidoyl, alkylsulfonyl, alkylsulfonylamino, still more preferably $R^{11}$, $R^{11'}$, $R^{12}$, $R^{12'}$ and $R^{16}$ are independently selected from H, halo preferably chloro and fluoro, cyano, nitro, alkyl preferably methyl, ethyl, isopropyl or isobutyl, haloalkyl preferably CF₃ or CHF₂, cycloalkyl preferably cyclohexyl, heterocyclyl preferably pyrrolidin-1-yl, 4-methylpiperidin-1-yl, aryl preferably phenyl, heteroaryl preferably thiophenyl, pyridinyl, pyrimidinyl, pyrazinyl, pyridazinyl, aralkyl preferably benzyl, alkoxy preferably methoxy, ethoxy or isopropyloxy, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridyloxymethyl, or two substituents form an haloalkylenedioxy group each of said substituents being optionally substituted by one or more further substituents selected from halo preferably chloro or fluoro, cyano, alkyl preferably methyl, haloalkyl preferably trifluoromethyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted by one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino.

Preferred compounds of formula Id-1g are those of formula Id-1h1:

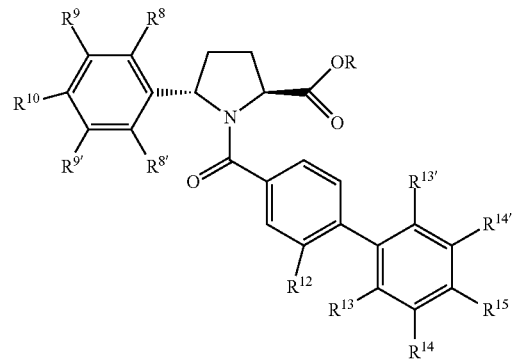

Id-1h1 and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Id-1g;
$R^{12}$ is as defined above in respect to formula Id-1g, preferably $R^{12}$ is H, fluoro, chloro, methyl, CF₃, nitro, cyano, methoxy or cyclopropylmethyloxy;
$R^{13}$, $R^{13'}$, $R^{14}$, $R^{14'}$ and $R^{15}$ are as defined above in respect to formula Id-1g, preferably $R^{13'}$, $R^{14}$, $R^{14'}$ and $R^{15}$ are H and $R^{13}$ is chloro, cyano, hydroxyl, methyl, trifluoromethyl, cyanomethyl, methoxy, isopropoxy, isobutyloxy, OCF₃, cyclopropylmethyloxy, phenoxy, cyclopropylmethyloxy, benzyloxy, (4-fluorobenzyl)oxy, methoxymethyl, 2-methoxyethoxy, carbamoylmethyloxy, or $R^{13}$, $R^{13'}$, $R^{14'}$ and $R^{15}$ are H and $R^{14}$ is chloro, methylsulfonylamino, or $R^{13}$, $R^{13'}$, $R^{14}$ and $R^{14'}$ are H and $R^{15}$ is chloro, methylsulfonylamino, $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{15}$ are H and both $R^{14}$ and $R^{14'}$ are fluoro, methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy, more preferably $R^{13'}$, $R^{14}$, $R^{14'}$ and $R^{15}$ are H and $R^{13}$ is chloro, cyano, trifluoromethyl, methoxy, isopropoxy, cyclopropylmethyloxy, or $R^{13}$, $R^{13'}$, $R^{14'}$ and $R^{15}$ are H and $R^{14}$ is chloro, or $R^{13}$, $R^{13'}$, $R^{14}$ and $R^{14'}$ are H and $R^{15}$ is chloro, methylsulfonylamino, or $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy.

Other preferred compounds of formula Id-1g are those of formula Id-1h':

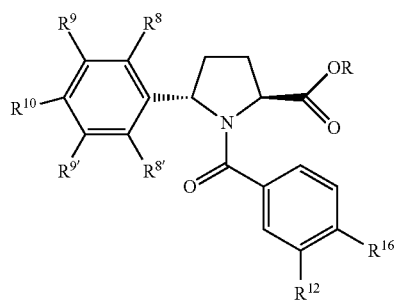

Id-1h' and pharmaceutically acceptable salts, solvates and prodrugs thereof, wherein

R is as defined above in respect to formula I;
$R^8$, $R^{8'}$, $R^9$, $R^{9'}$ and $R^{10}$ are as defined above in respect to formula Id-1g;
$R^{12}$ is as defined above in respect to formula Id-1g, preferably $R^{12}$ is H, fluoro, chloro, methyl, $CF_3$, or methoxy more preferably $R^{12}$ is H or methoxy;

$R^{16}$ is selected from the group of heteroaryl moieties consisting of:

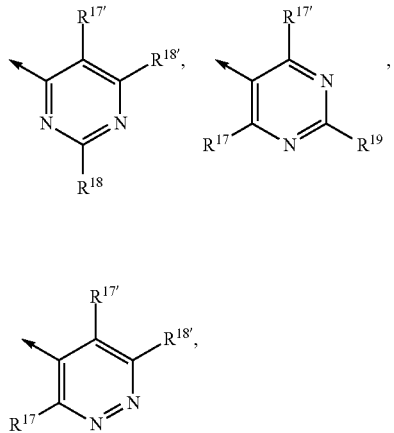

wherein the arrow marks the attachment point to the phenyl ring;

$R^{17}$, $R^{17'}$, $R^{18}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$ or $CHF_2$, hydroxyl, hydroxyalkyl, alkoxy preferably methoxy, ethoxy, isopropyloxy, haloalkoxy preferably $OCF_3$, $OCHF_2$, or 1,1,1-trifluoroethyloxy, alkoxyalkoxy, cycloalkyloxy, alkoxyalkyl preferably methoxymethyl, cycloalkylalkyloxy preferably cyclopropylmethyloxy, aralkyloxy preferably benzyloxy, haloalkoxyalkyl, amino, alkylamino, alkylcarbonylamino, haloalkylcarbonylamino, alkylcarbonylaminoalkyl, carbamoyl, hydroxycarbamoyl, alkylcarbamoyl, carbamoylamino, alkylcarbamoylamino, carbamimidoyl, hydroxycarbamimidoyl, alkylsulfonyl preferably methylsulfonyl, haloalkylsulfonyl, sulfamoyl, alkylsulfamoyl, alkylsulfonylamino preferably methylsulfonylamino, (N-methyl-N-methylsulfonyl)amino, haloalkylsulfonylamino, preferably $R^{17}$, $R^{17'}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$, alkoxy preferably methoxy, ethoxy, isopropyloxy, haloalkoxy preferably $OCF_3$, $OCHF_2$, or 1,1,1-trifluoroethyloxy, alkoxyalkyl preferably methoxymethyl, aralkyloxy preferably benzyloxy, amino, alkylcarbonylamino, carbamoyl, carbamimidoyl, hydroxycarbamimidoyl, alkylsulfonyl preferably methylsulfonyl, alkylsulfonylamino preferably methylsulfonylamino, (N-methyl-N-methylsulfonyl)amino, more preferably $R^{17}$, $R^{17'}$, $R^{18'}$, and $R^{19}$ are independently selected from H, halo preferably chloro, alkoxy preferably methoxy, even more preferably $R^{17}$, $R^{17'}$, $R^{18'}$ and $R^{19}$ are independently selected from H, halo preferably chloro, alkoxy preferably methoxy;

Preferred compounds of formula Id-1h' are those wherein $R^{16}$ is selected from 2-2-methoxypyrimidin-4-yl, 2,4-dibenzyloxypyrimidin-5-yl, 2,4-dimethoxypyrimidin-5-yl, 3,6-dimethoxypyridazin-5-yl, 2-methoxypyrimidin-5-yl, 2-methoxypyrimidin-3-yl.

In yet another embodiment, preferred compounds of Formula I are those of formula Ie:

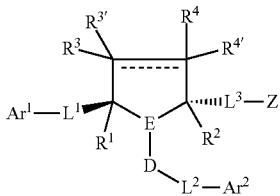

and pharmaceutically acceptable salts, solvates and prodrugs thereof, wherein
$A^1$, $Ar^2$, $L^1$, $L^2$, $L^3$, $R^1$, $R^2$, $R^3$, $R^{3'}$, $R^4$, $R^{4'}$, D, E and Z are as defined above in respect of formula I; and
the bond represented by the dotted line is either absent or present.

Preferred compounds of formula Ie and pharmaceutically acceptable salts, solvates and prodrugs thereof are those wherein the dotted line is absent.

Other preferred compounds of formula Ie are those of formula Ie-1b':

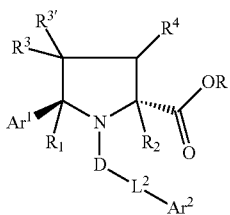

and pharmaceutically acceptable salts, solvates and prodrugs thereof, wherein
$R^2$ is as defined above in respect of formula Ie and R is as defined above in respect of formula I;
$R^1$ is H;
D is C=O;
$L^2$ is single bond;
$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy, preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl, phenyl, 2-chlorophenyl, 2-tolyl, 2-methoxyphenyl, 3-chlorophenyl, 4-chlorophenyl, 2-fluorophenyl, 3-fluorophenyl, 4-fluropheny 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;

$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl, cycloalkyl or heterocyclyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro or alkyl or cycloalkyl group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, alkoxyalkoxy, alkoxyalkyl, and haloalkoxyalkyl; preferably $Ar^2$ is an aryl or heteroaryl preferably pyridyl, pyrazinyl, cycloalkyl, heterocyclyl or $C_2$-$C_6$ alkyl group, each of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro or alkyl or cycloalkyl, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonylalkylsulfonylamino preferably methylsulfonylamino, (N-methyl-N-methylsulfonyl) amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably $Ar^2$ is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1,1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, 4-(2,6-dimethoxy-pyridin-3-yl)phenyl, 4-(2-(2-methoxyethoxy)-pyridin-3-yl) phenyl, 4-(pyrimidin-2-yl)phenyl, 4-(pyrimidin-5-yl) phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or $Ar^2$ is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro,2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyano methyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl) amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1, 1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxy-pyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

$R^4$ is H, cyano, $C_1$-$C_4$ alkyl.

Preferred compounds of formula Ie-1b' are those of formula Ie-1g:

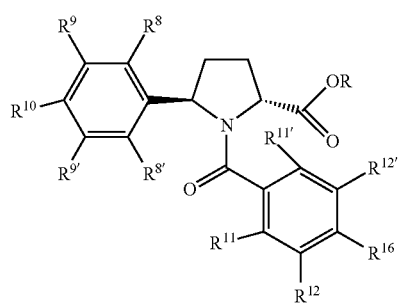

Ie-1g and pharmaceutically acceptable salts, solvates and prodrugs thereof, wherein R is as defined above in respect of formula I;

$R^8$, $R^{8'}$, $R^9$, $R^{9'}$ and $R^{10}$ are independently selected from H, halo preferably fluoro, chloro, bromo, cyano, alkyl, hydroxyalkyl, haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, haloalkoxy preferably $OCF_3$ or $OCHF_2$, heterocyclyloxy, alkylamino, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonylsulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, or one or more of $R^8$ and $R^9$, or $R^9$ and $R^{10}$, or $R^{10}$ and $R^{9'}$, or $R^{9'}$ and $R^{8'}$ form together a cycloalkyl, aryl, heterocycloalyl or heteroaryl moiety fused to the phenyl group they are attached to, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, preferably $R^8$, $R^{8'}$, $R^9$, $R^{9'}$ and $R^{10}$ are independently selected from H, halo preferably fluoro, chloro, bromo, cyano, alkyl, haloalkyl preferably $CF_3$ or $CHF_2$, cycloalkyl, aryl preferably phenyl, heteroaryl, hydroxyl, haloalkoxy preferably $OCF_3$ or $OCHF_2$, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy, haloalkoxy, more preferably $R^8$, $R^{8'}$, $R^9$, $R^{9'}$ and $R^{10}$ are independently selected from H, halo preferably bromo, fluoro or chloro, cyano, $C_1$-$C_4$ alkyl preferably methyl, aryl preferably phenyl, alkoxy preferably methoxy, still more preferably $R^8$, $R^{8'}$, $R^9$, $R^{9'}$ and $R^{10}$ are independently selected from H, halo preferably bromo, fluoro or chloro, alkyl preferably methyl, still more preferably $R^8$ is Br, Cl or F, preferably Cl and $R^{8'}$, $R^9$, $R^{9'}$ and $R^{10}$ are independently selected from H or F, or $R^9$ is Cl or F and $R^8$, $R^{8'}$, $R^{9'}$ and $R^{10}$ are H, or $R^9$ and $R^{9'}$ are F and $R^8$, $R^{8'}$ and $R^{10}$ are H, or $R^{10}$ is Cl or F and $R^8$, $R^{8'}$, $R^9$ and $R^{9'}$ are H, even more preferably $R^8$ is Br, Cl or F and $R^{8'}$, $R^9$, $R^{9'}$ and $R^{10}$ are H, or $R^8$ and $R^9$ are F and $R^{8'}$, $R^{9'}$ and $R^{10}$ are H, or $R^8$ and $R^{10}$ are F and $R^{8'}$, $R^9$ and $R^{9'}$ are H;

$R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkyloxycarbonyl, aminoalkyl alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together a cycloalkyl, aryl, heterocycloalkyl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, cycloalkylalkyl, aralkyl, heteroarylalkyl, heteroalkyl, hydroxyl, alkoxy, alkoxyalkoxy, haloalkoxy preferably trifluoromethoxt, 1,1,1-trifluoroethyloxy, alkoxyalkyl, haloalkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, cycloalkylcarbonyloxy, alkylcarbonylamino, haloalkcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, preferably $R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy preferably 1,1,1-trifluoroethyloxy, alkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, cycloalkylcarbonyloxy, alkylcarbonylamino, haloalkylcarbonylamino, carbamoyl, hydroxycarbamoyl, alkylcarbamoyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, more preferably $R^{11}$, $R^{11'}$, $R^{12}$, $R^{12'}$ and $R^{16}$ are independently selected from H, halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, cycloalkylalkyloxy, arylalkyloxy, heteroarylalkyloxy, alkoxyalkyl, aryloxyalkyl, heteroaryloxyalkyl, arylcarbonyl, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl, or heteroaryl moiety fused to the phenyl group they are attached to, each of said substituents being optionally substituted by one or more further substituents selected from halo preferably chloro or fluoro, cyano, alkyl preferably methyl, ethyl, propyl, isopropyl, tert-butyl, cyanomethyl, cycloalkyl, heterocyclyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylamino, alkylcarbonylamino, carbamoyl, hydroxycarbamimidoyl, alkylsulfonyl, alkylsulfonylamino, still more preferably $R^{11}$, $R^{11'}$, $R^{12}$, $R^{12'}$ and $R^{16}$ are independently selected from H, halo preferably chloro and fluoro, cyano, nitro, alkyl preferably methyl, ethyl, isopropyl or isobutyl, haloalkyl preferably $CF_3$ or $CHF_2$, cycloalkyl preferably cyclohexyl, heterocyclyl preferably pyrrolidin-1-yl, 4-methylpiperidin-1-yl, aryl preferably phenyl, heteroaryl preferably thiophenyl, pyridinyl, pyrimidinyl, pyrazinyl, pyridazinyl, aralkyl preferably benzyl, alkoxy preferably methoxy, ethoxy or isopropyloxy, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridyloxymethyl, or two substituents form an haloalkylenedioxy group each of said substituents being optionally substituted by one or more further substituents selected from halo preferably chloro or fluoro, cyano, alkyl preferably methyl, haloalkyl preferably trifluoromethyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted by one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl) amino.

Preferred compounds of formula Ie-1g are those of formula Ie-1h1:

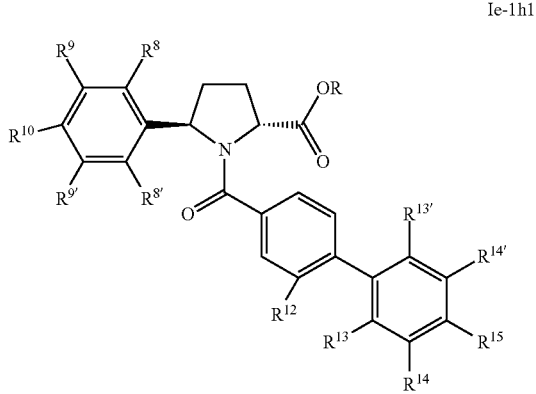

Ie-1h1 and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ie-1g;
$R^{12}$ is as defined above in respect to formula Ie-1g, preferably $R^{12}$ is H, fluoro, chloro, methyl, $CF_3$, nitro, cyano, methoxy or cyclopropylmethyloxy;
$R^{13}$, $R^{13'}$, $R^{14}$, $R^{14'}$ and $R^{15}$ are as defined above in respect to formula Ie-1g, preferably $R^{13'}$, $R^{14}$, $R^{14'}$ and $R^{15}$ are H and $R^{13}$ is chloro, cyano, hydroxyl, methyl, trifluoromethyl, cyanomethyl, methoxy, isopropoxy, isobutyloxy, $OCF_3$, cyclopropylmethyloxy, phenoxy, cyclopropylmethyloxy, benzyloxy, (4-fluorobenzyl)oxy, methoxymethyl, 2-methoxyethoxy, carbamoylmethyloxy, or $R^{13}$, $R^{13'}$, $R^{14'}$ and $R^{15}$ are H and $R^{14}$ is chloro, methylsulfonylamino, or $R^{13}$, $R^{13'}$, $R^{14}$ and $R^{14'}$ are H and $R^{15}$ is chloro, methylsulfonylamino, $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{15}$ are H and both $R^{14}$ and $R^{14'}$ are fluoro, methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy, more preferably $R^{13'}$, $R^{14}$, $R^{14'}$ and $R^{15}$ are H and $R^{13}$ is chloro, cyano, trifluoromethyl, methoxy, isopropoxy, cyclopropylmethyloxy, or $R^{13}$, $R^{13'}$, $R^{14'}$ and $R^{15}$ are H and $R^{14}$ is chloro, or $R^{13}$, $R^{13'}$, $R^{14}$ and $R^{14'}$ are H and $R^{15}$ is chloro, methylsulfonylamino, or $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy.

Other preferred compounds of formula Ie-1g are those of formula Ie-1h':

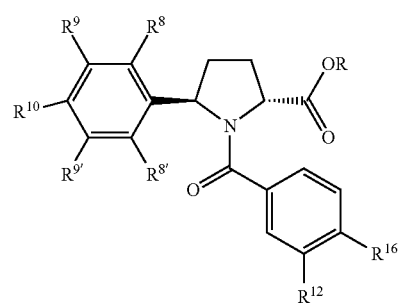

Ie-1h' and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ie-1g;
$R^{12}$ is as defined above in respect to formula Ie-1g, preferably $R^{12}$ is H, fluoro, chloro, methyl, $CF_3$, or methoxy more preferably $R^{12}$ is H or methoxy;
$R^{16}$ is selected from the group of heteroaryl moieties consisting of:

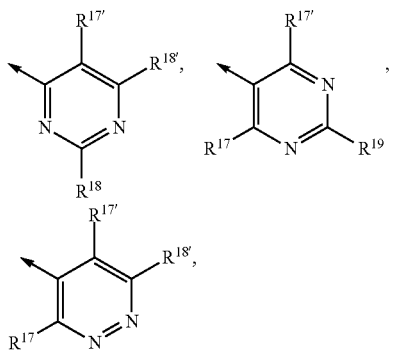

wherein
the arrow marks the attachment point to the phenyl ring;
$R^{17}$, $R^{17'}$, $R^{18}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$ or $CHF_2$, hydroxyl, hydroxyalkyl, alkoxy preferably methoxy, ethoxy, isopropyloxy, haloalkoxy preferably $OCF_3$, $OCHF_2$, or 1,1,1-trifluoroethyloxy, alkoxyalkoxy, cycloalkyloxy, alkoxyalkyl preferably methoxymethyl, cycloalkylalkyloxy preferably cyclopropylmethyloxy, aralkyloxy preferably benzyloxy, haloalkoxyalkyl, amino, alkylamino, alkylcarbonylamino, haloalkylcarbonylamino, alkylcarbonylaminoalkyl, carbamoyl, hydroxycarbamoyl, alkylcarbamoyl, carbamoylamino, alkylcarbamoylamino, carbamimidoyl, hydroxycarbamimidoyl, alkylsulfonyl preferably methylsulfonyl, haloalkylsulfonyl, sulfamoyl, alkylsulfamoyl, alkylsulfonylamino preferably methylsulfonylamino, (N-methyl-N-methylsulfonyl)amino, haloalkylsulfonylamino, preferably $R^{17}$, $R^{17'}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$, alkoxy preferably methoxy, ethoxy, isopropyloxy, haloalkoxy preferably $OCF_3$, $OCHF_2$, or 1,1,1-trifluoroethyloxy, alkoxyalkyl preferably methoxymethyl, aralkyloxy preferably benzyloxy, amino, alkylcarbonylamino, carbamoyl, carbamimidoyl, hydroxycarbamimidoyl, alkylsulfonyl preferably methylsulfonyl, alkylsulfonylamino preferably methylsulfonylamino, (N-methyl-N-methylsulfonyl)amino, more preferably $R^{17}$, $R^{17'}$, $R^{18'}$ and $R^{19}$ are independently selected from H, halo preferably chloro, alkoxy preferably methoxy, even more preferably $R^{17}$, $R^{17'}$, $R^{18'}$ and $R^{19}$ are independently selected from H, halo preferably chloro, alkoxy preferably methoxy;

Preferred compounds of formula Ie-1h' are those wherein $R^{16}$ is selected from 2-2-methoxypyrimidin-4-yl, 2,4-dibenzyloxypyrimidin-5-yl, 2,4-dimethoxypyrimidin-5-yl, 3,6-dimethoxypyridazin-5-yl, 2-methoxypyrimidin-5-yl, 2-methoxypyrimidin-3-yl.

Particularly preferred compounds of the invention are those listed in Table 1 hereafter:

TABLE 1

| Compound n° | Compound name | (M + H)⁺ |
|---|---|---|
| 1 | (2S,5R)-5-(2-chlorophenyl)-1-(2'-methoxy-[1,1'-biphenyl]-4-carbonyl)pyrrolidine-2-carboxylic acid | 436.9 |

TABLE 1-continued

| Compound n° | Compound name | (M + H)⁺ |
|---|---|---|
| 2 | (2S,5R)-5-(2-chlorophenyl)-1-(2'-methyl-[1,1'-biphenyl]-4-carbonyl)pyrrolidine-2-carboxylic acid | 420.9 |
| 3 | (2S,5R)-1-(3-((4-chlorobenzyl)oxy)-5-methoxybenzoyl)-5-(2-chlorophenyl)pyrrolidine-2-carboxylic acid | 501.4 |
| 4 | (2S,5R)-5-(2-chlorophenyl)-1-(2'-fluoro-[1,1'-biphenyl]-4-carbonyl)pyrrolidine-2-carboxylic acid | 424.9 |
| 5 | (2S,5R)-5-(2-chlorophenyl)-1-(4'-methyl-[1,1'-biphenyl]-4-carbonyl)pyrrolidine-2-carboxylic acid | 420.9 |
| 6 | (2S,5R)-5-(2-chlorophenyl)-1-(3-methoxy-5-phenethoxybenzoyl)pyrrolidine-2-carboxylic acid | 481.0 |
| 8 | (2S,5R)-1-([1,1'-biphenyl]-4-carbonyl)-5-(2-chlorophenyl)pyrrolidine-2-carboxylic acid | 406.9 |
| 9 | (2S,5R)-5-(2-chlorophenyl)-1-(3-(3,3-diphenylpropoxy)-5-methoxybenzoyl)pyrrolidine-2-carboxylic acid | 571.1 |
| 10 | (2S,5R)-5-(2-chlorophenyl)-1-(3'-fluoro-[1,1'-biphenyl]-4-carbonyl)pyrrolidine-2-carboxylic acid | 424.9 |
| 11 | (2S,5R)-5-(2-chlorophenyl)-1-(3'-methyl-[1,1'-biphenyl]-4-carbonyl)pyrrolidine-2-carboxylic acid | 420.9 |
| 12 | (2S,5R)-5-(2-chlorophenyl)-1-(3-methoxy-5-((4-(methylsulfonyl)benzyl)oxy)benzoyl)pyrrolidine-2-carboxylic acid | 545.0 |
| 13 | (2S,5R)-5-(2-chlorophenyl)-1-(3'-methoxy-[1,1'-biphenyl]-4-carbonyl)pyrrolidine-2-carboxylic acid | 436.9 |
| 14 | (2S,5R)-5-(2-chlorophenyl)-1-(3,5-dimethoxybenzoyl)pyrrolidine-2-carboxylic acid | 390.8 |
| 15 | (2S,5R)-5-(2-chlorophenyl)-1-(4-(phenoxymethyl)benzoyl)pyrrolidine-2-carboxylic acid | 436.9 |
| 16 | (2S,5R)-5-(2-chlorophenyl)-1-(4-((2-fluorobenzyl)oxy)benzoyl)pyrrolidine-2-carboxylic acid | 454.9 |
| 17 | (2S,5R)-1-(3-chloro-5-methoxybenzoyl)-5-(2-chlorophenyl)pyrrolidine-2-carboxylic acid | 395.2 |
| 18 | (2S,5R)-5-(2-chlorophenyl)-1-(4'-fluoro-[1,1'-biphenyl]-4-carbonyl)pyrrolidine-2-carboxylic acid | 424.9 |
| 19 | (2S,5R)-5-(2-chlorophenyl)-1-(4-phenethoxybenzoyl)pyrrolidine-2-carboxylic acid | 450.9 |
| 20 | (2S,5R)-5-(2-chlorophenyl)-1-(chroman-3-carbonyl)pyrrolidine-2-carboxylic acid | 386.8 |
| 21 | (2S,5R)-5-(2-chlorophenyl)-1-(3,5-diethoxybenzoyl)pyrrolidine-2-carboxylic acid | 418.9 |
| 23 | (2S,5R)-5-(2-chlorophenyl)-1-(3-phenethoxybenzoyl)pyrrolidine-2-carboxylic acid | 450.9 |
| 24 | (2S)-1-([1,1'-biphenyl]-4-carbonyl)-4-benzyl-5-phenylpyrrolidine-2-carboxylic acid | 462.6 |
| 25 | (2S,5R)-5-(2-chlorophenyl)-1-(1,2,3,4-tetrahydronaphthalene-2-carbonyl)pyrrolidine-2-carboxylic acid | 384.9 |
| 26 | (2S,5R)-5-(2-chlorophenyl)-1-(4-isobutylbenzoyl)pyrrolidine-2-carboxylic acid | 386.9 |
| 27 | (2S,5R)-5-(2-chlorophenyl)-1-(2,2-difluorobenzo[d][1,3]dioxole-6-carbonyl)pyrrolidine-2-carboxylic acid | 410.8 |
| 28 | (2S,5R)-1-([1,1'-biphenyl]-4-carbonyl)-5-phenylpyrrolidine-2-carboxylic acid | 372.4 |
| 29 | (2S,5R)-5-(2-chlorophenyl)-1-(3-fluoro-5-methoxybenzoyl)pyrrolidine-2-carboxylic acid | 378.8 |
| 30 | (2S,5R)-5-(2-chlorophenyl)-1-(6-phenylnicotinoyl)pyrrolidine-2-carboxylic acid | 407.9 |
| 31 | (2S,5R)-5-(2-chlorophenyl)-1-(3-methoxy-5-(2-methoxyethoxy)benzoyl)pyrrolidine-2-carboxylic acid | 434.9 |
| 32 | (2S,5R)-5-(2-chlorophenyl)-1-(3'-methoxy-[1,1'-biphenyl]-3-carbonyl)pyrrolidine-2-carboxylic acid | 436.9 |
| 33 | (2S,5R)-5-(2-chlorophenyl)-1-(3-methoxy-5-(trifluoromethyl)benzoyl)pyrrolidine-2-carboxylic acid | 428.8 |

TABLE 1-continued

| Compound n° | Compound name | (M + H)+ |
|---|---|---|
| 34 | (2S,5R)-5-(2-chlorophenyl)-1-(1-(4-methoxyphenyl)-5-phenyl-1H-pyrazole-3-carbonyl)pyrrolidine-2-carboxylic acid | 503.0 |
| 35 | (2S,5R)-5-(2-chlorophenyl)-1-(4-isopropoxybenzoyl)pyrrolidine-2-carboxylic acid | 388.9 |
| 36 | (2S,5R)-5-(2-chlorophenyl)-1-(3-((3,5-dimethylisoxazol-4-yl)methoxy)-5-methoxybenzoyl)pyrrolidine-2-carboxylic acid | 485.9 |
| 37 | (2S,5R)-5-(2-chlorophenyl)-1-(2,3-dihydro-1H-indene-2-carbonyl)pyrrolidine-2-carboxylic acid | 370.8 |
| 38 | (2S,5R)-5-(2-chlorophenyl)-1-(3-methyl-5-(trifluoromethoxy)benzoyl)pyrrolidine-2-carboxylic acid | 428.8 |
| 39 | (2S,5R)-1-(3-(benzyloxy)benzoyl)-5-(2-chlorophenyl)pyrrolidine-2-carboxylic acid | 436.9 |
| 40 | (2S,5R)-5-(2-chlorophenyl)-1-(3-methoxybenzoyl)pyrrolidine-2-carboxylic acid | 360.8 |
| 41 | (2S,5R)-5-(2-chlorophenyl)-1-(2-phenylpyrimidine-5-carbonyl)pyrrolidine-2-carboxylic acid | 408.9 |
| 42 | (2S,5R)-5-(2-chlorophenyl)-1-(4-(trifluoromethoxy)benzoyl)pyrrolidine-2-carboxylic acid | 414.8 |
| 43 | (2S,5R)-5-(2-chlorophenyl)-1-(4-(5-cyclopropyl-1,2,4-oxadiazol-3-yl)benzoyl)pyrrolidine-2-carboxylic acid | 438.9 |
| 44 | 4-((2S,5R)-2-carboxy-5-(2-chlorophenyl)pyrrolidine-1-carbonyl)-2,6-dimethoxypyrimidin-1-ium formate | 438.8 |
| 45 | (2S,5R)-5-(2-chlorophenyl)-1-(4-phenylbutanoyl)pyrrolidine-2-carboxylic acid | 372.9 |
| 46 | (2S,5R)-5-(2-chlorophenyl)-1-(3-methyl-5-(trifluoromethyl)benzoyl)pyrrolidine-2-carboxylic acid | 412.8 |
| 47 | (2S,5R)-1-([1,1'-biphenyl]-4-carbonyl)-5-(3-chloropyridin-2-yl)pyrrolidine-2-carboxylic acid | 407.9 |
| 48 | (2S,5R)-5-(2-chlorophenyl)-1-(3-hydroxy-5-(trifluoromethyl)benzoyl)pyrrolidine-2-carboxylic acid | 414.8 |
| 49 | (2S,5S)-5-(2-chlorophenyl)-1-(3-methoxybenzoyl)pyrrolidine-2-carboxylic acid | 360.8 |
| 50 | (2S,5R)-1-(3,5-dimethoxybenzoyl)-5-phenylpyrrolidine-2-carboxylic acid | 356.4 |
| 51 | (S)-5-([1,1'-biphenyl]-3-yl)-1-(3-methoxybenzoyl)pyrrolidine-2-carboxylic acid | 402.5 |
| 52 | (2S,5R)-5-(2-chlorophenyl)-1-(3-phenylpropanoyl)pyrrolidine-2-carboxylic acid | 358.8 |
| 53 | (2S,5S)-5-(2-chlorophenyl)-1-(2'-methoxy-[1,1'-biphenyl]-4-carbonyl)pyrrolidine-2-carboxylic acid | 436.9 |
| 54 | (2S,5R)-1-([1,1'-biphenyl]-4-carbonyl)-5-(pyridin-2-yl)pyrrolidine-2-carboxylic acid | 373.4 |
| 55 | (2S,5R)-5-(2-chlorophenyl)-1-(5-phenylpicolinoyl)pyrrolidine-2-carboxylic acid | 407.9 |
| 57 | (2S,5R)-5-(2-fluorophenyl)-1-(3-methoxybenzoyl)pyrrolidine-2-carboxylic acid | 344.3 |
| 58 | (2S,5R)-1-(2-([1,1'-biphenyl]-4-yl)acetyl)-5-(2-chlorophenyl)pyrrolidine-2-carboxylic acid | 420.9 |
| 59 | (2R,5S)-1-([1,1'-biphenyl]-4-carbonyl)-5-phenylpyrrolidine-2-carboxylic acid | 372.4 |
| 60 | (2S,5R)-5-phenyl-1-(2-phenylacetyl)pyrrolidine-2-carboxylic acid | 310.4 |
| 61 | (2R,5S)-5-phenyl-1-(2-phenylacetyl)pyrrolidine-2-carboxylic acid | 310.4 |
| 62 | (2S,5R)-1-(3-methoxybenzoyl)-5-(2-methoxyphenyl)pyrrolidine-2-carboxylic acid | 356.4 |
| 63 | (2R,5S)-5-(2-chlorophenyl)-1-(3-methoxybenzoyl)pyrrolidine-2-carboxylic acid | 360.8 |
| 64 | (2R,5R)-5-(2-chlorophenyl)-1-(3-methoxybenzoyl)pyrrolidine-2-carboxylic acid | 360.8 |
| 65 | (2S)-5-(4-chlorophenyl)-1-(3-methoxybenzoyl)pyrrolidine-2-carboxylic acid | 360.8 |
| 66 | (2S)-5-([1,1'-biphenyl]-4-yl)-1-(3-methoxybenzoyl)pyrrolidine-2-carboxylic acid | 402.5 |
| 67 | (2S,5R)-methyl 5-(2-chlorophenyl)-1-(3-methoxybenzoyl)pyrrolidine-2-carboxylate | 374.8 |
| 68 | (2S)-5-(2-chlorobenzyl)-1-(3-methoxybenzoyl)pyrrolidine-2-carboxylic acid | 374.8 |
| 69 | (2S)-5-cyclohexyl-1-(3-methoxybenzoyl)pyrrolidine-2-carboxylic acid | 332.4 |
| 70 | (2S,5R)-5-(2-chlorophenyl)-1-(2-(3-methoxyphenyl)acetyl)pyrrolidine-2-carboxylic acid | 374.8 |
| 71 | (2S,5S)-5-(2-chlorophenyl)-1-(3,5-dimethoxybenzoyl)pyrrolidine-2-carboxylic acid | 390.8 |
| 72 | (2S,5R)-5-([1,1'-biphenyl]-2-yl)-1-(3-methoxybenzoyl)pyrrolidine-2-carboxylic acid | 402.5 |
| 74 | 2-((2S,5R)-5-(2-chlorophenyl)-1-(3-methoxybenzoyl)pyrrolidin-2-yl)acetic acid | 374.8 |
| 75 | (2S,5R)-5-(2-chlorophenyl)-1-(6-phenylpyrimidine-4-carbonyl)pyrrolidine-2-carboxylic acid | 408.9 |
| 76 | (2S,5R)-5-(2-chlorophenyl)-1-(6-(2-fluorophenyl)nicotinoyl)pyrrolidine-2-carboxylic acid | 425.9 |
| 77 | (2S,5R)-5-(2-chlorophenyl)-1-(6-(2-chlorophenyl)nicotinoyl)pyrrolidine-2-carboxylic acid | 442.3 |
| 78 | (2S,5R)-5-(2-chlorophenyl)-1-(6-(2-methoxyphenyl)nicotinoyl)pyrrolidine-2-carboxylic acid | 437.9 |
| 79 | (2S,5R)-5-(2-chlorophenyl)-1-(6-(3-fluorophenyl)nicotinoyl)pyrrolidine-2-carboxylic acid | 425.9 |
| 80 | (2S,5R)-5-(2-chlorophenyl)-1-(6-(3-methoxyphenyl)nicotinoyl)pyrrolidine-2-carboxylic acid | 437.9 |
| 81 | (2S,5R)-5-(2-chlorophenyl)-1-(6-(4-methoxyphenyl)nicotinoyl)pyrrolidine-2-carboxylic acid | 437.9 |
| 82 | (2S,5R)-5-(2-chlorophenyl)-1-(6-(4-fluorophenyl)nicotinoyl)pyrrolidine-2-carboxylic acid | 425.9 |
| 83 | (2S,5R)-5-(2-chlorophenyl)-1-(2-(2-chlorophenyl)pyrimidine-5-carbonyl)pyrrolidine-2-carboxylic acid | 443.3 |
| 84 | (2S,5R)-5-(2-chlorophenyl)-1-(2-methyl-6-phenylnicotinoyl)pyrrolidine-2-carboxylic acid | 421.9 |
| 85 | (2S,5R)-1-(4-chloro-2-(pyridin-3-yl)pyrimidine-5-carbonyl)-5-(2-chlorophenyl)pyrrolidine-2-carboxylic acid | 444.3 |
| 86 | (2S,5R)-1-(4-chloro-2-(pyridin-2-yl)pyrimidine-5-carbonyl)-5-(2-chlorophenyl)pyrrolidine-2-carboxylic acid | 444.3 |
| 87 | (2S,5R)-1-(4-chloro-2-(pyridin-4-yl)pyrimidine-5-carbonyl)-5-(2-chlorophenyl)pyrrolidine-2-carboxylic acid | 444.3 |
| 88 | (2S,5R)-5-(2-chlorophenyl)-1-(4-(pyridin-2-yl)benzoyl)pyrrolidine-2-carboxylic acid | 407.9 |
| 89 | (2S,5R)-1-(4-((4-chlorophenoxy)methyl)benzoyl)-5-(2-chlorophenyl)pyrrolidine-2-carboxylic acid | 471.3 |
| 90 | (2S,5R)-5-(2-chlorophenyl)-1-(4-((4-fluorophenoxy)methyl)benzoyl)pyrrolidine-2-carboxylic acid | 454.9 |
| 91 | (2S,5R)-5-(2-chlorophenyl)-1-(4-((4-methoxyphenoxy)methyl)benzoyl)pyrrolidine-2-carboxylic acid | 466.9 |
| 92 | (2S,5R)-1-(4-((2-chlorophenoxy)methyl)benzoyl)-5-(2-chlorophenyl)pyrrolidine-2-carboxylic acid | 471.3 |
| 93 | (2S,5R)-5-(2-chlorophenyl)-1-(4-((2-methoxyphenoxy)methyl)benzoyl)pyrrolidine-2-carboxylic acid | 466.9 |
| 94 | (2S,5R)-5-(2-chlorophenyl)-1-(4-((3-methoxyphenoxy)methyl)benzoyl)pyrrolidine-2-carboxylic acid | 466.9 |
| 95 | (2S,5R)-1-(4-((3-chlorophenoxy)methyl)benzoyl)-5-(2-chlorophenyl)pyrrolidine-2-carboxylic acid | 471.3 |
| 96 | (2S,5R)-5-(2-chlorophenyl)-1-(4-((p-tolyloxy)methyl)benzoyl)pyrrolidine-2-carboxylic acid | 450.9 |
| 97 | (2S,5R)-5-(2-chlorophenyl)-1-(4-((3-methoxybenzyl)oxy)benzoyl)pyrrolidine-2-carboxylic acid | 466.9 |

TABLE 1-continued

| Compound n° | Compound name | (M + H)+ |
|---|---|---|
| 98 | (2S,5R)-1-(4-((3-chlorobenzyl)oxy)benzoyl)-5-(2-chlorophenyl)pyrrolidine-2-carboxylic acid | 471.3 |
| 99 | (2S,5R)-5-(2-chlorophenyl)-1-(4-((3,5-dimethylisoxazol-4-yl)methoxy)benzoyl)pyrrolidine-2-carboxylic acid | 455.9 |
| 100 | (2S,5R)-5-(2-chlorophenyl)-1-(4-((3,5-dimethyl-1H-pyrazol-1-yl)methoxy)benzoyl)pyrrolidine-2-carboxylic acid | 454.9 |
| 101 | (2S,5R)-5-(2-chlorophenyl)-1-(4-(pyridin-2-ylmethoxy)benzoyl)pyrrolidine-2-carboxylic acid | 437.9 |
| 102 | (2S,5R)-5-(2-chlorophenyl)-1-(4-(pyridin-4-ylmethoxy)benzoyl)pyrrolidine-2-carboxylic acid | 437.9 |
| 103 | (2S,5R)-5-(2-chlorophenyl)-1-(4-(pyridin-3-ylmethoxy)benzoyl)pyrrolidine-2-carboxylic acid | 437.9 |
| 104 | (2S,5R)-5-(2-chlorophenyl)-1-(4-(5-methyl-1H-pyrazol-1-yl)benzoyl)pyrrolidine-2-carboxylic acid | 410.9 |
| 105 | (2S,5R)-5-(2-chlorophenyl)-1-(4-(isoxazol-5-yl)benzoyl)pyrrolidine-2-carboxylic acid | 397.8 |
| 106 | (2S,5R)-1-(4-(4H-1,2,4-triazol-4-yl)benzoyl)-5-(2-chlorophenyl)pyrrolidine-2-carboxylic acid | 397.8 |
| 107 | (2S,5R)-5-(2-chlorophenyl)-1-(4-(5-(p-tolyl)-1H-1,2,3-triazol-1-yl)benzoyl)pyrrolidine-2-carboxylic acid | 488.0 |
| 108 | (2S,5R)-5-(2-chlorophenyl)-1-(4-(5-oxo-3-phenyl-4,5-dihydro-1H-pyrazol-1-yl)benzoyl)pyrrolidine-2-carboxylic acid | 488.9 |
| 109 | (2S,5R)-5-(2-chlorophenyl)-1-(4-(5-methyl-3-(trifluoromethyl)-1H-pyrazol-1-yl)benzoyl)pyrrolidine-2-carboxylic acid | 478.9 |
| 110 | (2S,5R)-1-(4-(1H-pyrazol-1-yl)benzoyl)-5-(2-chlorophenyl)pyrrolidine-2-carboxylic acid | 396.8 |
| 111 | (2S,5R)-5-(2-chlorophenyl)-1-(4-(oxazol-5-yl)benzoyl)pyrrolidine-2-carboxylic acid | 397.8 |
| 112 | (2S,5R)-5-(2-chlorophenyl)-1-(4-(3,5-dimethyl-1H-pyrazol-1-yl)benzoyl)pyrrolidine-2-carboxylic acid | 424.9 |
| 113 | (2S,5R)-5-(2-chlorophenyl)-1-(2',5'-dichloro-[1,1'-biphenyl]-4-carbonyl)pyrrolidine-2-carboxylic acid | 475.8 |
| 114 | (2S,5R)-5-(2-chlorophenyl)-1-(4-(pyrimidin-5-yl)benzoyl)pyrrolidine-2-carboxylic acid | 408.9 |
| 115 | (2S,5R)-5-(2-chlorophenyl)-1-(4-(furan-3-yl)benzoyl)pyrrolidine-2-carboxylic acid | 396.8 |
| 116 | (2S,5R)-5-(2-chlorophenyl)-1-(4-(6-methoxypyridin-3-yl)benzoyl)pyrrolidine-2-carboxylic acid | 437.9 |
| 117 | (2S,5R)-5-(2-chlorophenyl)-1-(4-(3-fluoropyridin-4-yl)benzoyl)pyrrolidine-2-carboxylic acid | 425.9 |
| 118 | (2S,5R)-5-(2-chlorophenyl)-1-(4-(pyridin-3-yl)benzoyl)pyrrolidine-2-carboxylic acid | 407.9 |
| 119 | (2S,5R)-5-(2-chlorophenyl)-1-(4-(6-(dimethylamino)pyridin-3-yl)benzoyl)pyrrolidine-2-carboxylic acid | 450.9 |
| 120 | (2S,5R)-5-(2-chlorophenyl)-1-(4-(pyridin-4-yl)benzoyl)pyrrolidine-2-carboxylic acid | 407.9 |
| 121 | (2S,5R)-5-(2-chlorophenyl)-1-(4-(6-methylpyridin-3-yl)benzoyl)pyrrolidine-2-carboxylic acid | 421.9 |
| 122 | (2S,5R)-5-(2-chlorophenyl)-1-(4-(2-methoxypyridin-3-yl)benzoyl)pyrrolidine-2-carboxylic acid | 437.9 |
| 123 | (2S,5R)-5-(2-chlorophenyl)-1-(4'-methoxy-[1,1'-biphenyl]-4-carbonyl)pyrrolidine-2-carboxylic acid | 436.9 |
| 124 | (2S,5R)-5-(2-chlorophenyl)-1-(4'-cyano-[1,1'-biphenyl]-4-carbonyl)pyrrolidine-2-carboxylic acid | 431.9 |
| 125 | (2S,5R)-5-(2-chlorophenyl)-1-(4-(4-methoxypyridin-3-yl)benzoyl)pyrrolidine-2-carboxylic acid | 437.9 |
| 126 | (2S,5R)-1-(4'-chloro-[1,1'-biphenyl]-4-carbonyl)-5-(2-chlorophenyl)pyrrolidine-2-carboxylic acid | 441.3 |
| 127 | (2S,5R)-1-(3'-chloro-[1,1'-biphenyl]-4-carbonyl)-5-(2-chlorophenyl)pyrrolidine-2-carboxylic acid | 441.3 |
| 128 | (2S,5R)-1-(2'-chloro-[1,1'-biphenyl]-4-carbonyl)-5-(2-chlorophenyl)pyrrolidine-2-carboxylic acid | 441.3 |
| 129 | (2S,5R)-5-(2-chlorophenyl)-1-(4'-(methylsulfonamido)-[1,1'-biphenyl]-4-carbonyl)pyrrolidine-2-carboxylic acid | 500.0 |
| 130 | (2S,5R)-5-(2-chlorophenyl)-1-(3'-(methylsulfonamido)-[1,1'-biphenyl]-4-carbonyl)pyrrolidine-2-carboxylic acid | 500.0 |
| 131 | (2S,5R)-5-(2-chlorophenyl)-1-(2'-(methylsulfonamido)-[1,1'-biphenyl]-4-carbonyl)pyrrolidine-2-carboxylic acid | 500.0 |
| 132 | (2S,5R)-5-(2-chlorophenyl)-1-(4-(naphthalen-2-yl)benzoyl)pyrrolidine-2-carboxylic acid | 456.9 |
| 133 | (2S,5R)-5-(2-chlorophenyl)-1-(3',5'-difluoro-[1,1'-biphenyl]-4-carbonyl)pyrrolidine-2-carboxylic acid | 442.9 |
| 134 | (2S,5R)-5-(2-chlorophenyl)-1-(2'-hydroxy-[1,1'-biphenyl]-4-carbonyl)pyrrolidine-2-carboxylic acid | 422.9 |
| 135 | (2S,5R)-5-(2-chlorophenyl)-1-(2'-(trifluoromethoxy)-[1,1'-biphenyl]-4-carbonyl)pyrrolidine-2-carboxylic acid | 490.9 |
| 136 | (2S,5R)-1-(2'-(benzyloxy)-[1,1'-biphenyl]-4-carbonyl)-5-(2-chlorophenyl)pyrrolidine-2-carboxylic acid | 513.0 |
| 137 | (2S,5R)-5-(2-chlorophenyl)-1-(2'-phenoxy-[1,1'-biphenyl]-4-carbonyl)pyrrolidine-2-carboxylic acid | 499.0 |
| 138 | (2S,5R)-5-(2-chlorophenyl)-1-(2'-isopropoxy-[1,1'-biphenyl]-4-carbonyl)pyrrolidine-2-carboxylic acid | 465.0 |
| 139 | (2S,5R)-5-(2-chlorophenyl)-1-(2'-isobutoxy-[1,1'-biphenyl]-4-carbonyl)pyrrolidine-2-carboxylic acid | 479.0 |
| 140 | (2S,5R)-5-(2-chlorophenyl)-1-(2'-(cyclopropylmethoxy)-[1,1'-biphenyl]-4-carbonyl)pyrrolidine-2-carboxylic acid | 477.0 |
| 141 | (2S,5R)-5-(2-chlorophenyl)-1-(2'-((4-fluorobenzyl)oxy)-[1,1'-biphenyl]-4-carbonyl)pyrrolidine-2-carboxylic acid | 531.0 |
| 142 | (2S,5R)-5-(2-chlorophenyl)-1-(4-(6-chloropyridin-3-yl)benzoyl)pyrrolidine-2-carboxylic acid | 442.3 |
| 143 | (2S,5R)-5-(2-chlorophenyl)-1-(4-(6-fluoropyridin-3-yl)benzoyl)pyrrolidine-2-carboxylic acid | 425.9 |
| 144 | (2S,5R)-5-(2-chlorophenyl)-1-(4-(2-chloropyridin-4-yl)benzoyl)pyrrolidine-2-carboxylic acid | 442.3 |
| 145 | (2S,5R)-1-(4-(2-chloro-3-fluoropyridin-4-yl)benzoyl)-5-(2-chlorophenyl)pyrrolidine-2-carboxylic acid | 460.3 |
| 146 | (2S,5R)-5-(2-chlorophenyl)-1-(4-(2-chloropyridin-3-yl)benzoyl)pyrrolidine-2-carboxylic acid | 442.3 |
| 147 | (2S,5R)-1-(4-(6-(benzyloxy)pyridin-3-yl)benzoyl)-5-(2-chlorophenyl)pyrrolidine-2-carboxylic acid | 514.0 |
| 148 | (2S,5R)-1-(4-(1H-pyrazol-4-yl)benzoyl)-5-(2-chlorophenyl)pyrrolidine-2-carboxylic acid | 396.8 |
| 149 | (2S,5R)-5-(2-chlorophenyl)-1-(4-(thiophen-3-yl)benzoyl)pyrrolidine-2-carboxylic acid | 412.9 |
| 150 | (2S,5R)-5-(2-chlorophenyl)-1-(4-cyclohexylbenzoyl)pyrrolidine-2-carboxylic acid | 412.9 |
| 151 | (2S,5R)-5-(2-chlorophenyl)-1-(4'-(methylsulfonyl)-[1,1'-biphenyl]-4-carbonyl)pyrrolidine-2-carboxylic acid | 485.0 |
| 152 | (2S,5R)-5-(2-chlorophenyl)-1-(9-oxo-9H-fluorene-2-carbonyl)pyrrolidine-2-carboxylic acid | 432.9 |
| 153 | (2S,5R)-5-(2-chlorophenyl)-1-(2'-(methylsulfonyl)-[1,1'-biphenyl]-4-carbonyl)pyrrolidine-2-carboxylic acid | 485.0 |
| 154 | (2S,5R)-5-(2-chlorophenyl)-1-(4-(tetrahydro-2H-pyran-4-yl)benzoyl)pyrrolidine-2-carboxylic acid | 414.9 |
| 155 | (2S,5R)-5-(2-chlorophenyl)-1-(9-methyl-9H-carbazole-2-carbonyl)pyrrolidine-2-carboxylic acid | 433.9 |
| 156 | (2S,5R)-5-(2-chlorophenyl)-1-(4-phenoxybenzoyl)pyrrolidine-2-carboxylic acid | 422.9 |
| 157 | (2S,5R)-1-(4-benzylbenzoyl)-5-(2-chlorophenyl)pyrrolidine-2-carboxylic acid | 420.9 |
| 158 | (2S,5R)-1-(4-benzoylbenzoyl)-5-(2-chlorophenyl)pyrrolidine-2-carboxylic acid | 434.9 |

TABLE 1-continued

| Compound n° | Compound name | (M + H)+ |
|---|---|---|
| 159 | (2S,5R)-5-(2-chlorophenyl)-1-(4-(pyrimidin-2-yl)benzoyl)pyrrolidine-2-carboxylic acid | 408.9 |
| 160 | (2S,5R)-5-(2-chlorophenyl)-1-(4-(4,6-dimethoxypyrimidin-2-yl)benzoyl)pyrrolidine-2-carboxylic acid | 468.9 |
| 161 | (2S,5R)-5-(2-chlorophenyl)-1-(4-(2,4-dimethoxypyrimidin-5-yl)benzoyl)pyrrolidine-2-carboxylic acid | 468.9 |
| 162 | (2S,5R)-5-(2-chlorophenyl)-1-(4-(2-methoxypyrimidin-5-yl)benzoyl)pyrrolidine-2-carboxylic acid | 438.9 |
| 163 | (2S,5R)-5-(2-chlorophenyl)-1-(4-(2-(dimethylamino)pyrimidin-5-yl)benzoyl)pyrrolidine-2-carboxylic acid | 451.9 |
| 164 | (2S,5R)-5-(2-chlorophenyl)-1-(4-(2-morpholinopyrimidin-5-yl)benzoyl)pyrrolidine-2-carboxylic acid | 494.0 |
| 165 | (2S,5R)-5-(2-chlorophenyl)-1-(4-(2-(piperidin-1-yl)pyrimidin-5-yl)benzoyl)pyrrolidine-2-carboxylic acid | 492.0 |
| 168 | (2S,5R)-5-(2-chlorophenyl)-1-(cyclohexanecarbonyl)pyrrolidine-2-carboxylic acid | 336.8 |
| 169 | (2S,5R)-5-(2-chlorophenyl)-1-(4-methylpentanoyl)pyrrolidine-2-carboxylic acid | 324.8 |
| 172 | (2S,5R)-5-(2-chlorophenyl)-1-(4-(4-methylpiperidin-1-yl)-3-nitrobenzoyl)pyrrolidine-2-carboxylic acid | 472.9 |
| 173 | (2S,5R)-5-(2-chlorophenyl)-1-(4-(2-oxopiperidin-1-yl)benzoyl)pyrrolidine-2-carboxylic acid | 427.9 |
| 174 | (2S,5R)-5-(2-chlorophenyl)-1-(3-methyl-4-morpholinobenzoyl)pyrrolidine-2-carboxylic acid | 429.9 |
| 175 | (2S,5R)-5-(2-chlorophenyl)-1-(4-(piperidin-1-yl)benzoyl)pyrrolidine-2-carboxylic acid | 413.9 |
| 176 | (2S,5R)-5-(2-chlorophenyl)-1-(4-morpholinobenzoyl)pyrrolidine-2-carboxylic acid | 415.9 |
| 177 | (2S,5R)-5-(2-chlorophenyl)-1-(1-(2-cyanophenyl)piperidine-4-carbonyl)pyrrolidine-2-carboxylic acid | 438.9 |
| 178 | (2S,5R)-5-(2-chlorophenyl)-1-(4-(4-chlorophenyl)cyclohexanecarbonyl)pyrrolidine-2-carboxylic acid | 447.4 |
| 179 | (2S,5R)-5-(2-chlorophenyl)-1-(4-phenylcyclohexanecarbonyl)pyrrolidine-2-carboxylic acid | 412.9 |
| 183 | ((2R,5S)-2-(2-chlorophenyl)-5-(1H-tetrazol-5-yl)pyrrolidin-1-yl)(2'-methoxy-[1,1'-biphenyl]-4-yl)methanone | 460.9 |
| 184 | (2R,5S)-5-(2-chlorophenyl)-1-(2'-methoxy-[1,1'-biphenyl]-4-carbonyl)pyrrolidine-2-carboxylic acid | 436.9 |
| 189 | (2S,5R)-5-(2-chlorophenyl)-1-(6-(2-fluorophenyl)nicotinoyl)pyrrolidine-2-carboxylic acid | 425.9 |
| 191 | (2S,5R)-5-(2-chlorophenyl)-1-(5-methoxy-6-phenylnicotinoyl)pyrrolidine-2-carboxylic acid | 437.9 |
| 192 | (2S,5R)-5-(2-chlorophenyl)-1-(4-(2-methoxyphenoxy)benzoyl)pyrrolidine-2-carboxylic acid | 452.9 |
| 193 | (2S,5R)-5-(2-chlorophenyl)-1-(4-(3-methoxypyridin-4-yl)benzoyl)pyrrolidine-2-carboxylic acid | 437.9 |
| 194 | (2S)-5-(2-chlorophenyl)-1-(2'-methoxy-[1,1'-biphenyl]-4-carbonyl)-4,4-dimethylpyrrolidine-2-carboxylic acid | 465.0 |
| 195 | (2S)-5-(2-chlorophenyl)-1-(2'-methoxy-[1,1'-biphenyl]-4-carbonyl)-4-methylpyrrolidine-2-carboxylic acid | 450.9 |
| 196 | (2S,5R)-5-(2-chlorophenyl)-1-(2-methoxy-[1,1'-biphenyl]-4-carbonyl)pyrrolidine-2-carboxylic acid | 436.9 |
| 197 | (2S,5R)-5-(2-chlorophenyl)-1-(2'-cyano-[1,1'-biphenyl]-4-carbonyl)pyrrolidine-2-carboxylic acid | 431.9 |
| 198 | (2S,5R)-5-(2-chlorophenyl)-1-(2',6'-dimethoxy-[1,1'-biphenyl]-4-carbonyl)pyrrolidine-2-carboxylic acid | 466.9 |
| 199 | (2S,5R)-5-(2-chlorophenyl)-1-(2',4'-dichloro-[1,1'-biphenyl]-4-carbonyl)pyrrolidine-2-carboxylic acid | 475.8 |
| 200 | (2S,5R)-5-(2-chlorophenyl)-1-(2'-(trifluoromethyl)-[1,1'-biphenyl]-4-carbonyl)pyrrolidine-2-carboxylic acid | 474.9 |
| 201 | (2S,5R)-5-(2-chlorophenyl)-1-(2,2'-dimethoxy-[1,1'-biphenyl]-4-carbonyl)pyrrolidine-2-carboxylic acid | 466.9 |
| 202 | (2S,5R)-1-(4'-chloro-2'-methoxy-[1,1'-biphenyl]-4-carbonyl)-5-(2-chlorophenyl)pyrrolidine-2-carboxylic acid | 471.3 |
| 203 | (2S,5R)-5-(2-chlorophenyl)-1-(4-(4-methoxypyrimidin-5-yl)benzoyl)pyrrolidine-2-carboxylic acid | 438.9 |
| 204 | (2S,5R)-5-(2-chlorophenyl)-1-(2',4'-dimethoxy-[1,1'-biphenyl]-4-carbonyl)pyrrolidine-2-carboxylic acid | 466.9 |
| 205 | (2S,5R)-1-([1,1'-biphenyl]-4-carbonyl)-5-(pyridin-3-yl)pyrrolidine-2-carboxylic acid | 373.4 |
| 206 | (2R,5R)-5-(2-chlorophenyl)-1-(2'-methoxy-[1,1'-biphenyl]-4-carbonyl)pyrrolidine-2-carboxylic acid | 436.9 |
| 207 | (2S,5R)-5-(2-chlorophenyl)-1-(1-phenyl-1H-benzo[d]imidazole-5-carbonyl)pyrrolidine-2-carboxylic acid | 446.9 |
| 208 | (2S,5R)-methyl 5-(2-chlorophenyl)-1-(2'-methoxy-[1,1'-biphenyl]-4-carbonyl)pyrrolidine-2-carboxylate | 450.9 |
| 211 | (2S,4S,5R)-5-(2-chlorophenyl)-4-(hydroxymethyl)-1-(2'-methoxy-[1,1'-biphenyl]-4-carbonyl)pyrrolidine-2-carboxylic acid | 466.9 |
| 217 | (2S,4S,5S)-5-(2-chlorophenyl)-1-(2'-methoxy-[1,1'-biphenyl]-4-carbonyl)-4-(phenylsulfonyl)pyrrolidine-2-carboxylic acid | 577.1 |
| 220 | (2S,5R)-5-(2-chlorophenyl)-4-cyano-1-(2'-methoxy-[1,1'-biphenyl]-4-carbonyl)pyrrolidine-2-carboxylic acid | 461.9 |
| 221 | (2S,3R,5R)-5-(2-chlorophenyl)-3-cyano-1-(2'-methoxy-[1,1'-biphenyl]-4-carbonyl)pyrrolidine-2-carboxylic acid | 461.9 |
| 224 | (2S,5R)-1-(4-chloro-[1,1'-biphenyl]-4-carbonyl)-5-(2-chlorophenyl)pyrrolidine-2-carboxylic acid | 441.3 |
| 225 | (2S,5R)-1-(2'-chloro-2-methoxy-[1,1'-biphenyl]-4-carbonyl)-5-(2-chlorophenyl)pyrrolidine-2-carboxylic acid | 471.3 |
| 226 | (2S,5R)-5-(2-chlorophenyl)-1-(2'-(2-methoxyethoxy)-[1,1'-biphenyl]-4-carbonyl)pyrrolidine-2-carboxylic acid | 481.0 |
| 227 | (2S,5R)-5-(2-chlorophenyl)-1-(4-(2-methylthiophen-3-yl)benzoyl)pyrrolidine-2-carboxylic acid | 426.9 |
| 228 | (2S,5R)-5-(2-chlorophenyl)-1-(2',6'-dichloro-[1,1'-biphenyl]-4-carbonyl)pyrrolidine-2-carboxylic acid | 475.8 |
| 229 | (2S,5R)-1-(2'-chloro-4'-methoxy-[1,1'-biphenyl]-4-carbonyl)-5-(2-chlorophenyl)pyrrolidine-2-carboxylic acid | 471.3 |
| 230 | (2S,5R)-5-(2-chlorophenyl)-1-(3-methoxy-4-(pyrimidin-5-yl)benzoyl)pyrrolidine-2-carboxylic acid | 438.9 |
| 231 | (2S,5R)-1-(2'-carbamimidoyl-[1,1'-biphenyl]-4-carbonyl)-5-(2-chlorophenyl)pyrrolidine-2-carboxylic acid | 448.9 |
| 232 | (2S,5R)-5-(2-fluorophenyl)-1-(2'-methoxy-[1,1'-biphenyl]-4-carbonyl)pyrrolidine-2-carboxylic acid | 420.4 |
| 233 | (2S,5R)-1-(2'-methoxy-[1,1'-biphenyl]-4-carbonyl)-5-(o-tolyl)pyrrolidine-2-carboxylic acid | 416.5 |
| 234 | (2S,5R)-1-(2'-methoxy-[1,1'-biphenyl]-4-carbonyl)-5-(2-methoxyphenyl)pyrrolidine-2-carboxylic acid | 432.5 |
| 235 | (2S,5R)-5-(2-chlorophenyl)-1-(2'-(methoxymethyl)-[1,1'-biphenyl]-4-carbonyl)pyrrolidine-2-carboxylic acid | 450.9 |
| 236 | (2S,5R)-5-(2-chlorophenyl)-1-(4-(2,6-dimethoxypyridin-3-yl)benzoyl)pyrrolidine-2-carboxylic acid | 467.9 |
| 237 | (2S,5R)-5-(2-chlorophenyl)-1-(3-methoxy-4-(2-methoxypyrimidin-5-yl)benzoyl)pyrrolidine-2-carboxylic acid | 468.9 |
| 238 | (2S,5R)-5-(2-chlorophenyl)-1-(4-(5-methoxypyrazin-2-yl)benzoyl)pyrrolidine-2-carboxylic acid | 438.9 |

TABLE 1-continued

| Compound n° | Compound name | (M + H)+ |
|---|---|---|
| 239 | (2S,5R)-5-(2-chlorophenyl)-1-(4-(2-(2-methoxyethoxy)pyridin-3-yl)benzoyl)pyrrolidine-2-carboxylic acid | 481.9 |
| 240 | (2S,5R)-5-(2-chlorophenyl)-1-(4-(3-methoxypyrazin-2-yl)benzoyl)pyrrolidine-2-carboxylic acid | 438.9 |
| 241 | (2S,5R)-1-(4-(2-chloro-4-(dimethylamino)pyrimidin-5-yl)benzoyl)-5-(2-chlorophenyl)pyrrolidine-2-carboxylic acid | 486.4 |
| 242 | (2S,5R)-5-(2-chlorophenyl)-1-(4-(2,6-dimethoxypyrimidin-4-yl)benzoyl)pyrrolidine-2-carboxylic acid | 468.9 |
| 243 | (2S,5R)-5-(2-chlorophenyl)-1-(2'-(dimethylamino)-[1,1'-biphenyl]-4-carbonyl)pyrrolidine-2-carboxylic acid | 449.9 |
| 244 | (2S,5R)-5-(2-chlorophenyl)-1-(4-(2-methoxypyrimidin-4-yl)benzoyl)pyrrolidine-2-carboxylic acid | 438.9 |
| 245 | (2S,5R)-5-(2-chlorophenyl)-1-(3-methoxy-4-(2-methoxypyrimidin-4-yl)benzoyl)pyrrolidine-2-carboxylic acid | 468.9 |
| 246 | (2S,5R)-5-(2-fluorophenyl)-1-(4-(2-methoxypyridin-3-yl)benzoyl)pyrrolidine-2-carboxylic acid | 421.4 |
| 247 | (2S,5R)-1-(4-(2,4-dimethoxypyrimidin-5-yl)benzoyl)-5-(2-fluorophenyl)pyrrolidine-2-carboxylic acid | 452.4 |
| 248 | (2S,5R)-5-(2-chlorophenyl)-1-(2-methyl-[1,1'-biphenyl]-4-carbonyl)pyrrolidine-2-carboxylic acid | 420.9 |
| 249 | (2S,5R)-5-(2-chlorophenyl)-1-(3-methoxy-[1,1'-biphenyl]-4-carbonyl)pyrrolidine-2-carboxylic acid | 436.9 |
| 250 | (2S,5R)-5-(2-chlorophenyl)-1-(2'-(2-oxopyrrolidin-1-yl)-[1,1'-biphenyl]-4-carbonyl)pyrrolidine-2-carboxylic acid | 490.0 |
| 251 | (2S,5R)-5-(2-chlorophenyl)-1-(5-phenylpyrazine-2-carbonyl)pyrrolidine-2-carboxylic acid | 408.9 |
| 252 | (2S,5R)-5-(2-chlorophenyl)-1-(5-methoxy-6-(2-methoxyphenyl)nicotinoyl)pyrrolidine-2-carboxylic acid | 467.9 |
| 253 | (2S,5R)-5-(2-chlorophenyl)-1-(4-(5-methoxypyrimidin-4-yl)benzoyl)pyrrolidine-2-carboxylic acid | 438.9 |
| 254 | (2S,5R)-5-(2-chlorophenyl)-1-(4-(pyridazin-4-yl)benzoyl)pyrrolidine-2-carboxylic acid | 408.9 |
| 255 | (2S,5R)-1-(4-(1H-1,2,3-triazol-1-yl)benzoyl)-5-(2-chlorophenyl)pyrrolidine-2-carboxylic acid | 397.8 |
| 256 | (2S,5R)-5-(2-chlorophenyl)-1-(4-(4-(p-tolyl)-1H-1,2,3-triazol-1-yl)benzoyl)pyrrolidine-2-carboxylic acid | 488.0 |
| 257 | (2S,5R)-5-(2-chlorophenyl)-1-(1-(2-methoxyphenyl)piperidine-4-carbonyl)pyrrolidine-2-carboxylic acid | 443.9 |
| 258 | (2S,5R)-5-(2-chlorophenyl)-1-(4-(2-methoxyphenyl)piperazine-1-carbonyl)pyrrolidine-2-carboxylic acid | 444.9 |
| 259 | (2S,5R)-5-(2-chlorophenyl)-1-(1-(4-methoxypyrimidin-5-yl)piperidine-4-carbonyl)pyrrolidine-2-carboxylic acid | 445.9 |
| 260 | (2S,5R)-5-(2-chlorophenyl)-1-(4-(4-methoxypyrimidin-5-yl)piperazine-1-carbonyl)pyrrolidine-2-carboxylic acid | 446.9 |
| 261 | (2S,5R)-5-(2-chlorophenyl)-1-(3-methoxy-4-(4-methylpiperidin-1-yl)benzoyl)pyrrolidine-2-carboxylic acid | 458.0 |
| 262 | (2S,5R)-5-(2-chlorophenyl)-1-(3-methoxy-4-(1-methylpiperidin-4-yl)benzoyl)pyrrolidine-2-carboxylic acid | 458.0 |
| 263 | (2S,5R)-5-(2-chlorophenyl)-1-(4-cyano-[1,1'-biphenyl]-4-carbonyl)pyrrolidine-2-carboxylic acid | 431.9 |
| 264 | (2S,5R)-5-(2-chlorophenyl)-1-(2-isobutoxy-[1,1'-biphenyl]-4-carbonyl)pyrrolidine-2-carboxylic acid | 479.0 |
| 265 | (2S,5R)-5-(2-chlorophenyl)-1-(4-(2,4-dichloropyrimidin-5-yl)benzoyl)pyrrolidine-2-carboxylic acid | 477.7 |
| 266 | (2S,5R)-5-(2-chlorophenyl)-1-(4-(2,4-dimethoxypyrimidin-5-yl)-3-methoxybenzoyl)pyrrolidine-2-carboxylic acid | 498.9 |
| 267 | (2S,5R)-1-(4-(2-chloro-4-methoxypyrimidin-5-yl)benzoyl)-5-(2-chlorophenyl)pyrrolidine-2-carboxylic acid | 473.3 |
| 268 | (2S,3S,5S)-5-(2-chlorophenyl)-1-(2'-methoxy-[1,1'-biphenyl]-4-carbonyl)-3-methylpyrrolidine-2-carboxylic acid | 450.9 |
| 269 | (2S,5R)-1-(4-(2,6-dimethoxypyridin-3-yl)benzoyl)-5-(2-fluorophenyl)pyrrolidine-2-carboxylic acid | 451.5 |
| 270 | (2S,5R)-1-(2'-(2-amino-2-oxoethoxy)-[1,1'-biphenyl]-4-carbonyl)-5-(2-chlorophenyl)pyrrolidine-2-carboxylic acid | 479.9 |
| 271 | (2S,5R)-5-(2-chlorophenyl)-1-(2-(cyclopropylmethoxy)-[1,1'-biphenyl]-4-carbonyl)pyrrolidine-2-carboxylic acid | 477.0 |
| 272 | (2S,5R)-1-(2'-methoxy-[1,1'-biphenyl]-4-carbonyl)-5-phenylpyrrolidine-2-carboxylic acid | 402.5 |
| 273 | (2S,5R)-5-(3-chlorophenyl)-1-(2'-methoxy-[1,1'-biphenyl]-4-carbonyl)pyrrolidine-2-carboxylic acid | 436.9 |
| 274 | (2S,5R)-5-(4-chlorophenyl)-1-(2'-methoxy-[1,1'-biphenyl]-4-carbonyl)pyrrolidine-2-carboxylic acid | 436.9 |
| 275 | (2S,5R)-5-(3-fluorophenyl)-1-(2'-methoxy-[1,1'-biphenyl]-4-carbonyl)pyrrolidine-2-carboxylic acid | 420.4 |
| 276 | (2S,5R)-5-(4-fluorophenyl)-1-(2'-methoxy-[1,1'-biphenyl]-4-carbonyl)pyrrolidine-2-carboxylic acid | 420.4 |
| 278 | (2S,5R)-4-acetyl-5-(2-chlorophenyl)-1-(2'-methoxy-[1,1'-biphenyl]-4-carbonyl)pyrrolidine-2-carboxylic acid | 478.9 |
| 279 | (2S,4S,5R)-5-(2-chlorophenyl)-1-(2'-methoxy-[1,1'-biphenyl]-4-carbonyl)-4-(methoxymethyl)pyrrolidine-2-carboxylic acid | 481.0 |
| 280 | (2S,5R)-5-(2-chlorophenyl)-1-(4-(2-methoxypyrimidin-4-yl)benzoyl)pyrrolidine-2-carboxylic acid | 438.9 |
| 281 | (2S,5R)-5-cyclohexyl-1-(2'-methoxy-[1,1'-biphenyl]-4-carbonyl)pyrrolidine-2-carboxylic acid | 408.5 |
| 283 | (2S,5R)-1-(4-(2-chloro-4-methoxypyrimidin-5-yl)benzoyl)-5-(2-chlorophenyl)pyrrolidine-2-carboxylic acid | 473.3 |
| 284 | (2S,5R)-5-(2-chlorophenyl)-1-(4-(3-methoxypyridin-2-yl)benzoyl)pyrrolidine-2-carboxylic acid | 437.9 |
| 285 | (2R,5R)-5-(2-fluorophenyl)-1-(2'-methoxy-[1,1'-biphenyl]-4-carbonyl)pyrrolidine-2-carboxylic acid | 420.4 |
| 286 | (2S,5S)-5-(2-fluorophenyl)-1-(2'-methoxy-[1,1'-biphenyl]-4-carbonyl)pyrrolidine-2-carboxylic acid | 420.4 |
| 287 | (2R,5S)-5-(2-fluorophenyl)-1-(2'-methoxy-[1,1'-biphenyl]-4-carbonyl)pyrrolidine-2-carboxylic acid | 420.4 |
| 288 | (2S,5R)-5-(2-chlorophenyl)-1-(2-(trifluoromethyl)-[1,1'-biphenyl]-4-carbonyl)pyrrolidine-2-carboxylic acid | 474.9 |
| 289 | (2S,5R)-5-(2-chlorophenyl)-1-(2',4'-difluoro-[1,1'-biphenyl]-4-carbonyl)pyrrolidine-2-carboxylic acid | 442.9 |
| 290 | (2S,5R)-5-(2-chlorophenyl)-1-(2-methyl-[1,1'-biphenyl]-4-carbonyl)pyrrolidine-2-carboxylic acid | 420.9 |
| 291 | (2S,5R)-5-(2,6-difluorophenyl)-1-(2'-methoxy-[1,1'-biphenyl]-4-carbonyl)pyrrolidine-2-carboxylic acid | 438.4 |
| 292 | (2S,5R)-5-(2,4-difluorophenyl)-1-(2'-methoxy-[1,1'-biphenyl]-4-carbonyl)pyrrolidine-2-carboxylic acid | 438.4 |
| 293 | (2S,5R)-5-(2,4-dichlorophenyl)-1-(2'-methoxy-[1,1'-biphenyl]-4-carbonyl)pyrrolidine-2-carboxylic acid | 471.3 |
| 294 | (2S,5R)-5-isobutyl-1-(2'-methoxy-[1,1'-biphenyl]-4-carbonyl)pyrrolidine-2-carboxylic acid | 382.5 |
| 295 | (2S,5R)-5-isopropyl-1-(2'-methoxy-[1,1'-biphenyl]-4-carbonyl)pyrrolidine-2-carboxylic acid | 368.4 |
| 296 | (2S,5R)-1-(3-chloro-4-(pyrimidin-4-yl)benzoyl)-5-(2-chlorophenyl)pyrrolidine-2-carboxylic acid | 443.3 |
| 297 | (2S,5R)-5-(2-chlorophenyl)-1-(2-fluoro-[1,1'-biphenyl]-4-carbonyl)pyrrolidine-2-carboxylic acid | 424.9 |
| 298 | (2S,5R)-5-(2-chlorophenyl)-1-(2'-fluoro-4'-methoxy-[1,1'-biphenyl]-4-carbonyl)pyrrolidine-2-carboxylic acid | 454.9 |
| 299 | (2S,5R)-5-(2-chlorophenyl)-1-(4'-fluoro-2'-methoxy-[1,1'-biphenyl]-4-carbonyl)pyrrolidine-2-carboxylic acid | 454.9 |

TABLE 1-continued

| Compound n° | Compound name | (M + H)+ |
|---|---|---|
| 300 | (2S,5R)-5-(2-chlorophenyl)-1-(4-(6-ethoxypyridin-3-yl)benzoyl)pyrrolidine-2-carboxylic acid | 451.9 |
| 301 | (2S,5R)-5-(2-chlorophenyl)-1-(4-(6-isopropoxypyridin-3-yl)benzoyl)pyrrolidine-2-carboxylic acid | 465.9 |
| 302 | (2S,5R)-5-(2-chlorophenyl)-1-(4-(6-methoxy-2-methylpyridin-3-yl)benzoyl)pyrrolidine-2-carboxylic acid | 451.9 |
| 303 | (2S,5R)-1-(3-chloro-4-(2-methoxypyrimidin-4-yl)benzoyl)-5-(2-chlorophenyl)pyrrolidine-2-carboxylic acid | 473.3 |
| 304 | (2S,5R)-1-(3-chloro-4-(pyrimidin-5-yl)benzoyl)-5-(2-chlorophenyl)pyrrolidine-2-carboxylic acid | 443.3 |
| 305 | (2S,5R)-5-(2-chlorophenyl)-4-cyano-1-(2'-methoxy-[1,1'-biphenyl]-4-carbonyl)-3-methylpyrrolidine-2-carboxylic acid | 475.9 |
| 306 | (2S,4S,5R)-5-(2-chlorophenyl)-4-cyano-1-(2'-methoxy-[1,1'-biphenyl]-4-carbonyl)-4-methylpyrrolidine-2-carboxylic acid | 475.9 |
| 307 | (2S,5R)-5-(2-chlorophenyl)-1-(2',3'-dimethoxy-[1,1'-biphenyl]-4-carbonyl)pyrrolidine-2-carboxylic acid | 466.9 |
| 308 | (2S,5R)-5-(2-chlorophenyl)-1-(3',4'-dimethoxy-[1,1'-biphenyl]-4-carbonyl)pyrrolidine-2-carboxylic acid | 466.9 |
| 309 | (2S,5R)-5-(2-chlorophenyl)-1-(2',3',4'-trimethoxy-[1,1'-biphenyl]-4-carbonyl)pyrrolidine-2-carboxylic acid | 497.0 |
| 310 | (2S,5R)-5-(2-chlorophenyl)-1-(2',3',6'-trimethoxy-[1,1'-biphenyl]-4-carbonyl)pyrrolidine-2-carboxylic acid | 497.0 |
| 311 | (2S,5R)-5-(2-chlorophenyl)-1-(3',5'-dimethoxy-[1,1'-biphenyl]-4-carbonyl)pyrrolidine-2-carboxylic acid | 466.9 |
| 312 | (2S,5R)-5-(2-chlorophenyl)-1-(2',5'-dimethoxy-[1,1'-biphenyl]-4-carbonyl)pyrrolidine-2-carboxylic acid | 466.9 |
| 313 | (2S,5R)-5-(2-chlorophenyl)-1-(2'-isopropyl-[1,1'-biphenyl]-4-carbonyl)pyrrolidine-2-carboxylic acid | 449.0 |
| 314 | (2S,5R)-1-(2,2'-dimethoxy-[1,1'-biphenyl]-4-carbonyl)-5-(2-fluorophenyl)pyrrolidine-2-carboxylic acid | 450.5 |
| 315 | (2S,5R)-1-(2-fluoro-2'-methoxy-[1,1'-biphenyl]-4-carbonyl)-5-(2-fluorophenyl)pyrrolidine-2-carboxylic acid | 438.4 |
| 316 | (2S,5R)-5-(2-chlorophenyl)-1-(2-fluoro-2'-methoxy-[1,1'-biphenyl]-4-carbonyl)pyrrolidine-2-carboxylic acid | 454.9 |
| 318 | (2S,5R)-5-cyclopentyl-1-(2'-methoxy-[1,1'-biphenyl]-4-carbonyl)pyrrolidine-2-carboxylic acid | 394.5 |
| 319 | (2S,5R)-5-(2-chlorophenyl)-1-(2'-ethyl-[1,1'-biphenyl]-4-carbonyl)pyrrolidine-2-carboxylic acid | 434.9 |
| 320 | (2S,5R)-5-(2-chlorophenyl)-1-(4-(2,6-dimethylpyridin-3-yl)benzoyl)pyrrolidine-2-carboxylic acid | 435.9 |
| 321 | (2S,5R)-1-(4-(2,4-bis(benzyloxy)pyrimidin-5-yl)benzoyl)-5-(2-chlorophenyl)pyrrolidine-2-carboxylic acid | 621.1 |
| 322 | (2S,5R)-1-([1,1':4',1''-terphenyl]-4-carbonyl)-5-(2-chlorophenyl)pyrrolidine-2-carboxylic acid | 483.0 |
| 323 | (2S,5R)-5-(2-chlorophenyl)-1-(4'-propyl-[1,1'-biphenyl]-4-carbonyl)pyrrolidine-2-carboxylic acid | 449.0 |
| 324 | (2S,5R)-1-(4'-(tert-butyl)-[1,1'-biphenyl]-4-carbonyl)-5-(2-chlorophenyl)pyrrolidine-2-carboxylic acid | 463.0 |
| 325 | (2S,5R)-1-(3-chloro-4-(2,4-dimethoxypyrimidin-5-yl)benzoyl)-5-(2-chlorophenyl)pyrrolidine-2-carboxylic acid | 503.3 |
| 326 | (2S,5R)-5-(2-chlorophenyl)-1-(5-(2-methoxyphenyl)pyrazine-2-carbonyl)pyrrolidine-2-carboxylic acid | 438.9 |
| 327 | (2S,5R)-5-(2-chlorophenyl)-1-(3-methoxy-4-(4-methoxypyridin-3-yl)benzoyl)pyrrolidine-2-carboxylic acid | 467.9 |
| 328 | (2S,5R)-5-(2-chlorophenyl)-1-(3-methoxy-4-(6-methoxypyridin-3-yl)benzoyl)pyrrolidine-2-carboxylic acid | 467.9 |
| 329 | (2S,5R)-1-(3-chloro-4-(2-methoxypyrimidin-5-yl)benzoyl)-5-(2-chlorophenyl)pyrrolidine-2-carboxylic acid | 473.3 |
| 330 | (2S,5R)-1-(3-chloro-4-(6-methoxypyridin-3-yl)benzoyl)-5-(2-chlorophenyl)pyrrolidine-2-carboxylic acid | 472.3 |
| 331 | (2S,5R)-5-(2-chlorophenyl)-1-(1-(4-(4-chlorophenyl)thiazol-2-yl)piperidine-4-carbonyl)pyrrolidine-2-carboxylic acid | 531.5 |
| 332 | (2S,5R)-5-(2-fluorophenyl)-1-(5-methoxy-6-(2-methoxyphenyl)nicotinoyl)pyrrolidine-2-carboxylic acid | 451.5 |
| 333 | (2S,5R)-1-(1-(benzo[d]oxazol-2-yl)piperidine-4-carbonyl)-5-(2-chlorophenyl)pyrrolidine-2-carboxylic acid | 454.9 |
| 334 | (2S,5R)-5-(2-chlorophenyl)-1-(3-methoxy-4-(pyrrolidin-1-yl)benzoyl)pyrrolidine-2-carboxylic acid | 429.9 |
| 335 | (2S,5R)-5-(2-chlorophenyl)-1-(5-methoxy-6-(2-methoxyphenyl)nicotinoyl)pyrrolidine-2-carboxylic acid | 467.9 |
| 336 | (2S,5R)-5-(2-chlorophenyl)-1-(1-(2-methoxyphenyl)piperidine-4-carbonyl)pyrrolidine-2-carboxylic acid | 443.9 |
| 337 | (2S,5R)-5-(2-chlorophenyl)-1-(4-(2,4-dimethoxypyrimidin-5-yl)-3-methoxybenzoyl)pyrrolidine-2-carboxylic acid | 498.9 |
| 338 | (2S,5R)-5-(2-bromophenyl)-1-(2'-methoxy-[1,1'-biphenyl]-4-carbonyl)pyrrolidine-2-carboxylic acid | 481.4 |
| 339 | (2S,5R)-5-(2-chlorophenyl)-1-(3'-cyano-[1,1'-biphenyl]-4-carbonyl)pyrrolidine-2-carboxylic acid | 431.9 |
| 340 | (2S,5R)-5-(2-chlorophenyl)-1-(3'-cyano-2'-methoxy-[1,1'-biphenyl]-4-carbonyl)pyrrolidine-2-carboxylic acid | 461.9 |
| 341 | (2S,5R)-5-(2-chlorophenyl)-1-(3'-cyano-2',4'-bis(2,2,2-trifluoroethoxy)-[1,1'-biphenyl]-4-carbonyl)pyrrolidine-2-carboxylic acid | 627.9 |
| 342 | (2S,5R)-1-(3'-amino-2'-methyl-[1,1'-biphenyl]-4-carbonyl)-5-(2-chlorophenyl)pyrrolidine-2-carboxylic acid | 435.9 |
| 343 | (2S,5R)-5-(2-chlorophenyl)-1-(2'-methyl-3'-(methylsulfonamido)-[1,1'-biphenyl]-4-carbonyl)pyrrolidine-2-carboxylic acid | 514.0 |
| 344 | (2S,5R)-1-(3'-acetamido-2'-methyl-[1,1'-biphenyl]-4-carbonyl)-5-(2-chlorophenyl)pyrrolidine-2-carboxylic acid | 478.0 |
| 345 | (2S,5R)-5-(2-chlorophenyl)-1-(5'-cyano-2'-methoxy-[1,1'-biphenyl]-4-carbonyl)pyrrolidine-2-carboxylic acid | 461.9 |
| 346 | (2S,5R)-5-(2-chlorophenyl)-1-(5'-cyano-2'-methyl-[1,1'-biphenyl]-4-carbonyl)pyrrolidine-2-carboxylic acid | 445.9 |
| 347 | (2S,5R)-5-(2-chlorophenyl)-1-(4-(4,6-dimethoxypyridin-3-yl)benzoyl)pyrrolidine-2-carboxylic acid | 467.9 |
| 348 | (2S,5R)-5-(2-chlorophenyl)-1-(4-(3,6-dimethoxypyridazin-4-yl)benzoyl)pyrrolidine-2-carboxylic acid | 468.9 |
| 349 | (2S,5S)-5-isopentyl-1-(2'-methoxy-[1,1'-biphenyl]-4-carbonyl)pyrrolidine-2-carboxylic acid | 396.5 |
| 350 | (2S,5R)-5-(2-chlorophenyl)-1-(2'-methoxy-4'-(methylsulfonamido)-[1,1'-biphenyl]-4-carbonyl)pyrrolidine-2-carboxylic acid | 530.0 |
| 351 | (2S,5R)-1-(4'-acetamido-2'-methoxy-[1,1'-biphenyl]-4-carbonyl)-5-(2-chlorophenyl)pyrrolidine-2-carboxylic acid | 494.0 |
| 352 | (2S,5R)-1-(3'-carbamimidoyl-[1,1'-biphenyl]-4-carbonyl)-5-(2-chlorophenyl)pyrrolidine-2-carboxylic acid | 448.9 |
| 353 | (2S,5R)-5-(2-chlorophenyl)-1-(3'-((E)—N'-hydroxycarbamimidoyl)-[1,1'-biphenyl]-4-carbonyl)pyrrolidine-2-carboxylic acid | 464.9 |
| 354 | (2S,5R)-5-(2-fluorophenyl)-1-(2'-methoxy-4'-(methylsulfonamido)-[1,1'-biphenyl]-4-carbonyl)pyrrolidine-2-carboxylic acid | 513.6 |

TABLE 1-continued

| Compound n° | Compound name | (M + H)+ |
|---|---|---|
| 355 | (2S,5R)-5-(2,4-difluorophenyl)-1-(4-(2,6-dimethoxypyridin-3-yl)benzoyl)pyrrolidine-2-carboxylic acid | 469.4 |
| 356 | (2S,5R)-5-(2-chlorophenyl)-1-(3-methoxy-4-(5-methoxypyridin-3-yl)benzoyl)pyrrolidine-2-carboxylic acid | 467.9 |
| 357 | (2S,5R)-1-(4'-amino-2'-methoxy-[1,1'-biphenyl]-4-carbonyl)-5-(2-chlorophenyl)pyrrolidine-2-carboxylic acid | 451.9 |
| 358 | (2S,5R)-5-(2-chlorophenyl)-1-(2',3,6'-trimethoxy-[2,3'-bipyridine]-5-carbonyl)pyrrolidine-2-carboxylic acid | 498.9 |
| 359 | (2S,5R)-1-(3'-carbamoyl-[1,1'-biphenyl]-4-carbonyl)-5-(2-chlorophenyl)pyrrolidine-2-carboxylic acid | 449.9 |
| 360 | (2S,5R)-5-(2-chlorophenyl)-1-(5'-cyano-2',3'-dimethoxy-[1,1'-biphenyl]-4-carbonyl)pyrrolidine-2-carboxylic acid | 491.9 |
| 361 | (2S,5R)-5-(2-chlorophenyl)-1-(2'-cyano-4',5'-dimethoxy-[1,1'-biphenyl]-4-carbonyl)pyrrolidine-2-carboxylic acid | 491.9 |
| 362 | (2S,5R)-5-(2-chlorophenyl)-1-(3',4',5'-trimethoxy-[1,1'-biphenyl]-4-carbonyl)pyrrolidine-2-carboxylic acid | 497.0 |
| 363 | (2S,5R)-5-(2-chlorophenyl)-1-(2'-(cyanomethyl)-4',5'-dimethoxy-[1,1'-biphenyl]-4-carbonyl)pyrrolidine-2-carboxylic acid | 506.0 |
| 364 | (2S,5R)-5-(2-chlorophenyl)-1-(3',4'-dicyano-[1,1'-biphenyl]-4-carbonyl)pyrrolidine-2-carboxylic acid | 456.9 |
| 365 | (2S,5R)-5-(2-chlorophenyl)-1-(5'-cyano-2'-fluoro-[1,1'-biphenyl]-4-carbonyl)pyrrolidine-2-carboxylic acid | 449.9 |
| 366 | (2S,5R)-5-(2-chlorophenyl)-1-(2-fluoro-3',4'-dimethoxy-[1,1'-biphenyl]-4-carbonyl)pyrrolidine-2-carboxylic acid | 484.9 |
| 367 | (2S,5R)-5-(2-chlorophenyl)-1-(4-(2,6-dimethoxypyridin-3-yl)-3-fluorobenzoyl)pyrrolidine-2-carboxylic acid | 485.9 |
| 368 | (2S,5R)-5-(2-chlorophenyl)-1-(3-fluoro-4-(6-methoxypyridin-3-yl)benzoyl)pyrrolidine-2-carboxylic acid | 455.9 |
| 369 | (2S,5R)-5-(2-chlorophenyl)-1-(1-(2-cyano-4-(trifluoromethyl)phenyl)piperidine-4-carbonyl)pyrrolidine-2-carboxylic acid | 506.9 |
| 370 | (2S,5R)-1-(1-(2-chloro-4-(trifluoromethyl)phenyl)piperidine-4-carbonyl)-5-(2-chlorophenyl)pyrrolidine-2-carboxylic acid | 516.4 |
| 371 | (2S,5R)-1-(5'-cyano-2'-methoxy-[1,1'-biphenyl]-4-carbonyl)-5-(2-fluorophenyl)pyrrolidine-2-carboxylic acid | 445.5 |
| 372 | (2S,5R)-1-(4-(2,6-dimethoxypyridin-3-yl)-3-fluorobenzoyl)-5-(2-fluorophenyl)pyrrolidine-2-carboxylic acid | 469.4 |
| 373 | (2S,5R)-1-(3-fluoro-4-(6-methoxypyridin-3-yl)benzoyl)-5-(2-fluorophenyl)pyrrolidine-2-carboxylic acid | 439.4 |
| 374 | (2S,5R)-1-(4-(3,6-dimethoxypyridazin-4-yl)benzoyl)-5-(2-fluorophenyl)pyrrolidine-2-carboxylic acid | 452.4 |
| 375 | (2S,5R)-1-(3'-carbamoyl-4'-cyano-[1,1'-biphenyl]-4-carbonyl)-5-(2-chlorophenyl)pyrrolidine-2-carboxylic acid | 474.9 |
| 376 | (2S,5R)-5-(2-chlorophenyl)-1-(1-(2-nitro-4-(trifluoromethyl)phenyl)piperidine-4-carbonyl)pyrrolidine-2-carboxylic acid | 526.9 |
| 377 | (2S,5R)-5-(2-chlorophenyl)-1-(1-(4-(morpholinosulfonyl)-2-nitrophenyl)piperidine-4-carbonyl)pyrrolidine-2-carboxylic acid | 608.1 |
| 378 | (2S,5R)-5-(2-chlorophenyl)-1-(1-(2-nitro-4-(piperidin-1-ylsulfonyl)phenyl)piperidine-4-carbonyl)pyrrolidine-2-carboxylic acid | 606.1 |
| 379 | (2S,5R)-5-(2-chlorophenyl)-1-(1-(4-(N,N-diethylsulfamoyl)-2-nitrophenyl)piperidine-4-carbonyl)pyrrolidine-2-carboxylic acid | 594.1 |
| 380 | (2S,5R)-5-(2-chlorophenyl)-1-(1-(4-methyl-2-nitrophenyl)piperidine-4-carbonyl)pyrrolidine-2-carboxylic acid | 472.9 |
| 381 | (2S,5R)-5-(2-chlorophenyl)-1-(1-(2-cyano-4-nitrophenyl)piperidine-4-carbonyl)pyrrolidine-2-carboxylic acid | 483.9 |
| 382 | (2S,5R)-5-(2-chlorophenyl)-1-(1-(4-nitrophenyl)piperidine-4-carbonyl)pyrrolidine-2-carboxylic acid | 458.9 |
| 383 | (2S,5R)-5-(2-chlorophenyl)-1-(1-(2-fluoro-4-nitrophenyl)piperidine-4-carbonyl)pyrrolidine-2-carboxylic acid | 476.9 |
| 384 | (2S,5R)-5-(2-chlorophenyl)-1-(1-(3-methoxy-4-nitrophenyl)piperidine-4-carbonyl)pyrrolidine-2-carboxylic acid | 488.9 |
| 385 | (2S,5R)-1-(1-(5-chloro-2-nitrophenyl)piperidine-4-carbonyl)-5-(2-chlorophenyl)pyrrolidine-2-carboxylic acid | 493.4 |
| 386 | (2S,5R)-5-(2-cyanophenyl)-1-(2'-methoxy-[1,1'-biphenyl]-4-carbonyl)pyrrolidine-2-carboxylic acid | 427.5 |
| 387 | (2S,5R)-5-(2-chlorophenyl)-1-(2'-cyano-4'-methoxy-[1,1'-biphenyl]-4-carbonyl)pyrrolidine-2-carboxylic acid | 461.9 |
| 388 | (2S,5R)-5-(2-chlorophenyl)-1-(2-fluoro-4'-(methylsulfonamido)-[1,1'-biphenyl]-4-carbonyl)pyrrolidine-2-carboxylic acid | 518.0 |
| 389 | (2S,5R)-5-(2-chlorophenyl)-1-(2-fluoro-3'-(methylsulfonamido)-[1,1'-biphenyl]-4-carbonyl)pyrrolidine-2-carboxylic acid | 518.0 |
| 390 | (2S,5R)-5-(2-chlorophenyl)-1-(2'-cyano-2-fluoro-[1,1'-biphenyl]-4-carbonyl)pyrrolidine-2-carboxylic acid | 449.9 |
| 391 | (2S,5R)-5-(2-chlorophenyl)-1-(1-(2-cyano-4-(methylsulfonamido)phenyl)piperidine-4-carbonyl)pyrrolidine-2-carboxylic acid | 532.0 |
| 392 | (2S,5R)-5-(2-chlorophenyl)-1-(1-(2-cyano-4-methoxyphenyl)piperidine-4-carbonyl)pyrrolidine-2-carboxylic acid | 468.9 |
| 393 | (2S,5R)-5-(2-chlorophenyl)-1-(1-(2-(methylsulfonamido)-4-(trifluoromethyl)phenyl)piperidine-4-carbonyl)pyrrolidine-2-carboxylic acid | 575.0 |
| 394 | (2S,5R)-5-(2-chlorophenyl)-1-(1-(2-nitrophenyl)piperidine-4-carbonyl)pyrrolidine-2-carboxylic acid | 458.9 |
| 395 | (2S,5R)-5-(2-chlorophenyl)-1-(1-(4-cyanophenyl)piperidine-4-carbonyl)pyrrolidine-2-carboxylic acid | 438.9 |
| 396 | (2S,5R)-5-(3,5-difluorophenyl)-1-(2'-methoxy-[1,1'-biphenyl]-4-carbonyl)pyrrolidine-2-carboxylic acid | 438.4 |
| 397 | (2S,5R)-5-(3,4-difluorophenyl)-1-(2'-methoxy-[1,1'-biphenyl]-4-carbonyl)pyrrolidine-2-carboxylic acid | 438.4 |
| 398 | (2S,5R)-5-(2,3-difluorophenyl)-1-(2'-methoxy-[1,1'-biphenyl]-4-carbonyl)pyrrolidine-2-carboxylic acid | 438.4 |
| 399 | (2S,5R)-5-(2,5-difluorophenyl)-1-(2'-methoxy-[1,1'-biphenyl]-4-carbonyl)pyrrolidine-2-carboxylic acid | 438.4 |
| 400 | (2S,5R)-5-([1,1'-biphenyl]-2-yl)-1-(2'-methoxy-[1,1'-biphenyl]-4-carbonyl)pyrrolidine-2-carboxylic acid | 478.6 |
| 401 | (2S,5R)-1-(2'-cyano-4'-methoxy-[1,1'-biphenyl]-4-carbonyl)-5-(2-fluorophenyl)pyrrolidine-2-carboxylic acid | 445.5 |
| 402 | (2S,5R)-5-(4-cyanophenyl)-1-(2'-methoxy-[1,1'-biphenyl]-4-carbonyl)pyrrolidine-2-carboxylic acid | 427.5 |
| 403 | (2S,5R)-5-(2-chlorophenyl)-1-(4-(5-methyl-4-(phenylsulfonyl)-1H-1,2,3-triazol-1-yl)benzoyl)pyrrolidine-2-carboxylic acid | 552.0 |
| 404 | (2S,5R)-5-(2-chlorophenyl)-1-(3'-cyano-4'-fluoro-[1,1'-biphenyl]-4-carbonyl)pyrrolidine-2-carboxylic acid | 449.9 |
| 405 | (2S,5R)-1-(2'-chloro-5'-cyano-[1,1'-biphenyl]-4-carbonyl)-5-(2-chlorophenyl)pyrrolidine-2-carboxylic acid | 466.3 |
| 406 | (2S,5R)-5-(2-chlorophenyl)-1-(2'-cyano-4'-(trifluoromethyl)-[1,1'-biphenyl]-4-carbonyl)pyrrolidine-2-carboxylic acid | 499.9 |

TABLE 1-continued

| Compound n° | Compound name | (M + H)+ |
|---|---|---|
| 407 | (2S,5R)-5-(2-chlorophenyl)-1-(1-(2-methoxy-4-(trifluoromethyl)phenyl)piperidine-4-carbonyl)pyrrolidine-2-carboxylic acid | 511.9 |
| 408 | (2S,5R)-5-(2-chlorophenyl)-1-(2'-methyl-3'-(N-methylmethylsulfonamido)-[1,1'-biphenyl]-4-carbonyl)pyrrolidine-2-carboxylic acid | 528.0 |
| 409 | (2S,5R)-5-(2-chlorophenyl)-1-(2'-methoxy-4'-(N-methylmethylsulfonamido)-[1,1'-biphenyl]-4-carbonyl)pyrrolidine-2-carboxylic acid | 544.0 |
| 410 | (2S,5R)-5-(2-chlorophenyl)-1-(6-(5-cyano-2-methoxyphenyl)-5-methoxynicotinoyl)pyrrolidine-2-carboxylic acid | 492.9 |
| 411 | (2S,5R)-5-(2-chlorophenyl)-1-(6-(2,4-dimethoxyphenyl)-5-methoxynicotinoyl)pyrrolidine-2-carboxylic acid | 497.9 |
| 412 | (2S,5R)-5-(2-chlorophenyl)-1-(6-(2,4-dimethoxyphenyl)nicotinoyl)pyrrolidine-2-carboxylic acid | 467.9 |
| 413 | (2S,5R)-1-(2'-cyano-4'-(trifluoromethyl)-[1,1'-biphenyl]-4-carbonyl)-5-(2-fluorophenyl)pyrrolidine-2-carboxylic acid | 483.4 |
| 414 | (2S,5R)-1-(3'-cyano-4'-fluoro-[1,1'-biphenyl]-4-carbonyl)-5-(2-fluorophenyl)pyrrolidine-2-carboxylic acid | 433.4 |
| 415 | (2S,5R)-1-(2'-chloro-5'-cyano-[1,1'-biphenyl]-4-carbonyl)-5-(2-fluorophenyl)pyrrolidine-2-carboxylic acid | 449.9 |
| 416 | (2S,5R)-5-(2-chlorophenyl)-1-(4-(3,6-dimethoxypyridazin-4-yl)-3-fluorobenzoyl)pyrrolidine-2-carboxylic acid | 486.9 |
| 417 | (2S,5R)-5-(2-fluorophenyl)-1-(2'-methyl-3'-(N-methylmethylsulfonamido)-[1,1'-biphenyl]-4-carbonyl)pyrrolidine-2-carboxylic acid | 511.6 |
| 418 | (2S,5R)-5-(2-fluorophenyl)-1-(2'-methoxy-4'-(N-methylmethylsulfonamido)-[1,1'-biphenyl]-4-carbonyl)pyrrolidine-2-carboxylic acid | 527.6 |
| 419 | (2S,5R)-5-(2-chlorophenyl)-1-(4-(4,6-dimethoxypyrimidin-5-yl)benzoyl)pyrrolidine-2-carboxylic acid | 468.9 |
| 420 | (2S,5R)-5-(2,3-difluorophenyl)-1-(4-(2,4-dimethoxypyrimidin-5-yl)benzoyl)pyrrolidine-2-carboxylic acid | 470.4 |
| 421 | (2S,5R)-1-(5'-cyano-2'-methyl-[1,1'-biphenyl]-4-carbonyl)-5-(2,3-difluorophenyl)pyrrolidine-2-carboxylic acid | 447.4 |
| 422 | (2S,5R)-5-(2,3-difluorophenyl)-1-(2'-methoxy-4'-(methylsulfonamido)-[1,1'-biphenyl]-4-carbonyl)pyrrolidine-2-carboxylic acid | 531.5 |
| 423 | (2S,5R)-5-(2,3-difluorophenyl)-1-(2'-methyl-3'-(methylsulfonamido)-[1,1'-biphenyl]-4-carbonyl)pyrrolidine-2-carboxylic acid | 515.5 |
| 424 | (2S,5R)-5-(2-fluorophenyl)-1-(2'-methyl-3'-(methylsulfonamido)-[1,1'-biphenyl]-4-carbonyl)pyrrolidine-2-carboxylic acid | 497.6 |
| 425 | (2S,5R)-5-(2,3-difluorophenyl)-1-(4-(2-methoxypyridin-3-yl)benzoyl)pyrrolidine-2-carboxylic acid | 439.4 |
| 426 | (2S,5R)-5-(2,3-difluorophenyl)-1-(3-methoxy-4-(2-methoxypyrimidin-5-yl)benzoyl)pyrrolidine-2-carboxylic acid | 470.4 |
| 427 | (2S,5R)-5-(2-fluorophenyl)-1-(3-methoxy-4-(2-methoxypyrimidin-5-yl)benzoyl)pyrrolidine-2-carboxylic acid | 452.4 |
| 428 | (2S,5R)-5-(2,3-difluorophenyl)-1-(4-(3,6-dimethoxypyridazin-4-yl)benzoyl)pyrrolidine-2-carboxylic acid | 470.4 |
| 429 | (2S,5R)-1-(5'-cyano-2'-methoxy-[1,1'-biphenyl]-4-carbonyl)-5-(2,3-difluorophenyl)pyrrolidine-2-carboxylic acid | 463.4 |
| 430 | (2S,5R)-1-(5'-cyano-2'-methyl-[1,1'-biphenyl]-4-carbonyl)-5-(2-fluorophenyl)pyrrolidine-2-carboxylic acid | 429.5 |
| 431 | (2S,5R)-5-(2,3-difluorophenyl)-1-(4-(3,6-dimethoxypyridazin-4-yl)-3-fluorobenzoyl)pyrrolidine-2-carboxylic acid | 488.4 |
| 432 | (2S,5R)-1-(4-(3,6-dimethoxypyridazin-4-yl)-3-fluorobenzoyl)-5-(2-fluorophenyl)pyrrolidine-2-carboxylic acid | 470.4 |

The compounds of table 1 were named using ChemDraw Ultra 12 purchased from CambridgeSoft (Cambridge, Mass., USA).

The compounds of formula I can be prepared by different ways with reactions known by the person skilled in the art. Reaction schemes as described in the example section illustrate by way of example different possible approaches.

The invention further provides processes for the preparation of compounds of the invention or a pharmaceutically acceptable salts or solvates thereof.

In one embodiment, the invention further provides a process for the preparation of a compound of formula Ib-1b'

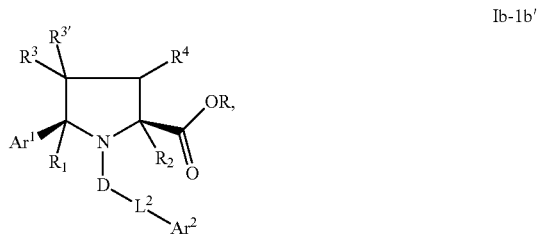

Ib-1b' wherein $Ar^2$ is as defined defined above in respect to formula Ib-1b';
$Ar^1$ is 2-chlorophenyl, 2-fluorophenyl, 2,3-difluorophenyl;
$R^1$, $R^2$, $R^3$, $R^{3'}$, $R^4$ and R are H;
D is C=O;
$L^2$ is a single bond;
which consists of:
a) the coupling of a compound of formula A

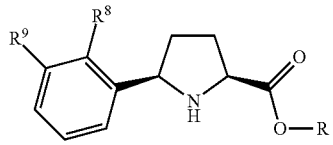

A wherein
$R^8$ is Cl or F and $R^9$ is H, or $R^8$ and $R^9$ are both F;
R is methyl, ethyl, tert-butyl, benzyl, allyl, phenacyl, methoxymethyl, methylthiomethyl, 2-methoxyethoxymethyl, 2-trimethylsilylethyl, tert-butyldiphenylsilyl, preferably R is methyl, ethyl, or tert-butyl;
with a compound of formula B

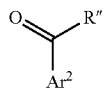

B wherein:
$Ar^2$ is as defined defined above in respect to formula Ib-1b';
R" is Cl or OL wherein L is a carboxylic acid activating group, followed by b) a alkaline or acidic treatment, hydrogenolysis or treatment with fluoride of the ester intermediate obtained in step a);

step b) being optionally followed by conversion of a compound of formula Ib-1b' to a pharmaceutically acceptable salt or solvate thereof.

In another embodiment the invention further provides a process for the preparation of a compound of formula Ib-1b'

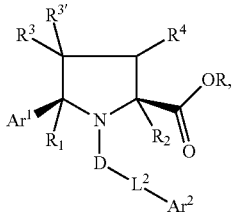

Ib-1b' wherein $Ar^1$ $R^3$, $R^{3'}$, $R^4$ are as defined above in respect to formula Ib-1b';
$R^1$, $R^2$, and R are H;
D is C=O;
$L^2$ is a single bond;
$Ar^2$ is selected from 4'-(2-methoxy-4-methylsulfonyl-1,1'-biphenyl), 4'-(2-methyl-3-methylsulfonylamino-1,1'-biphenyl), 4-(2-methoxypyridin-3-yl)phenyl, 4-(2,6-dimethoxypyrimidin-5-yl)phenyl, 3-methoxy-4-(2-methoxypyrimidin-5-yl)phenyl, 4-(3,6-dimethoxypyridazin-5-yl)phenyl, 4'-(5-cyano-2-methoxy-1,1'-biphenyl), 4'-(5-cyano-2-methyl-1,1'-biphenyl), 3-fluoro-4-(3,6-dimethoxypyridazin-5-yl)phenyl, (4-(4-methoxypyridin-3-yl)phenyl), (4'-(methylsulfonamido)-[1,1'-biphenyl]-4-yl), (3'-(methylsulfonamido)-[1,1'-biphenyl]-4-yl), (4-(2,4-dimethoxypyrimidin-5-yl)phenyl), (5-methoxy-6-phenylpyridin-3-yl), (4-(4-methoxypyrimidin-5-yl)phenyl), (2,2'-dimethoxy-[1,1'-biphenyl]-4-yl), (3-methoxy-4-(4-methoxypyridin-3-yl)phenyl), (4-(2,4-dimethoxypyrimidin-5-yl)-3-methoxyphenyl), (4'-acetamido-2'-methoxy-[1,1'-biphenyl]-4-yl), (2'-cyano-4',5'-dimethoxy-[1,1'-biphenyl]-4-yl), (2'-methoxy-4'-(N-methylmethylsulfonamido)-[1,1'-biphenyl]-4-yl), (6-(2,4-dimethoxyphenyl)pyridin-3-yl), (4-(4,6-dimethoxypyrimidin-5-yl)phenyl), (4-(3-methoxypyridin-4-yl)phenyl);

which consists of:
a) the coupling of a compound of formula C

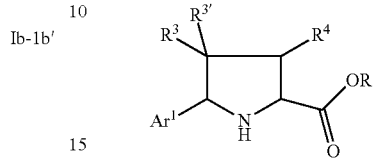

C wherein:
$Ar^1$, $R^3$, $R^{3'}$ and $R^4$ are as defined above in respect to formula Ib-1b';
R is methyl, ethyl, tert-butyl, benzyl, allyl, phenacyl, methoxymethyl, methylthiomethyl, 2-methoxyethoxymethyl, 2-trimethylsilylethyl, tert-butyldiphenylsilyl, preferably R is methyl, ethyl, or tert-butyl,
with a compound of formula D

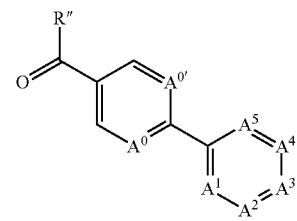

D wherein
R" is Cl or OL, wherein L is a carboxylic acid activating group;
$A^0$, $A^{0'}$, $A^1$, $A^2$, $A^3$, $A^4$ and $A^5$ are selected from the combinations 1 to 24:

| Combination n° | $A^0$ | $A^{0'}$ | $A^1$ | $A^2$ | $A^3$ | $A^4$ | $A^5$ |
|---|---|---|---|---|---|---|---|
| 1 | CH | CH | C—$OCH_3$ | CH | C—$NHSO_2CH_3$ | CH | CH |
| 2 | CH | CH | C—$CH_3$ | C—$NHSO_2CH_3$ | CH | CH | CH |
| 3 | CH | CH | C—$OCH_3$ | N | CH | CH | CH |
| 4 | CH | CH | C—$OCH_3$ | N | C—$OCH_3$ | N | CH |
| 5 | C—$OCH_3$ | CH | CH | N | C—$OCH_3$ | N | CH |
| 6 | CH | CH | C—$OCH_3$ | N | N | C—$OCH_3$ | CH |
| 7 | CH | CH | C—$OCH_3$ | CH | CH | C—CN | CH |
| 8 | CH | CH | C—$CH_3$ | CH | CH | C—CN | CH |
| 9 | C—F | CH | C—$OCH_3$ | N | N | C—$OCH_3$ | CH |
| 10 | CH | CH | CH | N | CH | CH | C—$OCH_3$ |
| 11 | CH | CH | CH | CH | C—$NHSO_2CH_3$ | CH | CH |
| 12 | CH | CH | CH | C—$NHSO_2CH_3$ | CH | CH | CH |
| 13 | CH | CH | CH | N | C—$OCH_3$ | N | C—$OCH_3$ |
| 14 | N | C—$OCH_3$ | CH | CH | CH | CH | CH |
| 15 | CH | CH | C—$OCH_3$ | N | CH | N | CH |
| 16 | CH | C—$OCH_3$ | C—$OCH_3$ | CH | CH | CH | CH |
| 17 | C—$OCH_3$ | CH | CH | N | CH | CH | C—$OCH_3$ |
| 18 | C—$OCH_3$ | CH | C—$OCH_3$ | N | C—$OCH_3$ | N | CH |
| 19 | CH | CH | C—$OCH_3$ | CH | C—$NHCOCH_3$ | CH | CH |
| 20 | CH | CH | C—CN | CH | C—$OCH_3$ | C—$OCH_3$ | CH |
| 21 | CH | CH | C—$OCH_3$ | CH | C—$N(CH_3)SO_2CH_3$ | CH | CH |
| 22 | N | CH | C—$OCH_3$ | CH | C—$OCH_3$ | CH | CH |
| 23 | CH | CH | C—$OCH_3$ | N | CH | N | C—$OCH_3$ |
| 24 | CH | CH | C—$OCH_3$ | CH | N | CH | CH | followed by
- b) an alkaline or acidic treatment, a hydrogenolysis or a treatment with fluoride of the ester intermediate obtained in step a);

step b) being optionally followed by conversion of a compound of formula Ib-1b' to a pharmaceutically acceptable salt or solvate thereof.

In yet another embodiment, the invention further provides a process for the preparation of a compound of the formula Ib-1h"

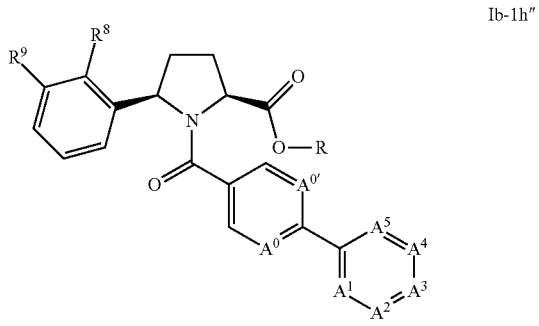

wherein
$R^8$ is F or Cl and $R^9$ is H, or both $R^8$ and $R^9$ are F;
R is H;
$A^0$, $A^{0'}$, $A^1$, $A^2$, $A^3$, $A^4$ and $A^5$ are selected from the combinations 1 to 24:

| Combination n° | $A^0$ | $A^{0'}$ | $A^1$ | $A^2$ | $A^3$ | $A^4$ | $A^5$ |
|---|---|---|---|---|---|---|---|
| 1 | CH | CH | C—OCH$_3$ | CH | C—NHSO$_2$CH$_3$ | CH | CH |
| 2 | CH | CH | C—CH$_3$ | C—NHSO$_2$CH$_3$ | CH | CH | CH |
| 3 | CH | CH | C—OCH$_3$ | N | CH | CH | CH |
| 4 | CH | CH | C—OCH$_3$ | N | C—OCH$_3$ | N | CH |
| 5 | C—OCH$_3$ | CH | CH | N | C—OCH$_3$ | N | CH |
| 6 | CH | CH | C—OCH$_3$ | N | N | C—OCH$_3$ | CH |
| 7 | CH | CH | C—OCH$_3$ | CH | CH | C—CN | CH |
| 8 | CH | CH | C—CH$_3$ | CH | CH | C—CN | CH |
| 9 | C—F | CH | C—OCH$_3$ | N | N | C—OCH$_3$ | CH |
| 10 | CH | CH | CH | N | CH | CH | C—OCH$_3$ |
| 11 | CH | CH | CH | CH | C—NHSO$_2$CH$_3$ | CH | CH |
| 12 | CH | CH | CH | C—NHSO$_2$CH$_3$ | CH | CH | CH |
| 13 | CH | CH | CH | N | C—OCH$_3$ | N | C—OCH$_3$ |
| 14 | N | C—OCH$_3$ | CH | CH | CH | CH | CH |
| 15 | CH | CH | C—OCH$_3$ | N | CH | N | CH |
| 16 | CH | C—OCH$_3$ | C—OCH$_3$ | CH | CH | CH | CH |
| 17 | C—OCH$_3$ | CH | CH | N | CH | CH | C—OCH$_3$ |
| 18 | C—OCH$_3$ | CH | C—OCH$_3$ | N | C—OCH$_3$ | N | CH |
| 19 | CH | CH | C—OCH$_3$ | CH | C—NHCOCH$_3$ | CH | CH |
| 20 | CH | CH | C—CN | CH | C—OCH$_3$ | C—OCH$_3$ | CH |
| 21 | CH | CH | C—OCH$_3$ | CH | C—N(CH$_3$)SO$_2$CH$_3$ | CH | CH |
| 22 | N | CH | C—OCH$_3$ | CH | C—OCH$_3$ | CH | CH |
| 23 | CH | CH | C—OCH$_3$ | N | CH | N | C—OCH$_3$ |
| 24 | CH | CH | C—OCH$_3$ | CH | N | CH | CH | which consists of:
- a) the coupling of a compound of formula A as defined above with a compound of formula B as defined above, followed by
- b) an alkaline or acidic treatment, a hydrogenolysis or a treatment with fluoride of the ester intermediate obtained in step a);

step b) being optionally followed by conversion of a compound of formula Ib-1h" to a pharmaceutically acceptable salt or solvate thereof.

In one variant of the process for the preparation of a compound of formula Ib-1h" as described above, the compound of formula Ib-1h" is selected from:

| | |
|---|---|
| 122 | (2S,5R)-5-(2-chlorophenyl)-1-(4-(2-methoxypyridin-3-yl)benzoyl)pyrrolidine-2-carboxylic acid |
| 125 | (2S,5R)-5-(2-chlorophenyl)-1-(4-(4-methoxypyridin-3-yl)benzoyl)pyrrolidine-2-carboxylic acid |
| 129 | (2S,5R)-5-(2-chlorophenyl)-1-(4'-(methylsulfonamido)-[1,1'-biphenyl]-4-carbonyl)pyrrolidine-2-carboxylic acid |
| 130 | (2S,5R)-5-(2-chlorophenyl)-1-(3'-(methylsulfonamido)-[1,1'-biphenyl]-4-carbonyl)pyrrolidine-2-carboxylic acid |
| 161 | (2S,5R)-5-(2-chlorophenyl)-1-(4-(2,4-dimethoxypyrimidin-5-yl)benzoyl)pyrrolidine-2-carboxylic acid |
| 191 | (2S,5R)-5-(2-chlorophenyl)-1-(5-methoxy-6-phenylnicotinoyl)pyrrolidine-2-carboxylic acid |
| 193 | (2S,5R)-5-(2-chlorophenyl)-1-(4-(3-methoxypyridin-4-yl)benzoyl)pyrrolidine-2-carboxylic acid |
| 203 | (2S,5R)-5-(2-chlorophenyl)-1-(4-(4-methoxypyrimidin-5-yl)benzoyl)pyrrolidine-2-carboxylic acid |
| 237 | (2S,5R)-5-(2-chlorophenyl)-1-(3-methoxy-4-(2-methoxypyrimidin-5-yl)benzoyl)pyrrolidine-2-carboxylic acid |
| 246 | (2S,5R)-5-(2-fluorophenyl)-1-(4-(2-methoxypyridin-3-yl)benzoyl)pyrrolidine-2-carboxylic acid |
| 247 | (2S,5R)-1-(4-(2,4-dimethoxypyrimidin-5-yl)benzoyl)-5-(2-fluorophenyl)pyrrolidine-2-carboxylic acid |
| 314 | (2S,5R)-1-(2,2'-dimethoxy-[1,1'-biphenyl]-4-carbonyl)-5-(2-fluorophenyl)pyrrolidine-2-carboxylic acid |
| 327 | (2S,5R)-5-(2-chlorophenyl)-1-(3-methoxy-4-(4-methoxypyridin-3-yl)benzoyl)pyrrolidine-2-carboxylic acid |
| 337 | (2S,5R)-5-(2-chlorophenyl)-1-(4-(2,4-dimethoxypyrimidin-5-yl)-3-methoxybenzoyl)pyrrolidine-2-carboxylic acid |

-continued

| | |
|---|---|
| 343 | (2S,5R)-5-(2-chlorophenyl)-1-(2'-methyl-3'-(methylsulfonamido)-[1,1'-biphenyl]-4-carbonyl)pyrrolidine-2-carboxylic acid |
| 345 | (2S,5R)-5-(2-chlorophenyl)-1-(5'-cyano-2'-methoxy-[1,1'-biphenyl]-4-carbonyl)pyrrolidine-2-carboxylic acid |
| 346 | (2S,5R)-5-(2-chlorophenyl)-1-(5'-cyano-2'-methyl-[1,1'-biphenyl]-4-carbonyl)pyrrolidine-2-carboxylic acid |
| 348 | (2S,5R)-5-(2-chlorophenyl)-1-(4-(3,6-dimethoxypyridazin-4-yl)benzoyl)pyrrolidine-2-carboxylic acid |

| | |
|---|---|
| 350 | (2S,5R)-5-(2-chlorophenyl)-1-(2'-methoxy-4'-(methylsulfonamido)-[1,1'-biphenyl]-4-carbonyl)pyrrolidine-2-carboxylic acid |
| 351 | (2S,5R)-1-(4'-acetamido-2'-methoxy-[1,1'-biphenyl]-4-carbonyl)-5-(2-chlorophenyl)pyrrolidine-2-carboxylic acid |
| 354 | (2S,5R)-5-(2-fluorophenyl)-1-(2'-methoxy-4'-(methylsulfonamido)-[1,1'-biphenyl]-4-carbonyl)pyrrolidine-2-carboxylic acid |
| 361 | (2S,5R)-5-(2-chlorophenyl)-1-(2'-cyano-4',5'-dimethoxy-[1,1'-biphenyl]-4-carbonyl)pyrrolidine-2-carboxylic acid |
| 371 | (2S,5R)-1-(5'-cyano-2'-methoxy-[1,1'-biphenyl]-4-carbonyl)-5-(2-fluorophenyl)pyrrolidine-2-carboxylic acid |
| 374 | (2S,5R)-1-(4-(3,6-dimethoxypyridazin-4-yl)benzoyl)-5-(2-fluorophenyl)pyrrolidine-2-carboxylic acid |
| 409 | (2S,5R)-5-(2-chlorophenyl)-1-(2'-methoxy-4'-(N-methylmethylsulfonamido)-[1,1'-biphenyl]-4-carbonyl)pyrrolidine-2-carboxylic acid |
| 412 | (2S,5R)-5-(2-chlorophenyl)-1-(6-(2,4-dimethoxyphenyl)nicotinoyl)pyrrolidine-2-carboxylic acid |
| 416 | (2S,5R)-5-(2-chlorophenyl)-1-(4-(3,6-dimethoxypyridazin-4-yl)-3-fluorobenzoyl)pyrrolidine-2-carboxylic acid |
| 419 | (2S,5R)-5-(2-chlorophenyl)-1-(4-(4,6-dimethoxypyrimidin-5-yl)benzoyl)pyrrolidine-2-carboxylic acid |
| 420 | (2S,5R)-5-(2,3-difluorophenyl)-1-(4-(2,4-dimethoxypyrimidin-5-yl)benzoyl)pyrrolidine-2-carboxylic acid |
| 421 | (2S,5R)-1-(5'-cyano-2'-methyl-[1,1'-biphenyl]-4-carbonyl)-5-(2,3-difluorophenyl)pyrrolidine-2-carboxylic acid |

Suitable carboxylic acid activating groups L for use in the above processes are benzotriazol-1-yl, 7-azabenzotriazol-1-yl, imidazol-1-yl, preferably 7-azabenzotriazol-1-yl.

In a typical procedure applicable to all of the aforementioned processes, the coupling reactions of a compound of formula B or D wherein R'' is OL, are done in the presence of a base such as triethylamine, diisopropylethylamine, preferably diisopropylethylamine, in a suitable solvent such as MeCN, DMF, DCM, preferably MeCN, at a suitable temperature ranging from room temperature to the boiling point of the solvent used, preferably at room temperature. Intermediates of formulae B and D are generated in situ from their corresponding carboxylic acid precursor which is reacted with HOBt, HOBt hydrate, HATU, CDI, pentafluorophenol, preferably with HATU. Preferably, the coupling with an activated carboxylic acid is made using HATU and DIEA in MeCN at room temperature.

In a typical procedure applicable to all of the above-mentioned processes, the coupling reactions of a compound of formula B or D wherein R is Cl, are done in the presence of a base such as triethylamine, diisopropylethylamine, preferably triethylamine, in a suitable solvent such as MeCN, DMF, DCM preferably DCM, at a suitable temperature ranging from room temperature to the boiling point of the solvent used, preferably at room temperature. Preferably, the coupling with an acyl chloride is made using triethylamine in DCM at room temperature.

In a typical procedure applicable to all of the aforementioned processes, the alkaline treatment of the intermediates obtained after coupling step a) and wherein R is methyl or ethyl, are done in the presence of a base such as sodium hydroxide, potassium hydroxide, lithium hydroxide, trimethyltin hydroxide, preferably lithium hydroxide, in a suitable solvent such as a 1/1 (v/v) mixture of water and THF, DCE, at a suitable temperature ranging from room temperature to the boiling point of the solvent used, preferably at room temperature.

In a typical procedure applicable to all of the above-mentioned processes, the acidic treatment of the intermediates obtained after coupling step a) and wherein R is tert-butyl, are done in the presence of a suitable acid such as HCl or TFA, in a suitable solvent such as DCM, dioxane, or in a miscible mixture of said solvents, at room temperature.

Those skilled in the art will appreciate that typical procedures applicable to all of the above-mentioned processes for step b) and wherein R is benzyl, allyl, phenacyl, methoxymethyl, methylthio methyl, 2-methoxyethoxymethyl, 2-trimethylsilylethyl or tert-butyldiphenylsilyl are well known and are indeed reported in Koscienski P. J., *Protecting Groups* 3$^{rd}$ *edition*, Thieme, 2005, 394-450.

In a particular embodiment, useful intermediates for the preparation of compounds of the invention are those of formula E:

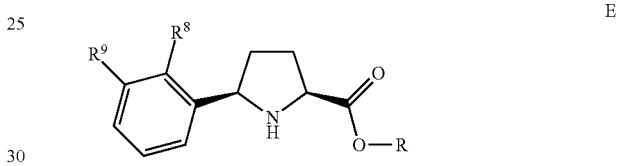

E wherein
$R^8$ is Cl or F and $R^9$ is H, or $R^8$ and $R^9$ are both F;
R is methyl, ethyl, benzyl, allyl, phenacyl, methoxymethyl, methylthiomethyl, 2-methoxyethoxymethyl, 2-trimethylsilyl ethyl, tert-butyldiphenylsilyl or R is tert-butyl when $R^8$ is F.

Preferred compounds of formula E are those wherein R is methyl, ethyl, or R is tert-butyl when $R^8$ is F.

In a particular embodiment, useful intermediates for the preparation of compounds of the invention are those of formula F:

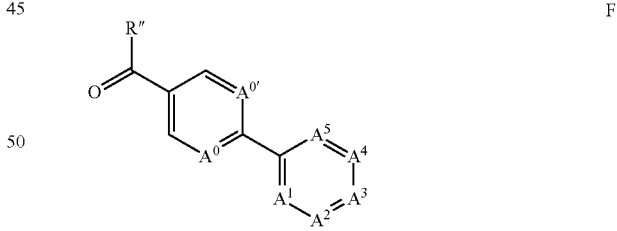

F wherein
R' is OH or Cl;
$A^0$, $A^{0'}$, $A^1$, $A^2$, $A^3$, $A^4$ and $A^5$ are selected from the combinations 1 to 7, 9, 10, 13 to 15, 17 to 21, 23 and 24:

| Combination n° | $A^0$ | $A^{0'}$ | $A^1$ | $A^2$ | $A^3$ | $A^4$ | $A^5$ |
|---|---|---|---|---|---|---|---|
| 1 | CH | CH | C—OCH$_3$ | CH | C—NHSO$_2$CH$_3$ | CH | CH |
| 2 | CH | CH | C—CH$_3$ | C—NHSO$_2$CH$_3$ | CH | CH | CH |
| 3 | CH | CH | C—OCH$_3$ | N | CH | CH | CH |
| 4 | CH | CH | C—OCH$_3$ | N | C—OCH$_3$ | N | CH |

| Combination n° | A⁰ | A⁰' | A¹ | A² | A³ | A⁴ | A⁵ |
|---|---|---|---|---|---|---|---|
| 5 | C—OCH₃ | CH | CH | N | C—OCH₃ | N | CH |
| 6 | CH | CH | C—OCH₃ | N | N | C—OCH₃ | CH |
| 7 | CH | CH | C—OCH₃ | CH | CH | C—CN | CH |
| 9 | C—F | CH | C—OCH₃ | N | N | C—OCH₃ | CH |
| 10 | CH | CH | CH | N | CH | CH | C—OCH₃ |
| 13 | CH | CH | CH | N | C—OCH₃ | N | C—OCH₃ |
| 14 | N | C—OCH₃ | CH | CH | CH | CH | CH |
| 15 | CH | CH | C—OCH₃ | N | CH | N | CH |
| 17 | C—OCH₃ | CH | CH | N | CH | CH | C—OCH₃ |
| 18 | C—OCH₃ | CH | C—OCH₃ | N | C—OCH₃ | N | CH |
| 19 | CH | CH | C—OCH₃ | CH | C—NHCOCH₃ | CH | CH |
| 20 | CH | CH | C—CN | CH | C—OCH₃ | C—OCH₃ | CH |
| 21 | CH | CH | C—OCH₃ | CH | C—N(CH₃)SO₂CH₃ | CH | CH |
| 23 | CH | CH | C—OCH₃ | N | CH | N | C—OCH₃ |
| 24 | CH | CH | C—OCH₃ | CH | N | CH | CH |

The invention further provides the use of the compounds of the invention or pharmaceutically acceptable salts, solvates or prodrugs thereof as agonists or partial agonists of G-protein coupled receptor 43 (GPR43).

Accordingly, in a particularly preferred embodiment, the invention relates to the use of compounds of formula I and subformulae in particular those of table 1 above, or pharmaceutically acceptable salts, solvates and prodrugs thereof, as GPR43 agonists or partial agonists.

[Applications]

The compounds of the invention are therefore useful in the prevention and/or treatment of type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

Preferred diseases are type II diabetes, lipid disorders such as dyslipidemia, hypertension, obesity, atherosclerosis and its sequelae.

In a particular preferred embodiment the diseases are type II diabetes and a lipid disorder such as dyslipidemia.

The invention also provides for a method for delaying in patient the onset of type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH) comprising the administration of a pharmaceutically effective amount of a compound of formula (I) or pharmaceutically acceptable salt thereof to a patient in need thereof.

Preferably, the patient is a warm-blooded animal, more preferably a human.

The invention further provides the use of a compound of formula (I) or a pharmaceutically acceptable salt or solvates thereof for the manufacture of a medicament for use in treating a patient and/or preventing a patient from developing a disease selected from the group consisting of type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

Preferably, the patient is a warm-blooded animal, more preferably a human.

According to a further feature of the present invention there is provided a method for modulating GPR43 receptor activity, in a patient, preferably a warm blooded animal, and even more preferably a human, in need of such treatment, which comprises administering to said animal an effective amount of compound of the present invention, or a pharmaceutically acceptable salt or solvate thereof.

According to one embodiment, the compounds of the invention, their pharmaceutical acceptable salts, solvates or prodrugs may be administered as part of a combination therapy. Thus, are included within the scope of the present invention embodiments comprising coadministration of, and compositions and medicaments which contain, in addition to a compound of the present invention, a pharmaceutically acceptable salt or solvate thereof as active ingredient, additional therapeutic agents and/or active ingredients. Such multiple drug regimens, often referred to as combination therapy, may be used in the treatment and/or prevention of any of the diseases or conditions mediated by or associated with GPR43 receptor modulation, particularly type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH). The use of such combinations of therapeutic agents is especially pertinent with respect to the treatment of the above-mentioned list of diseases within a patient in need of treatment or one at risk of becoming such a patient.

In addition to the requirement of therapeutic efficacy, which may necessitate the use of active agents in addition to the GPR43 agonist or partial agonist compounds of Formula I or their pharmaceutical acceptable salts, solvates or prodrugs thereof, there may be additional rationales which compel or highly recommend the use of combinations of drugs involving active ingredients which represent adjunct therapy, i.e., which complement and supplement the function performed by the GPR43 receptor agonist or partial agonist compounds of the present invention. Suitable supplementary therapeutic agents used for the purpose of auxiliary treatment include drugs which, instead of directly treating or preventing a disease or condition mediated by or associated with GPR43 receptor modulation, treat diseases or conditions which directly result from or indirectly accompany the basic or underlying GPR43 receptor modulated disease or condition.

Thus, the methods of treatment and pharmaceutical compositions of the present invention may employ the compounds of Formula I or their pharmaceutical acceptable salts, solvates or prodrugs thereof in the form of monotherapy, but said methods and compositions may also be used in the form of multiple therapy in which one or more compounds of Formula I or their pharmaceutically acceptable salts, solvates and prodrugs are coadministered in combination with one or more other therapeutic agents such as those described in detail further herein.

Examples of other active ingredients that may be administered in combination with a compound of Formula I or a pharmaceutically acceptable salt or solvate thereof, and either administered separately or in the same pharmaceutical composition, include but are not limited to:

(a) PPARγ agonists and partial agonists, including both glitazones and non-glitazones (e.g. troglitazone, pioglitazone, englitazone, MCC-555, rosiglitazone, balaglitazone, netoglitazone, T-131, LY-300512 and LY-818;
(b) Biguanides such as metformin and phenformin;
(c) Protein tyrosine phosphatase-1B (PTP-1B) inhibitors,
(d) Dipeptidyl peptidase IV (DP-IV) inhibitor, such as MK-0431 and LAF-237;
(e) Insulin or insulin mimetics;
(f) Sulfonylureas such as tolbutamide and glipizide or related materials;
(g) α-glucosidase inhibitors (such as acarbose);
(h) agents which improve a patient's lipid profile such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors such as for example ezetimibe, (vi) acyl CoA: cholesterol acyltransferase (ACAT) inhibitors such as avasimibe, (vii) CETP inhibitors such as torcetrapib and (viii) phenolic anti-oxidants such as probucol;
(i) PPARα/γ dual agonists such as muraglitazar, tesaglitazar, farglitazar and JT-501;
(j) PPARδ agonists such those disclosed in WO97/28149;
(k) Antiobesity compounds such as fenfluramine, dextenfluramine, phentiramine, subitramine, orlistat, neuropeptide Y5 inhibitors, MC4R agonists, cannabinoid receptor 1 antagonists/inverse agonists and β3 adrenergic receptor agonists;
(l) Ileal bile acid transporter inhibitors;
(m) Agents intended for use in inflammatory conditions such as aspirin, non-steroidal, anti-inflammatory drugs, glucocorticoids, azulfidine and cyclo-oxygenase 2 selective inhibitors;
(n) Glucagon receptor antagonists;
(o) GLP-1;
(p) GIP-1;
(q) GLP-1 analogs, such as exendins, for example exenitide, and
(r) Hydroxysterol dehydrogenase-1 (HSD-1) inhibitors.

The above combinations include combinations of a compound of the present invention or a pharmaceutically acceptable salt or solvate not only with one other active compound but also with two or more active compounds. Non limiting examples include combinations of compounds having Formula I with two or more active compounds selected from biguanides, sulfonylureas, HMG-CoA reductase inhibitors, other PPAR agonists, PTP-1B inhibitors, DP-IV inhibitors and anti-obesity compounds.

In the above-described embodiment combinations of the present invention, the compound of Formula I, a pharmaceutically acceptable salt or solvate thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions comprising a compound of formula I or a pharmaceutically acceptable salt or solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt or solvate thereof as active ingredient, additional therapeutic agents and/or active ingredients.

Another object of this invention is a medicament comprising at least one compound of the invention, or a pharmaceutically acceptable salt or solvate thereof, as active ingredient.

The invention also provides the use of a compound of formula I or a pharmaceutically acceptable salt or solvate thereof for the manufacture of a medicament. Preferably, the medicament is used for the treatment and/or prevention of type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

Preferred diseases are type II diabetes, lipid disorders such as dyslipidemia, hypertension, obesity, atherosclerosis and its sequelae.

In a particular preferred embodiment the disease are type II diabetes and a lipid disorder such as dyslipidemia.

According to a further feature of the present invention there is provided the use of a compound of formula I or a pharmaceutically acceptable salt or solvate thereof for the manufacture of a medicament for modulating GPR43 receptor activity, in a patient, in need of such treatment, which comprises administering to said patient an effective amount of compound of the present invention, or a pharmaceutically acceptable salt or solvate thereof.

Preferably, the patient is a warm-blooded animal, more preferably a human.

As set forth above, the compounds of the invention, their pharmaceutically acceptable salts, solvates and prodrugs may be used in monotherapy or in combination therapy. Thus, according to one embodiment, the invention provides the use of a compound of the invention for the manufacture of a medicament for at least one of the purposes described above, wherein said medicament is administered to a patient in need thereof, preferably a warm-blooded animal, and even more preferably a human, in combination with at least one additional therapeutic agent and/or active ingredient. The benefits and advantages of such a multiple drug regimen, possible administration regimens as well as suitable additional therapeutic agents and/or active ingredients are those described above.

Generally, for pharmaceutical use, the compounds of the inventions may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, of at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.01 to 100 mg per kilogram, more often between 0.1 and 50 mg, such as between 1 and 25 mg, for example about 0.5, 1, 5, 10, 15, 20 or 25 mg, per kilogram body weight of the patient per day, which may be administered as a single daily dose, divided over one or more daily doses, or essentially continuously, e.g. using a drip infusion.

Definitions

The definitions and explanations below are for the terms as used throughout the entire application, including both the specification and the claims.

When describing the compounds of the invention, the terms used are to be construed in accordance with the following definitions, unless indicated otherwise.

Where groups may be substituted, such groups may be substituted with one or more substituents, and preferably with one, two or three substituents. Substituents may be selected from but not limited to, for example, the group comprising halogen, hydroxyl, oxo, cyano, nitro, amido, carboxy, amino, cyano haloalkoxy, and haloalkyl.

As used herein the terms such as "alkyl, aryl, or cycloalkyl, each being optionally substituted with . . . " or "alkyl, aryl, or cycloalkyl, optionally substituted with . . . " encompasses "alkyl optionally substituted with . . . ", "aryl optionally substituted with . . . " and "cycloalkyl optionally substituted with . . . ".

The term "halo" or "halogen" means fluoro, chloro, bromo, or iodo. Preferred halo groups are fluoro and chloro.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. $C_{x-y}$-alkyl and Cx-Cy-alkyl refer to alkyl groups which comprise from x to y carbon atoms.

Suitable alkyl groups include methyl, ethyl, n-propyl, i-propyl, n-butyl, i-butyl, s-butyl and tert-butyl, pentyl and its isomers (e.g. n-pentyl, iso-pentyl), and hexyl and its isomers (e.g. n-hexyl, iso-hexyl). Preferred alkyl groups include methyl, ethyl, n-propyl, i-propyl, n-butyl, i-butyl, s-butyl and tert-butyl.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

The term "alkenyl" as used herein refers to an unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkynyl" as used herein refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Non limiting examples of alkynyl groups are ethynyl, 2-propynyl, 2-butynyl, 3-butynyl, 2-pentynyl and its isomers, 2-hexynyl and its isomers- and the like. The terms "alkenylene" and "alkynylene" respectively mean an alkenyl group or an alkinyl group as defined above having two single bonds as points of attachment to other groups.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

When the suffix "ene" is used in conjunction with a cyclic group, this is intended to mean the cyclic group as defined herein having two single bonds as points of attachment to other groups.

Therefore, "cycloalkylene" herein refers to a saturated homocyclic hydrocarbyl biradical of Formula $C_nH_{2n-2}$. Suitable cycloalkylene groups are $C_{3-6}$ cycloalkylene group, preferably a $C_{3-5}$ cycloalkylene (i.e. 1,2cyclopropylene, 1,1-cyclopropylene, 1,1-cyclobutylene, 1,2-cyclobutylene, 1,3-cyclobutylene, 1,3-cyclopentylene, or 1,1-cyclopentylene), more preferably a $C_{3-4}$ cycloalkylene (i.e. 1,3-cyclopropylene, 1,1-cyclopropylene, 1,1-cyclobutylene, 1,2-cyclobutylene).

Where at least one carbon atom in a cycloalkyl group is replaced with a heteroatom, the resultant ring is referred to herein as "heterocycloalkyl" or "heterocyclyl".

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more Spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

The ring atoms of heterocyclyl and heterocyclylene moieties are numbered based on scheme below

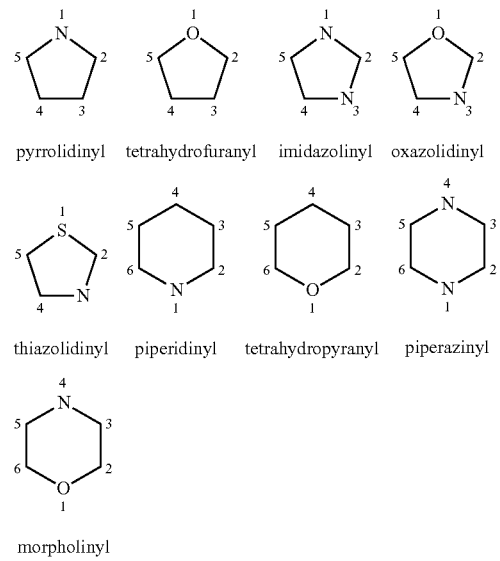

pyrrolidinyl  tetrahydrofuranyl  imidazolinyl  oxazolidinyl thiazolidinyl  piperidinyl  tetrahydropyranyl  piperazinyl morpholinyl The term "aryl" as used herein refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "arylene" as used herein is intended to include divalent carbocyclic aromatic ring systems such as phenylene, biphenylylene, naphthylene, indenylene, pentalenylene, azulenylene and the like. Arylene is also intended to include the partially hydrogenated derivatives of the carbocyclic systems enumerated above. Non-limiting examples of such partially hydrogenated derivatives are 1,2,3,4-tetrahydronaphthylene, 1,4-dihydronaphthylene and the like.

The term "arylalkyl" or "aralkyl" refers to a linear or branched alkyl group where one carbon is attached to an aryl ring. Non limiting examples of aralkyl comprise benzyl, phenethyl, (naphtalen-1-yl) or (naphtalen-2-yl)methyl. When an aralkyl group is substituted, the substituent(s) is/are attached either on the alkyl group or on the aryl ring. A "x-membered aralkyl" refers to a linear or branched alkyl group where one carbon is attached to a x-membered aryl ring. Where at least one carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxopyridazin-1(6H)-yl, 2-oxopyridin-1(2H)-yl, 6-oxopyridazin-1(6H)-yl, 2-oxopyridin-1(2H)-yl, 1,3-benzodioxolyl, quinolinyl, isoquinolinyl, cinnolinyl, quinazolinyl, quinoxalinyl.

The term "heteroarylene" as used herein means divalent carbocyclic aromatic ring systems including pyridinylene and the like.

The ring atoms of heteroaryl or heteroarylene moieties are numbered on scheme below:

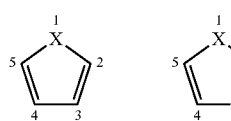

X is selected from:  X is selected from:  X is selected from:
N, O or S            N, O or S            N, O or S
Examples:            Examples:            Examples:
pyrrolyl             imidazolyl           pyrazolyl
furanyl              oxazolyl             isooxazolyl
thiophenyl           thiazolyl            isothiazolyl

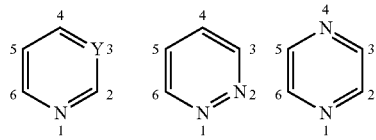

Y is selected from:  pyridazinyl   pyrazinyl
C, N
Examples:
pyridyl
pyrimidinyl

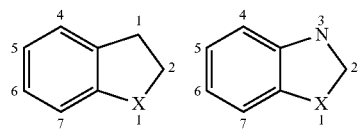

X is selected from:      X is selected from:
N, O or S                N, O or S
Examples:                Examples:
indolyl                  benzimidazolyl
benzofuranyl             benzoxazolyl
benzothiophenyl          benzothiazolyl The term "biaryl" as used herein designates two aryl moieties as defined herein linked via a single bond. Non-limiting examples of such biaryl moieties include biphenyl.

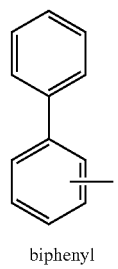

biphenyl

The term "heterobiaryl" as used herein designates two heteroaryl moieties as defined herein or a heteroaryl moiety and an aryl moity as defined herein linked via a single bond. Non-limiting examples of such heterobiaryl moieties include pyridinylphenyl which is meant to include (2-pyridinyl)phenyl, (3-pyridinyl)phenyl and (4-pyridinyl)phenyl, bipyridinyl.

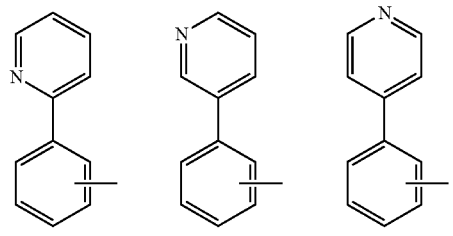

(2-pyridinyl)phenyl  (3-pyridinyl)phenyl  (4-pyridinyl)phenyl

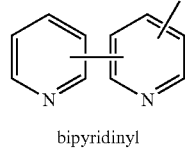

bipyridinyl

The term "alkylamino" as used herein means an amino group substituted with one or two alkyl groups. This includes monoalkylamino and dialkylamino groups.

The term "carbamoyl" as used herein means a group of formula

wherein the arrow defines the attachment point.

The term "carbamimidoyl" as used herein means a group of formula

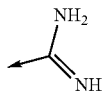

wherein the arrow defines the attachment point.

The term "carbamimidoyl" as used herein means a group of formula

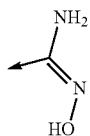

wherein the arrow defines the attachment point.

The compounds of Formula I and subformulae thereof contain at least one asymmetric center and thus may exist as different stereoisomeric forms. Accordingly, the present invention includes all possible stereoisomers and includes not only racemic compounds but the individual enantiomers and their non racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be effected by any suitable method known in the art. See, for example, Stereochemistry of Organic Compounds by E. L. Eliel, S. H. Wilen, and L. N. Mander (Wiley—Interscience, 1994), incorporated by reference with regard to stereochemistry.

The bonds from an asymmetric carbon in compounds of the present invention may be depicted herein using a solid line (—), a zigzag line ( ~~~ ), a solid wedge ( ▬ ) or a dotted wedge ( ······ ), a solid bar ( ■■ ) or a dotted bar ( ········ ). The use of a solid line to depict bonds from an asymmetric carbon atom is meant to indicate that all possible stereoisomers are meant to be included, unless it is clear from the context that a specific stereoisomer is intended. The use of either a solid or dotted wedge to depict bonds from an asymmetric carbon atom is meant to indicate that only the stereoisomer shown is meant to be included.

The compounds of the invention may also contain more than one asymmetric carbon atom. In those compounds, the use of a solid line to depict bonds from asymmetric carbon atoms is meant to indicate that all possible stereoisomers are meant to be included, unless it is clear from the context that a specific stereoisomer is intended. In those compounds, the use of solid or dotted bars is meant to indicate relative stereochemistry. As an example,

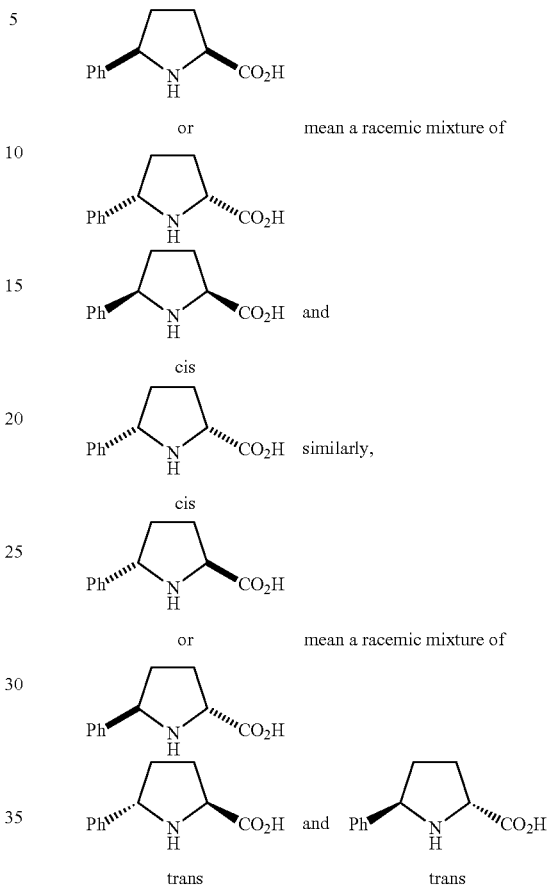

The compounds of the invention may be in the form of pharmaceutically acceptable salts. Pharmaceutically acceptable salts of the compounds of formula I include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I may be prepared by one or more of these methods:

(i) by reacting the compound of Formula I with the desired acid;

(ii) by reacting the compound of Formula I with the desired base;

(iii) by removing an acid- or base-labile protecting group from a suitable precursor of the compound of Formula I or by ring-opening a suitable cyclic precursor, for example, a lactone or lactam, using the desired acid; or (iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a molecular complex comprising the compound of the invention and one or more pharmaceutically acceptable solvent molecules, for example, ethanol. The term 'hydrate' is employed when said solvent is water.

All references to compounds of formula I include references to salts, solvates, multi-component complexes and liquid crystals thereof.

The compounds of the invention include compounds of formula I as hereinbefore defined, including all polymorphs and crystal habits thereof, prodrugs and isomers thereof (including optical, geometric and tautomeric isomers) and isotopically-labeled compounds of formula I.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

The invention also generally covers all pharmaceutically acceptable predrugs and prodrugs of the compounds of Formula I.

The term "prodrug" as used herein means the pharmacologically acceptable derivatives of compounds of formula I such as esters whose in vivo biotransformation product is the active drug. Prodrugs are characterized by increased bioavailability and are readily metabolized into the active compounds in vivo. Suitable prodrugs for the purpose of the invention include carboxylic esters, in particular alkyl esters, aryl esters, acyloxyalkyl esters, and dioxolene carboxylic esters; ascorbic acid esters as well as compounds of formula I in which Z is a substituent selected from the table 2 below.

TABLE 2

| Z | Q |
|---|---|
| —C(O)SQ | Alkyl or aryl |
| —C(O)NQ$^1$Q$^2$ | Q$^1$ and Q$^2$ independently selected from: H, alkyl, aryl, OH or NH$_2$ |
| —C(O)OCHQ$^1$O(O)CQ$^2$ | Q$^1$ = H or phenyl<br>Q$^2$ = alkyl or aryl |
| —C(O)OCHQCl | H or aryl |
| —C(OQ)$_3$ | Alkyl |
| —C(O)OC(O)OQ | Alkyl or aryl |
| —C(O)CH$_2$Q | SMe, SOMe, SO$_2$Me |

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting or receiving medical care or is or will be the object of a medical procedure.

The term "human" refers to subject of both genders and at any stage of development (i.e. neonate, infant, juvenile, adolescent, adult).

The terms "treat", "treating" and "treatment, as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e. g. GPR43 agonist or partial agonist) which is sufficient to achieve the desired therapeutic or prophylactic effect in the individual to which it is administered.

The term "administration", or a variant thereof (e.g., "administering"), means providing the active agent or active ingredient (e.g. a GPR43 agonist or partial agonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "agonist" as used herein means a ligand that activates an intracellular response when it binds to a receptor. An agonist according to the invention may promote internalization of a cell surface receptor such that the cell surface concentration of a receptor is decreased or remove.

The term "partial agonist" as used herein means an agonist which is unable to induce maximal activation of a receptor, regardless of the amount of compound applied on the receptor.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The term "lipid disorder" as used herein means any plasma lipid disorder including but not limited to dyslipidemia such as mixed or diabetic dyslipidemia, hypercholesterolemia, low HDL cholesterol, high LDL cholesterol, hyperlipidemia and hypertriglyceridemia.

The present invention will be better understood with reference to the following examples. These examples are intended to representative of specific embodiments of the invention, and are not intended as limiting the scope of the invention.

CHEMISTRY EXAMPLES

All temperatures are expressed in ° C. and all reactions were carried out at room temperature (RT) unless otherwise stated.

Analytical thin layer chromatography (TLC) was used to monitor reactions, establish flash chromatography conditions and verify purity of intermediates or final products. TLC plates used were Merck TLC aluminium sheet silica gel 60 $F_{254}$. TLC plates were revealed using ultraviolet irradiation (wavelength=254 nm) at RT or bromocresol green spray reagent at 0.1% in propan-2-ol or $KMnO_4$ revelator ($KMnO_4$, $Na_2CO_3$, NaOH, $H_2O$) upon heating at 160° C.

HPLC-MS spectra were obtained on Agilent LCMS using Electropsray ionization (ESI). The Agilent instrument includes an Autosampler 1200, a binary pump 1100, a 5 wave length detector 1100 and a 6100 Single Quad. The column used was an XBridge C18.

Eluent was a mixture of solution A (0.1% TFA in $H_2O$) and solution B (0.1% TFA in ACN). Gradients used are as follows: gradient A (intermediates characterization): held the initial conditions of 5% solution B for 1 min, increased linearly to 95% solution B in 4 min, held at 95% during 1 min, returned to initial conditions in 0.5 min and maintained for 1 min; gradient B (examples characterization): held the initial conditions of 5% solution B for 1 min, increased linearly to 60% in 10 min, increased linearly to 95% in 0.5 min, held at 95% during 3 min, returned to initial conditions in 0.5 min and maintained for 1 min.

Determination of enantiomeric excess was performed on an Agilent 1100 (binary pump and 5 wavelengths detector) with manual or automatic (Autosampler 1100) injection. Columns used were CHIRALPAK IA CHTRALPAK IB or CHTRALPAK IC in isocratic mode. Mixtures of eluents were selected depending on the separation obtained of enantiomers or diastereosiomers. Usual mixtures were:
 Hexane and Ethanol (0.1% TFA)
 Hexane and Propanol (0.1% TFA)
 Hexane and Ethyl acetate (0.1% TFA)
 Hexane and Dichloromethane (0.1% TFA)
 Hexane and tert-butyl methyl ether (0.1% TFA)

Preparative HPLC purifications were carried out on Fractionlynx instrument, from Waters. This instrument consists of a Fraction Collector, a 2767 Sample Manager, a pump control a module II, a 515 HPLC Pump, a 2525 Binary Gradient Module, a Switching Valve, a 2996 Photodiode Array Detector and a Micromass ZQ. The column used was a Waters Sunfire C18 Eluent was a mixture of solution A (0.1% TFA in $H_2O$) and solution B (0.1% TFA in ACN). The gradient was adapted depending on impurities present in samples, to allow sufficient separation between impurities and target compound.

Chiral preparative HPLC purification were performed on an Agilent 1100 instrument (binary pump and 5 wavelengths detector) with manual injection using a CHIRALPAK IA or a CHIRALPAK IB column in isocratic mode. Mixtures of eluents were selected depending on the separation of enantiomers or diastereosiomers obtained with the analytical method. Usual mixtures were the same as those used for the determination of ee.

$^1$H and $^{13}$C NMR spectra were recorded on a Bruker ARX 300 MHz. Chemical shifts are expressed in parts per million, (ppm, δ units). Coupling constants are expressed in Hertz units (Hz). Splitting patterns describe apparent multiplicities and are described as s (singlet), d (doublet), t (triplet), q (quintet), m (multiplet), or br (broad).

Solvents, reagents and starting materials were purchased from well known chemical suppliers such as for example Sigma Aldrich, Acros Organics, VWR Int., Sopachem or Polymer labs and the following abbreviations are used:

ACN or MeCN: Acetonitrile,
DCM: Dichloromethane,
DCE: 1,2-Dichloroethane,
EtOAc or AcOEt: Ethyl acetate,
EtOH: Ethanol,
MeOH: Methanol,
IPA: isopropanol,
PE: Petroleumether,
NMP: N-methylpyrrolidinone,
RT: Room temperature,
DIEA: N,N-diisopropylethylamine,
HATU: O-(7-azabenzotriazol-1-yl)-N,N,N',N'-tretramethyluronium hexafluorophosphate,
HOBt: 1-hydroxybenzotriazole or 1-hydroxybenzotriazole hydrate,
DMAP: N, N-Dimethylaminopyridine
Y: Yield,
g: Grams,
mg: Milligrams,
L: Liters,
mL: Milliliters,
μL: Microliters,
mol: Moles,
mmol: Millimoles,
h: Hours,
min or mn: Minutes,
TLC: Thin layer chromatography,
MW: Molecular weight,
eq: Equivalent,
THF: Tetrahydrofuran,
TFA: Trifluoroacetic acid,
Ac: Acetyl,
ee: Enantiomeric excess,
tBu: tert-Butyl
P: UV purity at 254 nm determined by HPLC-MS,
rt: Retention time,
BuLi: butyllithium,
CDI: carbonyldiimidazole,
TBDPS: tert-butyl-diphenylsilyl,
$Boc_2O$: di-tert-butyldicarbonate,
TBAF: tetrabutylammonium fluoride,
S-Phos: 2-Dicyclohexylphosphino-2',6'-dimethoxybiphenyl,
RM: reaction mixture,
Nu: Nucleophile,
DMF: N,N-dimethylformamide,
TMS: trimethylsilyl.

General Synthetic Schemes

A general method for the synthesis of most compounds of the invention is outlined in scheme 1.

Scheme 1: A general method for the synthesis of most compounds of the invention

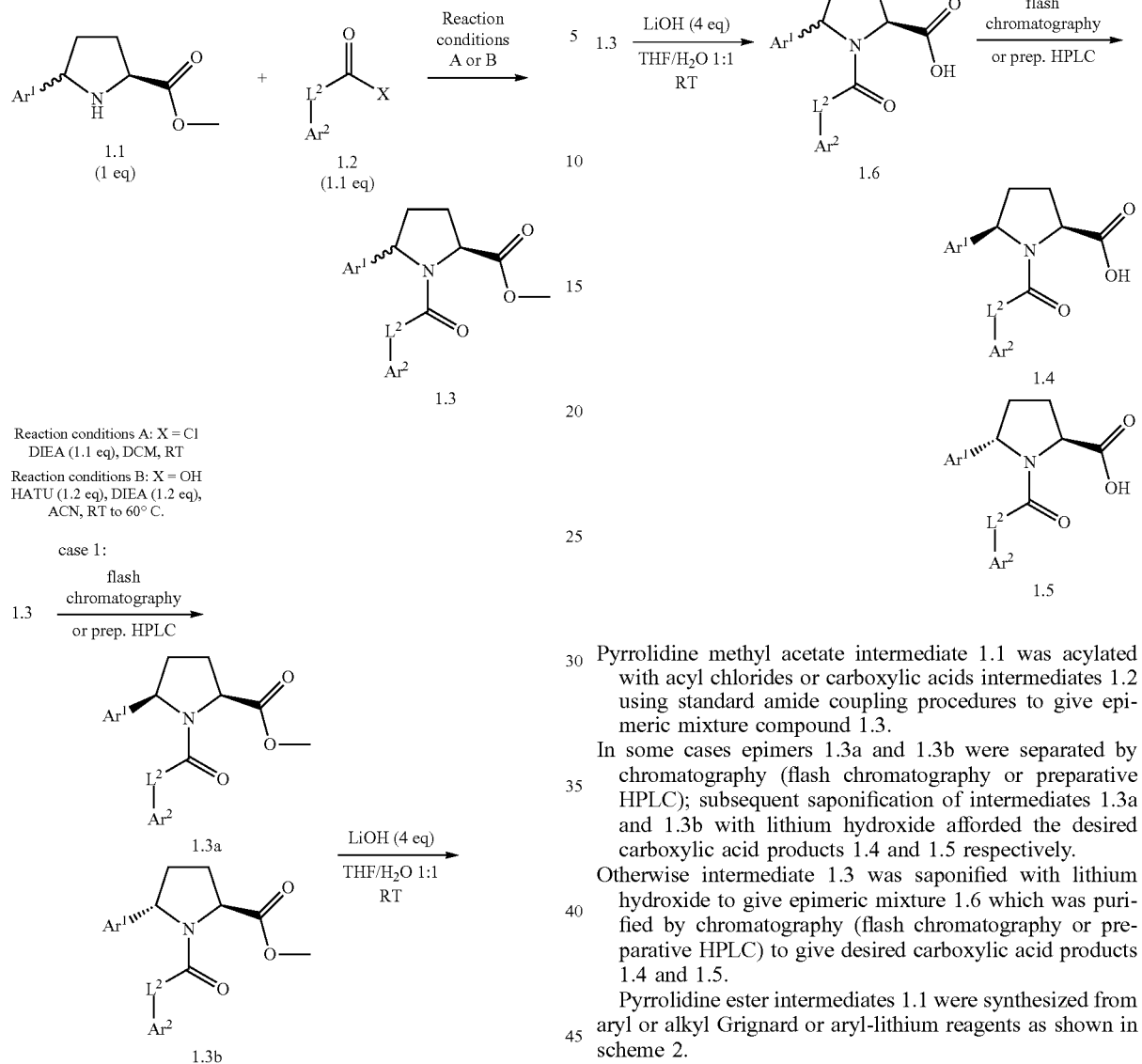

Pyrrolidine methyl acetate intermediate 1.1 was acylated with acyl chlorides or carboxylic acids intermediates 1.2 using standard amide coupling procedures to give epimeric mixture compound 1.3.

In some cases epimers 1.3a and 1.3b were separated by chromatography (flash chromatography or preparative HPLC); subsequent saponification of intermediates 1.3a and 1.3b with lithium hydroxide afforded the desired carboxylic acid products 1.4 and 1.5 respectively.

Otherwise intermediate 1.3 was saponified with lithium hydroxide to give epimeric mixture 1.6 which was purified by chromatography (flash chromatography or preparative HPLC) to give desired carboxylic acid products 1.4 and 1.5.

Pyrrolidine ester intermediates 1.1 were synthesized from aryl or alkyl Grignard or aryl-lithium reagents as shown in scheme 2.

Scheme 2: Synthetic scheme for the preparation of pyrrolidine ester intermediates

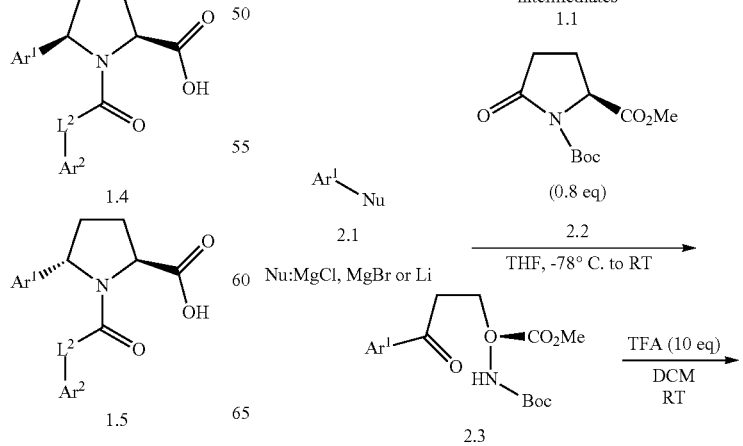

-continued

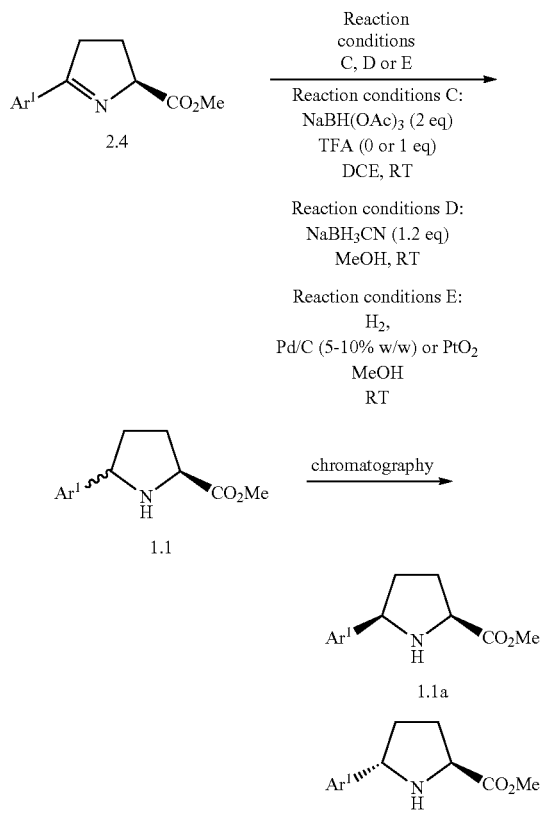

Addition of aryl or alkyl Grignard or aryl-lithium 2.1 to N-Boc-L-pyroglutamic acid methyl ester 2.2 provided intermediate 2.3, as described by Colandrea et al. in *Bioorg. & Med. Chem. Lett.* 2006, 16, 2905-2908 and Ying-zi Xu et al. in *J. Org. Chem.* 1999, 64, 4069-4078. One pot Boc deprotection and cyclic imine formation under acidic conditions afforded cyclic imine intermediate 2.4 which could be reduced either by hydrogenation or by borohydride reagent to give the pyrrolidine ester intermediate 1.1. In some cases epimers 1.1a and 1.1b were separated by flash chromatography.

Aryl or alkyl Grignard and aryl-lithium reagents 2.1 were prepared using the methodologies shown in scheme Scheme 3: Synthetic scheme for the preparation of aryl or alkyl magnesium and aryl-lithium reagents Route 1

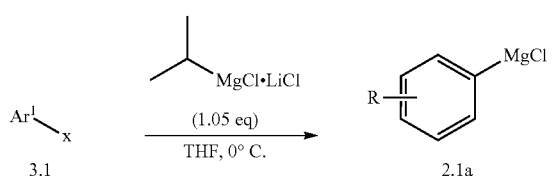

Route 2

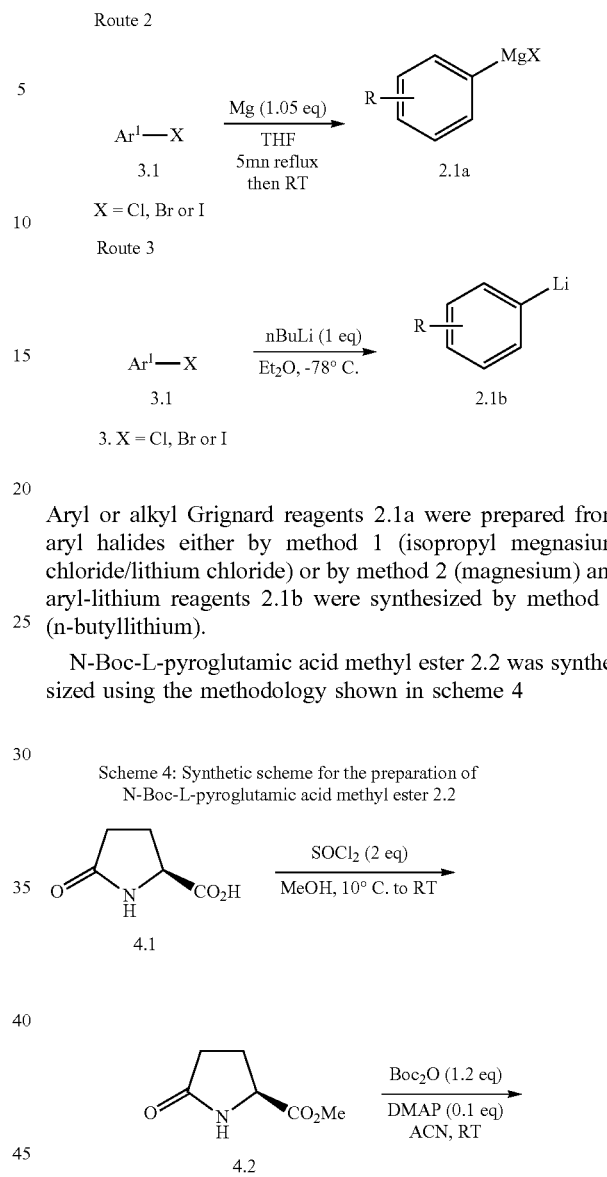

Aryl or alkyl Grignard reagents 2.1a were prepared from aryl halides either by method 1 (isopropyl megnasium chloride/lithium chloride) or by method 2 (magnesium) and aryl-lithium reagents 2.1b were synthesized by method 3 (n-butyllithium).

N-Boc-L-pyroglutamic acid methyl ester 2.2 was synthesized using the methodology shown in scheme 4

Scheme 4: Synthetic scheme for the preparation of N-Boc-L-pyroglutamic acid methyl ester 2.2

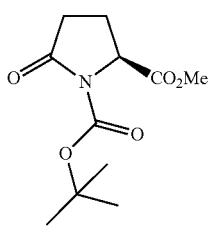

L-pyroglutamic acid 4.1 was converted to the methyl ester 4.2 which upon Boc protection with di-tert-butyl dicarbonate afforded intermediate 2.2.

Biaryl and heterobiaryl carboxylic acid intermediates 1.2a were synthesized using one of the three routes (a, b or c) shown in scheme 5.

Scheme 5: Synthetic scheme for the preparation of biaryl carboxylic acid intermediates 1.2a
Route a:

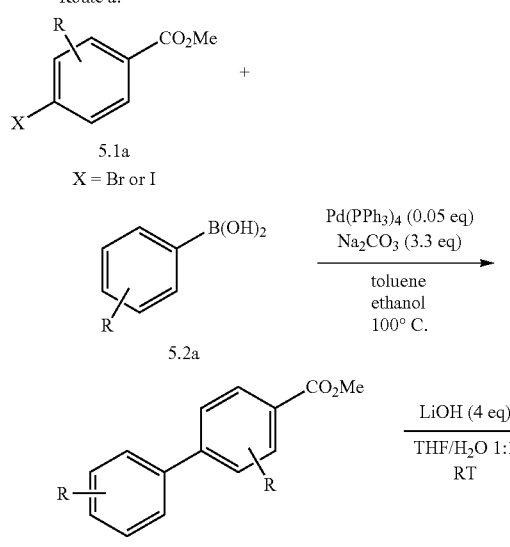

Route b:

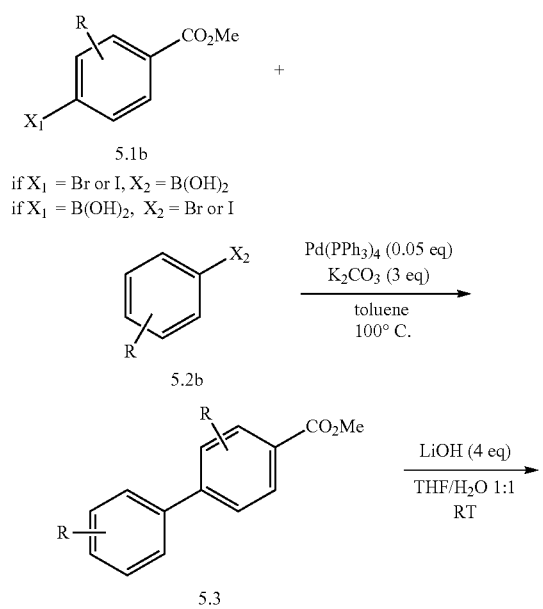

Route c:

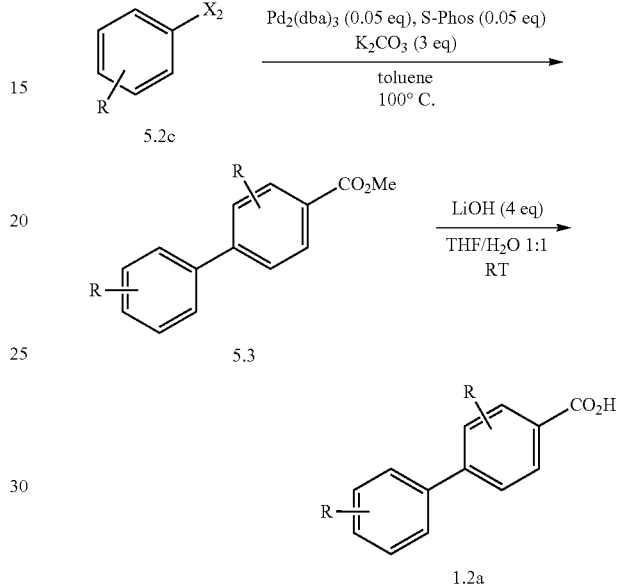

Suzuki coupling between 5.1 and 5.2 provided biaryl ester intermediate 5.3, subsequent saponification with lithium hydroxide afforded biaryl carboxylic acid intermediate 1.2a.

Aralkyloxyaryl carboxylic acid intermediates 1.2 were synthesized using the methodology shown in scheme 6 for benzyloxybenzoic acid intermediates 1.2b.

Scheme 6: Synthetic scheme for the preparation of benzyloxybenzoic acid intermediates 1.2b

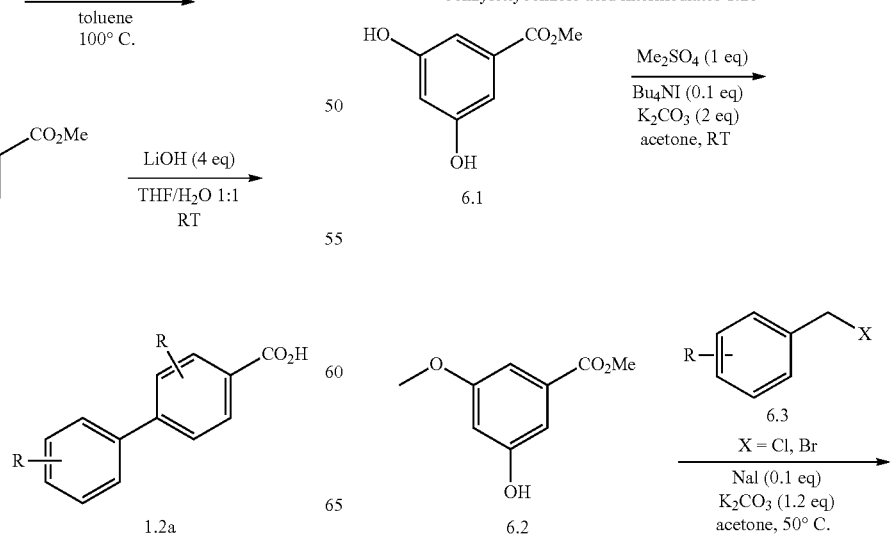

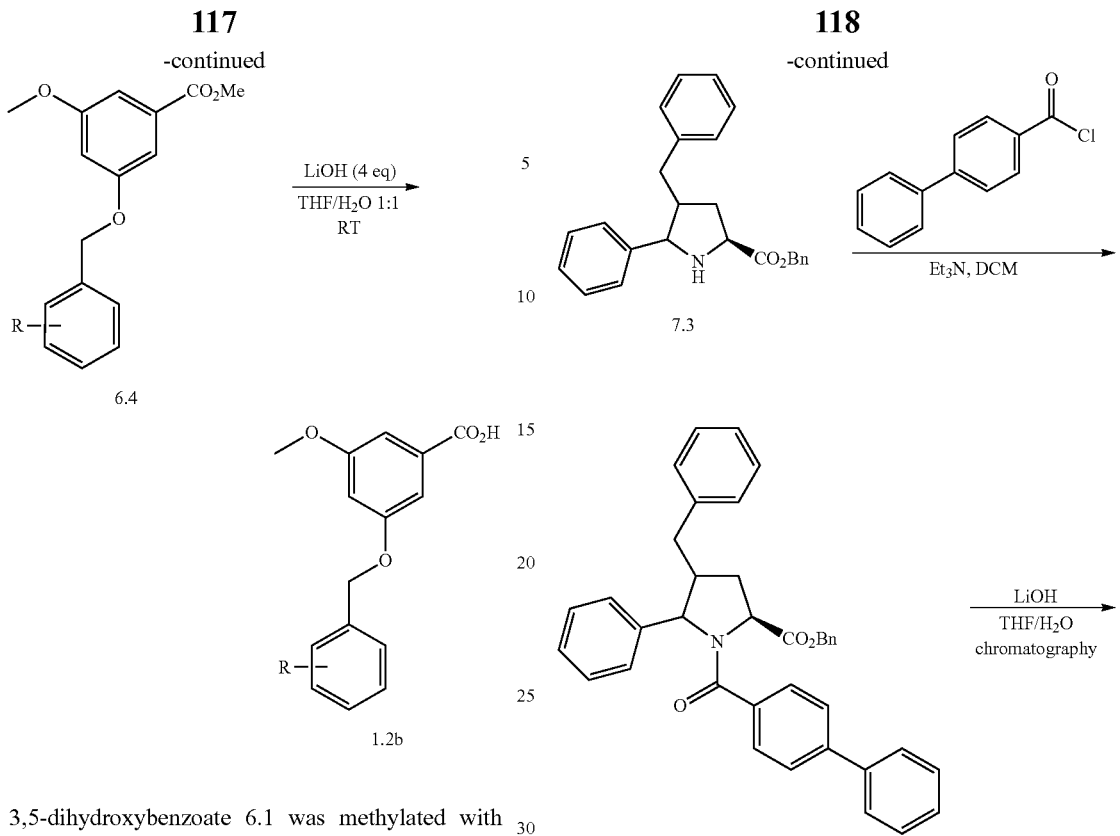

Methyl 3,5-dihydroxybenzoate 6.1 was methylated with dimehylsulfate to give intermediate 6.2. Benzylation with benzyl halide reagent 6.3 provided ester intermediate 6.4 which upon subsequent saponification with lithium hydroxide afforded benzyloxybenzoic acid intermediates 1.2b Additional Synthetic Schemes Synthesis of compound no24 is depicted in scheme 7.

Scheme 7: Synthesis of compound n°24

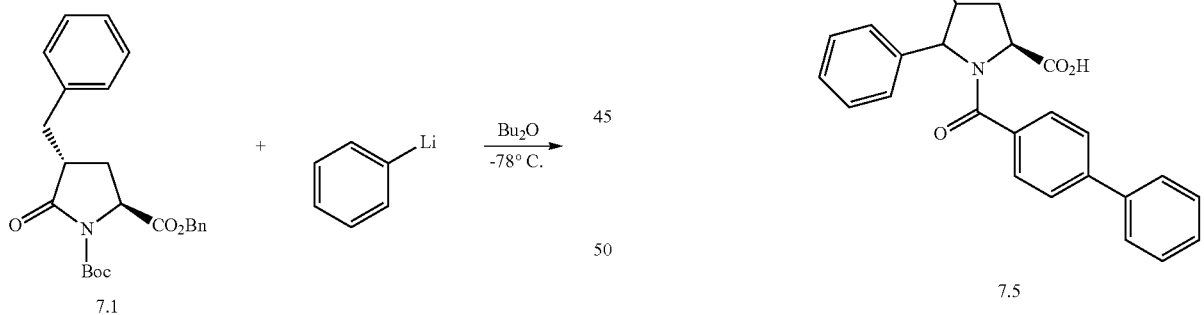

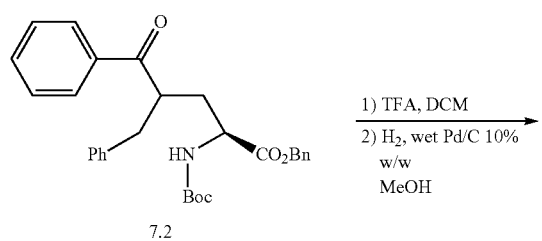

Synthesis of methyl substituted pyrrolidinone intermediates 2.2 is depicted in scheme 8.

Scheme 8: Synthesis of methyl substituted pyrrolidinone intermediates

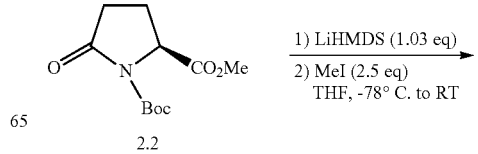

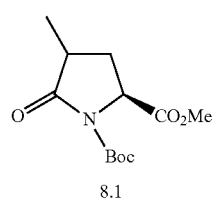
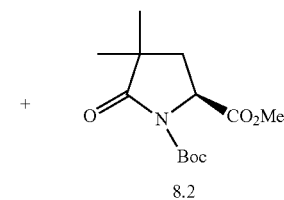
Dipolar cycloaddition methodology is exemplified with the synthesis of compound no217 and is depicted in scheme 9.
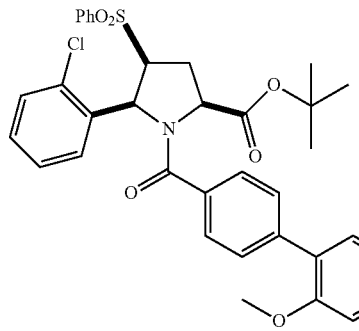
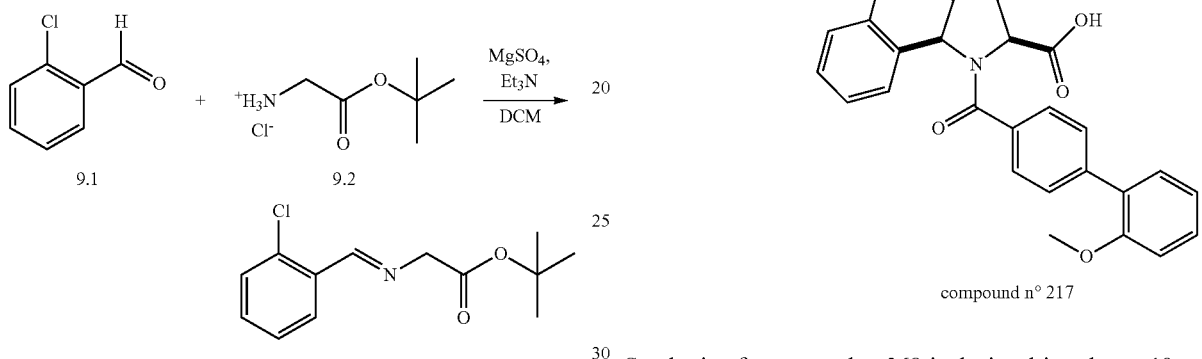
Synthesis of compound no268 is depicted in scheme 10.
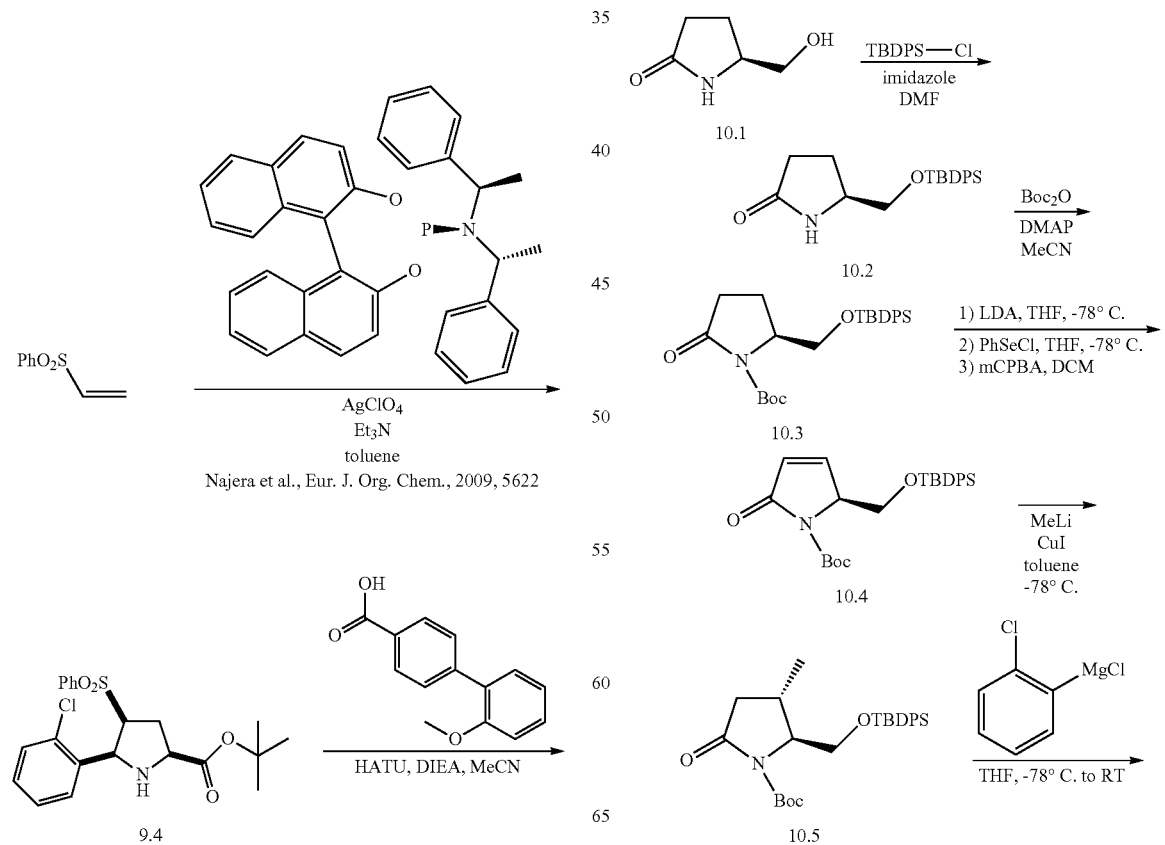

121
-continued
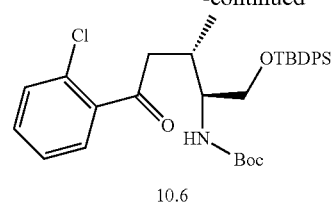
10.6
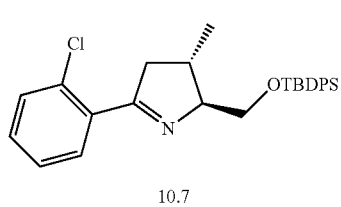
10.7
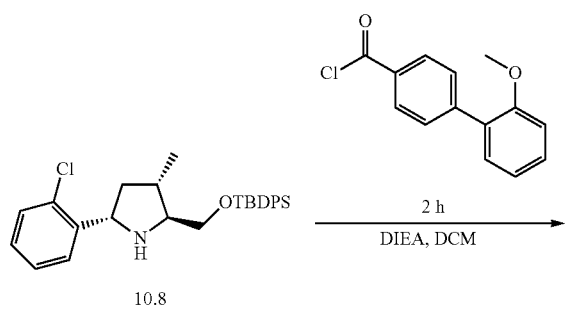
10.8
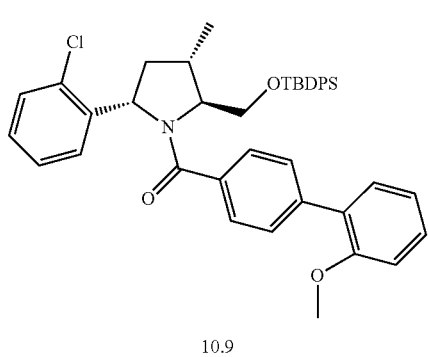
10.9
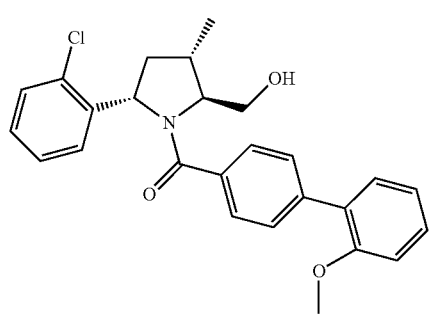
10.10
122
-continued
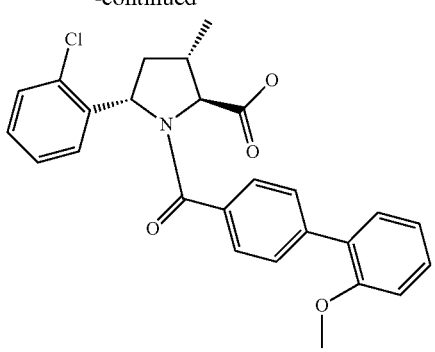
compound n° 268
Synthesis of intermediate 3-methoxy-4-(4-methylpiperidin-1-yl)benzoic acid used in the preparation of compound no261 is depicted in scheme 11.
Scheme 11: Synthesis of intermediate 3-methoxy-4-(4-methylpiperidin-1-yl)benzoic acid
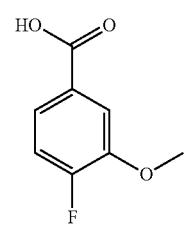
11.1
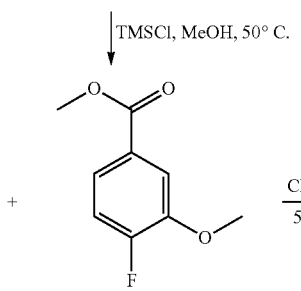
xx 11.2    11.3
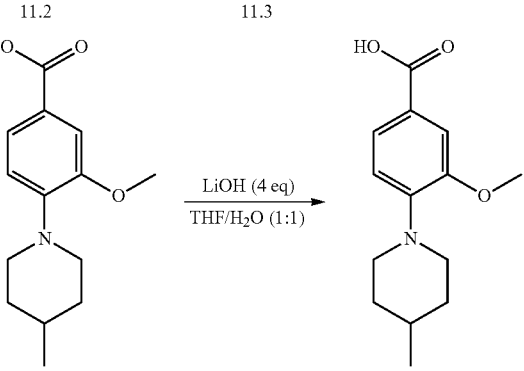
11.4    11.5

The synthesis of compound no393 is depicted in scheme 12.
Scheme 12: synthesis of compound n° 393.
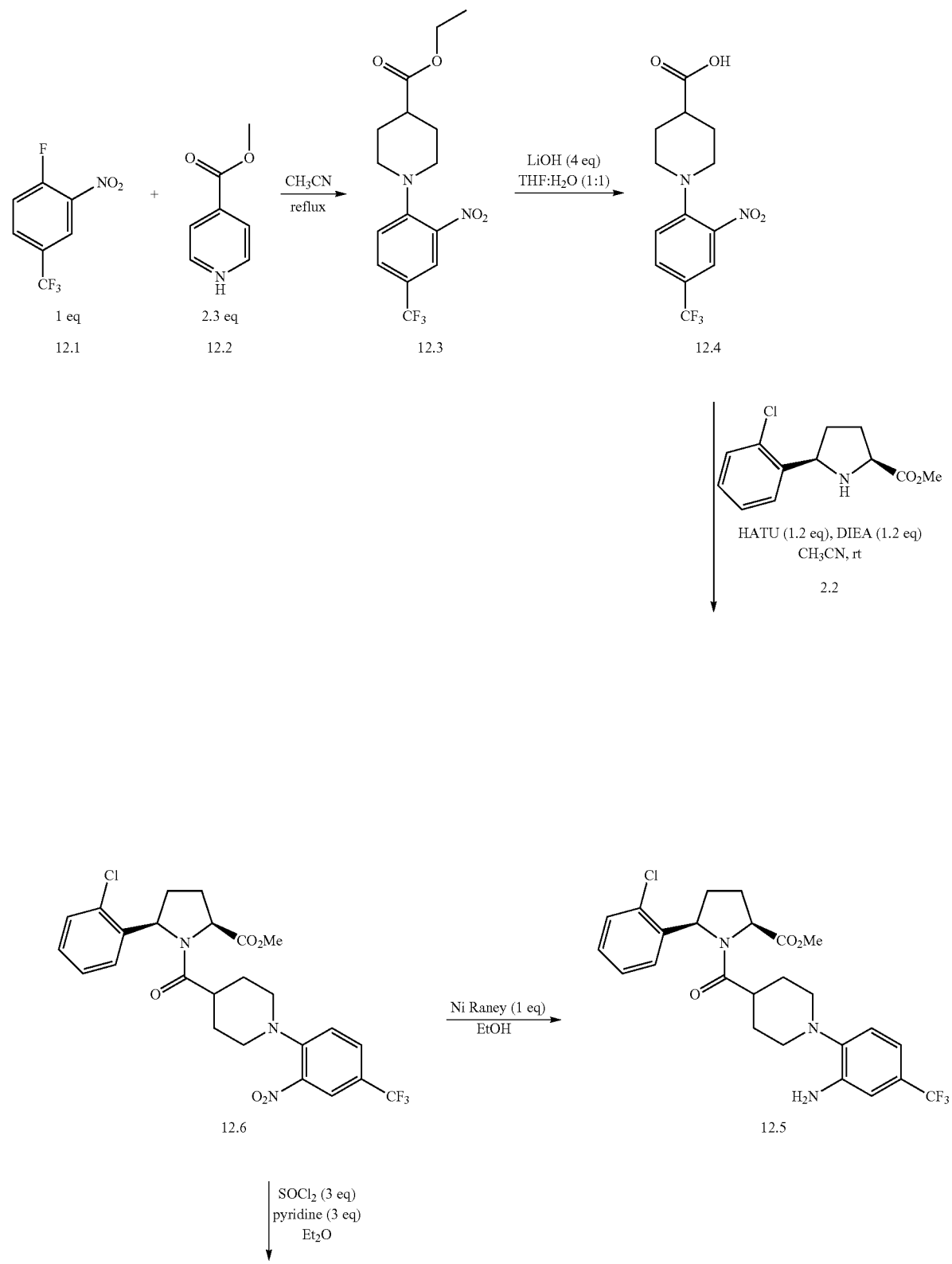

125 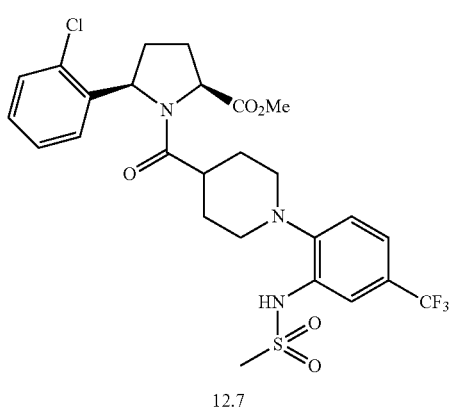 126 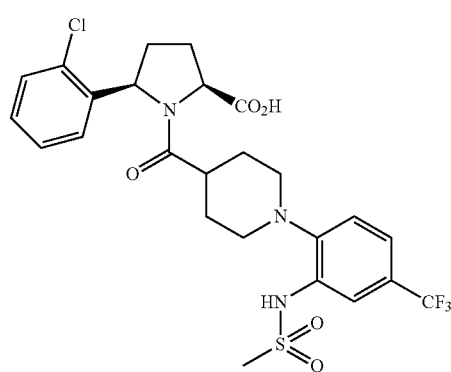
-continued
The synthesis of compound no369 is depicted in scheme 13.
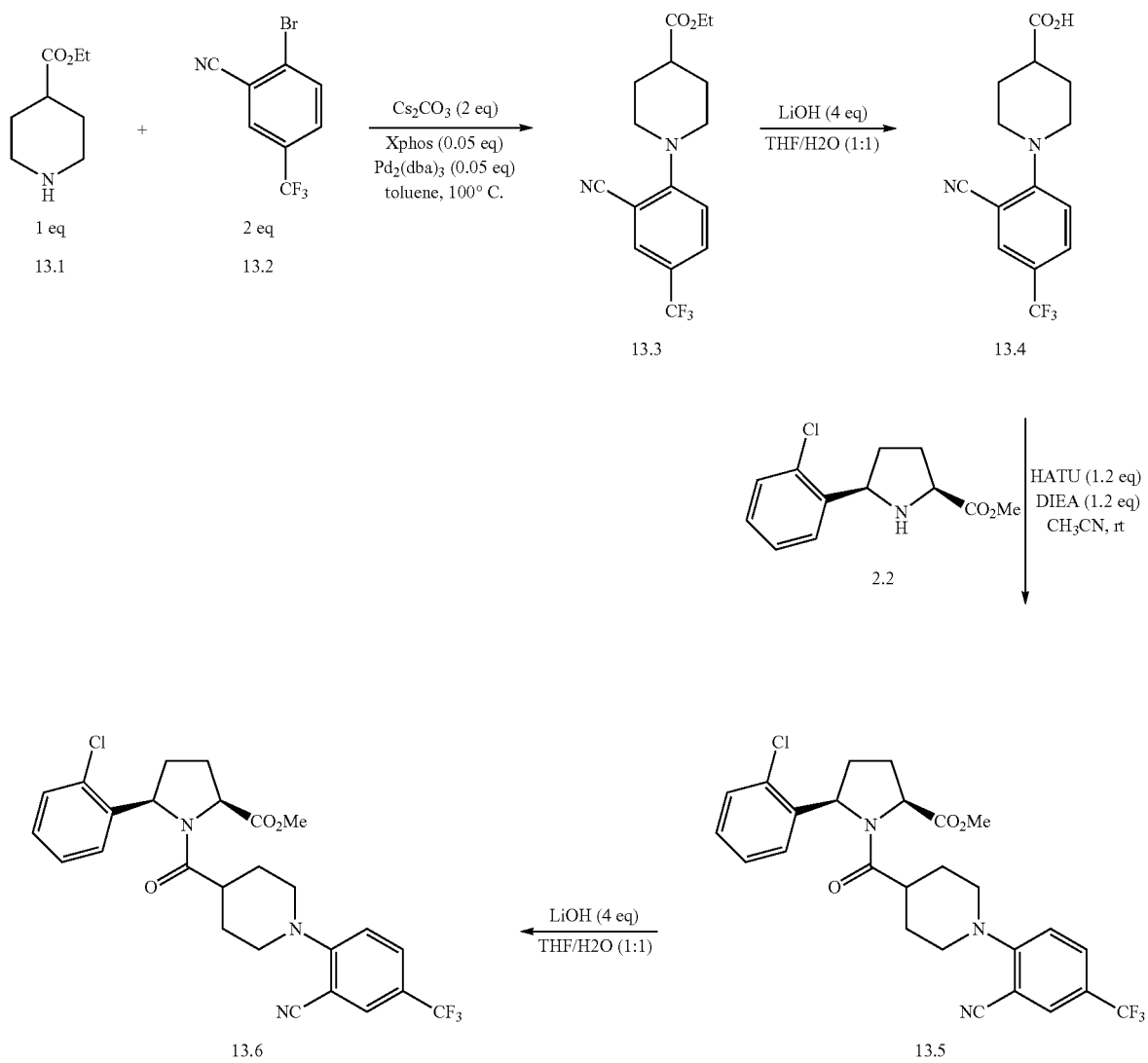
Scheme 13: synthesis of compound n° 369.

Synthesis of compound no279 is depicted in scheme

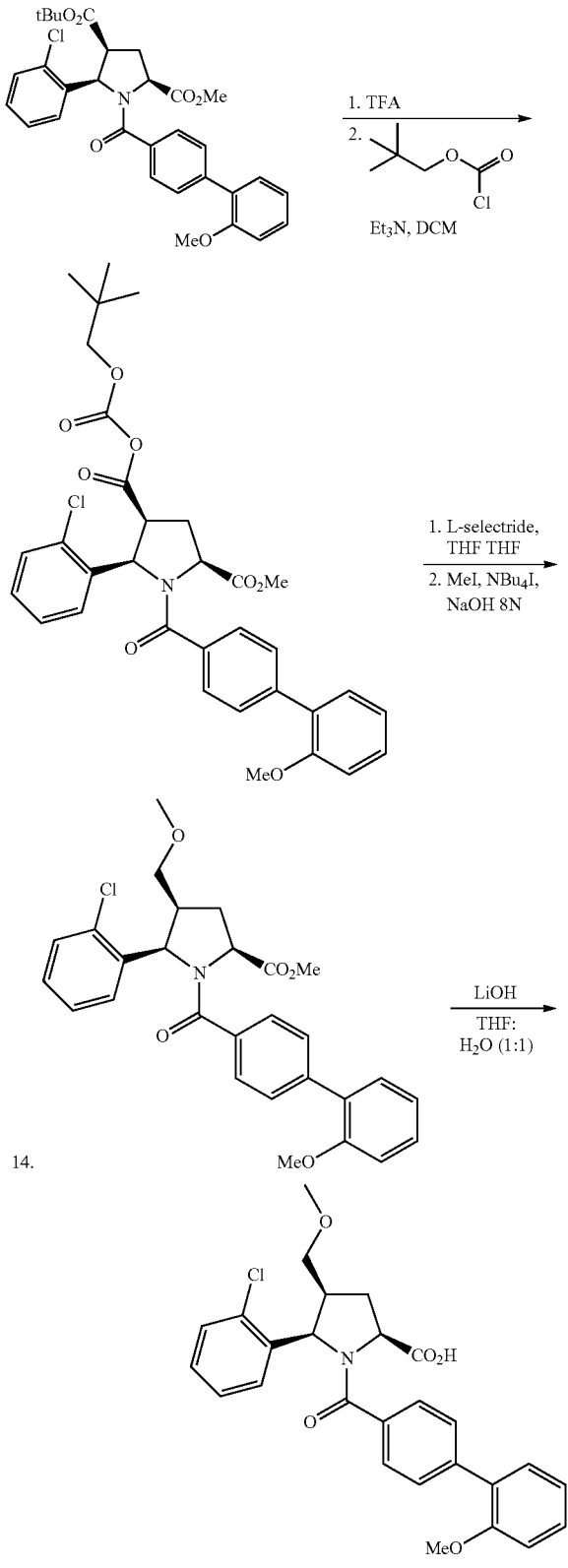

Scheme 14: synthesis of compound n° 279.

14.

General Methods

General Method A: Synthesis of Pyrrolidine Ester Intermediates 1.1

General method A is exemplified with the synthesis of intermediate 1a (2S,5R)-methyl 5-(2-chlorophenyl)pyrrolidine-2-carboxylate, intermediate 1b (2S,5S)-methyl 5-(2-chlorophenyl)pyrrolidine-2-carboxylate and intermediate 1f (2S,5R)-methyl 5-(pyridin-2-yl)pyrrolidine-2-carboxylate from 2-bromopyridine (route 3, conditions E).

Step 1: Synthesis of (2-chlorophenyl)magnesium chloride: Route 1

To a 2M solution of isopropylmagnesium chloride in anhydrous THF (5.76 mmol) was added lithium chloride (5.76 mmol) in distilled THF in a Schlenk tube under Ar atmosphere at RT. The reaction mixture was cooled to −15° C. and 1-bromo-2-chlorobenzene (5.35 mmol) was added and the RM was stirred at −15° C. for another 3 h. This crude solution of (2-chlorophenyl)magnesium chloride was cooled to −40° C. and used as such in step 2.

Step 2: Synthesis of (S)-methyl 2-((tert-butoxycarbonyl)amino)-5-(2-chlorophenyl)-5-oxopentanoate To the crude solution of (2-chlorophenyl)magnesium chloride obtained in step 1 was added at −40° C. under Ar a solution of (S)-1-tert-butyl 2-methyl 5-oxopyrrolidine-1,2-dicarboxylate (4.11 mmol) in distilled THF (4 mL). The reaction mixture was stirred at −40° C. for 2 h and then quenched with 10 mL of a saturated aqueous solution of ammonium chloride. The mixture was extracted three times with AcOEt, combined organics were dried over anhydrous $MgSO_4$ and concentrated in vacuo. Crude was purified by flash chromatography (eluent: cyclohexane/AcOEt) to yield title compound. Y: 425 mg (29%), P: >95%, rt=4.24 min, $(M+H)^+=256$.

Step 3: Synthesis of (S)-methyl 5-(2-chlorophenyl)-3,4-dihydro-2H-pyrrole-2-carboxylate TFA (2 mL) was added to a solution of (S)-methyl 2-((tert-butoxycarbonyl)amino)-5-(2-chlorophenyl)-5-oxopentanoate (1.08 mmol) in DCM (2 mL) and the reaction mixture was stirred at RT for 2 h. The RM was evaporated to dryness to yield title compound. Y: 574 mg (56%), P: >95%, rt=2.85 min, $(M+H)^-=238$.

Step 4

Reaction conditions C: synthesis of intermediate 1a (2S,5R)-methyl 5-(2-chlorophenyl)pyrrolidine-2-carboxylate and intermediate 1b (2S,5S)-methyl 5-(2-chlorophenyl)pyrrolidine-2-carboxylate.

Sodium triacetoxyborohydride (0.091 mol) was added portionwise to a stirred solution of (S)-methyl 5-(2-chlorophenyl)-3,4-dihydro-2H-pyrrole-2-carboxylate (0.076 mol) in 1,2-dichloroethane (200 mL) at RT under a nitrogen atmosphere. TFA (0.76 mol) was added and the reaction mixture was stirred at RT for 1.5 h. LCMS showed starting material still remaining so further TFA (~10 mL) was added (to give pH 3-4) and stirring continued for a further 1.5 h. All starting material was consumed, water (30 mL) was added followed by saturated aqueous $NaHCO_3$ (~400 mL) until neutral pH. The separated aqueous layer was extracted with DCM (2×300 ml) and the combined organics dried over anhydrous $MgSO_4$ and evaporated in vacuo to give a yellow oil (17.5 g). Crude was purified by column chromatography (eluent: PE/EtOAc) to give, as colourless oils, intermediate 1a: Y: 12 g (66%), P: >95%, rt=2.73 min, (M+H)⁺=240 and intermediate 1b Y: 3 g (16%), P: >95%, (M+H)⁺=240.

Reaction conditions D: synthesis of Intermediate (2S)-methyl 5-(2-chlorophenyl)pyrrolidine-2-carboxylate.

Sodium cyanobrorohydride (2.9 mmol) was added to a solution of (S)-methyl 5-(2-chlorophenyl)-3,4-dihydro-2H-pyrrole-2-carboxylate (2.42 mmol) in anhydrous MeOH (20 mL) and the reaction mixture was stirred at RT for 1 h. The RM was quenched with water and extracted with DCM. Combined organics were dried over anhydrous MgSO₄ and concentrated in vacuo to yield title compound. Y: 338 mg (59%), P: >95%, rt=2.73 min, (M+H)⁺=240.

Reaction conditions E: synthesis of intermediate 1f: (2S, 5R)-methyl 5-(pyridin-2-yl)pyrrolidine-2-carboxylate from 2-bromopyridine (route 3).

In a 10 mL round bottomed flask was dissolved (S)-methyl 5-(pyridin-2-yl)-3,4-dihydro-2H-pyrrole-2-carboxylate (0.208 mmol) in IPA (550 µL) to give a brown solution. Palladium on carbon (3.95 µmol) (10% w/w) was added, and reaction was stirred under H₂ atmosphere.
Reaction mixture was stirred overnight at RT. The mixture was filtered through celite and concentrated under reduced pressure to give intermediate if in a quantitative yield. Y: 12 g (66%), P: >95%, rt=2.34 min, (M+H)⁺=207.

The following intermediates were synthesized from ad-hoc reagents using general method A:

intermediate 1c: (2S,5R)-methyl 5-(3-chloropyridin-2-yl)pyrrolidine-2-carboxylate from 2-bromo-3-chloropyridine (route 3, conditions C);
intermediate 1e: (2S)-methyl 5-([1,1'-biphenyl]-3-yl)pyrrolidine-2-carboxylate from biphenyl-3-ylmagnesium bromide (conditions C);
intermediate 1g: (2S)-methyl 5-(2-fluorophenyl)pyrrolidine-2-carboxylate from 1-bromo-2-fluorobenzene (route 1, conditions C), rt=2.5 min (gradient A);
intermediate 1i: (2S)-methyl 5-(2-methoxyphenyl)pyrrolidine-2-carboxylate 1-bromo-2-methoxybenzene (route 1, conditions D);
intermediate 1j: (2R)-methyl 5-(2-chlorophenyl)pyrrolidine-2-carboxylate from 1-bromo-2-chlorobenzene (route 1, conditions D);
intermediate 1k: (2S)-methyl 5-(4-chlorophenyl)pyrrolidine-2-carboxylate from 4-chlorophenylmagnesium bromide (conditions C);
intermediate 1l: (2S)-methyl 5-([1,1'-biphenyl]-4-yl)pyrrolidine-2-carboxylate from [1,1'-biphenyl]-4-ylmagnesium bromide (conditions C);
intermediate 1m: (2S)-methyl 5-(2-chlorobenzyl)pyrrolidine-2-carboxylate from 2-chlorobenzylmagnesium chloride (conditions C);
intermediate 1n: (2S)-methyl 5-cyclohexylpyrrolidine-2-carboxylate from cyclohexylmagnesium chloride (conditions C);
intermediate 1o: (2S)-methyl 5-([1,1'-biphenyl]-2-yl)pyrrolidine-2-carboxylate from [1,1'-biphenyl]-2-ylmagnesium bromide (conditions C);
intermediate 1p: (2S,5R)-methyl 5-(2-chlorophenyl)-4,4-dimethylpyrrolidine-2-carboxylate (conditions C), starting from (S)-1-tert-butyl 2-methyl-4,4-dimethyl-5-oxopyrrolidine-1,2-dicarboxylate obtained using the synthetic route described in scheme 8;
intermediate 1q: (2S,5R)-methyl 5-(2-chlorophenyl)-4-methylpyrrolidine-2-carboxylate (conditions C), starting from (S)-1-tert-butyl 2-methyl-4-dimethyl-5-oxopyrrolidine-1,2-dicarboxylate;
intermediate 1r: (2S,5R)-methyl 5-(pyridin-3-yl)pyrrolidine-2-carboxylate;
intermediate 1s: (2S,5R)-methyl 5-(o-tolyl)pyrrolidine-2-carboxylate;
intermediate 1t: (2S,5R)-methyl 5-phenylpyrrolidine-2-carboxylate (condition E);
intermediate 1u: (2S,5R)-methyl 5-(3-chlorophenyl)pyrrolidine-2-carboxylate (route 1, conditions C);
intermediate 1v: (2S,5R)-methyl 5-(4-chlorophenyl)pyrrolidine-2-carboxylate (route 1, conditions C);
intermediate 1w: (2S,5R)-5-(3-fluorophenyl)pyrrolidine-2-carboxylic acid (route 1, conditions E);
intermediate 1x: (2S,5R)-methyl 5-(4-fluorophenyl)pyrrolidine-2-carboxylate (route 1, conditions E);
intermediate 1y: (2S,5R)-methyl 5-cyclohexylpyrroldine-2-carboxylate was synthesized by hydrogenation of intermediate 1t using PtO₂ in MeOH,
intermediate 1z: (2R,5R)-methyl 5-(2-fluorophenyl)pyrrolidine-2-carboxylate (route 1, conditions C);
intermediate 1a1: (2S,5S)-methyl 5-(2-fluorophenyl)pyrrolidine-2-carboxylate (route 1, conditions C);
intermediate 1b1: (2R,5S)-methyl 5-(2-fluorophenyl)pyrrolidine-2-carboxylate (route 1, conditions C);
intermediate 1c1: (2S,5R)-methyl 5-(2,6-difluorophenyl)pyrrolidine-2-carboxylate (route 1, conditions E);
intermediate 1d1: (2S,5R)-methyl 5-(2,4-difluorophenyl)pyrrolidine-2-carboxylate (route 1, conditions E);
intermediate 1e1: (2S,5R)-methyl 5-(2,4-dichlorophenyl)pyrrolidine-2-carboxylate (route 1, conditions C);
intermediate 1f1: (2S,5R)-methyl 5-isobutylpyrrolidine-2-carboxylate (route 2, conditions E);
intermediate 1g1: (2S,5R)-methyl 5-isopropylpyrrolidine-2-carboxylate (route 1, conditions E);
intermediate 1h1: (2S,5R)-methyl 5-cyclopentylpyrrolidine-2-carboxylate (conditions E);
intermediate 1i1: (2S,5R)-methyl 5-(2-bromophenyl)pyrrolidine-2-carboxylate (route 1, conditions C);
intermediate 1j1: (2S,5S)-methyl 5-isopentylpyrrolidine-2-carboxylate (route 2, conditions E);
intermediate 1k1: (2S,5R)-methyl 5-(2,4-difluorophenyl)pyrrolidine-2-carboxylate (route 1, conditions E);
intermediate 1l1: (2S,5R)-methyl 5-(3,5-difluorophenyl)pyrrolidine-2-icarboxylate (route 1, conditions C);
intermediate 1m1: (2S,5R)-methyl 5-(3,4-difluorophenyl)pyrrolidine-2-carboxylate (route 1, conditions C);
intermediate 1n1: (2S,5R)-methyl 5-(2,3-difluorophenyl)pyrrolidine-2carboxylate (route 1, conditions C), rt=2.6 min (gradient A);
intermediate 1o1: (2S,5R)-methyl 5-(2,5-difluorophenyl)pyrrolidine-2-carboxylate (route 1, conditions C);
intermediate 1p1: (2S,5R)-methyl 5-(4-cyanophenyl)pyrrolidine-2-carboxylate. (route 1, conditions C).

General Method B: Synthesis of Aryloxyaryl Carboxylic Acid Intermediates 1.2b

General method B is exemplified with the synthesis of intermediate 2a 3-(benzyloxy)-5-methoxybenzoic acid.

Step 1: Synthesis of methyl 3-hydroxy-5-methoxybenzoate

To a solution of methyl 3,5-dihydroxybenzoate (29.76 mmol) in anhydrous acetone (40 mL) was added dimethylsulfate (29.69 mmol), tetrabutylammonium iodide (2.97 mmol) and potassium carbonate (59.42 mmol). The reaction mixture was stirred at RT overnight. The RM was diluted with water and extracted with AcOEt. Combined organics were dried over anhydrous MgSO₄ and concentrated in vacuo. Crude was purified by flash chromatography (eluent: PE/AcOEt) to yield title compound. Y: 1.7 g (31%), P: >95%, rt=3.75 min, (M+H)$^+$=183.

Step 2: Synthesis of methyl 3-(benzyloxy)-5-methoxybenzoate

To a solution of methyl 3-hydroxy-5-methoxybenzoate (0.55 mmol) in anhydrous acetone (2 mL) was added benzyl bromide (0.55 mmol), potassium carbonate (0.66 mmol) and sodium iodide (0.055 mmol). The reaction mixture was stirred at 55° C. for 5 h. The RM was diluted with AcOEt and a 1M aqueous solution of sodium hydroxide. The organic layer was separated, dried over anhydrous MgSO$_4$ and concentrated in vacuo. Crude was purified by flash chromatography (eluent: PE/AcOEt) to yield title compound. Y: 104 mg (69%), P: >95%, rt=4.53 min, (M+H)$^+$=273.

Step 3: Synthesis of intermediate 2a 3-(benzyloxy)-5-methoxybenzoic Acid

To a solution of methyl 3-(benzyloxy)-5-methoxybenzoate (0.38 mmol) in THF (1 mL) was added a solution of lithium hydroxide (1.53 mmol) in water (1 mL). The reaction mixture was stirred at RT overnight. The RM was quenched with a 1M HCl aqueous solution and extracted three times with DCM. Combined organics were dried over anhydrous MgSO$_4$ and concentrated in vacuo to yield title compound. Y: 92 mg (94%), P: >95%, rt=3.95 mn, (M+H)$^+$=259.

The following intermediates were synthesized from ad-hoc reagents using general method B:

intermediate 2b: 3((4-chlorobenzypoxy)-5-methoxybenzoic acid, intermediate 2c: 3-methoxy-5-phenethoxybenzoic acid, intermediate 2d: 3-(3,3-diphenylpropoxy)-5-methoxybenzoic acid, intermediate 2e: 3-methoxy-5-((4-(methylsulfonyl)benzyl)oxy)benzoic acid, intermediate 2f: 3-methoxy-5-(2-methoxyethoxy)benzoic acid, intermediate 2g: 34(3,5-dimethylisoxazol-4-yl)methoxy)-5-methoxybenzoic acid, General Method C: Synthesis of Most Compounds of the Invention General method C is exemplified with the synthesis of Example 1: compound no1: (2S,5R)-5-(2-chlorophenyl)-1-(2'-methoxy-[1,1'-biphenyl]-4-carbonyl)pyrrolidine-2-carboxylic acid.

Step 1: Synthesis of (2S,5R)-methyl 5-(2-chlorophenyl)-1-(2'-methoxy-[1,1'-biphenyl]-4-carbonyl)pyrrolidine-2-carboxylate Conditions A:

In a 100 mL round bottom flask, under argon, was dissolved 2'-methoxybiphenyl-4-carboxylic acid (15.714 g, 68.8 mmol) in DCM (138 mL). A white suspension was obtained to which were successively added thionyl chloride (7.49 mL, 103 mmol) and DMF (0.107 mL, 1.377 mmol). Reaction mixture was heated at reflux (40° C.) 3 hours. The solution was allowed to reach spontaneously RT (yellow-orange solution). RM was concentrated under reduced pressure. Removal of the excess of thionyl chloride was done by two co-evaporation cycles with DCM. The resulting brown residue was dried under vacuum to afford 17 g of a brown solid. Crude product was used without further purification in the next step.

In a 500 mL, round bottom flask were introduced under argon methyl (2S,5R)-5-(2-chlorophenyl)pyrrolidine-2-carboxylate (15 g, 62.6 mmol), DCM (62.4 mL) and Et$_3$N (9.59 mL, 68.8 mmol). To this solution cooled to 0° C., was added dropwise (via an addition funnel) a solution of 2'-methoxybiphenyl-4-carbonyl chloride (16.98 g, 68.8 mmol) in DCM (83 mL) (dark brown solution). The RM was stirred from 0° C. to RT overnight. The RM was transferred to a separation funnel and washed with 25 mL of HCl 6M diluted with 75 mL water. The organic layer was dried under stirring with MgSO$_4$ in the presence of 0.3 g of Norit AS, filtered and concentrated to afford 34 g of a light brown foaming oily residue. Purification by column chromatography (eluent: EtOAc/PE: 1/2) yielded desired product as a beige solid. Y: 25.4 g (90%), P>95%.

Conditions B: To a solution of 2'-methoxybiphenyl-4-carboxylic acid 2b (1.1 mmol) in anhydrous ACN (2 mL) was added HATU (1.1 mmol). After 5 min was added (2S,5R)-methyl 5-(2-chlorophenyl)pyrrolidine-2-carboxylate 1a (1 mmol) and DIEA (1.2 mmol). Reaction mixture was stirred at RT for 4 days. Reaction mixture was diluted with AcOEt and washed with saturated aqueous solution of NaHCO$_3$ and with water. The organic phase was dried over MgSO$_4$ and evaporated. Crude was purified by flash chromatography (eluent: cyclohexane/AcOEt) to yield title compound. Y: 300 mg (67%), P>95%, rt=4.85 min (M+H)$^+$=451.

Step 2: Synthesis of Example 1: Compound no1: (2S,5R)-5-(2-chlorophenyl)-1-(2'-methoxy-[1,1'-biphenyl]-4-carbonyl)pyrrolidine-2-carboxylic Acid To a solution of (2S,5R)-methyl 5-(2-chlorophenyl)-1-(2'-methoxy-[1,1'-biphenyl]-4-carbonyl)pyrrolidine-2-carboxylate (0.67 mmol) in THF (5 mL) was added a solution of lithium hydroxide (2.67 mmol) in water (5 mL). The reaction mixture was stirred at RT overnight. The RM was quenched with a 1M HCl aqueous solution and extracted twice with AcOEt. Combined organics were dried over anhydrous MgSO$_4$ and concentrated in vacuo to yield title compound as a colorless solid. Y: 250 mg (86%), P: >95%, rt=6.05 min, (M+H)$^+$=436.

General Method D: Synthesis of Biaryl Carboxylic Acid Intermediates 1.2a

Three routes (a, b and c) were used in the preparation of biaryl or heterobiaryl intermediates.

Route a is exemplified with the synthesis of intermediate 2h 2'-methoxy-[1,1'-biphenyl]-4-carboxylic acid.

Step 1: Synthesis of methyl 2'-methoxy-[1,1'-biphenyl]-4-carboxylate

A mixture of methyl-4-iodobenzoate (86.2 g, 0.33 mol) and 2-methoxyphenyl boronic acid (50.0 g, 0.33 mol) in toluene (975 mL) and EtOH (525 mL) was degassed with nitrogen bubbling for 30 minutes. Pd(PPh$_3$)$_4$ (19.0 g, 16.5 mmol) and 4M aqueous Na$_2$CO$_3$ (271.5 mL, 1.09 mol) were added and the mixture stirred at 100° C. under a nitrogen atmosphere overnight. After cooling to room temperature, EtOAc (1.5 L) and water (1.5 L) were added, and the separated organic layer was dried (Na$_2$SO$_4$) and evaporated in vacuo to leave a brown oily solid (107 g). The residue was purified by column chromatography using an increasing gradient from 5-50% EtOAc/petrol to give title product as a yellow solid. Y: 51 g (64%), P>80%.

Step 2: Synthesis of Intermediate 2h 2'-methoxy-[1,1'-biphenyl]-4-carboxylic Acid LiOH.H$_2$O (89 g, 2.1 mol) was added to a stirred suspension of methyl 2'-methoxy-[1,1'-biphenyl]-4-carboxylate (51 g, 0.21 mol) in a mixture of THF (500 mL) and H$_2$O (1 L). Further amounts of THF (~500 mL) and H$_2$O (~1 L) were added to dissolve the majority of the solids. After stirring overnight at room temperature, more solids had precipitated and starting material still remained. The mixture was heated to 50° C. for 4 hours, after which time all solids had dissolved and no starting material remained. After cooling to room temperature, saturated aqueous citric acid was added until pH=6-7, which produced a white precipitate. THF was removed by evaporation in vacuo and the resulting suspension filtered. The solid was washed with water several times and dried at 50° C. overnight to give intermediate 2 h as an off-white solid. Y: 43 g (90%), P>90%.

Route b is exemplified with the synthesis of intermediate 2s2 4-(2-methoxypyrimidin-4-yl)benzoic acid.

Step 1: Synthesis of methyl 4-(2-methoxypyrimidin-4-yl)benzoate

In an oven dried glass tube, were introduced under argon 4-methoxycarbonylphenylboronic acid (381 mg, 2.116 mmol) and 4-bromo-2-methoxypyrimidine (200 mg, 1.058 mmol). Three vacuum/Argon cycles were performed and toluene (5 mL) was added, followed by a 2M aqueous solution of K$_2$CO$_3$ (0.106 mmol). The resulting mixture was degassed (argon bubbling into the solution for 5-10 minutes).

Tetrakis(triphenylphosphine)palladium(0) (0.1 mmol) was then added and the mixture was heated to 95° C. overnight. The mixture was cooled down to room temperature and then diluted with EtOAc and washed with brine. The aqueous layer was further extracted with EtOAc and the combined organic layers were dried and concentrated. The residue was purified on silica gel (cyclohexane/EtOAc), furnishing 243 mg of desired product as a pale yellow solid (94% yield).

Step 2: Synthesis of Intermediate 2s2 4-(2-methoxypyrimidin-4-yl)benzoic acid

The same conditions as in step 2 of route a were used.
The following intermediates were synthesized from ad-hoc reagents using general method D route b:
intermediate 2i: 2',5'-dichloro-[1,1'-biphenyl]-4-carboxylic acid;
intermediate 2j: 4-(pyrimidin-5-yl)benzoic acid;
intermediate 2k: 4-(furan-3-yl)benzoic acid;
intermediate 2l: 4-(6-methoxypyridin-3-yl)benzoic acid,
intermediate 2m: 4-(3-fluoropyridin-4-yl)benzoic acid;
intermediate 2n: 4-(pyridin-3-yl)benzoic acid;
intermediate 2o: 4-(6-(dimethylamino)pyridin-3-yl)benzoic acid;
intermediate 2p: 4-(pyridin-4-yl)benzoic acid;
intermediate 2q: 4-(6-methylpyridin-3-yl)benzoic acid;
intermediate 2r: 4-(2-methoxypyridin-3-yl)benzoic acid, rt=3.4 min (gradient A);
intermediate 2s: 4'-methoxy-[1,1'-biphenyl]-4-carboxylic acid;
intermediate 2t: 4'-cyano-[1,1'-biphenyl]-4-carboxylic acid;
intermediate 2u: 4-(4-methoxypyridin-3-yl)benzoic acid;
intermediate 2v: 4'-chloro-[1,1'-biphenyl]-4-carboxylic acid;
intermediate 2w: 3'-chloro-[1,1'-biphenyl]-4-carboxylic acid;
intermediate 2x: 2'-chloro-[1,1'-biphenyl]-4-carboxylic acid;
intermediate 2y: 4'-(methylsulfonamido)-[1,1'-biphenyl]-4-carboxylic acid;
intermediate 2z: 3'-(methylsulfonamido)-[1,1'-biphenyl]-4-carboxylic acid;
intermediate 2a1: 2'-(methylsulfonamido)-[1,1'-biphenyl]-4-carboxylic acid;
intermediate 2b1: 4-(naphthalen-2-yl)benzoic acid;
intermediate 2c1: 3',5'-difluoro-[1,1'-biphenyl]-4-carboxylic acid;
intermediate 2d1: 2'-hydroxy-[1,1'-biphenyl]-4-carboxylic acid;
intermediate 2e1: 2'-(trifluoromethoxy)-[1,1'-biphenyl]-4-carboxylic acid;
intermediate 2f1: 4-(3-fluoropyridin-4-yl)benzoic acid;
intermediate 2g1: 4-(6-chloropyridin-3-yl)benzoic acid;
intermediate 2h1: 4-(6-fluoropyridin-3-yl)benzoic acid;
intermediate 2i1: 5-methoxy-6-phenylnicotinic acid;
intermediate 2j1: 4-(3-methoxypyridin-4-yl)benzoic acid;
intermediate 2k1: 2-methoxy-[1,1'-biphenyl]-4-carboxylic acid;
intermediate 2l1: 4-(6-chloropyridin-3-yl)benzoic acid;
intermediate 2m1: 4-(6-fluoropyridin-3-yl)benzoic acid;
intermediate 2n1: 4-(thiophen-3-yl)benzoic acid;
intermediate 2o1: 4-cyclohexylbenzoic acid;
intermediate 2p1: 2'-(methylsulfonyl)-[1,1'-biphenyl]-4-carboxylic acid;
intermediate 2q1: 4-(pyrimidin-2-yl)benzoic acid;
intermediate 2r1: 4-(4,6-dimethoxypyrimidin-2-yl)benzoic acid;
intermediate 2s1: 4-(2,4-dimethoxypyrimidin-5-yl)benzoic acid, rt=3.4 min (gradient A);
intermediate 2t1: 4-(2-methoxypyrimidin-5-yl)benzoic acid;
intermediate 2u1: 4-(pyridin-2-yl)benzoic acid;
intermediate 2v1: 2'-cyano-[1,1'-biphenyl]-4-carboxylic acid;
intermediate 2w1: 2',6'-dimethoxy-[1,1'-biphenyl]-4-carboxylic acid,
intermediate 2x1: 2',4'-dichloro-[1,1'-biphenyl]-4-carboxylic acid;
intermediate 2y1: 2'-(trifluoromethyl)-[1,1'-biphenyl]-4-carboxylic acid;
intermediate 2z1: 2,2'-dimethoxy-[1,1'-biphenyl]-4-carboxylic acid;
intermediate 2a2: 4'-chloro-2'-methoxy-[1,1'-biphenyl]-4-carboxylic acid;
intermediate 2b2: 4-(4-methoxypyrimidin-5-yl)benzoic acid;
intermediate 2c2: 4-(3-fluoropyridin-4-yl)benzoic acid;
intermediate 2d2: 2-chlorobiphenyl-4-carboxylic acid;
intermediate 2e2: 2'-chloro-2-methoxybiphenyl-4-carboxylic acid,
intermediate 2f2: 3-methoxy-4-(pyrimidin-5-yl)benzoic acid;
intermediate 2g2: 2'-(methoxymethyl)biphenyl-4-carboxylic acid;
intermediate 2h2: 4-(2,6-dimethoxypyridin-3-yl)benzoic acid;

intermediate 2i2: 3-methoxy-4-(2-methoxypyrimidin-5-yl)benzoic acid, rt=3.2 min (gradient A);

intermediate 2j2: 4-(5-methoxypyrazin-2-yl)benzoic acid;

intermediate 2k2: 4-(3-methoxypyrazin-2-yl)benzoic acid;

intermediate 2l2: 4-(2-chloro-4-(dimethylamino)pyrimidin-5-yl)benzoic acid;

intermediate 2m2: 4-(2,6-dimethoxypyrimidin-4-yl)benzoic acid;

intermediate 2n2: 4-(2-methylthiophen-3-yl)benzoic acid;

intermediate 2o2: methyl 2',6'-dichlorobiphenyl-4-carboxylate;

intermediate 2p2: 2'-chloro-4'-methoxy-[1,1'-biphenyl]-4-carboxylic acid;

intermediate 2q2: 2'-(dimethylamino)-[1,1'-biphenyl]-4-carboxylic acid;

intermediate 2r2: 3-methoxy-[1,1'-biphenyl]-4-carboxylic acid;

intermediate 2t2: 4-(2-chloro-4-methoxypyrimidin-5-yl)benzoic acid;

intermediate 2u2: 4-(3-methoxypyridin-2-yl)benzoic acid;

intermediate 2v2: 2-(trifluoromethyl)-[1,1'-biphenyl]-4-carboxylic acid;

intermediate 2w2: 2',4'-difluoro-[1,1'-biphenyl]-4-carboxylic acid;

intermediate 2x2: 2-methyl-[1,1'-biphenyl]-4-carboxylic acid;

intermediate 2y2: 3-chloro-4-(pyrimidin-4-yl)benzoic acid;

intermediate 2z2: 2-fluoro-[1,1'-biphenyl]-4-carboxylic acid;

intermediate 2a3: 2'-fluoro-4'-methoxy-[1,1'-biphenyl]-4-carboxylic acid;

intermediate 2b3: 4'-fluoro-2'-methoxy-[1,1'-biphenyl]-4-carboxylic acid;

intermediate 2c3: 4-(6-ethoxypyridin-3-yl)benzoic acid;

intermediate 2d3: 4-(6-isopropoxypyridin-3-yl)benzoic acid;

intermediate 2e3: 4-(6-methoxy-2-methylpyridin-3-yl)benzoic acid;

intermediate 2f3: 3-chloro-4-(2-methoxypyrimidin-4-yl)benzoic acid;

intermediate 2g3: 3-chloro-4-(pyrimidin-5-yl)benzoic acid; intermediate 2h3: 2',3'-dimethoxy-[1,1'-biphenyl]-4-carboxylic acid;

intermediate 2i3: 3',4'-dimethoxy-[1,1'-biphenyl]-4-carboxylic acid;

intermediate 2j3: 2',3',4'-trimethoxy-[1,1'-biphenyl]-4-carboxylic acid;

intermediate 2k3: 2',3',6'-trimethoxy-[1,1'-biphenyl]-4-carboxylic acid;

intermediate 2l3: 3',5'-dimethoxy-[1,1'-biphenyl]-4-carboxylic acid;

intermediate 2m3: 2',5'-dimethoxy-[1,1'-biphenyl]-4-carboxylic acid;

intermediate 2n3: 2'-isopropyl-[1,1'-biphenyl]-4-carboxylic acid;

intermediate 2o3; 2'-ethyl-[1,1'-biphenyl]-4-carboxylic acid;

intermediate 2p3: 4-(2,6-dimethylpyridin-3-yl)benzoic acid;

intermediate 2q3: 4-(2,4-bis(benzyloxy)pyrimidin-5-yl)benzoic acid;

intermediate 2r3: 3-chloro-4-(6-methoxypyridin-3-yl)benzoic acid;

intermediate 2s3: 5-methoxy-6-(2-methoxyphenyl)nicotinic acid;

intermediate 2t3: 5-methoxy-6-(2-methoxyphenyl)nicotinic acid;

intermediate 2u3: 3'-cyano-2'-methoxy-[1,1'-biphenyl]-4-carboxylic acid;

intermediate 2v3: 3'-cyano-2',4'-bis(2,2,2-trifluoroethoxy)-[1,1'-biphenyl]-4-carboxylic acid;

intermediate 2w3: 3'-amino-2'-methyl-[1,1'-biphenyl]-4-carboxylic acid;

intermediate 2x3: 2'-methyl-3'-(methylsulfonamido)-[1,1'-biphenyl]-4-carboxylic acid was obtained by sulfonylation of methyl 3'-amino-2'-methyl-[1,1'-biphenyl]-4-carboxylate (which was synthesized using general method D, route b) and subsequent saponification. Sulfonylation procedure (as in *J. Org. Chem.* 2003, 68, 5300-5309): methyl 3'-amino-2'-methylbiphenyl-4-carboxylate (0.83 mmol) was dissolved in dry $Et_2O$ (5 mL) and cooled to 0° C. Then pyridine (5.00 mmol) was added, followed by dropwise addition of methanesulfonyl chloride (5.00 mmol). The reaction was stirred at RT for 2 h. The precipitate was filtered and washed with $Et_2O$. The organic layer was washed with HCl 1M aqueous solution, brine, dried and concentrated, furnishing 265 mg of desired product as a brown oil in a quantitative yield;

intermediate 2y3: 3'-acetamido-2'-methyl-[1,1'-biphenyl]-4-carboxylic acid was obtained by acetylation of methyl 3'-amino-2'-methyl-[1,1'-biphenyl]-4-carboxylate (which was synthesized using general method D, route b) and subsequent saponification. Acetylation procedure: to a solution of methyl 3'-amino-2'-methylbiphenyl-4-carboxylate (0.83 mmol) in dry DCM (5 mL) under $N_7$ was added acetyl chloride (0.95 mmol), followed by $Et_3N$ (0.91 mmol). The RM was stirred at RT overnight. The RM was then concentrated and the crude purified on silica gel (cyclohexane/EtOAc), furnishing 205 mg of desired product as a yellow oil (87% yield);

intermediate 2z3: 5'-cyano-2'-methoxy-[1,1'-biphenyl]-4-carboxylic acid, rt=3.7 min (gradient A);

intermediate 2a4: 5 cyano-2'-methyl-[1,1'-biphenyl]-4-carboxylic acid, rt=3.9 min (gradient A);

intermediate 2b4: 4-(4,6-dimethoxypyridin-3-yl)benzoic acid;

intermediate 2c4: 4'-acetamido-2'-methoxy-[1,1'-biphenyl]-4-carboxylic acid was obtained by the nitro group reduction of methyl 2'-methoxy-4'-nitro-[1,1'-biphenyl]-4-carboxylate (which was synthesized using general method D, route b) followed by acetylation with acetyl chloride (procedure described in the synthesis of intermediate 2y3) and saponification;

intermediate 2d4: 3-methoxy-4-(5-methoxypyridin-3-yl)benzoic acid;

intermediate 2e4: 2',3,6'-trimethoxy-[2,3'-bipyridine]-5-carboxylic acid;

intermediate 2f4: 5'-cyano-2',3'-dimethoxy-[1,1'-biphenyl]-4-carboxylic acid;

intermediate 2g4: 2'-cyano-4',5'-dimethoxy-[1,1'-biphenyl]-4-carboxylic acid;

intermediate 2h4: 3',4',5'-trimethoxy-[1,1'-biphenyl]-4-carboxylic acid;

intermediate 2i4: 2'-(cyanomethyl)-4',5'-dimethoxy-[1,1'-biphenyl]-4-carboxylic acid;

intermediate 2j4: 3',4'-dicyano-[1,1'-biphenyl]-4-carboxylic acid;

intermediate 2k4: 5'-cyano-2'-fluoro-[1,1'-biphenyl]-4-carboxylic acid;

intermediate 2l4: 2-fluoro-3',4'-dimethoxy-[1,1'-biphenyl]-4-carboxylic acid;

intermediate 2m4: 4-(2,6-dimethoxypyridin-3-yl)-3-fluorobenzoic acid;

intermediate 2n4: 3-fluoro-4-(6-methoxypyridin-3-yl)benzoic acid;

intermediate 2r4: 4-(3,6-dimethoxypyridazin-4-yl)benzoic acid, rt=3.2 min (gradient A);

intermediate 2s4: 2'-cyano-4'-methoxy-[1,1'-biphenyl]-4-carboxylic acid;

intermediate 2u4: 3'-cyano-4'-fluoro-[1,1'-biphenyl]-4-carboxylic acid;

intermediate 2v4: 2'-chloro-5'-cyano-[1,1'-biphenyl]-4-carboxylic acid;

intermediate 2w4: 2'-cyano-4'-(trifluoromethyl)-[1,1'-biphenyl]-4-carboxylic acid;

intermediate 2x4: 2'-methyl-3'-(N-methylmethylsulfonamido)-[1,1'-biphenyl]-4-carboxylic acid was obtained by sulfonylation of methyl 3'-amino-2'-methyl-[1,1'-biphenyl]-4-carboxylate, followed by sulfonamide N-methylation with iodomethane, and subsequent saponification. Methyl 3'-amino-2'-methyl-[1,1'-biphenyl]-4-carboxylate was synthesized using general method D (route b); sulfonamide N-methylation procedure: in a glass tube was introduced methyl 2'-methyl-3'-(methylsulfonamido)biphenyl-4-carboxylate (0.438 mmol) and sodium hydride (0.570 mmol) in dry DMF (2 mL) at room temperature under argon atmosphere. After 30 minutes at room temperature, iodomethane (1.315 mmol) was added and the mixture was stirred at room temperature for 1.5 h. Brine was then added and the aqueous layer was extracted with EtOAc. The organic layer was dried over MgSO$_4$ and concentrated under reduced pressure, furnishing crude desired product as a pale yellow oil in a quantitative yield; rt=3.4 min (gradient A)

intermediate 2y4: 6-(5-cyano-2-methoxyphenyl)-5-methoxynicotinic acid;

intermediate 2z4: 6-(2,4-dimethoxyphenyl)-5-methoxynicotinic acid;

intermediate 2a5: 6-(2,4-dimethoxyphenyl)nicotinic acid; intermediate 2f5: 4-(4,6-dimethoxypyrimidin-5-yl)benzoic acid.

Route c is exemplified for the synthesis of intermediate 2g5 3-chloro-4-(2,4-dimethoxypyrimidin-5-yl)benzoic acid Step 1: Synthesis of methyl
3-chloro-4-(2,4-dimethoxypyrimidin-5-yl)benzoate In a oven dried glass tube were introduced under argon 2-chloro-4-(methoxycarbonyl)phenylboronic acid (2.0 mmol) and 5-iodo-2,4-dimethoxypyrimidine (1.0 mmol). The tube was subjected to three vacuum/argon cycles and toluene (5 mL) was added, followed by a 2M aqueous solution of K$_2$CO$_3$ (3.0 mmol). The resulting mixture was degassed (argon bubbling into the solution for 5-10 minutes). Tris(dibenzylideneacetone)dipalladium(0) (5%) and S-Phos (10%) were then added and mixture was heated to 95° C. overnight. The mixture was cooled down to room temperature and then diluted with EtOAc and washed with brine. The aqueous layer was further extracted with EtOAc and the combined organic layers were dried and concentrated. The residue was purified on silica gel (cyclohex/EtOAc), furnishing 143 mg of desired product as a pale yellow solid (93% yield).

Step 2: Saponification Using Same Procedure of 2h Synthesis

The following intermediates were synthesized from ad-hoc reagents using general method D route c:

intermediate 2h5: 2-fluoro-2'-methoxy-[1,1'-biphenyl]-4-carboxylic acid;

intermediate 2j5: 5-(2-methoxyphenyl)pyrazine-2-carboxylic acid;

intermediate 2k5: 3-methoxy-4-(4-methoxypyridin-3-yl)benzoic acid;

intermediate 2l5: 3-methoxy-4-(6-methoxypyridin-3-yl)benzoic acid;

intermediate 2m5: 3-chloro-4-(2-methoxypyrimidin-5-yl)benzoic acid (exemplified above);

intermediate 2n5: 4-(2,4-dimethoxypyrimidin-5-yl)-3-methoxybenzoic acid;

intermediate 2r4: 4-(3,6-dimethoxypyridazin-4-yl)benzoic acid;

intermediate 2p5: 2'-methoxy-4'-(methylsulfonamido)-[1,1'-biphenyl]-4-carboxylic acid was obtained by the nitro group reduction of methyl 2'-methoxy-4'-nitro-[1,1'-biphenyl]-4-carboxylate (which was synthesized using general method D, route c) followed by sulfonylation with methanesulfonyl chloride (procedure described in the synthesis of intermediate 2x3) and saponification. Nitro reduction procedure: to a solution of methyl 2'-methoxy-4'-nitrobiphenyl-4-carboxylate (1.184 mmol) in anhydrous EtOH (35 ml) was added a slurry of Raney Ni in water (0.4 mL). The mixture was stirred at 50° C. overnight. The RM was filtered on celite, and the solid was washed with MeOH. The filtrate was evaporated to yield desired product which was used without further purification;

intermediate 2q5: 4-(2,6-dimethoxypyridin-3-yl)benzoic acid;

intermediate 2s5: 2-fluoro-4'-(methylsulfonamido)-[1,1'-biphenyl]-4-carboxylic acid was obtained by sulfonylation of methyl 4'-amino-2-fluoro-[1,1'-biphenyl]-4-carboxylate and subsequent saponification. methyl 4'-amino-2-fluoro-[1,1'-biphenyl]-4-carboxylate was synthetized using general method D, route c;

intermediate 2t5: 2-fluoro-3'-(methylsulfonamido)-[1,1'-biphenyl]-4-carboxylic acid was obtained by sulfonylation of methyl 3'-amino-2-fluoro-[1,1'-biphenyl]-4-carboxylate and subsequent saponification. methyl 3'-amino-2-fluoro-[1,1'-biphenyl]-4-carboxylate was synthetized using general method D, route c;

intermediate 2u5: 2'-cyano-2-fluoro-[1,1'-biphenyl]-4-carboxylic acid;

intermediate 2v5: 2'-methoxy-4'-(N-methylmethylsulfonamido)-[1,1'-biphenyl]-4-carboxylic acid was obtained by the nitro group reduction of 2'-methoxy-4'-nitro-[1,1'-biphenyl]-4-carboxylate, followed by sulfonylation with methanesulfonyl chloride, followed by sulfonamide N-methylation with iodomethane, and subsequent saponification; rt=3.7 min (gradient A). Methyl 2'-methoxy-4'-nitro-[1,1'-biphenyl]-4-carboxylate was synthesized using general method D (route c).

Intermediate 2w5 4-(3,6-dimethoxypyridazin-4-yl)-3-fluorobenzoic acid which was obtained from methyl 4-bromo-3-fluorobenzoate and (3,6-dimethoxypyridazin-4-yl)boronic acid using a suzuki coupling procedure described in the literature (*J. Org. Chem.*, 2008, 73, 2176-2181); rt=3.5 min (gradient A).

Unless otherwise stated compounds in examples 2 to 44 were synthesized from intermediate 1a and commercially available carboxylic acids or acyl chlorides using general method C.

Example 2

Compound no2: (2S,5R)-5-(2-chlorophenyl)-1-(2'-methyl-[1,1'-biphenyl]-4-carbonyl)pyrrolidine-2-carboxylic acid.

Example 3

Compound no3: (2S,5R)-1-(3-((4-chlorobenzyl)oxy)-5-methoxybenzoyl)-5-(2-chlorophenyl)pyrrolidine-2-carboxylic acid.

Example 4

Compound no4: (2S,5R)-5-(2-chlorophenyl)-1-(2'-fluoro-[1,1'-biphenyl]-4-carbonyl)pyrrolidine-2-carboxylic acid was synthesized from intermediates 1a and 2b using general method C.

Example 5

Compound no5: (2S,5R)-5-(2-chlorophenyl)-1-(4'-methyl-[1,1'-biphenyl]-4-carbonyl)pyrrolidine-2-carboxylic acid.

Example 6

Compound no6: (2S,5R)-5-(2-chlorophenyl)-1-(3-methoxy-5-phenethoxybenzoyl)pyrrolidine-2-carboxylic acid was synthesized from intermediates 1a and 2c using general method C.

Example 8

Compound no8: (2S,5R)-1-([1,1'-biphenyl]-4-carbonyl)-5-(2-chlorophenyl)pyrrolidine-2-carboxylic acid.

Example 9

Compound no9: (2S,5R)-5-(2-chlorophenyl)-1-(3-(3,3-diphenylpropoxy)-5-methoxybenzoyl)pyrrolidine-2-carboxylic acid was synthesized from intermediates 1a and 2d using general method C.

Example 10

Compound no10: (2S,5R)-5-(2-chlorophenyl)-1-(3'-fluoro-[1,1'-biphenyl]-4-carbonyl)pyrrolidine-2-carboxylic acid.

Example 11

Compound no11: (2S,5R)-5-(2-chlorophenyl)-1-(3'-methyl-[1,1'-biphenyl]-4-carbonyl)pyrrolidine-2-carboxylic acid.

Example 12

Compound no12: (2S,5R)-5-(2-chlorophenyl)-1-(3-methoxy-5-((4-(methylsulfonyl)benzyl)oxy)benzoyl)pyrrolidine-2-carboxylic acid was synthesized from intermediates 1a and 2e using general method C.

Example 13

Compound no13: (2S,5R)-5-(2-chlorophenyl)-1-(3'-methoxy-[1,1'-biphenyl]-4-carbonyl)pyrrolidine-2-carboxylic acid.

Example 14

Compound no14: (2S,5R)-5-(2-chlorophenyl)-1-(3,5-dimethoxybenzoyl)pyrrolidine-2-carboxylic acid.

Example 15

Compound no15: (2S,5R)-5-(2-chlorophenyl)-1-(4-(phenoxymethyl)benzoyl)pyrrolidine-2-carboxylic acid.

Example 16

Compound no16: (2S,5R)-5-(2-chlorophenyl)-1-(4-((2-fluorobenzyl)oxy)benzoyl)pyrrolidine-2-carboxylic acid.

Example 17

Compound no17: (2S,5R)-1-(3-chloro-5-methoxybenzoyl)-5-(2-chlorophenyl)pyrrolidine-2-carboxylic acid.

Example 18

Compound no18: (2S,5R)-5-(2-chlorophenyl)-1-(4'-fluoro-[1,1'-biphenyl]-4-carbonyl)pyrrolidine-2-carboxylic acid.

Example 19

Compound no19: (2S,5R)-5-(2-chlorophenyl)-1-(4-phenethoxybenzoyl)pyrrolidine-2-carboxylic acid.

Example 20

Compound no20: (2S,5R)-5-(2-chlorophenyl)-1-(chroman-3-carbonyl)pyrrolidine-2-carboxylic acid.

Example 21

Compound no21: (2S,5R)-5-(2-chlorophenyl)-1-(3,5-diethoxybenzoyl)pyrrolidine-2-carboxylic acid.

Example 23

Compound no23: (2S,5R)-5-(2-chlorophenyl)-1-(3-phenethoxybenzoyl)pyrrolidine-2-carboxylic acid.

Example 24

Compound no24: (2S)-1-([1,1'-biphenyl]-4-carbonyl)-4-benzyl-5-phenylpyrrolidine-2-carboxylic acid was synthesized as described in scheme 24.

Example 25

Compound no25: (2S,5R)-5-(2-chlorophenyl)-1-(1,2,3,4-tetrahydronaphthalene-2-carbonyl)pyrrolidine-2-carboxylic acid.

Example 26

Compound no26: (2S,5R)-5-(2-chlorophenyl)-1-(4-isobutylbenzoyl)pyrrolidine-2-carboxylic acid.

Example 27

Compound no27: (2S,5R)-5-(2-chlorophenyl)-1-(2,2-difluorobenzo[d][1,3]dioxole-6-carbonyl)pyrrolidine-2-carboxylic acid.

Example 28

Compound no28: (2S,5R)-1-([1,1'-biphenyl]-4-carbonyl)-5-phenylpyrrolidine-2-carboxylic acid.

Example 29

Compound no29: (2S,5R)-5-(2-chlorophenyl)-1-(3-fluoro-5-methoxybenzoyl)pyrrolidine-2-carboxylic acid.

Example 30

Compound no30: (2S,5R)-5-(2-chlorophenyl)-1-(6-phenylnicotinoyl)pyrrolidine-2-carboxylic acid.

Example 31

Compound no31: (2S,5R)-5-(2-chlorophenyl)-1-(3-methoxy-5-(2-methoxyethoxy)benzoyl)pyrrolidine-2-carboxylic acid was synthesized from intermediates 1a and 2f using general method C.

Example 32

Compound no32: (2S,5R)-5-(2-chlorophenyl)-1-(3'-methoxy-[1,1'-biphenyl]-3-carbonyl)pyrrolidine-2-carboxylic acid.

Example 33

Compound no33: (2S,5R)-5-(2-chlorophenyl)-1-(3-methoxy-5-(trifluoromethyl)benzoyl)pyrrolidine-2-carboxylic acid.

Example 34

Compound no34: (2S,5R)-5-(2-chlorophenyl)-1-(1-(4-methoxyphenyl)-5-phenyl-1H-pyrazole-3-carbonyl)pyrrolidine-2-carboxylic acid.

Example 35

Compound no35: (2S,5R)-5-(2-chlorophenyl)-1-(4-isopropoxybenzoyl)pyrrolidine-2-carboxylic acid.

Example 36

Compound no36: (2S,5R)-5-(2-chlorophenyl)-1-(3-((3,5-dimethylisoxazol-4-yl) methoxy)-5-methoxybenzoyl)pyrrolidine-2-carboxylic acid was synthesized from intermediates 1a and 2g using general method C.

Example 37

Compound no37: (2S,5R)-5-(2-chlorophenyl)-1-(2,3-dihydro-1H-indene-2-carbonyl)pyrrolidine-2-carboxylic acid.

Example 38

Compound no38: (2S,5R)-5-(2-chlorophenyl)-1-(3-methyl-5-(trifluoromethoxy)benzoyl)pyrrolidine-2-carboxylic acid.

Example 39

Compound no39: (2S,5R)-1-(3-(benzyloxy)benzoyl)-5-(2-chlorophenyl)pyrrolidine-2-carboxylic acid.

Example 40

Compound no40: (2S,5R)-5-(2-chlorophenyl)-1-(3-methoxybenzoyl)pyrrolidine-2-carboxylic acid.

Example 41

Compound no41: (2S,5R)-5-(2-chlorophenyl)-1-(2-phenylpyrimidine-5-carbonyl)pyrrolidine-2-carboxylic acid.

Example 42

Compound no42: (2S,5R)-5-(2-chlorophenyl)-1-(4-(trifluoromethoxy)benzoyl)pyrrolidine-2-carboxylic acid.

Example 43

Compound no43: (2S,5R)-5-(2-chlorophenyl)-1-(4-(5-cyclopropyl-1,2,4-oxadiazol-3-yl)benzoyl)pyrrolidine-2-carboxylic acid.

Example 44

Compound no44: 4-((2S,5R)-2-carboxy-5-(2-chlorophenyl)pyrrolidine-1-carbonyl)-2,6-dimethoxypyrimidin-1-ium formate.

Example 45

Compound no45: (2S,5R)-5-(2-chlorophenyl)-1-(4-phenylbutanoyl)pyrrolidine-2-carboxylic acid.

Example 46

Compound no46: (2S,5R)-5-(2-chlorophenyl)-1-(3-methyl-5-(trifluoromethyl)benzoyl)pyrrolidine-2-carboxylic acid.

Example 47

Compound no47: (2S,5R)-1-([1,1'-biphenyl]-4-carbonyl)-5-(3-chloropyridin-2-yl)pyrrolidine-2-carboxylic acid intermediate 1c using general method C.

Example 48

Compound no48: (2S,5R)-5-(2-chlorophenyl)-1-(3-hydroxy-5-(trifluoromethyl)benzoyl)pyrrolidine-2-carboxylic acid.

Example 49

Compound no49: (2S,5S)-5-(2-chlorophenyl)-1-(3-methoxybenzoyl)pyrrolidine-2-carboxylic acid was synthesized from intermediate 1b using general method C.

Example 50

Compound no50: (2S,5R)-1-(3,5-dimethoxybenzoyl)-5-phenylpyrrolidine-2-carboxylic acid was synthesized from intermediate 1d ((2S,5R)-methyl 5-phenylpyrrolidine-2-carboxylate). 1d was synthesized from commercially available (2S,5R)-1-(tert-butoxycarbonyl)-5-phenylpyrrolidine-2-carboxylic acid using the synthetic steps described in scheme 4.

Example 51

Compound no51: (S)-5-([1,1'-biphenyl]-3-yl)-1-(3-methoxybenzoyl)pyrrolidine-2-carboxylic acid was synthesized from intermediate 1e using general method C.

Example 52

Compound no52: (2S,5R)-5-(2-chlorophenyl)-1-(3-phenylpropanoyl)pyrrolidine-2-carboxylic acid.

Example 53

Compound no53: (2S,5S)-5-(2-chlorophenyl)-1-(2'-methoxy-[1,1'-biphenyl]-4-carbonyl)pyrrolidine-2-carboxylic acid was synthesized from intermediate 1b using general method C.

Example 54

Compound no54: (2S,5R)-1-([1,1'-biphenyl]-4-carbonyl)-5-(pyridin-2-yl)pyrrolidine-2-carboxylic acid was synthesized from intermediate 1f using general method C.

Example 55

Compound no55: (2S,5R)-5-(2-chlorophenyl)-1-(5-phenylpicolinoyl)pyrrolidine-2-carboxylic acid.

Example 57

Compound no57: (2S,5R)-5-(2-fluorophenyl)-1-(3-methoxybenzoyl)pyrrolidine-2-carboxylic acid was synthesized from intermediate 1g using general method C.

Example 58

Compound no58: (2S,5R)-1-(2-([1,1'-biphenyl]-4-yl)acetyl)-5-(2-chlorophenyl)pyrrolidine-2-carboxylic acid.

Example 59

Compound no59: (2R,5S)-1-([1,1'-biphenyl]-4-carbonyl)-5-phenylpyrrolidine-2-carboxylic acid was synthesized from intermediate 1h using general method C. 1h was synthesized from commercially available (2R,5S)-1-(tert-butoxycarbonyl)-5-phenylpyrrolidine-2-carboxylic acid using the synthetic steps described in scheme 4.

Example 60

Compound no60: (2S,5R)-5-phenyl-1-(2-phenylacetyl)pyrrolidine-2-carboxylic acid was synthesized from intermediate 1d using general method C.

Example 61

Compound no61: (2R,5S)-5-phenyl-1-(2-phenylacetyl)pyrrolidine-2-carboxylic acid was synthesized from intermediate 1h using general method C.

Example 62

Compound no62: (2S,5R)-1-(3-methoxybenzoyl)-5-(2-methoxyphenyl)pyrrolidine-2-carboxylic acid was synthesized from intermediate 1i using general method C.

Example 63

Compound no63: (2R,5S)-5-(2-chlorophenyl)-1-(3-methoxybenzoyl)pyrrolidine-2-carboxylic acid was synthesized from intermediate 1j using general method C.

Example 64

Compound no64: (2R,5R)-5-(2-chlorophenyl)-1-(3-methoxybenzoyl)pyrrolidine-2-carboxylic acid was synthesized from intermediate 1j using general method C.

Example 65

Compound no65: (2S)-5-(4-chlorophenyl)-1-(3-methoxybenzoyl)pyrrolidine-2-carboxylic acid was synthesized from intermediate 1k using general method C.

Example 66

Compound no66: (2S)-5-([1,1'-biphenyl]-4-yl)-1-(3-methoxybenzoyl)pyrrolidine-2-carboxylic acid was synthesized from intermediate 1l using general method C.

Example 67

Compound no67: (2S,5R)-methyl 5-(2-chlorophenyl)-1-(3-methoxybenzoyl)pyrrolidine-2-carboxylate was synthesized using general method C without the last saponification step.

Example 68

Compound no68: (2S)-5-(2-chlorobenzyl)-1-(3-methoxybenzoyl)pyrrolidine-2-carboxylic acid was synthesized from intermediate 1m using general method C.

Example 69

Compound no69: (2S)-5-cyclohexyl-1-(3-methoxybenzoyl)pyrrolidine-2-carboxylic acid was synthesized from intermediate 1n using general method C.

Example 70

Compound no70: (2S,5R)-5-(2-chlorophenyl)-1-(2-(3-methoxyphenyl)acetyl)pyrrolidine-2-carboxylic acid.

Example 71

Compound no71: (2S,5S)-5-(2-chlorophenyl)-1-(3,5-dimethoxybenzoyl)pyrrolidine-2-carboxylic acid was synthesized from intermediate 1b using general method C.

Example 72

Compound no72: (2S,5R)-5-([1,1'-biphenyl]-2-yl)-1-(3-methoxybenzoyl)pyrrolidine-2-carboxylic acid was synthesized from intermediate 1o using general method C.

Example 74

Compound no74: 2-((2S,5R)-5-(2-chlorophenyl)-1-(3-methoxybenzoyl)pyrrolidin-2-yl)acetic acid. Compound no40 was reacted with ethyl chloroformate (1.03 eq) in THF in the presence of triethylamine (1.03 eq) and then was added a solution of diazomethane in diethyl ether (2 eq), the mixture was stirred at RT for 2.5 days. Reaction mixture was quenched with a 10% aqueous solution of citric acid and diluted with diethyl ether. The organic layer was washed with a saturated aqueous solution of sodium bicarbonate and brine, then concentrated in vacuo. The residue was dissolved in MeOH and silver benzoate (1 eq) and triethylamine (2 eq) were added. The RM was stirred at RT for 45 min and diluted with AcOEt, washed with a saturated aqueous solution of sodium bicarbonate and brine 1M aqueous HCl, dried over anhydrous $MgSO_4$ and evaporated to dryness to yield title compound.

Example 75

Compound no75: (2S,5R)-5-(2-chlorophenyl)-1-(6-phenylpyrimidine-4-carbonyl)pyrrolidine-2-carboxylic acid.

Example 76

Compound no77: (2S,5R)-5-(2-chlorophenyl)-1-(6-(2-chlorophenyl)nicotinoyl)pyrrolidine-2-carboxylic acid.

Example 77

Compound no78: (2S,5R)-5-(2-chlorophenyl)-1-(6-(2-methoxyphenyl)nicotinoyl)pyrrolidine-2-carboxylic acid.

Example 78

Compound no79: (2S,5R)-5-(2-chlorophenyl)-1-(6-(3-fluorophenyl)nicotinoyl)pyrrolidine-2-carboxylic acid.

Example 79

Compound no80: (2S,5R)-5-(2-chlorophenyl)-1-(6-(3-methoxyphenyl)nicotinoyl)pyrrolidine-2-carboxylic acid.

Example 80

Compound no81: (2S,5R)-5-(2-chlorophenyl)-1-(6-(4-methoxyphenyl)nicotinoyl)pyrrolidine-2-carboxylic acid.

Example 81

Compound no82: (2S,5R)-5-(2-chlorophenyl)-1-(6-(4-fluorophenyl)nicotinoyl)pyrrolidine-2-carboxylic acid.

Example 82

Compound no83: (2S,5R)-5-(2-chlorophenyl)-1-(2-(2-chlorophenyl)pyrimidine-5-carbonyl)pyrrolidine-2-carboxylic acid.

Example 83

Compound no84: (2S,5R)-5-(2-chlorophenyl)-1-(2-methyl-6-phenylnicotinoyl)pyrrolidine-2-carboxylic acid.

Example 84

Compound no88: (2S,5R)-5-(2-chlorophenyl)-1-(4-(pyridin-2-yl)benzoyl)pyrrolidine-2-carboxylic acid was was synthesized from intermediates 1a and 2u1 using general method C.

Example 85

Compound no89: (2S,5R)-1-(4-((4-chlorophenoxy)methyl)benzoyl)-5-(2-chlorophenyl)pyrrolidine-2-carboxylic acid.

Example 86

Compound no91: (2S,5R)-5-(2-chlorophenyl)-1-(4-((4-methoxyphenoxy)methyl)benzoyl)pyrrolidine-2-carboxylic acid Example 87

Compound no92: (2S,5R)-1-(4-((2-chlorophenoxy)methyl)benzoyl)-5-(2-chlorophenyl)pyrrolidine-2-carboxylic acid was synthesized from intermediate 1b using general method C.

Example 88

Compound no95: (2S,5R)-1-(4-((3-chlorophenoxy)methyl)benzoyl)-5-(2-chlorophenyl)pyrrolidine-2-carboxylic acid.

Example 89

Compound no96: (2S,5R)-5-(2-chlorophenyl)-1-(4-((p-tolyloxy)methyl)benzoyl)pyrrolidine-2-carboxylic acid.

Example 90

Compound no99: (2S,5R)-5-(2-chlorophenyl)-1-(4-((3,5-dimethylisoxazol-4-yl)methoxy)benzoyl)pyrrolidine-2-carboxylic acid.

Example 91

Compound no102: (2S,5R)-5-(2-chlorophenyl)-1-(4-(pyridin-4-ylmethoxy)benzoyl)pyrrolidine-2-carboxylic acid.

Example 92

Compound no104: (2S,5R)-5-(2-chlorophenyl)-1-(4-(5-methyl-1H-pyrazol-1-yl)benzoyl)pyrrolidine-2-carboxylic acid.

Example 93

Compound no105: (2S,5R)-5-(2-chlorophenyl)-1-(4-(isoxazol-5-yl)benzoyl)pyrrolidine-2-carboxylic acid.

Example 94

Compound no106: (2S,5R)-1-(4-(4H-1,2,4-triazol-4-yl)benzoyl)-5-(2-chlorophenyl)pyrrolidine-2-carboxylic acid.

Example 95

Compound no107: (2S,5R)-5-(2-chlorophenyl)-1-(4-(5-(p-tolyl)-1H-1,2,3-triazol-1-yl)benzoyl)pyrrolidine-2-carboxylic acid.

Example 96

Compound no108: (2S,5R)-5-(2-chlorophenyl)-1-(4-(5-oxo-3-phenyl-4,5-dihydro-1H-pyrazol-1-yl)benzoyl)pyrrolidine-2-carboxylic acid.

Example 97

Compound no109: (2S,5R)-5-(2-chlorophenyl)-1-(4-(5-methyl-3-(trifluoromethyl)-1H-pyrazol-1-yl)benzoyl)pyrrolidine-2-carboxylic acid.

Example 98

Compound no110: (2S,5R)-1-(4-(1H-pyrazol-1-yl)benzoyl)-5-(2-chlorophenyl)pyrrolidine-2-carboxylic acid.

Example 99

Compound no111: (2S,5R)-5-(2-chlorophenyl)-1-(4-(oxazol-5-yl)benzoyl)pyrrolidine-2-carboxylic acid.

Example 100

Compound no112: (2S,5R)-5-(2-chlorophenyl)-1-(4-(3,5-dimethyl-1H-pyrazol-1-yl)benzoyl)pyrrolidine-2-carboxylic acid.

Example 101

Compound no113: (2S,5R)-5-(2-chlorophenyl)-1-(2',5'-dichloro-[1,1'-biphenyl]-4-carbonyl)pyrrolidine-2-carboxylic acid was synthesized from intermediates 1a and 2i using general method C.

Example 102

Compound no114: (2S,5R)-5-(2-chlorophenyl)-1-(4-(pyrimidin-5-yl)benzoyl)pyrrolidine-2-carboxylic acid was synthesized from intermediates 1a and 2j using general method C.

Example 103

Compound no115: (2S,5R)-5-(2-chlorophenyl)-1-(4-(furan-3-yl)benzoyl)pyrrolidine-2-carboxylic acid was synthesized from intermediates 1a and 2k using general method C.

Example 104

Compound no116: (2S,5R)-5-(2-chlorophenyl)-1-(4-(6-methoxypyridin-3-yl)benzoyl)pyrrolidine-2-carboxylic acid was synthesized from intermediates 1a and 2l using general method C.

Example 105

Compound no117: (2S,5R)-5-(2-chlorophenyl)-1-(4-(3-fluoropyridin-4-yl)benzoyl)pyrrolidine-2-carboxylic acid was synthesized from intermediates 1a and 2m using general method C.

Example 106

Compound no118: (2S,5R)-5-(2-chlorophenyl)-1-(4-(pyridin-3-yl)benzoyl)pyrrolidine-2-carboxylic acid was synthesized from intermediates 1a and 2n using general method C.

Example 107

Compound no119: (2S,5R)-5-(2-chlorophenyl)-1-(4-(6-(dimethylamino)pyridin-3-yl)benzoyl)pyrrolidine-2-carboxylic acid was synthesized from intermediates 1a and 2o using general method C.

Example 108

Compound no120: (2S,5R)-5-(2-chlorophenyl)-1-(4-(pyridin-4-yl)benzoyl)pyrrolidine-2-carboxylic acid was synthesized from intermediates 1a and 2p using general method C.

Example 109

Compound no121: (2S,5R)-5-(2-chlorophenyl)-1-(4-(6-methylpyridin-3-yl)benzoyl)pyrrolidine-2-carboxylic acid was synthesized from intermediates 1a and 2q using general method C.

Example 110

Compound no122: (2S,5R)-5-(2-chlorophenyl)-1-(4-(2-methoxypyridin-3-yl)benzoyl)pyrrolidine-2-carboxylic acid was synthesized from intermediates 1a and 2r using general method C.

Example 111

Compound no123: (2S,5R)-5-(2-chlorophenyl)-1-(4'-methoxy-[1,1'-biphenyl]-4-carbonyl)pyrrolidine-2-carboxylic acid was synthesized from intermediates 1a and 2s using general method C.

Example 112

Compound no124: (2S,5R)-5-(2-chlorophenyl)-1-(4'-cyano-[1,1'-biphenyl]-4-carbonyl)pyrrolidine-2-carboxylic acid was synthesized from intermediates 1a and 2t using general method C.

Example 113

Compound no125: (2S,5R)-5-(2-chlorophenyl)-1-(4-(4-methoxypyridin-3-yl)benzoyl)pyrrolidine-2-carboxylic acid was synthesized from intermediates 1a and 2u using general method C.

Example 114

Compound no126: (2S,5R)-1-(4'-chloro-[1,1'-biphenyl]-4-carbonyl)-5-(2-chlorophenyl)pyrrolidine-2-carboxylic acid was synthesized from intermediates 1a and 2v using general method C.

Example 115

Compound no127: (2S,5R)-1-(3'-chloro-[1,1'-biphenyl]-4-carbonyl)-5-(2-chlorophenyl)pyrrolidine-2-carboxylic acid was synthesized from intermediates 1a and 2w using general method C.

Example 116

Compound no128: (2S,5R)-1-(2'-chloro-[1,1'-biphenyl]-4-carbonyl)-5-(2-chlorophenyl)pyrrolidine-2-carboxylic acid was synthesized from intermediates 1a and 2x using general method C.

Example 117

Compound no129: (2S,5R)-5-(2-chlorophenyl)-1-(4'-(methylsulfonamido)-[1,1'-biphenyl]-4-carbonyl)pyrrolidine-2-carboxylic acid was synthesized from intermediates 1a and 2y using general method C.

Example 118

Compound no130: (2S,5R)-5-(2-chlorophenyl)-1-(3'-(methylsulfonamido)-[1,1'-biphenyl]-4-carbonyl)pyrrolidine-2-carboxylic acid was synthesized from intermediates 1a and 2z using general method C.

Example 119

Compound no131: (2S,5R)-5-(2-chlorophenyl)-1-(2'-(methylsulfonamido)-[1,1'-biphenyl]-4-carbonyl)pyrrolidine-2-carboxylic acid was synthesized from intermediates 1a and 2a1 using general method C.

Example 120

Compound no132: (2S,5R)-5-(2-chlorophenyl)-1-(4-(naphthalen-2-yl)benzoyl)pyrrolidine-2-carboxylic acid was synthesized from intermediates 1a and 2b1 using general method C.

Example 121

Compound no133: (2S,5R)-5-(2-chlorophenyl)-1-(3',5'-difluoro-[1,1'-biphenyl]-4-carbonyl)pyrrolidine-2-carboxylic acid was synthesized from intermediates 1a and 2c1 using general method C.

Example 122

Compound no134: (2S,5R)-5-(2-chlorophenyl)-1-(2'-hydroxy-[1,1'-biphenyl]-4-carbonyl)pyrrolidine-2-carboxylic acid was synthesized from intermediates 1a and 2d1 using general method C.

Example 123

Compound no135: (2S,5R)-5-(2-chlorophenyl)-1-(2'-(trifluoromethoxy)-[1,1'-biphenyl]-4-carbonyl)pyrrolidine-2-carboxylic acid was synthesized from intermediates 1a and 2e1 using general method C.

Example 124

Compound no136: (2S,5R)-1-(2'-benzyloxy)-[1,1'-biphenyl]-4-carbonyl)-5-(2-chlorophenyl)pyrrolidine-2-carboxylic acid.

Example 125

Compound no137: (2S,5R)-5-(2-chlorophenyl)-1-(2'-phenoxy-[1,1'-biphenyl]-4-carbonyl)pyrrolidine-2-carboxylic acid.

Example 126

Compound no138: (2S,5R)-5-(2-chlorophenyl)-1-(2'-isopropoxy-[1,1'-biphenyl]-4-carbonyl)pyrrolidine-2-carboxylic acid.

Example 127

Compound no139: (2S,5R)-5-(2-chlorophenyl)-1-(2'-isobutoxy-[1,1'-biphenyl]-4-carbonyl)pyrrolidine-2-carboxylic acid.

Example 128

Compound no140: (2S,5R)-5-(2-chlorophenyl)-1-(2'-(cyclopropylmethoxy)-[1,1'-biphenyl]-4-carbonyl)pyrrolidine-2-carboxylic acid.

Example 129

Compound no141: (2S,5R)-5-(2-chlorophenyl)-1-(2'-((4-fluorobenzyl)oxy)-[1,1'-biphenyl]-4-carbonyl)pyrrolidine-2-carboxylic acid.

Example 130

Compound no142: (2S,5R)-5-(2-chlorophenyl)-1-(4-(6-chloropyridin-3-yl)benzoyl)pyrrolidine-2-carboxylic acid was synthesized from intermediates 1a and 2l1 using general method C.

Example 131

Compound no143: (2S,5R)-5-(2-chlorophenyl)-1-(4-(6-fluoropyridin-3-yl)benzoyl)pyrrolidine-2-carboxylic acid was synthesized from intermediates 1a and 2m1 using general method C.

Example 132

Compound no149: (2S,5R)-5-(2-chlorophenyl)-1-(4-(thiophen-3-yl)benzoyl)pyrrolidine-2-carboxylic acid was synthesized from intermediates 1a and 2n1 using general method C.

Example 133

Compound no150: (2S,5R)-5-(2-chlorophenyl)-1-(4-cyclohexylbenzoyl)pyrrolidine-2-carboxylic acid was synthesized from intermediates 1a and 2o1 using general method C.

Example 134

Compound no152: (2S,5R)-5-(2-chlorophenyl)-1-(9-oxo-9H-fluorene-2-carbonyl)pyrrolidine-2-carboxylic acid.

Example 135

Compound no153: (2S,5R)-5-(2-chlorophenyl)-1-(2'-(methylsulfonyl)-[1,1'-biphenyl]-4-carbonyl)pyrrolidine-2-carboxylic acid was synthesized from intermediates 1a and 2p1 using general method C.

Example 136

Compound no155: (2S,5R)-5-(2-chlorophenyl)-1-(9-methyl-9H-carbazole-2-carbonyl)pyrrolidine-2-carboxylic acid.

Example 137

Compound no156: (2S,5R)-5-(2-chlorophenyl)-1-(4-phenoxybenzoyl)pyrrolidine-2-carboxylic acid.

Example 138

Compound no157: (2S,5R)-1-(4-benzylbenzoyl)-5-(2-chlorophenyl)pyrrolidine-2-carboxylic acid.

Example 139

Compound no158: (2S,5R)-1-(4-benzoylbenzoyl)-5-(2-chlorophenyl)pyrrolidine-2-carboxylic acid.

Example 140

Compound no159: (2S,5R)-5-(2-chlorophenyl)-1-(4-(pyrimidin-2-yl)benzoyl)pyrrolidine-2-carboxylic acid was synthesized from intermediates 1a and 2q1 using general method C.

Example 141

Compound no160: (2S,5R)-5-(2-chlorophenyl)-1-(4-(4,6-dimethoxypyrimidin-2-yl)benzoyl)pyrrolidine-2-carboxylic acid was synthesized from intermediates 1a and 2r1 using general method C.

Example 142

Compound no161: (2S,5R)-5-(2-chlorophenyl)-1-(4-(2,4-dimethoxypyrimidin-5-yl)benzoyl)pyrrolidine-2-carboxylic acid was synthesized from intermediates 1a and 2s1 using general method C.

Example 143

Compound no162: (2S,5R)-5-(2-chlorophenyl)-1-(4-(2-methoxypyrimidin-5-yl)benzoyl)pyrrolidine-2-carboxylic acid was synthesized from intermediates 1a and 2t1 using general method C.

Example 144

Compound no168: (2S,5R)-5-(2-chlorophenyl)-1-(cyclohexanecarbonyl)pyrrolidine-2-carboxylic acid.

Example 145

Compound no169: (2S,5R)-5-(2-chlorophenyl)-1-(4-methylpentanoyl)pyrrolidine-2-carboxylic acid.

Example 146

Compound no172: (2S,5R)-5-(2-chlorophenyl)-1-(4-(4-methylpiperidin-1-yl)-3-nitrobenzoyl)pyrrolidine-2-carboxylic acid.

Example 147

Compound no173: (2S,5R)-5-(2-chlorophenyl)-1-(4-(2-oxopiperidin-1-yl)benzoyl)pyrrolidine-2-carboxylic acid.

Example 148

Compound no174: (2S,5R)-5-(2-chlorophenyl)-1-(3-methyl-4-morpholinobenzoyl)pyrrolidine-2-carboxylic acid.

Example 149

Compound no175: (2S,5R)-5-(2-chlorophenyl)-1-(4-(piperidin-1-yl)benzoyl)pyrrolidine-2-carboxylic acid.

Example 150

Compound no176: (2S,5R)-5-(2-chlorophenyl)-1-(4-morpholinobenzoyl)pyrrolidine-2-carboxylic acid.

Example 151

Compound no177: (2S,5R)-5-(2-chlorophenyl)-1-(1-(2-cyanophenyl)piperidine-4-carbonyl)pyrrolidine-2-carboxylic acid.

Example 152

Compound no178: (2S,5R)-5-(2-chlorophenyl)-1-(4-(4-chlorophenyl)cyclohexanecarbonyl)pyrrolidine-2-carboxylic acid.

Example 153

Compound no179: (2S,5R)-5-(2-chlorophenyl)-1-(4-phenylcyclohexanecarbonyl)pyrrolidine-2-carboxylic acid.

Example 154

Compound no183: ((2R,5S)-2-(2-chlorophenyl)-5-(1H-tetrazol-5-yl)pyrrolidin-1-yl)(2'-methoxy-[1,1'-biphenyl]-4-yl)methanone:

Step 1: Synthesis of (2S,5R)-5-(2-chlorophenyl)-1-(2'-methoxy-[1,1'-biphenyl]-4-carbonyl)pyrrolidine-2-carboxamide In a glass tube containing compound no1 (0.2 g, 0.459 mmol) in THF (5 mL) were added CDI (0.167 g, 0.11 mmol). The RM was stirred at RT for 30 mn, then $NH_3$ bubbling in the RM for 1 mn. The RM was diluted with HCl 1M and extracted with EtOAc. The organic layer was dried overnight over MgSO4. The concentrated in vacuo and the residue (164 mg) diluted in MeCN and passed through a new PE-AX (2 g) cartridge. The filtrate was concentrated to yield title intermediate. Y: 0.14 g (70%), P>80%, rt=4.08 nm (gradient A).

Step 2: Synthesis of (2S,5R)-5-(2-chlorophenyl)-1-(2'-methoxy-[1,1'-biphenyl]-4-carbonyl)pyrrolidine-2-carbonitrile In a 50 mL round bottom flask containing (2S,5R)-5-(2-chlorophenyl)-1-(2'-methoxy-[1,1'-biphenyl]-4-carbonyl)

pyrrolidine-2-carboxamide (0.14 g, 0.322 mmol) were added DMF (3.22 mL). The RM was degassed and placed under Ar. Cyanuric chloride (0.059 g, 0.322 mmol) was added and the RM stirred at RT for 90 mn. The RM was diluted with NaHCO$_3$ (aqueous saturated solution) and extracted with AcOEt. The organic phase was washed with brine (2×), dried over MgSO$_4$ filtered and concentrated to afford 126 mg of title product. Y: 0.126 g (94%), P>80%, rt=4.53 mn (gradient A), (M+H)$^+$=417/419.

Step 3: Synthesis of Compound no 183

In a oven-dried glass tube were added under Ar sodium azide (0.086 g, 1.330 mmol) and THF (5 mL). Were added successively aluminium chloride (0.101 g, 0.756 mmol) and (2S,5R)-5-(2-chlorophenyl)-1-(2'-methoxy-[1,1'-biphenyl]-4-carbonyl)pyrrolidine-2-carbonitrile (0.126 g, 0.302 mmol) diluted in 1 mL THF. The RM was heated at 60° C. overnight. Sodium azide (0.086 g, 1.33 mmol) and aluminium chloride (0.101 g, 0.756 mmol) were added and the RM stirred at 60° C. for another 7 h. The RM was allowed to reach RT and quenched with HCl 6N and extracted with AcOEt (2×). The organic layer was dried over MgSO$_4$, filtered and concentrated to afford 160 mg of crude product as a yellow oil. Crude was purified by flash chromatography (DCM/MeOH: 95/5) and SPE using a PEAX cartridge and elution with ACN, then ACN+HCl. Crude in MeCN solution from the PEAX fractions were concentrated in vacuo. Residue lyophilized in ACN/Water (2 mL/1 mL). Y: 13 mg (9%), P=100%, rt=5.19 mn (gradient B), (M+H)$^+$=460.

Example 155

Compound no184: (2R,5S)-5-(2-chlorophenyl)-1-(2'-methoxy-[1,1'-biphenyl]-4-carbonyl)pyrrolidine-2-carboxylic acid was synthesized from intermediates 1j and 2h using general method C.

Example 160

Compound no189: (2S,5R)-5-(2-chlorophenyl)-1-(6-(2-fluorophenyl)nicotinoyl)pyrrolidine-2-carboxylic acid.

Example 162

Compound no191: (2S,5R)-5-(2-chlorophenyl)-1-(5-methoxy-6-phenylnicotinoyl)pyrrolidine-2-carboxylic acid was synthesized from intermediates 1a and 2i1 using general method C.

Example 163

Compound no192: (2S,5R)-5-(2-chlorophenyl)-1-(4-(2-methoxyphenoxy)benzoyl)pyrrolidine-2-carboxylic acid.

Example 164

Compound no193: (2S,5R)-5-(2-chlorophenyl)-1-(4-(3-methoxypyridin-4-yl)benzoyl)pyrrolidine-2-carboxylic acid was synthesized from intermediates 1a and 2j1 using general method C.

Example 165

Compound no194: (2S)-5-(2-chlorophenyl)-1-(2'-methoxy-[1,1'-biphenyl]-4-carbonyl)-4,4-dimethylpyrrolidine-2-carboxylic acid was synthesized from intermediates 1p and 2h using general method C.

Example 166

Compound no195: (2S)-5-(2-chlorophenyl)-1-(2'-methoxy-[1,1'-biphenyl]-4-carbonyl)-4-methylpyrrolidine-2-carboxylic acid was synthesized from intermediates 1q and 2h using general method C.

Example 167

Compound no196: (2S,5R)-5-(2-chlorophenyl)-1-(2-methoxy-[1,1'-biphenyl]-4-carbonyl)pyrrolidine-2-carboxylic acid was synthesized from intermediates 1a and 2k1 using general method C.

Example 168

Compound no197: (2S,5R)-5-(2-chlorophenyl)-1-(2'-cyano-[1,1'-biphenyl]-4-carbonyl)pyrrolidine-2-carboxylic acid was synthesized from intermediates 1a and 2v1 using general method C.

Example 169

Compound no198: (2S,5R)-5-(2-chlorophenyl)-1-(2',6'-dimethoxy-[1,1'-biphenyl]-4-carbonyl)pyrrolidine-2-carboxylic acid was synthesized from intermediates 1a and 2w1 using general method C.

Example 170

Compound no199: (2S,5R)-5-(2-chlorophenyl)-1-(2',4'-dichloro-[1,1'-biphenyl]-4-carbonyl)pyrrolidine-2-carboxylic acid was synthesized from intermediates 1a and 2x1 using general method C.

Example 171

Compound no200: (2S,5R)-5-(2-chlorophenyl)-1-(2'-(trifluoromethyl)-[1,1'-biphenyl]-4-carbonyl)pyrrolidine-2-carboxylic acid was synthesized from intermediates 1a and 2y1 using general method C.

Example 172

Compound no201: (2S,5R)-5-(2-chlorophenyl)-1-(2,2'-dimethoxy-[1,1'-biphenyl]-4-carbonyl)pyrrolidine-2-carboxylic acid was synthesized from intermediates 1a and 2z1 using general method C.

Example 173

Compound no202: (2S,5R)-1-(4'-chloro-2'-methoxy-[1,1'-biphenyl]-4-carbonyl)-5-(2-chlorophenyl)pyrrolidine-2-carboxylic acid was synthesized from intermediates 1a and 2a2 using general method C.

Example 174

Compound no203: (2S,5R)-5-(2-chlorophenyl)-1-(4-(4-methoxypyrimidin-5-yl)benzoyl)pyrrolidine-2-carboxylic acid was synthesized from intermediates 1a and 2b2 using general method C.

Example 175

Compound no204: (2S,5R)-5-(2-chlorophenyl)-1-(2',4'-dimethoxy-[1,1'-biphenyl]-4-carbonyl)pyrrolidine-2-carboxylic acid was synthesized from intermediates 1a and 2c2 using general method C.

Example 176

Compound no205: (2S,5R)-1-([1,1'-biphenyl]-4-carbonyl)-5-(pyridin-3-yl)pyrrolidine-2-carboxylic acid was synthesized from intermediates 1r using general method C.

Example 177

Compound no206: (2R,5R)-5-(2-chlorophenyl)-1-(2'-methoxy-[1,1'-biphenyl]-4-carbonyl)pyrrolidine-2-carboxylic acid was synthesized from intermediate 1j using general method C.

Example 178

Compound no207: (2S,5R)-5-(2-chlorophenyl)-1-(1-phenyl-1H-benzo[d]imidazole-5-carbonyl)pyrrolidine-2-carboxylic acid.

Example 179

Compound no208: (2S,5R)-methyl 5-(2-chlorophenyl)-1-(2'-methoxy-[1,1'-biphenyl]-4-carbonyl)pyrrolidine-2-carboxylate was obtained in step 1 of general method C.

Example 180

Compound no217: (2S,4 S,5S)-5-(2-chlorophenyl)-1-(2'-methoxy-[1,1'-biphenyl]-4-carbonyl)-4-(phenylsulfonyl)pyrrolidine-2-carboxylic acid was synthesized using the methodology described in scheme 9.

Example 181

Compound no220: (2S,5R)-5-(2-chlorophenyl)-4-cyano-1-(2'-methoxy-[1,1'-biphenyl]-4-carbonyl)pyrrolidine-2-carboxylic acid was synthesized using the methodology described in scheme 9.

Example 182

Compound no224: (2S,5R)-1-(2-chloro-[1,1'-biphenyl]-4-carbonyl)-5-(2-chlorophenyl)pyrrolidine-2-carboxylic acid was synthesized from intermediates 1a and 2d2 using general method C.

Example 183

Compound no225: (2S,5R)-1-(2'-chloro-2-methoxy-[1,1'-biphenyl]-4-carbonyl)-5-(2-chlorophenyl)pyrrolidine-2-carboxylic acid was synthesized from intermediates 1a and 2e2 using general method C.

Example 184

Compound no226: (2S,5R)-5-(2-chlorophenyl)-1-(2'-(2-methoxyethoxy)-[1,1'-biphenyl]-4-carbonyl)pyrrolidine-2-carboxylic acid was synthesized from intermediate 1a and 2'-(2-methoxyethoxy)biphenyl-4-carboxylic acid which was obtained by saponification of methyl 2'-(2-methoxyethoxy)biphenyl-4-carboxylate. The latter intermediate was prepared using Mitsunobu chemistry:

To a solution of methyl 2'-hydroxybiphenyl-4-carboxylate (300 mg, 1.31 mmol), triphenylphosphine (517 mg, 1.97 mmol) and 2-methoxyethanol (130 µL, 1.64 mmol) in THF (12.5 mL) was added slowly diisopropylazodicarboxylate (388 µL, 1.97 mmol) at 0° C. The mixture was stirred at RT overnight and the reaction was quenched with methanol. The reaction mixture was diluted with water and extracted with DCM (25 mL). The organic layer was washed with water, dried and concentrated in vacuo. Crude was purified by column chromatography (cyclohexane/EtOAc=1/1) to yield 2'-(2-methoxyethoxy)biphenyl-4-carboxylate as a yellow oil. Y: 450 mg (78%), P: 65%, rt=2.5 mn (gradient A), Rf (cyclohexane/EtOAc=95/5)=0.75.

Example 185

Compound no230: (2S,5R)-5-(2-chlorophenyl)-1-(3-methoxy-4-(pyrimidin-5-yl)benzoyl)pyrrolidine-2-carboxylic acid was synthesized from intermediates 1a and 2f2 using general method C.

Example 186

Compound no231: (2S,5R)-1-(2'-carbamimidoyl-[1,1'-biphenyl]-4-carbonyl)-5-(2-chlorophenyl)pyrrolidine-2-carboxylic acid.

Step 1:

To a solution of compound no197 precursor (2S,5R)-methyl 5-(2-chlorophenyl)-1-(2'-cyano-[1,1'-biphenyl]-4-carbonyflpyrrolidine-2-carboxylate (100 mg, 0.225 mmol) and hydoxylamine hydrochloride (32 mg, 0.45 mmol) in EtOH (1 mL) was triethylamine (64 µL, 0.45 mmol) dropwise at room temperature. The mixture was stirred at reflux for 2 days. The mixture was cooled to RT and concentrated. Crude was purified by column chromatography (DCM/MeOH=98/2) to yield (2S,5R)-methyl5-(2-chlorophenyl)-1-(2'-((E)-N'-hydroxycarbamimidoyl)biphenylcarbonyl)pyrrolidine-2-carboxylate as a colorless solid. Y: 113 mg (63%), P: >80%, rt=3.6 mn (gradient A), Rf (DCM/MeOH=9/1)=0.3.

Step 2:

A solution of (2S,5R)-methyl5-(2-chlorophenyl)-1-(2'-((E)-N'-hydroxycarbamimidoyl)biphenylcarbonyl)pyrrolidine-2-carboxylate in (EtOH/THF/AcOH=1/1/0.025) (2 mL) was hydrogenated at RT for 45 min. under atmospheric pressure of $H_2$ using a slurry solution of Raney nickel catalyst in water (2 vacuum/N2 cycles and then 2 vacuum/$H_2$ cycles). The catalyst was filtered off over Celite and the filtrate was concentrated in vacuo to yield (2S,5R)-methyl 1-(2'-carbamimidoylbiphenylcarbonyl)-5-(2-chlorophenyl)pyrrolidine-2-carboxylate as a greenish solid. Y: 64 mg (99%), P: 70%, rt=3.5 mn (gradient A).

Step 3:

(2S,5R)-methyl 1-(2'-carbamimidoylbiphenylcarbonyl)-5-(2-chlorophenyl)pyrrolidine-2-carboxylate was saponified as exemplified in general method C to provide compound no231.

Example 187

Compound no232: (2S,5R)-5-(2-fluorophenyl)-1-(2'-methoxy-[1,1'-biphenyl]-4-carbonyl)pyrrolidine-2-carboxylic acid was synthesized from intermediates 1g using general method C.

Example 188

Compound no233: (2S,5R)-1-(2'-methoxy-[1,1'-biphenyl]-4-carbonyl)-5-(o-tolyppyrrolidine-2-carboxylic acid was synthesized from intermediates 1s using general method C.

Example 189

Compound no234: (2S,5R)-1-(2'-methoxy-[1,1'-biphenyl]-4-carbonyl)-5-(2-methoxyphenyl)pyrrolidine-2-carboxylic acid was synthesized from intermediates 1i using general method C.

Example 190

Compound no235: (2S,5R)-5-(2-chlorophenyl)-1-(2'-(methoxymethyl)-[1,1'-biphenyl]-4-carbonyl)pyrrolidine-2-carboxylic acid was synthesized from intermediates 1a and 2g2 using general method C.

Example 191

Compound no236: (2S,5R)-5-(2-chlorophenyl)-1-(4-(2,6-dimethoxypyridin-3-yl)benzoyl)pyrrolidine-2-carboxylic acid was synthesized from intermediates 1a and 2h2 using general method C.

Example 192

Compound no237: (2S,5R)-5-(2-chlorophenyl)-1-(3-methoxy-4-(2-methoxypyrimidin-5-yl)benzoyl)pyrrolidine-2-carboxylic acid was synthesized from intermediates 1a and 2i2 using general method C.

Example 193

Compound no238: (2S,5R)-5-(2-chlorophenyl)-1-(4-(5-methoxypyrazin-2-yl)benzoyl)pyrrolidine-2-carboxylic acid was synthesized from intermediates 1a and 2j2 using general method C.

Example 194

Compound no239: (2S,5R)-5-(2-chlorophenyl)-1-(4-(2-(2-methoxyethoxy)pyridin-3-yl)benzoyl)pyrrolidine-2-carboxylic acid was synthesized from intermediate 1a and 4-(2-(2-methoxyethoxy)pyridin-3-yl)benzoic acid which was obtained by saponification of methyl 4-(2-(2-methoxyethoxy)pyridin-3-yl)benzoate. The latter intermediate was prepared using Mitsunobu chemistry as described for the synthesis of compound no226.

Example 195

Compound no240: (2S,5R)-5-(2-chlorophenyl)-1-(4-(3-methoxypyrazin-2-yl)benzoyl)pyrrolidine-2-carboxylic acid was synthesized from intermediates 1a and 2k2 using general method C.

Example 196

Compound no241: (2S,5R)-1-(4-(2-chloro-4-(dimethylamino)pyrimidin-5-yl)benzoyl)-5-(2-chlorophenyl)pyrrolidine-2-carboxylic acid was synthesized from intermediates 1a and 2l2 using general method C.

Example 197

Compound no242: (2S,5R)-5-(2-chlorophenyl)-1-(4-(2,6-dimethoxypyrimidin-4-yl)benzoyl)pyrrolidine-2-carboxylic acid was synthesized from intermediates 1a and 2m2 using general method C.

Example 198

Compound no227: (2S,5R)-5-(2-chlorophenyl)-1-(4-(2-methylthiophen-3-yl)benzoyl)pyrrolidine-2-carboxylic acid was synthesized from intermediates 1a and 2n2 using general method C and further purified by preparative HPLC.

Example 199

Compound no228: (2S,5R)-5-(2-chlorophenyl)-1-(2',6'-dichloro-[1,1'-biphenyl]-4-carbonyl)pyrrolidine-2-carboxylic acid was synthesized from intermediates 1a and 2o2 using general method C.

Example 200

Compound no229: (2S,5R)-1-(2'-chloro-4'-methoxy-[1,1'-biphenyl]-4-carbonyl)-5-(2-chlorophenyl)pyrrolidine-2-carboxylic acid was synthesized from intermediates 1a and 2p2 using general method C.

Example 201

Compound no243: (2S,5R)-5-(2-chlorophenyl)-1-(2'-(dimethylamino)-[1,1'-biphenyl]-4-carbonyl)pyrrolidine-2-carboxylic acid was synthesized from intermediates 1a and 2q2 using general method C.

Example 202

Compound no246: (2S,5R)-5-(2-fluorophenyl)-1-(4-(2-methoxypyridin-3-yl)benzoyl)pyrrolidine-2-carboxylic acid was synthesized from intermediates 1g and 2r using general method C.

Example 203

Compound no247: (2S,5R)-1-(4-(2,4-dimethoxypyrimidin-5-yl)benzoyl)-5-(2-fluorophenyl)pyrrolidine-2-carboxylic acid was synthesized from intermediates 1g and 2s1 using general method C.

Example 204

Compound no249: (2S,5R)-5-(2-chlorophenyl)-1-(3-methoxy-[1,1'-biphenyl]-4-carbonyl)pyrrolidine-2-carboxylic acid was synthesized from intermediates 1a and 2r2 using general method C.

Example 205

Compound no269: (2S,5R)-1-(4-(2,6-dimethoxypyridin-3-yl)benzoyl)-5-(2-fluorophenyl)pyrrolidine-2-carboxylic acid was synthesized from intermediates 1g and 2h2 using general method C.

Example 206

Compound no261: (2S,5R)-5-(2-chlorophenyl)-1-(3-methoxy-4-(4-methylpiperidin-1-yl)benzoyl)pyrrolidine-2- carboxylic acid was synthesized from intermediates 1a and 3-methoxy-4-(4-methylpiperidin-1-yl)benzoic acid using general method C (condition B). The synthesis of 3-methoxy-4-(4-methylpiperidin-1-yl)benzoic acid is depicted in scheme 11.

Example 207

Compound no272: (2S,5R)-1-(2'-methoxy-[1,1'-biphenyl]-4-carbonyl)-5-phenylpyrrolidine-2-carboxylic acid was synthesized from intermediates 1t and 2h using general method C (condition A).

Example 208

Compound no273: (2S,5R)-5-(3-chlorophenyl)-1-(2'-methoxy-[1,1'-biphenyl]-4-carbonyl)pyrrolidine-2-carboxylic acid was synthesized from intermediates 1u and 2h using general method C (condition A).

Example 209

Compound no274: (2S,5R)-5-(4-chlorophenyl)-1-(2'-methoxy-[1,1'-biphenyl]-4-carbonyl)pyrrolidine-2-carboxylic acid was synthesized from intermediates 1v and 2h using general method C (condition A).

Example 210

Compound no275: (2S,5R)-5-(3-fluorophenyl)-1-(2'-methoxy-[1,1'-biphenyl]-4-carbonyl)pyrrolidine-2-carboxylic acid was synthesized from intermediates 1w and 2h using general method C (condition A).

Example 211

Compound no276: (2S,5R)-5-(4-fluorophenyl)-1-(2'-methoxy-[1,1'-biphenyl]-4-carbonyl)pyrrolidine-2-carboxylic acid was synthesized from intermediates 1x and 2h using general method C (condition A).

Example 212

Compound no278: (2S,5R)-4-acetyl-5-(2-chlorophenyl)-1-(2'-methoxy-[1,1'-biphenyl]-4-carbonyl)pyrrolidine-2-carboxylic acid was synthesized from (2S,4 S,5R)-methyl 4-acetyl-5-(2-chlorophenyl)pyrrolidine-2-carboxylate using the same dipolar cycloaddition methodology as shown in scheme 9, except for the last step (Me$_3$SnOH (10 eq), DCE, 90° C.) instead of (TFA, DCM).

Example 213

Compound no279: (2S,4 S,5R)-5-(2-chlorophenyl)-1-(2'-methoxy-[1,1'-biphenyl]-4-carbonyl)-4-(methoxymethyl) pyrrolidine-2-carboxylic acid was synthesized from (2S,4S, 5R)-4-tert-butyl 2-methyl 5-(2-chlorophenyl)-1-(2'-methoxy-[1,1'-biphenyl]-4-carbonyl)pyrrolidine-2,4-dicarboxylate which was obtained using the dipolar cycloaddition methodology shown in scheme 9. Last steps to perform the synthesis of compound no279 are depicted in scheme 14.

Example 214

Compound no280: (2S,5R)-5-(2-chlorophenyl)-1-(4-(2-methoxypyrimidin-4-yl)benzoyl)pyrrolidine-2-carboxylic acid was synthesized from intermediates 1a and 2s2 using general method C (condition B).

Example 215

Compound no281: (2S,5R)-5-cyclohexyl-1-(2'-methoxy-[1,1'-biphenyl]-4-carbonyl)pyrrolidine-2-carboxylic acid was synthesized from intermediates 1y and 2h using general method C (condition B).

Example 216

Compound no283: (2S,5R)-1-(4-(2-chloro-4-methoxypyrimidin-5-yl)benzoyl)-5-(2-chlorophenyl)pyrrolidine-2-carboxylic acid was synthesized from intermediates 1a and 2t2 using general method C (condition B).

Example 217

Compound no284: (2S,5R)-5-(2-chlorophenyl)-1-(4-(3-methoxypyridin-2-yl)benzoyl)pyrrolidine-2-carboxylic acid was synthesized from intermediates 1a and 2u2 using general method C (condition B).

Example 218

Compound no285: (2R,5R)-5-(2-fluorophenyl)-1-(2'-methoxy-[1,1'-biphenyl]-4-carbonyl)pyrrolidine-2-carboxylic acid was synthesized from intermediates 1z and 2h using general method C (condition A).

Example 219

Compound no286: (2S,5S)-5-(2-fluorophenyl)-1-(2'-methoxy-[1,1'-biphenyl]-4-carbonyl)pyrrolidine-2-carboxylic acid was synthesized from intermediates 1a1 and 2h using general method C (condition A).

Example 220

Compound no287: (2R,5S)-5-(2-fluorophenyl)-1-(2'-methoxy-[1,1'-biphenyl]-4-carbonyl)pyrrolidine-2-carboxylic acid was synthesized from intermediates 1b1 and 2h using general method C (condition A).

Example 221

Compound no288: (2S,5R)-5-(2-chlorophenyl)-1-(2-(trifluoromethyl)-[1,1'-biphenyl]-4-carbonyl)pyrrolidine-2-carboxylic acid was synthesized from intermediates 1a and 2v2 using general method C (condition B).

Example 222

Compound no289: (2S,5R)-5-(2-chlorophenyl)-1-(2',4'-difluoro-[1,1'-biphenyl]-4-carbonyl)pyrrolidine-2-carboxylic acid was synthesized from intermediates 1a and 2w2 using general method C (condition B).

Example 223

Compound no290: (2S,5R)-5-(2-chlorophenyl)-1-(2-methyl-[1,1'-biphenyl]-4-carbonyl)pyrrolidine-2-carboxylic acid was synthesized from intermediates 1a and 2x2 using general method C (condition B).

Example 224

Compound no291: (2S,5R)-5-(2,6-difluorophenyl)-1-(2'-methoxy-[1,1'-biphenyl]-4-carbonyl)pyrrolidine-2-carboxylic acid was synthesized from intermediates 1d and 2h using general method C (condition A).

Example 225

Compound no292: (2S,5R)-5-(2,4-difluorophenyl)-1-(2'-methoxy-[1,1'-biphenyl]-4-carbonyl)pyrrolidine-2-carboxylic acid was synthesized from intermediates 1d1 and 2h using general method C (condition A).

Example 226

Compound no293: (2S,5R)-5-(2,4-dichlorophenyl)-1-(2'-methoxy-[1,1'-biphenyl]-4-carbonyl)pyrrolidine-2-carboxylic acid was synthesized from intermediates 1e1 and 2h using general method C (condition A).

Example 227

Compound no294: (2S,5R)-5-isobutyl-1-(2'-methoxy-[1,1'-biphenyl]-4-carbonyl)pyrrolidine-2-carboxylic acid was synthesized from intermediates 1f1 and 2h using general method C (condition A).

Example 228

Compound no295: (2S,5R)-5-isopropyl-1-(2'-methoxy-[1,1'-biphenyl]-4-carbonyl)pyrrolidine-2-carboxylic acid was synthesized from intermediates 1g1 and 2h using general method C (condition A).

Example 229

Compound no296: (2S,5R)-1-(3-chloro-4-(pyrimidin-4-yl)benzoyl)-5-(2-chlorophenyl)pyrrolidine-2-carboxylic acid was synthesized from intermediates 1a and 2y2 using general method C (condition B).

Example 230

Compound no297: (2S,5R)-5-(2-chlorophenyl)-1-(2-fluoro-[1,1'-biphenyl]-4-carbonyl)pyrrolidine-2-carboxylic acid was synthesized from intermediates 1a and 2z2 using general method C (conditions B).

Example 231

Compound no298: (2S,5R)-5-(2-chlorophenyl)-1-(2'-fluoro-4'-methoxy-[1,1'-biphenyl]-4-carbonyl)pyrrolidine-2-carboxylic acid was synthesized from intermediates 1a and 2a3 using general method C (conditions B).

Example 232

Compound no299: (2S,5R)-5-(2-chlorophenyl)-1-(4'-fluoro-2'-methoxy-[1,1'-biphenyl]-4-carbonyl)pyrrolidine-2-carboxylic acid was synthesized from intermediates 1a and 2b3 using general method C (conditions B).

Example 233

Compound no300: (2S,5R)-5-(2-chlorophenyl)-1-(4-(6-ethoxypyridin-3-yl)benzoyl)pyrrolidine-2-carboxylic acid was synthesized from intermediates 1a and 2c3 using general method C (conditions B).

Example 234

Compound no301: (2S,5R)-5-(2-chlorophenyl)-1-(4-(6-isopropoxypyridin-3-yl)benzoyl)pyrrolidine-2-carboxylic acid was synthesized from intermediates 1a and 2d3 using general method C (condition B).

Example 234

Compound no302: (2S,5R)-5-(2-chlorophenyl)-1-(4-(6-methoxy-2-methylpyridin-3-yl)benzoyl)pyrrolidine-2-carboxylic acid was synthesized from intermediates 1a and 2e3 using general method C (condition B).

Example 235

Compound no303: (2S,5R)-1-(3-chloro-4-(2-methoxypyrimidin-4-yl)benzoyl)-5-(2-chlorophenyl)pyrrolidine-2-carboxylic acid was synthesized from intermediates 1a and 2f3 using general method C (condition B).

Example 236

Compound no304: (2S,5R)-1-(3-chloro-4-(pyrimidin-5-yl)benzoyl)-5-(2-chlorophenyl)pyrrolidine-2-carboxylic acid was synthesized from intermediates 1a and 2g3 using general method C (condition B).

Example 237

Compound no305: (2S,5R)-5-(2-chlorophenyl)-4-cyano-1-(2'-methoxy-[1,1'-biphenyl]-4-carbonyl)-3-methylpyrrolidine-2-carboxylic acid was synthesized using the 1,3-dipolar cycloaddition shown in scheme 9.

Example 238

Compound no306: (2S,4S,5R)-5-(2-chlorophenyl)-4-cyano-1-(2'-methoxy-[1,1'-biphenyl]-4-carbonyl)-4-methylpyrrolidine-2-carboxylic acid was synthesized using the 1,3-dipolar cycloaddition shown in scheme 9.

Example 239

Compound no307: (2S,5R)-5-(2-chlorophenyl)-1-(2',3'-dimethoxy-[1,1'-biphenyl]-4-carbonyl)pyrrolidine-2-carboxylic acid was synthesized from intermediates 1a and 2h3 using general method C (condition B).

Example 240

Compound no308: (2S,5R)-5-(2-chlorophenyl)-1-(3',4'-dimethoxy-[1,1'-biphenyl]-4-carbonyl)pyrrolidine-2-carboxylic acid was synthesized from intermediates 1a and 2i3 using general method C (condition B).

Example 241

Compound no309: (2S,5R)-5-(2-chlorophenyl)-1-(2',3',4'-trimethoxy-[1,1'-biphenyl]-4-carbonyl)pyrrolidine-2-carboxylic acid was synthesized from intermediates 1a and 2j3 using general method C (condition B).

Example 242

Compound no310: (2S,5R)-5-(2-chlorophenyl)-1-(2',3',6'-trimethoxy-[1,1'-biphenyl]-4-carbonyl)pyrrolidine-2-carboxylic acid was synthesized from intermediates 1a and 2k3 using general method C (condition B).

Example 243

Compound no311: (2S,5R)-5-(2-chlorophenyl)-1-(3',5'-dimethoxy-[1,1'-biphenyl]-4-carbonyl)pyrrolidine-2-carboxylic acid was synthesized from intermediates 1a and 2l3 using general method C (condition B).

Example 244

Compound no312: (2S,5R)-5-(2-chlorophenyl)-1-(2',5'-dimethoxy-[1,1'-biphenyl]-4-carbonyl)pyrrolidine-2-carboxylic acid was synthesized from intermediates 1a and 2m3 using general method C (condition B).

Example 245

Compound no313: (2S,5R)-5-(2-chlorophenyl)-1-(2'-isopropyl-[1,1'-biphenyl]-4-carbonyl)pyrrolidine-2-carboxylic acid was synthesized from intermediates 1a and 2n3 using general method C (condition B).

Example 246

Compound no314: (2S,5R)-1-(2,2'-dimethoxy-[1,1'-biphenyl]-4-carbonyl)-5-(2-fluorophenyl)pyrrolidine-2-carboxylic acid was synthesized from intermediates 1g and 2z1 using general method C (condition B).

Example 247

Compound no315: (2S,5R)-1-(2-fluoro-2'-methoxy-[1,1'-biphenyl]-4-carbonyl)-5-(2-fluorophenyl)pyrrolidine-2-carboxylic acid was synthesized from intermediates 1g and 2h5 using general method C (condition B).

Example 248

Compound no316: (2S,5R)-5-(2-chlorophenyl)-1-(2-fluoro-2'-methoxy-[1,1'-biphenyl]-4-carbonyl)pyrrolidine-2-carboxylic acid was synthesized from intermediates 1a and 2h5 using general method C (condition B).

Example 249

Compound no318: (2S,5R)-5-cyclopentyl-1-(2'-methoxy-[1,1'-biphenyl]-4-carbonyl)pyrrolidine-2-carboxylic acid was synthesized from intermediates 1h1 and 2h using general method C (condition A).

Example 250

Compound no319: (2S,5R)-5-(2-chlorophenyl)-1-(2'-ethyl-[1,1'-biphenyl]-4-carbonyl)pyrrolidine-2-carboxylic acid was synthesized from intermediates 1a and 2o3 using general method C (condition B).

Example 251

Compound no320: (2S,5R)-5-(2-chlorophenyl)-1-(4-(2,6-dimethylpyridin-3-yl)benzoyl)pyrrolidine-2-carboxylic acid was synthesized from intermediates 1a and 2p3 using general method C (condition B).

Example 252

Compound no321: (2S,5R)-1-(4-(2,4-bis(benzyloxy)pyrimidin-5-yl)benzoyl)-5-(2-chlorophenyl)pyrrolidine-2-carboxylic acid was synthesized from intermediates 1a and 2q3 using general method C (conditions B).

Example 253

Compound no322: (2S,5R)-1-([1,1':4',1''-terphenyl]-4-carbonyl)-5-(2-chlorophenyl)pyrrolidine-2-carboxylic acid was synthesized from intermediate 1a and commercial 1,1':4',1''-terphenyl]-4-carboxylic acid using general method C (conditions B).

Example 254

Compound no323: (2S,5R)-5-(2-chlorophenyl)-1-(4'-propyl-[1,1'-biphenyl]-4-carbonyl)pyrrolidine-2-carboxylic acid was synthesized from intermediate 1a and commercial 4'-propyl-[1,1'-biphenyl]-4-carboxylic acid using general method C (conditions B).

Example 255

Compound no324: (2S,5R)-1-(4'-(tert-butyl)-[1,1'-biphenyl]-4-carbonyl)-5-(2-chlorophenyl)pyrrolidine-2-carboxylic acid was synthesized from intermediate 1a and commercial 4'-(tert-butyl)-[1,1'-biphenyl]-4-carboxylic acid using general method C (conditions B).

Example 256

Compound no325: (2S,5R)-1-(3-chloro-4-(2,4-dimethoxypyrimidin-5-yl)benzoyl)-5-(2-chlorophenyl)pyrrolidine-2-carboxylic acid was synthesized from intermediates 1a and 2g5 using general method C (conditions B).

Example 257

Compound no326: (2S,5R)-5-(2-chlorophenyl)-1-(5-(2-methoxyphenyl)pyrazine-2-carbonyl)pyrrolidine-2-carboxylic acid was synthesized from intermediates 1a and 2j5 using general method C (conditions B).

Example 258

Compound no327: (2S,5R)-5-(2-chlorophenyl)-1-(3-methoxy-4-(4-methoxypyridin-3-yl)benzoyl)pyrrolidine-2-carboxylic acid was synthesized from intermediates 1a and 2k5 using general method C (conditions B).

Example 259

Compound no328: (2S,5R)-5-(2-chlorophenyl)-1-(3-methoxy-4-(6-methoxypyridin-3-yl)benzoyl)pyrrolidine-2-carboxylic acid was synthesized from intermediates 1a and 2l5 using general method C (conditions B).

Example 260

Compound no329: (2S,5R)-1-(3-chloro-4-(2-methoxypyrimidin-5-yl)benzoyl)-5-(2-chlorophenyl)pyrrolidine-2-carboxylic acid was synthesized from intermediates 1a and 2m5 using general method C (conditions B).

Example 261

Compound no330: (2S,5R)-1-(3-chloro-4-(6-methoxypyridin-3-yl)benzoyl)-5-(2-chlorophenyl)pyrrolidine-2-carboxylic acid was synthesized from intermediates 1a and 2r3 using general method C (conditions B).

Example 262

Compound no331: (2S,5R)-5-(2-chlorophenyl)-1-(1-(4-(4-chlorophenyl)thiazol-2-yl)piperidine-4-carbonyl)pyrrolidine-2-carboxylic acid was synthesized from intermediate 1a and commercial 1-(4-(4-chlorophenyl)thiazol-2-yl)piperidine-4-carboxylic acid using general method C (conditions B).

Example 263

Compound no332: (2S,5R)-5-(2-fluorophenyl)-1-(5-methoxy-6-(2-methoxyphenyl)nicotinoyl)pyrrolidine-2-carboxylic acid was synthesized from intermediates 1g and 2s3 using general method C (conditions B).

Example 264

Compound no333: (2S,5R)-1-(1-(benzo[d]oxazol-2-yl)piperidine-4-carbonyl)-5-(2-chlorophenyl)pyrrolidine-2-carboxylic acid was synthesized from intermediate 1a and commercial 1-(benzo[d]oxazol-2-yl)piperidine-4-carboxylic acid using general method C (conditions B).

Example 265

Compound no334: (2S,5R)-5-(2-chlorophenyl)-1-(3-methoxy-4-(pyrrolidin-1-yl)benzoyl)pyrrolidine-2-carboxylic acid was synthesized using the same methodology as shown in scheme 11, replacing 4-methylpiperidine with pyrrolidine.

Example 266

Compound no335: (2S,5R)-5-(2-chlorophenyl)-1-(5-methoxy-6-(2-methoxyphenyl)nicotinoyl)pyrrolidine-2-carboxylic acid was synthesized from intermediates 1a and 2t3 using general method C (conditions B).

Example 267

Compound no336: (2S,5R)-5-(2-chlorophenyl)-1-(1-(2-methoxyphenyl)piperidine-4-carbonyl)pyrrolidine-2-carboxylic acid was synthesized using the same methodology as shown in scheme 13 replacing 2-cyano-4-trifluoromethyl-bromobenzene with 2-methoxy-bromobenzene.

Example 268

Compound no337: (2S,5R)-5-(2-chlorophenyl)-1-(4-(2,4-dimethoxypyrimidin-5-yl)-3-methoxybenzoyl)pyrrolidine-2-carboxylic acid was synthesized from intermediates 1a and 2n5 using general method C (conditions B).

Example 269

Compound no338: (2S,5R)-5-(2-bromophenyl)-1-(2'-methoxy-[1,1'-biphenyl]-4-carbonyl)pyrrolidine-2-carboxylic acid was synthesized from intermediates 1i1 and 2h using general method C (conditions A).

Example 270

Compound no339: (2S,5R)-5-(2-chlorophenyl)-1-(3'-cyano-[1,1'-biphenyl]-4-carbonyl)pyrrolidine-2-carboxylic acid was synthesized from intermediate 1a and commercial 3'-cyano-[1,1'-biphenyl]-4-carboxylic acid using general method C (conditions B).

Example 271

Compound no340: (2S,5R)-5-(2-chlorophenyl)-1-(3'-cyano-2'-methoxy-[1,1'-biphenyl]-4-carbonyl)pyrrolidine-2-carboxylic acid was synthesized from intermediates 1a and 2u3 using general method C (conditions A).

Example 272

Compound no341: (2S,5R)-5-(2-chlorophenyl)-1-(3'-cyano-2',4'-bis(2,2,2-trifluoroethoxy)-[1,1'-biphenyl]-4-carbonyflpyrrolidine-2-carboxylic acid was synthesized from intermediates 1a and 2v3 using general method C (conditions B).

Example 273

Compound no342: (2S,5R)-1-(3'-amino-2'-methyl-[1,1'-biphenyl]-4-carbonyl)-5-(2-chlorophenyl)pyrrolidine-2-carboxylic acid was synthesized from intermediates 1a and 2w3 using general method C (conditions B).

Example 274

Compound no343: (2S,5R)-5-(2-chlorophenyl)-1-(2'-methyl-3'-(methylsulfonamido)-[1,1'-biphenyl]-4-carbonyl)pyrrolidine-2-carboxylic acid was synthesized from intermediates 1a and 2x3 using general method C (conditions B).

Example 275

Compound no344: (2S,5R)-1-(3'-acetamido-2'-methyl-[1,1'-biphenyl]-4-carbonyl)-5-(2-chlorophenyl)pyrrolidine-2-carboxylic acid was synthesized from intermediates 1a and 2y3 using general method C (conditions B).

Example 276

Compound no345: (2S,5R)-5-(2-chlorophenyl)-1-(5'-cyano-2'-methoxy-[1,1'-biphenyl]-4-carbonyl)pyrrolidine-2-carboxylic acid was synthesized from intermediates 1a and 2z3 using general method C (conditions B).

Example 277

Compound no346: (2S,5R)-5-(2-chlorophenyl)-1-(5'-cyano-2'-methyl-[1,1'-biphenyl]-4-carbonyl)pyrrolidine-2-carboxylic acid was synthesized from intermediates 1a and 2a4 using general method C (conditions B).

Example 278

Compound no347: (2S,5R)-5-(2-chlorophenyl)-1-(4-(4,6-dimethoxypyridin-3-yl)benzoyl)pyrrolidine-2-carboxylic acid was synthesized from intermediates 1a and 2b4 using general method C (conditions B).

Example 279

Compound no348: (2S,5R)-5-(2-chlorophenyl)-1-(4-(3,6-dimethoxypyridazin-4-yl)benzoyl)pyrrolidine-2-carboxylic acid was synthesized from intermediates 1a and 2r4 using general method C (conditions B).

Example 280

Compound no349: (2S,5S)-5-isopentyl-1-(2'-methoxy-[1,1'-biphenyl]-4-carbonyl)pyrrolidine-2-carboxylic acid was synthesized from intermediates 1j1 and 2h using general method C (conditions A).

Example 281

Compound no350: (2S,5R)-5-(2-chlorophenyl)-1-(2'-methoxy-4'-(methylsulfonamido)-[1,1'-biphenyl]-4-carbonyl)pyrrolidine-2-carboxylic acid was synthesized from intermediates 1a and 2p5 using general method C (conditions B).

Example 282

Compound no351: (2S,5R)-1-(4'-acetamido-2'-methoxy-[1,1'-biphenyl]-4-carbonyl)-5-(2-chlorophenyl)pyrrolidine-2-carboxylic acid was synthesized from intermediates 1a and 2c4 using general method C (conditions B).

Example 283

Compound no352: (2S,5R)-1-(3'-carbamimidoyl-[1,1'-biphenyl]-4-carbonyl)-5-(2-chlorophenyl)pyrrolidine-2-carboxylic acid was synthesized from (2S,5R)-methyl 5-(2-chlorophenyl)-1-(3'-cyanobiphenylcarbonyl)pyrrolidine-2-carboxylate which was obtained from intermediate 1a and commercial 3'-cyanobiphenyl-4-carboxylic acid using general method C (conditions B).

Step 1: To a solution of (2S,5R)-methyl 5-(2-chlorophenyl)-1-(3'-cyanobiphenylcarbonyl)pyrrolidine-2-carboxylate (1.0 mmol) and hydoxylamine hydrochloride (2.0 mmol) in dry EtOH (5 mL) under $N_2$ was added $NEt_3$ (2.0 mmol) dropwise at RT. The mixture was stirred under reflux overnight. The mixture was cooled down to RT, concentrated and purified on silica gel (cyclohex/EtOAc), furnishing 300 mg of (2S,5R)-methyl 5-(2-chlorophenyl)-1-(3'-((4E)-N'-hydroxycarbamimidoyl)biphenylcarbonyl)pyrrolidine-2-carboxylate as a white solid (60% yield).

Step 2: A solution of (2S,5R)-methyl 5-(2-chlorophenyl)-1-(3'-((E)-N'-hydroxycarbamimidoyl)biphenylcarbonyl)pyrrolidine-2-carboxylate (0.42 mmol) in EtOH/THF/AcOH (3 mL/3 mL/0.1 mL) was hydrogenated at RT under atmospheric pressure using a slurry solution of Raney nickel catalyst in water (0.5 mL) for 5 h. The catalyst was filtered off over Celite and the filtrate was concentrated, furnishing 160 mg of white solid (83% yield).

Step 3: Saponification using standard methodology described in general method C.

Example 284

Compound no353: (2S,5R)-5-(2-chlorophenyl)-1-(3'-((E)-N'-hydroxycarbamimidoyl)-[1,1'-biphenyl]-4-carbonyl)pyrrolidine-2-carboxylic acid was obtained from (2S,5R)-methyl 5-(2-chlorophenyl)-1-(3'-((4E)-N'-hydroxycarbamimidoyl)biphenylcarbonyl)pyrrolidine-2-carboxylate (step 1 of synthesis of compound no352) using the saponification standard methodology described in general method C: (2S,5R)-1-(3'-carbamoyl-[1,1'-biphenyl]-4-carbonyl)-5-(2-chlorophenyl)pyrrolidine-2-carboxylic acid was obtained by hydrolysis and saponification using LiOH of (2S,5R)-methyl 5-(2-chlorophenyl)-1-(3'-cyanobiphenylcarbonyl)pyrrolidine-2-carboxylate which was obtained from intermediate 1a and commercial 3'-cyanobiphenyl-4-carboxylic acid using general method C (conditions B).

Example 285

Compound no360: (2S,5R)-5-(2-chlorophenyl)-1-(5'-cyano-2',3'-dimethoxy-[1,1'-biphenyl]-4-carbonyl)pyrrolidine-2-carboxylic acid was synthesized from intermediates 1a and 2f4 using general method C (conditions B).

Example 286

Compound no361: (2S,5R)-5-(2-chlorophenyl)-1-(2'-cyano-4',5'-dimethoxy-[1,1'-biphenyl]-4-carbonyl)pyrrolidine-2-carboxylic acid was synthesized from intermediates 1a and 2g4 using general method C (conditions B).

Example 287

Compound no362: (2S,5R)-5-(2-chlorophenyl)-1-(3',4',5'-trimethoxy-[1,1'-biphenyl]-4-carbonyl)pyrrolidine-2-carboxylic acid was synthesized from intermediates 1a and 2h4 using general method C (conditions B).

Example 288

Compound no363: (2S,5R)-5-(2-chlorophenyl)-1-(2'-(cyanomethyl)-4',5'-dimethoxy-[1,1'-biphenyl]-4-carbonyl)pyrrolidine-2-carboxylic acid was synthesized from intermediates 1a and 2i4 using general method C (conditions B).

Example 289

Compound no364: (2S,5R)-5-(2-chlorophenyl)-1-(3',4'-dicyano-[1,1'-biphenyl]-4-carbonyl)pyrrolidine-2-carboxylic acid was synthesized from intermediates 1a and 2j4 using general method C (conditions B).

Example 290

Compound no365: (2S,5R)-5-(2-chlorophenyl)-1-(5'-cyano-2'-fluoro-[1,1'-biphenyl]-4-carbonyl)pyrrolidine-2-carboxylic acid was synthesized from intermediates 1a and 2k4 using general method C (conditions B).

Example 291

Compound no366: (2S,5R)-5-(2-chlorophenyl)-1-(2-fluoro-3',4'-dimethoxy-[1,1'-biphenyl]-4-carbonyl)pyrrolidine-2-carboxylic acid was synthesized from intermediates 1a and 2l4 using general method C (conditions B).

Example 292

Compound no367: (2S,5R)-5-(2-chlorophenyl)-1-(4-(2,6-dimethoxypyridin-3-yl)-3-fluorobenzoyl)pyrrolidine-2-carboxylic acid was synthesized from intermediates 1a and 2m4 using general method C (conditions B).

Example 293

Compound no368: (2S,5R)-5-(2-chlorophenyl)-1-(3-fluoro-4-(6-methoxypyridin-3-yl)benzoyl)pyrrolidine-2-carboxylic acid was synthesized from intermediates 1a and 2n4 using general method C (conditions B).

Example 294

Compound no369: (2S,5R)-5-(2-chlorophenyl)-1-(1-(2-cyano-4-(trifluoromethyl)phenyl)piperidine-4-carbonyl)pyrrolidine-2-carboxylic acid was synthesized using the methodology shown in scheme 13.

Example 295

Compound no370: (2S,5R)-1-(1-(2-chloro-4-(trifluoromethyl)phenyl)piperidine-4-carbonyl)-5-(2-chlorophenyl)pyrrolidine-2-carboxylic acid was synthesized using the methodology shown in scheme 13 replacing 2-cyano-4-trifluoromethyl-bromobenzene with 2-chloro-4-trifluoromethyl-bromobenzene.

Example 296

Compound no371: (2S,5R)-1-(5'-cyano-2'-methoxy-[1,1'-biphenyl]-4-carbonyl)-5-(2-fluorophenyl)pyrrolidine-2-carboxylic acid was synthesized from intermediates 1g and 2z3 using general method C (conditions B).

Example 297

Compound no372: (2S,5R)-1-(4-(2,6-dimethoxypyridin-3-yl)-3-fluorobenzoyl)-5-(2-fluorophenyl)pyrrolidine-2-carboxylic acid was synthesized from intermediates 1g and 2m4 using general method C (conditions B).

Example 298

Compound no373: (2S,5R)-1-(3-fluoro-4-(6-methoxypyridin-3-yl)benzoyl)-5-(2-fluorophenyl)pyrrolidine-2-carboxylic acid was synthesized from intermediates 1g and 2n4 using general method C (conditions B).

Example 299

Compound no374: (2S,5R)-1-(4-(3,6-dimethoxypyridazin-4-yl)benzoyl)-5-(2-fluorophenyl)pyrrolidine-2-carboxylic acid was obtained from intermediates 1a and intermediate 2r4 using general method C (conditions B).

Example 300

Compound no375: (2S,5R)-1-(3'-carbamoyl-4'-cyano-[1,1'-biphenyl]-4-carbonyl)-5-(2-chlorophenyl)pyrrolidine-2-carboxylic acid was obtained by the hydrolysis of the nitrile moiety of (2S,5R)-methyl 5-(2-chlorophenyl)-1-(3',4'-dicyano-[1,1'-biphenyl]-4-carbonyl)pyrrolidine-2-carboxylate and subsequent saponification using LiOH. (2S,5R)-methyl 5-(2-chlorophenyl)-1-(3',4'-dicyano-[1,1'-biphenyl]-4-carbonyl)pyrrolidine-2-carboxylate was obtained from intermediates 1a and intermediate 2j4 using general method C (conditions B).

Example 302

Compound no376: (2S,5R)-5-(2-chlorophenyl)-1-(1-(2-nitro-4-(trifluoromethyl)phenyl)piperidine-4-carbonyl)pyrrolidine-2-carboxylic acid was synthesized from intermediate 1a and commercial 1-(2-nitro-4-(trifluoromethyl)phenyl)piperidine-4-carboxylic acid using general method C (conditions B).

Example 303

Compound no377: (2S,5R)-5-(2-chlorophenyl)-1-(1-(4-(morpholinosulfonyl)-2-nitrophenyl)piperidine-4-carbonyl)pyrrolidine-2-carboxylic acid was synthesized from intermediate 1a and commercial 1-(2-nitro-4-(piperidin-1-ylsulfonyl)phenyl)piperidine-4-carboxylic acid using general method C (conditions B).

Example 304

Compound no378: (2S,5R)-5-(2-chlorophenyl)-1-(1-(2-nitro-4-(piperidin-1-ylsulfonyl)phenyl)piperidine-4-carbonyl)pyrrolidine-2-carboxylic acid was synthesized from intermediate 1a and commercial 1-(4-(N,N-diethylsulfamoyl)-2-nitrophenyl)piperidine-4-carboxylic acid using general method C (conditions B).

Example 305

Compound no379: (2S,5R)-5-(2-chlorophenyl)-1-(1-(4-(N,N-diethylsulfamoyl)-2-nitrophenyl)piperidine-4-carbonyl)pyrrolidine-2-carboxylic acid was synthesized from intermediate 1a and commercial 1-(4-methyl-2-nitrophenyl)piperidine-4-carboxylic acid using general method C (conditions B).

Example 306

Compound no380: (2S,5R)-5-(2-chlorophenyl)-1-(1-(4-methyl-2-nitrophenyl)piperidine-4-carbonyl)pyrrolidine-2-carboxylic acid was synthesized using the same methodology as depicted in scheme 12, replacing 2-nitro-4-trifluoromethyl-fluorobenzene by 2-nitro-4-methyl-fluorobenzene.

Example 307

Compound no381: (2S,5R)-5-(2-chlorophenyl)-1-(1-(2-cyano-4-nitrophenyl)piperidine-4-carbonyl)pyrrolidine-2-carboxylic acid was synthesized using the same methodology as depicted in scheme 12, replacing 2-nitro-4-trifluoromethyl-fluorobenzene by 2-cyano-4-methyl-fluorobenzene.

Example 308

Compound no382: (2S,5R)-5-(2-chlorophenyl)-1-(1-(4-nitrophenyl)piperidine-4-carbonyl)pyrrolidine-2-carboxylic acid was synthesized from intermediate 1a and commercial 1-(4-nitrophenyl)piperidine-4-carboxylic acid using general method C (conditions B).

Example 309

Compound no383: (2S,5R)-5-(2-chlorophenyl)-1-(1-(2-fluoro-4-nitrophenyl)piperidine-4-carbonyl)pyrrolidine-2-carboxylic acid was synthesized using the same methodology as depicted in scheme 13, replacing 2-cyano-4-trifluoromethyl-bromobenzene by 2-fluoro-4-nitro-bromobenzene.

Example 310

Compound no384: (2S,5R)-5-(2-chlorophenyl)-1-(1-(3-methoxy-4-nitrophenyl)piperidine-4-carbonyl)pyrrolidine-2-carboxylic acid was synthesized from intermediate 1a and commercial 1-(3-methoxy-4-nitrophenyl)piperidine-4-carboxylic acid using general method C (conditions B).

Example 311

Compound no385: (2S,5R)-1-(1-(5-chloro-2-nitrophenyl)piperidine-4-carbonyl)-5-(2-chlorophenyl)pyrrolidine-2-carboxylic acid was synthesized from intermediate 1a and commercial 1-(5-chloro-2-nitrophenyl)piperidine-4-carboxylic acid using general method C (conditions B).

Example 312

Compound no386: (2S,5R)-5-(2-cyanophenyl)-1-(2'-methoxy-[1,1'-biphenyl]-4-carbonyl)pyrrolidine-2-carboxylic acid was obtained by cyanation of (2S,5R)-methyl 5-(2-bromophenyl)-1-(2'-methoxy-[1,1'-biphenyl]-4-carbonyl)pyrrolidine-2-carboxylate and subsequent saponification. (2S,5R)-methyl 5-(2-bromophenyl)-1-(2'-methoxy-[1, 1'-biphenyl]-4-carbonyl)pyrrolidine-2-carboxylate was obtained from intermediates 1i1 and 2h using general method C, (conditions A). Cyanation method of cyanation: In a carrousel tube were introduced NMP (0.2 mL), i-PrOH (9.7 µL), sodium carbonate (0.021 g, 0.202 mmol), palladium(II) acetate (0.908 mg, 4.05 µmol) and (2S,5R)-methyl 5-(2-bromophenyl)-1-(2'-methoxy-[1,1'-biphenyl]-4-carbonyl)pyrrolidine-2-carboxylate (0.1 g, 0.202 mmol). The RM was heated at 140° C. and potassium ferrocyanide.3H$_2$O (0.026 g, 0.061 mmol) was added. Heating was stopped and the RM was stirred overnight. The RM was diluted with water and extracted with three times with EtOAc. The aqueous layer was acidified (a color change from brown to blue was observed) and extracted twice with diethyl ether. The combined organic layers were dried over MgSO$_4$, filtered and concentrated to afford a brown residue. Crude was purified by flash chromatography (EtOAc/PE: 1/2) to yield compound no386. Y=10%, P>90%.

Example 313

Compound no387: (2S,5R)-5-(2-chlorophenyl)-1-(2'-cyano-4'-methoxy-[1,1'-biphenyl]-4-carbonyl)pyrrolidine-2-carboxylic acid was obtained from intermediates 1a and intermediate 2s4 using general method C (conditions B).

Example 314

Compound no388: (2S,5R)-5-(2-chlorophenyl)-1-(2-fluoro-4'-(methylsulfonamido)-[1,1'-biphenyl]-4-carbonyl)pyrrolidine-2-carboxylic acid was obtained from intermediates 1a and intermediate 2s5 using general method C (conditions B).

Example 315

Compound no389: (2S,5R)-5-(2-chlorophenyl)-1-(2-fluoro-3'-(methylsulfonamido)-[1,1'-biphenyl]-4-carbonyl)pyrrolidine-2-carboxylic acid was obtained from intermediates 1a and intermediate 2t5 using general method C (conditions B).

Example 316

Compound no390: (2S,5R)-5-(2-chlorophenyl)-1-(2'-cyano-2-fluoro-[1,1'-biphenyl]-4-carbonyl)pyrrolidine-2-carboxylic acid was obtained from intermediates 1a and intermediate 2u5 using general method C (conditions B).

Example 317

Compound no391: (2S,5R)-5-(2-chlorophenyl)-1-(1-(2-cyano-4-(methylsulfonamido)phenyl)piperidine-4-carbonyl)pyrrolidine-2-carboxylic acid was obtained by reduction of nitro, sulfonylation and saponification of (2S,5R)-methyl 5-(2-chlorophenyl)-1-(1-(2-cyano-4-nitrophenyl)piperidine-4-carbonyl)pyrrolidine-2-carboxylate which was obtained from intermediate 1a and commercial 1-(2-cyano-4-nitrophenyl)piperidine-4-carboxylic acid using general method C, condition B.

Example 318

Compound no392: (2S,5R)-5-(2-chlorophenyl)-1-(1-(2-cyano-4-methoxyphenyl)piperidine-4-carbonyl)pyrrolidine-2-carboxylic acid was obtained using the same methodology as shown in scheme 13 replacing 2-cyano-4-trifluoromethyl-bromobenzene with 2-cyano-4-methoxy-bromobenzene.

Example 319

Compound no393: (2S,5R)-5-(2-chlorophenyl)-1-(1-(2-(methylsulfonamido)-4-(trifluoromethyl)phenyl)piperidine-4-carbonyl)pyrrolidine-2-carboxylic acid was obtained by reduction of the nitro group of (2S,5R)-methyl 5-(2-chlorophenyl)-1-(1-(2-nitro-4-(trifluoromethyl)phenyl)piperidine-4-carbonyl)pyrrolidine-2-carboxylate, followed by sulfonylation with methane sulfonyl chloride, and subsequent saponification. (2S,5R)-methyl-5-(2-chlorophenyl)-1-(1-(2-nitro-4-(trifluoromethyl)phenyl)piperidine-4-carbonyl)pyrrolidine-2-carboxylate was obtained from intermediates 1a and commercial 1-(2-nitro-4-(trifluoromethyl)phenyl)piperidine-4-carboxylic acid using general method C (conditions B).

Example 320

Compound no394: (2S,5R)-5-(2-chlorophenyl)-1-(1-(2-nitrophenyl)piperidine-4-carbonyl)pyrrolidine-2-carboxylic acid was synthesized from intermediate 1a and commercial 1-(2-nitrophenyl)piperidine-4-carboxylic acid using general method C (conditions B).

Example 321

Compound no395: (2S,5R)-5-(2-chlorophenyl)-1-(1-(4-cyanophenyl)piperidine-4-carbonyl)pyrrolidine-2-carboxylic acid was synthesized from intermediate 1a and commercial 1-(4-cyanophenyl)piperidine-4-carboxylic acid using general method C (conditions B).

Example 322

Compound no396: (2S,5R)-5-(3,5-difluorophenyl)-1-(2'-methoxy-[1,1'-biphenyl]-4-carbonyl)pyrrolidine-2-carboxylic acid was obtained from intermediates 1l1 and intermediate 2h using general method C (conditions A).

Example 323

Compound no397: (2S,5R)-5-(3,4-difluorophenyl)-1-(2'-methoxy-[1,1'-biphenyl]-4-carbonyl)pyrrolidine-2-carboxylic acid was obtained from intermediates 1m1 and intermediate 2h using general method C (conditions A).

Example 324

Compound no398: (2S,5R)-5-(2,3-difluorophenyl)-1-(2'-methoxy-[1,1'-biphenyl]-4-carbonyl)pyrrolidine-2-carboxylic acid was obtained from intermediates 1n1 and intermediate 2h using general method C (conditions A).

Example 325

Compound no399: (2S,5R)-5-(2,5-difluorophenyl)-1-(2'-methoxy-[1,1'-biphenyl]-4-carbonyl)pyrrolidine-2-carboxylic acid was obtained from intermediates 1o1 and intermediate 2h using general method C (conditions A).

Example 326

Compound no400: (2S,5R)-5-([1,1'-biphenyl]-2-yl)-1-(2'-methoxy-[1,1'-biphenyl]-4-carbonyl)pyrrolidine-2-carboxylic acid was obtained by Suzuki coupling (2S,5R)-methyl 5-(2-bromophenyl)-1-(2'-methoxy-[1,1'-biphenyl]-4-carbonyl)pyrrolidine-2-carboxylate with phenylboronic acid and subsequent saponification. (2S,5R)-methyl 5-(2-bromophenyl)-1-(2'-methoxy-[1,1'-biphenyl]-4-carbonyl)pyrrolidine-2-carboxylate was obtained from intermediates 1i1 and 2h using general method C (conditions A).

Example 327

Compound no401: (2S,5R)-1-(2'-cyano-4'-methoxy-[1,1'-biphenyl]-4-carbonyl)-5-(2-fluorophenyl)pyrrolidine-2-carboxylic acid was obtained from intermediates 1g and 2s4 using general method C (conditions B).

Example 328

Compound no402: (2S,5R)-5-(4-cyanophenyl)-1-(2'-methoxy-[1,1'-biphenyl]-4-carbonyl)pyrrolidine-2-carboxylic acid was obtained from intermediates 1p1 and 2h using general method C (conditions A).

Example 329

Compound no403: (2S,5R)-5-(2-chlorophenyl)-1-(4-(5-methyl-4-(phenylsulfonyl)-1H-1,2,3-triazol-1-yl)benzoyl)pyrrolidine-2-carboxylic acid was synthesized from intermediate 1a and commercial 4-(5-methyl-4-(phenylsulfonyl)-1H-1,2,3-triazol-1-yl)benzoic acid using general method C (conditions B).

Example 330

Compound no404: (2S,5R)-5-(2-chlorophenyl)-1-(3'-cyano-4'-fluoro-[1,1'-biphenyl]-4-carbonyl)pyrrolidine-2-carboxylic acid was obtained from intermediates 1a and intermediate 2u4 using general method C (conditions B).

Example 331

Compound no405: (2S,5R)-1-(2'-chloro-5'-cyano-[1,1'-biphenyl]-4-carbonyl)-5-(2-chlorophenyl)pyrrolidine-2-carboxylic acid was obtained from intermediates 1a and intermediate 2v4 using general method C (conditions B).

Example 332

Compound no406: (2S,5R)-5-(2-chlorophenyl)-1-(2'-cyano-4'-(trifluoromethyl)-[1,1'-biphenyl]-4-carbonyl)pyrrolidine-2-carboxylic acid was obtained from intermediates 1a and intermediate 2w4 using general method C (conditions B).

Example 333

Compound no407: (2S,5R)-5-(2-chlorophenyl)-1-(1-(2-methoxy-4-(trifluoromethyl)phenyl)piperidine-4-carbonyl)pyrrolidine-2-carboxylic acid was obtained using the same methodology as depicted in scheme 12, replacing 2-nitro-4-trifluoromethyl-fluorobenzene by 2-methoxy-4-trifluoromethyl-fluorobenzene.

Example 334

Compound no408: (2S,5R)-5-(2-chlorophenyl)-1-(2'-methyl-3'-(N-methylmethylsulfonamido)-[1,1'-biphenyl]-4-carbonyl)pyrrolidine-2-carboxylic acid was obtained from intermediates 1a and intermediate 2x4 using general method C (conditions B).

Example 335

Compound no409: (2S,5R)-5-(2-chlorophenyl)-1-(2'-methoxy-4'-(N-methylmethylsulfonamido)-[1,1'-biphenyl]-4-carbonyl)pyrrolidine-2-carboxylic acid was obtained from intermediates 1a and intermediate 2v5 using general method C (conditions B).

Example 336

Compound no410: (2S,5R)-5-(2-chlorophenyl)-1-(6-(5-cyano-2-methoxyphenyl)-5-methoxynicotinoyl)pyrrolidine-2-carboxylic acid was obtained from intermediates 1a and intermediate 2y4 using general method C (conditions B).

Example 337

Compound no411: (2S,5R)-5-(2-chlorophenyl)-1-(6-(2,4-dimethoxyphenyl)-5-methoxynicotinoyl)pyrrolidine-2-carboxylic acid was obtained from intermediates 1a and intermediate 2z4 using general method C (conditions B).

Example 338

Compound no412: (2S,5R)-5-(2-chlorophenyl)-1-(6-(2,4-dimethoxyphenyl)nicotinoyl)pyrrolidine-2-carboxylic acid was obtained from intermediates 1a and intermediate 2a5 using general method C (conditions B).

Example 339

Compound no413: (2S,5R)-1-(2'-cyano-4'-(trifluoromethyl)-[1,1'-biphenyl]-4-carbonyl)-5-(2-fluorophenyl)pyrrolidine-2-carboxylic acid was obtained from intermediates 1g and intermediate 2w4 using general method C (conditions B).

Example 340

Compound no414: (2S,5R)-1-(3'-cyano-4'-fluoro-[1,1'-biphenyl]-4-carbonyl)-5-(2-fluorophenyl)pyrrolidine-2-carboxylic acid was obtained from intermediates 1g and intermediate 2u4 using general method C (conditions B).

Example 341

Compound no415: (2S,5R)-1-(2'-chloro-5'-cyano-[1,1'-biphenyl]-4-carbonyl)-5-(2-fluorophenyl)pyrrolidine-2-carboxylic acid was obtained from intermediates 1g and intermediate 2v4 using general method C (conditions B).

Example 342

Compound no416: (2S,5R)-5-(2-chlorophenyl)-1-(4-(3,6-dimethoxypyridazin-4-yl)-3-fluorobenzoyl)pyrrolidine-2-carboxylic acid was synthetized from 1a and 2w5 using general method C (conditions B).

Example 343

Compound no417: (2S,5R)-5-(2-fluorophenyl)-1-(2'-methyl-3'-(N-methylmethylsulfonamido)-[1,1'-biphenyl]-4- carbonyl)pyrrolidine-2-carboxylic acid was synthetized from intermediates 1g and 2x4 using general method C (conditions B).

Example 344

Compound no418: (2S,5R)-5-(2-fluorophenyl)-1-(2'-methoxy-4'-(N-methylmethylsulfonamido)-[1,1'-biphenyl]-4-carbonyl)pyrrolidine-2-carboxylic acid was synthetized from 1g and 2v5 using general method C (conditions B).

Example 345

Compound no419: (2S,5R)-5-(2-chlorophenyl)-1-(4-(4,6-dimethoxypyrimidin-5-yl)benzoyl)pyrrolidine-2-carboxylic acid was synthetized from 1a and 2f5 using general method C (conditions B).

Example 346

Compound no420: (2S,5R)-5-(2,3-difluorophenyl)-1-(4-(2,4-dimethoxypyrimidin-5-yl)benzoyl)pyrrolidine-2-carboxylic acid was synthetized from intermediates 1n1 and 2s1 using general method C (conditions B).

Example 347

Compound no421: (2S,5R)-1-(5'-cyano-2'-methyl-[1,1'-biphenyl]-4-carbonyl)-5-(2,3-difluorophenyl)pyrrolidine-2-carboxylic acid was synthetized from intermediates 1n1 and 2a4 using general method C (conditions B).

Example 348

Compound no354: (2S,5R)-5-(2-fluorophenyl)-1-(2'-methoxy-4'-(methylsulfonamido)-[1,1'-biphenyl]-4-carbonyl)pyrrolidine-2-carboxylic acid was synthetized from intermediates 1g and 2p5 using general method C (conditions B).

Example 349

Compound no355: (2S,5R)-5-(2,4-difluorophenyl)-1-(4-(2,6-dimethoxypyridin-3-yl)benzoyl)pyrrolidine-2-carboxylic acid was synthetized from intermediates 1k1 and 2q5 using general method C (conditions B).

Example 350

Compound no356: (2S,5R)-5-(2-chlorophenyl)-1-(3-methoxy-4-(5-methoxypyridin-3-yl)benzoyl)pyrrolidine-2-carboxylic acid was synthetized from intermediates 1a and 2d4 using general method C (conditions B).

Example 351

Compound no357: (2S,5R)-1-(4'-amino-2'-methoxy-[1,1'-biphenyl]-4-carbonyl)-5-(2-chlorophenyl)pyrrolidine-2-carboxylic acid was synthetized from intermediate 1a and methyl 2'-methoxy-4'-amino-[1,1'-biphenyl]-4-carboxylate obtained in the synthesis of intermediate 2p5.

Example 352

Compound no358: (2S,5R)-5-(2-chlorophenyl)-1-(2',3,6'-trimethoxy-[2,3'-bipyridine]-5-carbonyl)pyrrolidine-2-carboxylic acid was synthetized from intermediates 1a and 2e4 using general method C (conditions B).

BIOLOGY EXAMPLES

Brief Description of the Drawings

FIG. 1 represents the effect of compounds 1; 2; 4; 5; 8; 10; 11 and 13 on isoprenaline-induced lipolysis in adipocytes isolated from normal rat. Compounds are tested at 30 µM final concentration.

FIGS. 2A and 2B represent the inhibition of blood glucose concentration in OGTT assay following bi-daily injection (at 50 mg/kg) of compound 1 during 28 days.

MEMBRANE BINDING ASSAY: GTPγS BINDING ASSAY

The following assay can be used for determination of GPR43 activation. When a GPCR is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyses the GTP to GDP, at which point the receptor normally is deactivated. Activated receptors continue to exchange GDP for GTP. The non-hydrolysable GTP analog, [$^{35}$S]GTPγS, was used to demonstrate enhance binding of [$^{35}$S]GTPγS to membranes expressing receptors. The assay uses the ability of GPCR to stimulate [$^{35}$S]GTPγS binding to membranes expressing the relevant receptors. The assay can, therefore, be used in the direct identification method to screen candidate compounds to endogenous or not endogenous GPCR.

Preparation of Membrane Extracts:

Membrane extracts were prepared from cells expressing the human GPR43 receptor (hGPR43) as follows: the medium was aspirated and the cells were scraped from the plates in $Ca^{++}$ and $Mg^{++}$-free Phosphate-buffered saline (PBS). The cells were then centrifuged for 3 min at 1500 g and the pellets were resuspended in buffer A (15 mM Tris-HCl pH 7.5, 2 mM $MgCl_2$, 0.3 mM EDTA, 1 mM EGTA) and homogenized in a glass homogenizer. The crude membrane fraction was collected by two consecutive centrifugation steps at 40.000×g for 25 min separated by a washing step in buffer A. The final pellet was resuspended in 500 µl of buffer B (75 mM Tris-HCl pH 7.5, 12.5 mM $MgCl_2$, 0.3 mM EDTA, 1 mM EGTA, 250 mM sucrose) and flash frozen in liquid nitrogen. Protein content was assayed by the Folin method.

GTPγS Assay (SPA Method):

The assay was used to determine the activity of the compounds of the invention. The [$^{35}$S]GTPγS assay was incubated in 20 mM HEPES pH7.4, 100 mM NaCl, 10 µg/ml saponin, 30 mM of $MgCl_2$, 10 µM of GDP, 5 µg membrane-expressing hGPR43, 250 µg of wheatgerm agglutinin beads (Amersham, ref: RPNQ001), a range concentration of compounds of the invention (from 30 µM to 1 nM) in a final volume of 100 µl for 30 min at room temperature. The SCFA propionate was used at 1 mM final concentration as positive control. The plates were then centrifuged for 10 minutes at 2000 rpm, incubated for 2 hours at room temperature and counted for 1 min in a scintillation counter (TopCount, PerkinElmer). The results of the tested compounds are reported as the concentration of the compound required to reach 50% ($EC_{50}$) of the maximum level of the activation induced by these compounds.

When tested in the assay described above and by way of illustration the compounds in Table 3 activate GPR43 receptor. The $EC_{50}$ value obtained is represented as follows: "+++" means $EC_{50} < 200$ nM; "++" means $200\ \text{nM} \leq EC_{50} \leq 1\ \mu M$; "+" means $EC_{50} > 1\ \mu M$.

TABLE 3

Compounds $EC_{50}$ values in GTPγ$^{35}$S assay.

| Compound n° | $EC_{50}$ (nM) |
|---|---|
| 1 | +++ |
| 2 | +++ |
| 3 | +++ |
| 4 | +++ |
| 5 | +++ |
| 6 | +++ |
| 8 | ++ |
| 9 | ++ |
| 10 | ++ |
| 11 | ++ |
| 12 | ++ |
| 13 | ++ |
| 14 | ++ |
| 15 | ++ |
| 16 | ++ |
| 17 | ++ |
| 18 | ++ |
| 19 | ++ |
| 20 | ++ |
| 21 | ++ |
| 23 | + |
| 24 | + |
| 26 | + |
| 27 | + |
| 30 | + |
| 31 | + |
| 32 | + |
| 33 | + |
| 34 | + |
| 35 | + |
| 36 | + |
| 38 | + |
| 39 | + |
| 40 | + |
| 41 | + |
| 42 | + |
| 43 | + |
| 44 | + |
| 45 | + |
| 47 | + |
| 48 | + |
| 49 | + |
| 52 | + |
| 53 | + |
| 58 | + |
| 59 | + |
| 77 | +++ |
| 78 | ++ |
| 83 | + |
| 88 | + |
| 89 | ++ |
| 91 | ++ |
| 96 | ++ |
| 99 | ++ |
| 102 | + |
| 105 | + |
| 107 | + |
| 108 | + |
| 109 | + |
| 113 | +++ |
| 114 | + |
| 116 | ++ |
| 117 | ++ |
| 120 | + |
| 121 | ++ |
| 122 | +++ |
| 123 | +++ |
| 125 | ++ |
| 126 | +++ |
| 127 | +++ |
| 128 | +++ |
| 129 | +++ |
| 130 | +++ |
| 131 | + |
| 132 | +++ |
| 133 | ++ |
| 134 | ++ |
| 135 | +++ |
| 136 | ++ |
| 137 | ++ |
| 138 | +++ |
| 140 | +++ |
| 141 | ++ |
| 143 | + |
| 149 | ++ |
| 150 | ++ |
| 151 | ++ |
| 153 | + |
| 155 | + |
| 156 | ++ |
| 157 | +++ |
| 160 | ++ |
| 161 | +++ |
| 162 | + |
| 169 | + |
| 174 | + |
| 176 | + |
| 177 | + |
| 178 | ++ |
| 179 | + |
| 183 | + |
| 184 | ++ |
| 189 | ++ |
| 191 | ++ |
| 192 | ++ |
| 193 | +++ |
| 194 | ++ |
| 195 | ++ |
| 196 | +++ |
| 197 | +++ |
| 198 | +++ |
| 199 | +++ |
| 200 | +++ |
| 201 | +++ |
| 202 | +++ |
| 203 | ++ |
| 204 | +++ |
| 206 | + |
| 207 | + |
| 224 | +++ |
| 225 | +++ |
| 226 | ++ |
| 227 | +++ |
| 228 | +++ |
| 229 | +++ |
| 230 | + |
| 231 | + |
| 232 | +++ |
| 233 | ++ |
| 234 | + |
| 235 | +++ |
| 236 | +++ |
| 237 | ++ |
| 239 | ++ |
| 240 | ++ |
| 242 | ++ |
| 246 | +++ |
| 247 | +++ |
| 261 | ++ |
| 268 | +++ |
| 269 | +++ |
| 272 | ++ |
| 273 | ++ |
| 274 | ++ |
| 275 | +++ |

TABLE 3-continued

Compounds EC$_{50}$ values in GTPγ$^{35}$S assay.

| Compound n° | EC$_{50}$ (nM) |
|---|---|
| 276 | ++ |
| 278 | ++ |
| 279 | + |
| 280 | + |
| 281 | ++ |
| 283 | +++ |
| 284 | ++ |
| 285 | + |
| 286 | + |
| 287 | ++ |
| 288 | ++ |
| 289 | +++ |
| 290 | +++ |
| 291 | ++ |
| 292 | +++ |
| 293 | ++ |
| 294 | ++ |
| 295 | + |
| 296 | + |
| 297 | +++ |
| 298 | +++ |
| 299 | +++ |
| 300 | ++ |
| 301 | ++ |
| 302 | +++ |
| 303 | ++ |
| 304 | + |
| 305 | + |
| 306 | + |
| 307 | +++ |
| 308 | +++ |
| 309 | ++ |
| 310 | ++ |
| 311 | +++ |
| 312 | +++ |
| 313 | ++ |
| 314 | +++ |
| 315 | +++ |
| 316 | +++ |
| 318 | + |
| 319 | ++ |
| 320 | +++ |
| 321 | ++ |
| 322 | ++ |
| 323 | ++ |
| 324 | ++ |
| 325 | +++ |
| 326 | + |
| 327 | ++ |
| 328 | +++ |
| 329 | ++ |
| 330 | ++ |
| 331 | ++ |
| 332 | + |
| 333 | + |
| 334 | ++ |
| 335 | + |
| 336 | + |
| 337 | +++ |
| 338 | +++ |
| 339 | ++ |
| 340 | +++ |
| 341 | + |
| 342 | +++ |
| 343 | +++ |
| 344 | ++ |
| 345 | +++ |
| 346 | +++ |
| 347 | +++ |
| 348 | +++ |
| 349 | ++ |
| 350 | +++ |
| 351 | +++ |
| 352 | + |
| 353 | ++ |
| 354 | +++ |
| 355 | +++ |
| 356 | +++ |
| 357 | +++ |
| 358 | ++ |
| 359 | ++ |
| 360 | +++ |
| 361 | +++ |
| 362 | +++ |
| 363 | ++ |
| 364 | + |
| 365 | ++ |
| 366 | +++ |
| 367 | +++ |
| 368 | +++ |
| 369 | ++ |
| 370 | + |
| 371 | +++ |
| 372 | +++ |
| 373 | ++ |
| 374 | ++ |
| 375 | ++ |
| 386 | ++ |
| 387 | +++ |
| 388 | +++ |
| 389 | +++ |
| 390 | +++ |
| 391 | + |
| 392 | + |
| 393 | + |
| 395 | ++ |
| 396 | ++ |
| 397 | ++ |
| 398 | +++ |
| 399 | +++ |
| 400 | ++ |
| 401 | +++ |
| 402 | + |
| 403 | + |
| 404 | ++ |
| 405 | +++ |
| 406 | +++ |
| 407 | ++ |
| 408 | +++ |
| 409 | +++ |
| 410 | ++ |
| 411 | ++ |
| 412 | ++ |
| 413 | +++ |
| 414 | + |
| 415 | +++ |
| 416 | +++ |
| 417 | +++ |
| 418 | ++ |
| 419 | +++ |
| 420 | +++ |
| 421 | +++ |

Radioligand Binding (RLB) Assay with Cell Membrane Extracts from Human GPR43 Recombinant Cell Line Human GPR43 radioligand binding assay is performed by adding successively in the wells of a 96 well plate (Master Block, Greiner, 786201), 50 μl of compound of the invention at increasing concentrations (diluted in assay buffer: 50 mM Tris pH 7.4), 25 μl radiolabeled antagonist (i.e. compound no277 described in EP10305100.9) diluted in assay buffer and 25 μl cell membrane extracts (10 protein/well). The final concentration of radiolabeled antagonist in the assay is 10 nM. The plate is incubated 60 min at 25° C. in a water bath and then filtered over GF/B filters (Perkin Elmer, 6005177, presoaked in 0.05% Brij for 2 h at room temperature) with a Filtration unit (Perkin Elmer). The filters are washed 3 times with 0.5 ml of ice-cold wash buffer (50 mM Tris pH 7.4). 50 μl of Microscint 20 (Packard), is added and the plate is incubated 15 min on an orbital shaker and then counted with a TopCount™ for 1 min/well.

In Table 4 biological results obtained using the RLB assay as described above with compounds of the invention are set out in tabulated form. In this table, the constant of inhibition of radioligand binding carried out by the compound of the invention (Ki) is given. The Ki values (nM) obtained is represented as follows: "+++" means Ki<1 μM; "++" means 1 μM≤Ki≤2 μM; "+" means 2 μM<Ki.

TABLE 4

Compounds Ki values in RLB assay.

| Compound n° | Ki (nM) |
| --- | --- |
| 376 | +++ |
| 377 | + |
| 378 | ++ |
| 379 | + |
| 380 | ++ |
| 381 | ++ |
| 382 | + |
| 383 | + |
| 384 | + |
| 385 | +++ |
| 394 | + |

Cell Based Assay: Calcium Flux. The Aequorin-Based Assay.

The following assay can be used for determination of GPR43 activation. The aequorin assay uses the responsiveness of mitochondrial apoaequorin to intracellular calcium release induced by the activation of GPCRs (Stables et al., 1997, Anal. Biochem. 252:115-126; Detheux et al., 2000, J. Exp. Med., 192 1501-1508). Briefly, GPCR-expressing clones are transfected to coexpress mitochondrial apoaequorin and Gα16. Cells expressing GPR43 receptor are incubated with 5 μM Coelenterazine H (Molecular Probes) for 4 hours at room temperature, washed in DMEM-F12 culture medium and resuspended at a concentration of $0.5\times10^6$ cells/ml (the amount can be changed for optimization). Cells are then mixed with test compounds and light emission by the aequorin is recorded with a luminometer for 30 sec. Results are expressed as Relative Light Units (RLU). Controls include assays using cells not expressing GPR43 (mock transfected), in order to exclude possible non-specific effects of the candidate compound.

Aequorin activity or intracellular calcium levels are "changed" if light intensity increases or decreases by 10% or more in a sample of cells, expressing a GPR43 and treated with a compound of the invention, relative to a sample of cells expressing the GPR43 but not treated with the compound of the invention or relative to a sample of cells not expressing the GPR43 (mock-transfected cells) but treated with the compound of the invention.

Cell Based Assay: Intracellular Inositol-Phosphate Accumulation Assay. (Gq-Associated Receptor)

The following assay can be used for determination of GPR43 activation. On day 1, GPR43-expressing cells in mid-log phase are detached with PBS-EDTA, centrifuged at 2000×g for 2 min and resuspended in medium without antibiotics. After counting, cells are resuspended at $4\times10^5$ cells/ml (the amount can be changed for optimization) in medium without antibiotics, distributed in a 96 well plate (10 μl/well) and the plate is incubated overnight at 37° C. with 5% $CO_2$. On day 2, the medium is removed and the compounds of the invention, at increasing concentrations, are added (24 μl/well) and the plate is incubated for 30 min. at 37° C. in a humidified atmosphere of 95% air with 5% $CO_2$. The IPI concentrations are then estimated using the IPI-HTRF assay kit (Cisbio international, France) following the manufacturer recommendations.

Cell Based Assay: cAMP Accumulation Assay ($G_{i/o}$ Associated Receptor)

The following assay can be used for determination of GPR43 activation. Cells expressing GPR43 in mid-log phase and grown in media without antibiotics are detached with PBS-EDTA, centrifuged and resuspended in media without antibiotics. Cells are counted and resuspended in assay buffer at $4.2\times10^5$ cells/ml. 96 well plates are filled with 12 μl of cells ($5\times10^3$ cells/well), 6 μl of compound of the invention at increasing concentrations and 6 μl of Forskolin (final concentration of 10 μM). The plate is then incubated for 30 min. at room temperature. After addition of the lysis buffer, cAMP concentrations are estimated, according to the manufacturer specification, with the HTRF kit from Cis-Bio International.

In Vitro Assays to Assess Compound Activity in 3T3-L1 Cell Line.

3T3-L1 adipocytes cell line has been described as cellular model to assess compounds mimicking insulin-mediated effect such as inhibition of lipolysis and activation of glucose uptake.

Lipolysis.

3T3-L1 cells (ATCC) are cultured in Dulbecco's modified eagle's medium (DMEM) containing 10% (v/v) bovine serum (fresh regular medium) in 24 well plate. On day 0 (2 days after 3T3-L1 preadipocytes reached confluence), cells are induced to differentiate by insulin (10 μg/ml), IBMX (0.5 mM) and dexamethasone (1 μM). On day 3 and every other $3^{rd}$ day thereafter, fresh regular medium is substituted until day 14.

On day 14, the medium is removed and cells are washed twice with 1 ml of a wash buffer (Hank's balanced salt solution). The wash solution is removed and the SCFA or the tested compounds, or a combination of both, are added at the desired concentration in Hank's buffer supplemented with 2% BSA-FAF and incubated for 10 minutes à 37° C. Then, isoproterenol (100 nM) is added to induce lipolysis and incubate for 30 minutes at 37° C. The supernatants are collected in a glycerol-free container. 25 μl (the amount can be changed for optimization) of cell-free supernatants are dispensed in 96-well microtiter plate, 25 μl of free glycerol assay reagent (Chemicon, the amount can be changed for optimization) is added in each well and the assay plate is incubated for 15 minutes at room temperature. The absorbance is recorded with a spectrophotometer at 540 or 560 nm. Using the supernatants, the free fatty acids amount can be assessed using the NEFA assay kit (Wako) according the manufacturer's recommendations.

Glucose Uptake.

3T3-L1 cells are differentiated as described previously with or without of 30 μM of tested compounds (the concentration can be changed for optimization) during the 14 days of differentiation. The day of the experiment, the cells are washed twice with a KREBS-Ringer bicarbonate (pH 7.3) supplemented with 2 mM sodium pyruvate and starved for 30 minutes in the same buffer at 37° C. in an atmosphere containing 5% CO2 and 95% O2. Various amount of SCFA, tested compounds or combination of both are then added with or without 10 nM of insulin (the amount can be changed for optimization) for 30 minutes at 37° C. in an atmosphere containing 5% CO2 and 95% O2. Then, D-($^3$H)-2 deoxyglucose (0.2 μCi/well) and D-2-deoxyglucose (0.1 mM) is added for 30 minutes. To stop the reaction, the cells are immersed in ice-cold saline buffer, washed for 30 min, and then dissolved in NaOH 1M at 55° C. for 60 minutes. NaOH is neutralized with HCl 1M. The 3H labeled radioactivity of an aliquot of the extract is counted in the presence of a scintillation buffer.

In Vitro Assays to Assess Compound Activity in NCI-H716 Cell Line.

Human intestinal cell line NCI-H716 has been described as cellular model to assess compounds mimicking nutrient-mediated effect such as glucagon-like peptide-1 (GLP-1) secretion.

GLP-1 Release.

NCI-H716 cells (ATCC, Manassas) are cultured in Dulbecco's modified eagle's medium (DMEM) containing 10% (v/v) bovine serum, 2 mM L-glutamine, 100 IU/ml penicillin and 100 µg/ml streptomycin in 75 ml flask. Cell adhesion and endocrine differentiation is initiated by growing cells in 96-well plate coated with matrigel in High Glucose DMEM containing 10% (v/v) bovine serum, 2 mM L-glutamine, 100 IU/ml penicillin and 100 µg/ml streptomycin for 2 days.

On day 2, the medium is removed and cells are washed once with a pre-warmed wash buffer (Phosphate Buffered salt solution). The wash solution is removed and the SCFA or the tested compounds, or a combination of both, are added at the desired concentration in High Glucose DMEM containing 0.1% (v/v) bovine serum and incubated for 2 hours at 37° C. The supernatants are collected in a container. Using the cell-free supernatants, the GLP-1 amount is assessed using a GLP-1 specific ELISA assay kit according the manufacturer's recommendations (ALPCON).

Ex Vivo Assays to Assess Compound Activity in Adipocytes from Normal Rat or Mice and High-Fat Diet Fed Mice.

Mice C56Black6 male are housed in Makrolon type IV group housing cages (56×35×20 cm$^3$) throughout the experimental phase. Animals' cages litters are changed once a week. They are housed in groups of 10 animals at 12 light dark (at 8 h 30 pm lights off), 22+/−2° C. and 50+/−5% relative humidity. Animals are acclimated one week. During the whole phase, standard diet or diet high in energy from fat (Research Diets, New Brunswick, N.J.) and tap water are provided ad libitum. The animals are 16 weeks old at the time of the study.

For keeping only mice that have responded to the high fat diet, fasted glycemia are measured in these mice just before performing the ex-vivo study.

Glucose Uptake Assay in Isolated Adipocytes.

Animals are killed by cervical dislocation and epididymal fat pads are removed and digested in collagenase buffer at 370° C./120 rpm for approximately 50 minutes. The digest is filtered through gauze to recover the adipocytes, which are washed and resuspended in Krebs-Ringer Hepes (KRH) buffer containing 1% BSA, 200 nM adenosine and 2 mM glucose.

Isolated adipocytes are washed in glucose-free KRH-buffer and resuspended to 30%. Adipocytes are then incubated at 370° C./80 rpm with either the tested compound (30 µM, 10 µM and 1 µM) in the presence or absence of insulin (10 nM) for 30 min 2-deoxyglucose and 2-deoxy-D-[1-$^3$H]-glucose ($^3$H-2-DOG) are added and incubation continued for 10 min. The reactions are then stopped by addition of cytochalasin b followed by centrifugation through dinonyl-phthalate to recover the adipocytes. The uptake of $^3$H-2-DOG- was measured by scintillation. Each data point is investigated in triplicates in two independent experiments.

Lipolysis Assay in Isolated Adipocytes.

Isolated adipocytes are diluted to 5% in KRH-buffer and are pre-treated with the tested compound (30 µM, 100/1 and 10/1) for 30 min at 370° C./120 rpm. After the pre-treatment, Isoprenaline (1 µM) is added to the adipocytes followed by 30 min incubation at 37° C./150 rpm. The reactions are put on ice and the buffer is assayed spectrophotometrically for the production of NADH$^+$ from glycerol breakdown in reactions catalyzed by glycerol kinase and glycerol-3-phosphate dehydrogenase and/or Non Esterified Fatty Acid (NEFA). Each data point is investigated in triplicates in two independent experiments.

According to the method described above and by way of illustration the compounds no1; 2; 4; 5; 8; 10; 11 and 13 inhibit isoprenaline-induced lipolysis in adipocytes from normal rat, at the concentration of 30 µM (FIG. 1).

In Vivo Assay to Assess Compound Activity in Rodent Diabetes Model.

Genetic Rodent Models:

Rodent models of T2D associated with obesity and insulin resistance have been developed. Genetic models such as db/db and ob/ob in mice and fa/fa in Zucker rats have been developed for understanding the pathophysiology of disease and testing candidate therapeutic compounds. The homozygous animals, C57 Black/6-db/db mice developed by Jackson Laboratory are obese, hyperglycemic, hyperinsulinemic and insulin resistant (J Clin Invest, 1990, 85:962-967), whereas heterozygotes are lean and normoglycemic. In the db/db model, mice progressively develop insulinopenia with age, a feature commonly observed in late stages of human T2D when sugar levels are insufficiently controlled. Since this model resembles that of human T2D, the compounds are tested for activities including, but not limited to, lowering of plasma glucose and triglycerides. Zucker (fa/fa) rats are severely obese, hyperinsulinemic, and insulin resistant, and the fa/fa mutation may be the rat equivalent of the murine db mutation. Genetically altered obese diabetic mice (db/db) (male, 7-9 weeks old) are housed under standard laboratory conditions at 22° C. and 50% relative humidity, and maintained on a diet of Purina rodent chow and water ad libitum. Prior to treatment, blood is collected from the tail vein of each animal and blood glucose concentrations are determined using one touch basic glucose monitor system (Lifescan). Mice that have plasma glucose levels between 250 to 500 mg/dl are used. Each treatment group consists of several mice that are distributed so that the mean of glucose levels are equivalent in each group at the start of the study. Db/db mice are dosed by micro-osmotic pumps, inserted using isoflurane anesthesia, to provide compounds of the invention, saline, or an irrelevant compound to the mice intravenously (i.v). Blood is sampled from the tail vein at intervals thereafter and analyzed for blood glucose concentrations. Significant differences between groups (comparing compounds of the invention to saline-treated) are evaluated using Student t-test.

Ob/ob or obese mice are leptin-deficient mice that eat excessively and become profoundly obese, hyperinsulinemic and hyperglycemic. It is an animal model of type II diabetes. Such model can be used for oral glucose tolerance tests (OGTTs). A total of sixteen (16) male ob/ob mice (6 weeks of age) were obtained from Harlan. Upon arrival to the animal unit, mice were housed 4 per cage in rodent cages mounted with feeders containing regular chow. The mice were put in a 12/12 h light-dark cycle (light from 0600-1800 h) with controlled temperature conditions (22-24° C.). Fed blood glucose and body-weight was measured on day −2 in the morning between 08:00 AM and 09:00 AM. Animals were randomized into 2 groups according to fed glucose levels (on day −2). The 16 mice with blood glucose and body-weight closest to the mean were distributed into the following groups: Group 1: Vehicle p.o. bi-daily, (n=8) and Group 2: Compound of the invention, p.o., bi-daily, (n=8).

Day 1 is the first day of dosing. Animals were dosed with compounds of the invention at 07:00 AM and 04:00 PM for 28 days. On the evening of day 27, food was removed and mice were transferred to clean cages. Mice were fasted for the subsequent 17 hours until the OGTT was performed. At −15 min, blood glucose was measured (using a glucose analyzer) and animals were dosed with compounds of the invention or vehicle. At time point 0, blood glucose was measured again and glucose was administered by oral gavage (1 g/kg glucose). The blood glucose was then measured at time points 15, 30, 45, 60 and 120 minutes. The blood glucose area under the curve (AUC) from time −15 to 120 min was then calculated (GraphPad software). The percentages of AUC inhibition induced by compounds of the invention were calculated as follows: % of AUC inhibition: [1−(AUC compound/AUC vehicle)]*100.

When tested in the above-described assay, the compound 1 showed a % of AUC inhibition of 40%, indicating that compound 1 is able to significantly reduce the level of blood glucose in diabetic animal model (FIGS. 2A and 2B).

The High-Fat Diet Fed Mouse:

This model was originally introduced by Surwit et al. in 1988. The model has shown to be accompanied by insulin resistance, as determined by intravenous glucose tolerance tests, and of insufficient islet compensation to the insulin resistance. The model has, accordingly, been used in studies on pathophysiology of impaired glucose tolerance (IGT) and type 2 diabetes and for development of new treatments.

C57BL/6J mice are maintained in a temperature-controlled room (22° C.) on a 12-h light-dark cycle. One week after arrival, mice are divided into two groups and are fed either a high-fat diet or received continuous feeding of a normal diet for up to 12 months. On caloric basis, the high-fat diet consist of 58% fat from lard, 25.6% carbohydrate, and 16.4% protein (total 23.4 kJ/g), whereas the normal diet contains 11.4% fat, 62.8% carbohydrate, and 25.8% protein (total 12.6 kJ/g). Food intake and body weight are measured once a week, and blood samples are taken at indicated time points from the intraorbital retrobulbar plexus from nonfasted anesthetized mice.

For intravenous glucose tolerance tests (IVGTTs), 4-h fasted mice are anesthetized with 7.2 mg/kg fluanison/fenlanyl and 15.3 mg/kg midazolam. Thereafter a blood sample is taken from the retrobulbar, intraorbital, capillary plexus, after which D-glucose (1 g/kg) is injected intravenously in a tail vein (volume load 10 l/g). Additional blood samples are taken at 1, 5, 10, 20, 50, and 75 min after injection. Following immediate centrifugation at 4 C, plasma is separated and stored at −20 C until analysis. For oral glucose tolerance tests (OGTTs), 16-h fasted anesthetized mice are given 150 mg glucose by gavage through a gastric tube (outer diameter 1.2 mm), which is inserted in the stomach. Blood samples are taken at 0, 15, 30, 60, 90, and 120 min after glucose administration and handled as above.

Administration of the compounds: Five-week-old mice are fed a high-fat or a normal diet for 8 weeks. After 4 weeks, the mice are additionally given the compound of the invention in their drinking water (0.3 mg/ml, the amount can be changed for optimization. Control groups are given tap water without compound. After another 4 weeks, the mice are subjected to an OGTT as described above. Insulin and glucose measurements: Insulin is determined enzymatically using an ELISA assay kit (Linco Research, St. Charles, Mo.). Plasma glucose is determined by the glucose oxidase method.

In Vivo Assay to Assess Compound Anti-Obesity Activity in Rodent Model.

Mouse Acute Food Intake and Weight Change:

Male C57BL/6N wild-type mice are weighed and vehicle or the tested compounds are administered by oral gavage to male mice approximately 30 min prior to the onset of the dark phase of the light cycle. Mice are fed ad libitum in the dark phase following dosing. A preweighed aliquot of a highly palatable medium high fat diet is provided in the food hopper of the cage 5 min prior to the onset of the dark phase of the light cycle and weighed 2 and 18 h after the onset of the dark phase of the light cycle.

Acute Studies in Diet-Induced Obesity (DIO) Rats:

For acute experiments, male Sprague-Dawley DIO rats from Charles River Laboratories are raised from 4 weeks of age on a diet moderately high fat (32% kcal) and high in sucrose (25% kcal). Animals are used at 12 weeks of age and are maintained on a 12/12 h light dark cycle. The rats are randomized into groups (n=6/group) for the tested compounds and vehicle dosing. Rats are weighed 17 h after dosing to determine effects on overnight body weight gain. The tested compounds are administered orally or s.c. at amount desired 1 h before the start of the dark cycle. Powdered food is provided in food cups which are weighed continuously at 5 min intervals over 18 h and the data are recorded using a computerized system.

Chronic Studies in Diet-Induced Obesity Rats:

For the 14-day chronic experiment, male Sprague-Dawley DIO rats are obtained as described above. Animals are used at 15 weeks of age and are maintained on a 12/12 hour light-dark cycle. Rats are conditioned to dosing for 4 days prior to baseline measurements, using an oral gavage or a s.c. route of vehicle. Thereafter, animals are dosed daily with vehicle or compound by oral gavage or s.c. The tested compound or vehicle is administered 1 h before the dark cycle for 14 days. Body composition is measured by dual energy X-ray densitometry (DEXAscan) 5 days prior to the study and at the end of the 14-day study. Daily endpoints included body weight and food intake.

In Vivo Assay to Assess Compound Anti-Lipolytic Activity in Rodent Model.

Male C57BL/6N wild-type are housed one per cage in a room maintained on a 12 h light/dark cycle under constant temperature (22-25° C.) with ad libitum access to food and water. The anti-lipolytic effects of the tested compounds are studied in awake mice. Animals are fasted overnight before experimental use. On the day of the experiment, animals are put in metabolic cages and left undisturbed to acclimate to the environment for 1-2 h. blood samples are taken at indicated time points from the intraorbital retrobulbar plexus. A 1% sodium citrate saline solution is used to flush the lines. A pre-treatment blood sample is obtained from each animal to determine baseline values for free fatty acids (FFA) and triglycerides (TG). The tested compounds are given via oral gavage, sc injection, iv injection or ip injection for each different series of experiments. Blood samples are collected into pre-cooled tubes pre-coated with heparin (200 µl blood, Li-heparin, Sarstedt) for determination triglycerides and glycerol and in tri-potassium EDTA added sodium fluoride (200 µl blood, $K_3$-EDTA, 1.6 mg/mL+1% NaF, Sarstedt) for determination of plasma free fatty acids. The tubes are placed on wet ice pending processing. Blood samples will be centrifuged at 4000×g, at 4° C., 15 min the resulting plasma will be transferred into non-coated tubes and stored at −80° C. until analyses. The plasma is thawed at 4° C. for determinations of FFA and TG using commercial kits (Wako Chemicals).

While embodiments of the invention have been illustrated and described, it is not intended that these embodiments illustrate and describe all possible forms of the invention. Rather, the words used in the specification are words of description rather than limitation ant it is understood that various changes may be made without departing from the spirit and scope of the invention.

The invention claimed is:

1. A process for the preparation of a compound of formula Ib-1b':

$$\text{Ib-1b'}$$

wherein:
D is —C(=O)—;
$L^2$ is a single bond;
R, $R^1$, $R^2$, $R^3$, $R^{3'}$ and $R^4$ are independently —H;
$Ar^1$ is 2-chlorophenyl, 2-fluorophenyl or 2,3-difluorophenyl; and
$Ar^2$ is aryl, heteroaryl, cycloalkyl or monocyclic heterocyclyl, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxy, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino and oxo, wherein each of said substituent group(s) may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; or two $Ar^2$ substituents form an alkylenedioxy group or a haloalkylenedioxy group, wherein each of said alkylenedioxy or haloalkylenedioxy groups may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; or fused to the $Ar^2$ cycloalkyl group may be one or more aryl or heteroaryl moieties, wherein each of said aryl or heteroaryl moieties may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl;

wherein the process consists of:

a) coupling a compound of formula A:

$$A$$

wherein:
R is methyl, ethyl, tert-butyl, benzyl, allyl, phenacyl, methoxymethyl, methylthiomethyl, 2-methoxyethoxymethyl, 2-trimethylsilylethyl or tert-butyldiphenylsilyl; and
(i) $R^8$ is —Cl or —F; and
$R^9$ is —H; or
(ii) $R^8$ is —F; and
$R^9$ is —F;

with a compound of formula B:

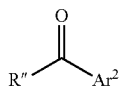

wherein:
R" is —Cl or -OL, wherein L is benzotriazol-1-yl, 7-azabenzotriazol-1-yl or imidazol-1-yl; and
Ar² is aryl, heteroaryl, cycloalkyl or monocyclic heterocyclyl, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxy, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino and oxo, wherein each of said substituent group(s) may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; or
two Ar² substituents form an alkylenedioxy group or a haloalkylenedioxy group, wherein each of said alkylenedioxy or haloalkylenedioxy groups may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; or
fused to the Ar² cycloalkyl group may be one or more aryl or heteroaryl moieties, wherein each of said aryl or heteroaryl moieties may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl;
in the presence of a base, to provide a compound of the formula:

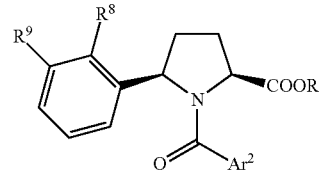

wherein:
R is methyl, ethyl, tert-butyl, benzyl, allyl, phenacyl, methoxymethyl, methylthiomethyl, 2-methoxyethoxymethyl, 2-trimethylsilylethyl or tert-butyldiphenylsilyl;
(i) $R^8$ is —Cl or —F; and
$R^9$ is —H; or
$R^8$ is —F; and
$R^9$ is —F; and
Ar² is aryl, heteroaryl, cycloalkyl or monocyclic heterocyclyl, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxy, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino and oxo, wherein each of said substituent group(s) may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; or two $Ar^2$ substituents form an alkylenedioxy group or a haloalkylenedioxy group, wherein each of said alkylenedioxy or haloalkylenedioxy groups may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; or fused to the $Ar^2$ cycloalkyl group may be one or more aryl or heteroaryl moieties, wherein each of said aryl or heteroaryl moieties may be optionally substituted by one or more further substituents selected from halo, cyano, nitro, alkyl, hydroxyalkyl, haloalkyl, cyanomethyl, cycloalkyl, heterocyclyl, $C_5$-$C_{12}$ aryl optionally substituted by a chloro or methyl group, heteroaryl, heteroalkyl, hydroxy, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; and b) (i) treating the compound provided in step a) above with a base, an acid or a fluoride; or
(ii) hydrogenolysis of the compound provided in step a) above,
to provide a compound of formula Ib-1b'.

2. The process according to claim 1, wherein the compound of formula A is methyl (2S,5R)-5-(2-chlorophenyl) pyrrolidine-2-carboxylate.

3. The process according to claim 1, wherein the compound of formula B is 2' methoxybiphenyl-4-carbonyl chloride.

* * * * *